(12) United States Patent
Griffin et al.

(10) Patent No.: US 6,566,509 B1
(45) Date of Patent: May 20, 2003

(54) MULTIVALENT MACROLIDE ANTIBIOTICS

(75) Inventors: John H. Griffin, Atherton, CA (US); John L. Pace, San Anselmo, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 09/327,899

(22) Filed: Jun. 8, 1999

Related U.S. Application Data

(60) Provisional application No. 60/093,072, filed on Jul. 16, 1998, and provisional application No. 60/088,448, filed on Jun. 8, 1998.

(51) Int. Cl.[7] .................. C07H 17/08; A01N 43/04; A61K 31/70; C07D 413/00; C07D 417/00
(52) U.S. Cl. .................. 536/7.4; 424/449; 424/456; 424/465; 424/489; 435/7.1; 435/7.2; 435/76; 436/501; 436/518; 514/28; 514/29; 514/31; 544/137; 544/138; 544/139; 544/140; 544/369; 536/6.5; 536/7.1; 536/7.2
(58) Field of Search .................. 435/7.1, 7.2, 76; 514/29, 28, 31; 536/7.2, 7.4, 6.5, 7.1; 436/501, 515; 544/137–140, 369; 424/456, 449, 465, 489

(56) References Cited

U.S. PATENT DOCUMENTS

| | | | |
|---|---|---|---|
| 5,023,252 | A | 6/1991 | Hseih |
| 5,463,564 | A | 10/1995 | Agrafiotis et al. |
| 5,693,791 | A | 12/1997 | Truett |
| 5,846,839 | A | 12/1998 | Gallop et al. |

FOREIGN PATENT DOCUMENTS

| | | |
|---|---|---|
| CA | 2240325 | 7/1998 |
| WO | 93/06121 | 4/1993 |
| WO | 95/07271 | 3/1995 |
| WO | 97/35195 | 9/1997 |

OTHER PUBLICATIONS

Sundram et al. J. Am. Chem. Soc., vol. 118, No. 51, pp. 13107–13108, Dec. 1996.*
Wang et al. Book of Abstracts, 213th ACS National Meeting, San Francisco, Apr. 13–17 (1997), CARB–064. American Chemical Society: Washington, D.C., Nov. 1997.*
Brickner et al. J. Med. Chem. vol. 39, No. 3, pp. 673–679, Oct. 1997.*
Rao et al. J. Am. Chem. Soc., vol. 119, No. 43, pp. 10286–10290, Oct. 1997.*
Brickner, S. J., et al. "Synthesis and Antibacterial Activity of U–100592 and u–100766, Two Oxazolidinone Antibacterial Agents for the Potential Treatment of Multidrug–Resistant Gram–Positive Bacterial Infections." *J. Med. Chem.* 39:673–679 (1986).
Holmes, et al. "Novel Dimeric Penicillin Derived Inhibitors of HIV–1 Proteinase: Interaction with the Catalytic Aspartases." *Bioorg. Med. Chem. Lett.* 3(4): 503–508 (1993).
Portoghese, P.S. The Role of Concepts in Structure–Activity Relationship Studies of Opioid Ligands. *J. med. Chem.* 35(11): 1927–1937 (1992).
Rao, et al. "Tight Binding of a Dimeric Dervative of Vancomycin with Dimeris L–Lys–D–Ala–D–Ala." *J. Am. Chem. Soc.* 119(43): 10286–10290 (1997).
Salvi, et al. "Formation of Bis (Fmoc–amino ethyl)–N–g-lycine derivatives by reductive amination of Fmoc–amino aldehydes with $NaBH_3CN$." *Tetrahedron Letters*. 35: 1181–1184 (1994).
Shuker, et al. "Discovering High–Affinity Ligands for Proteins: SAR by NMR." *Science*. 274: 1531–1534 (1996).
Sundram, U.N., et al. "Novel Vancomycin Dimers with Activity againt Vancomycin–Resistant Enterococci." *J. Am. Chem. Soc.* 118: 13107–13108 (1996).
Tucker, J. A., et al. "Piperazinyl Oxazolidinone Antibacterial Agents Containing a pyridine, Diazene, or Triazene Heteroaromatic Ring." *J. Med Chem.* 41:3727–3735 (1988).
Zeng, et al. Automated Analytical/Preparative High–performance Liquid Chromatography–Mass Spectrometry System for the Rapid Characterization and Purification of Compound Libraries. *J. Chrom. A.* 794:3–13 (1998).
Ahonkhai, V. I. et al. "In Vitro Activity of U–57930E, a New Clindamycin Analog, Against Aerobic Gram–Positive Bacteria." *Antimicrobial Agents and Chemotherapy*. 21(6):902–905 (1982).
Ballesta, J. P., et al. "Peptidyltransferase inhibitors: Structure–Activity Relationship Analysis by Chemical Modification." *The Ribosome.* Ch. 44, pp 502–510, Hill, et al, eds. (1982).
Barden, T. C., et al. "Glycylcyclines. 3. 9–Aminodoxycyclinecarboxamides." *J. Med. Chem.* 37(20):3205–3211 (1994).
Blackwood, R. K., et al. "Some Transformations of Tetracycline at the 4–Position." *Can. J. Chem.* 43:1382–1388 (1965).
Brenner, et al. "Encoded combinatorial chemistry." *Proc. Natl. Acad. Sci., USA*. 89:5381–5383 (1992).
CAS 1771–31–9, 53864—51–0.

(List continued on next page.)

*Primary Examiner*—Maurie Baker
(74) *Attorney, Agent, or Firm*—David E. Boone; Jeffrey A. Hagenah; Joyce Cohen

(57) ABSTRACT

Disclosed are multibinding compounds which include macrolide antibiotics, aminoglycosides, lincosamides, oxazolidinones, streptogramins, tetracycline and/or other compounds at which bind to bacterial ribosomal RNA and/or to one or more proteins involved in ribosomal protein synthesis in the bacterium, which are useful in treating bacterial infections. The compounds adversely affect protein expression and have an antibacterial effect. The multibinding compounds of this invention containing from 2 to 10 ligands covalently attached to one or more linkers. Each ligand is macrolide antibiotic, aminoglycoside, lincosamide, oxazolidinone, streptogramin, tetracycline or other compound which binds to bacterial ribosomal RNA and/or one or more proteins involved in ribosomal protein synthesis in the bacterium.

7 Claims, 57 Drawing Sheets

OTHER PUBLICATIONS

Cooperman, B.S. et al. "Antiobiotic Probes of *Escherichia coli* Ribosomal Peptidyltransferase." *The Ribosome.* Ch. 42, pp 491–502, Hill, et al. eds. (1990).

Cooperman. "Affintiy labelling of Ribosomes." *Methods Enzymol.* 164: 341–361 (1988).

Cundliffe, E. "Recognition Sites for Antibiotics within rRNA." *The Ribosome.* Chapter 41, pp 479–510, Hill, et al. eds. (1990).

Delaware, D. L., et al. "Aminoglycoside Antibiotics (Dihydrostreptomycin Analogues)." *J. Antibiotics*, XXXIX(2):251–258 91986).

Herrinton, P. M., et al. "Oxidation and Alkylation of Spectinomycin Derivatives; Synthesis of Trospectomycin from Spectinomycin." *J. Org. Chem.* 678–682 (1993).

Jaynes, et al. "Photoinduced Affinity Labeling of the *Escherichia coli* Ribosome Puromycin Site." *Biochemistry.* 17: 561–569 (1978).

Kirst, Ph.D., H. A. "2 Semi–synthetic derivatives of Erythromycin." *Prog. Med. Chem.*, 30(2):57–88 (1993) (Ellis and Luscombe, eds.).

Lemieux, R. U., et al. "The Chemistry of Streptomycin." *Advances in Carbohydrate Chemistry.* 52:337–384 (1948).

Mossa, J. S., et al. "Streptomycin." *Analytical Profiles of Drug Substances.* 16:507, 531–535,587 (1987) (Flored, ed.).

Rosenbrook, Jr., W., et al. "Spectinomycin Modification." ACS Symposium, Series 125, 133–144 (1980).

Spahn, C. M. T., et al. "Throwing a spanner in the works: antibiotics and the translation apparatus." *J. Mol. Med.* 74:423–439 (1996).

Thomas, R. C., et al. "Synthesis of Spectinomycin Analogs." ACS Symposium, Series 125, 121–131 (1980).

Tohma, S., et al. "Ashimycins A and B, new streptomycin Analogues." *J. Antibiotics.* XLII(8):1205–1212 (1989).

White, D. R., et al. "The Synthesis of Trospectomycin (6'–n–Propylspectinomycin, U–63,366F) From Spectinomycin." *Tetrahedron Letters.* 30(12): 1469–1472 (1989).

* cited by examiner

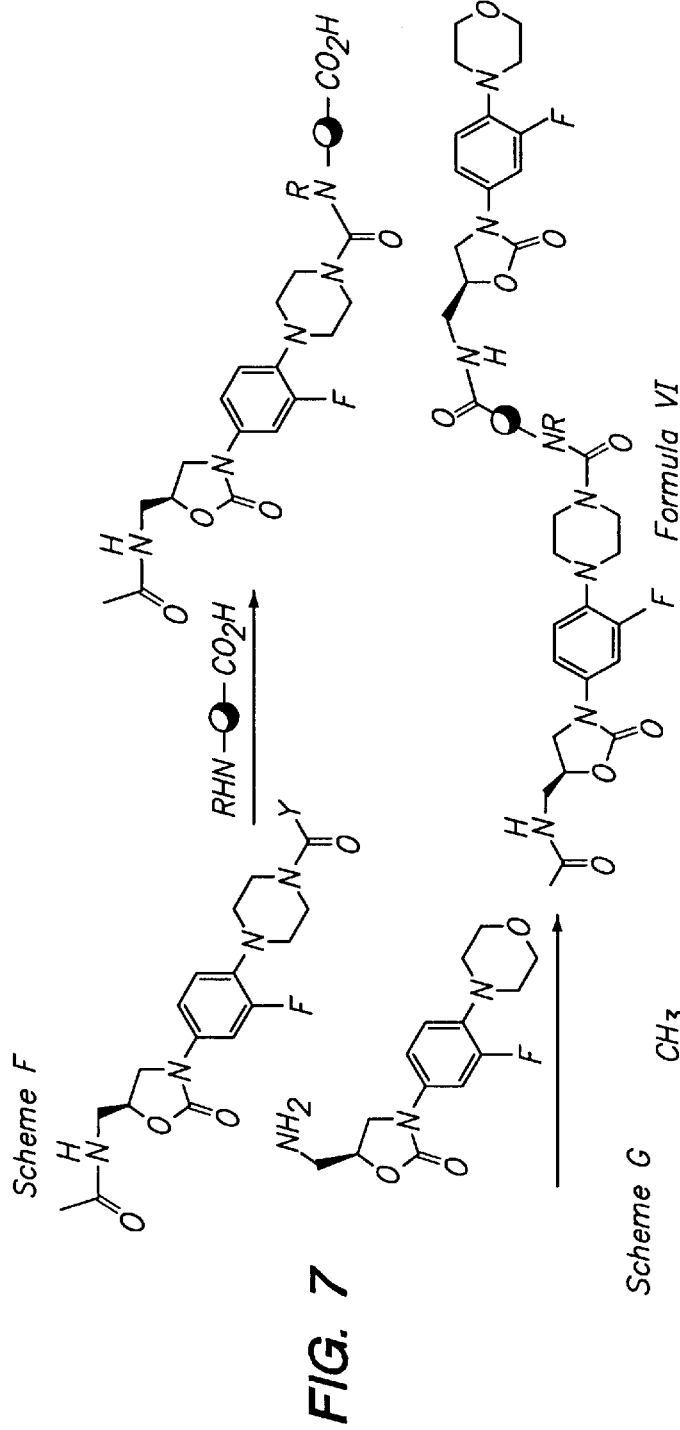
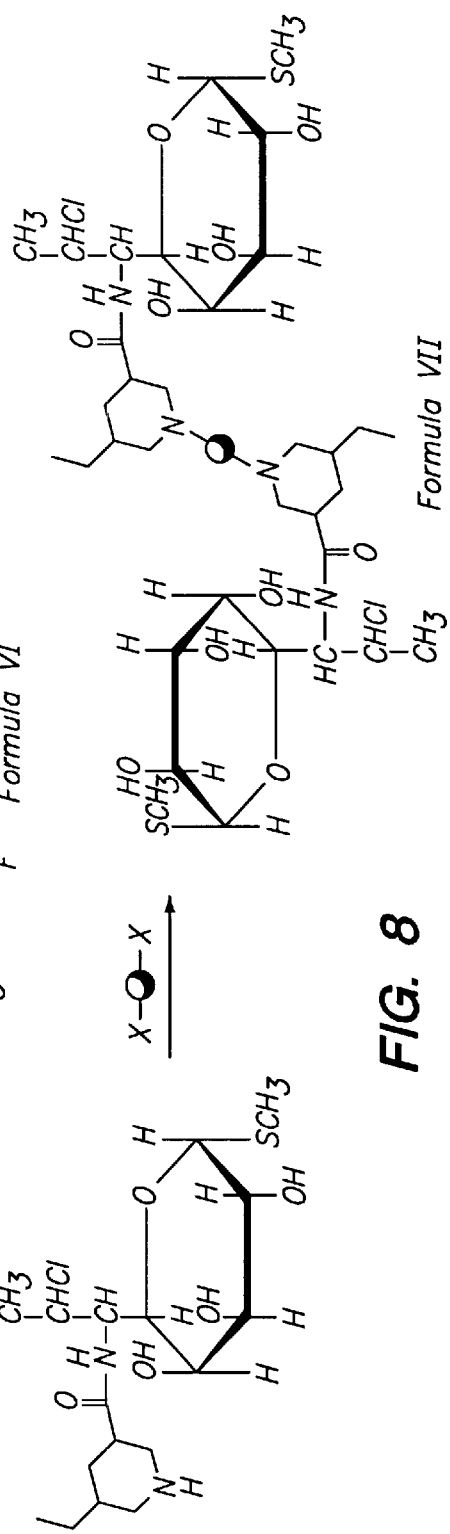
FIG. 7
FIG. 8

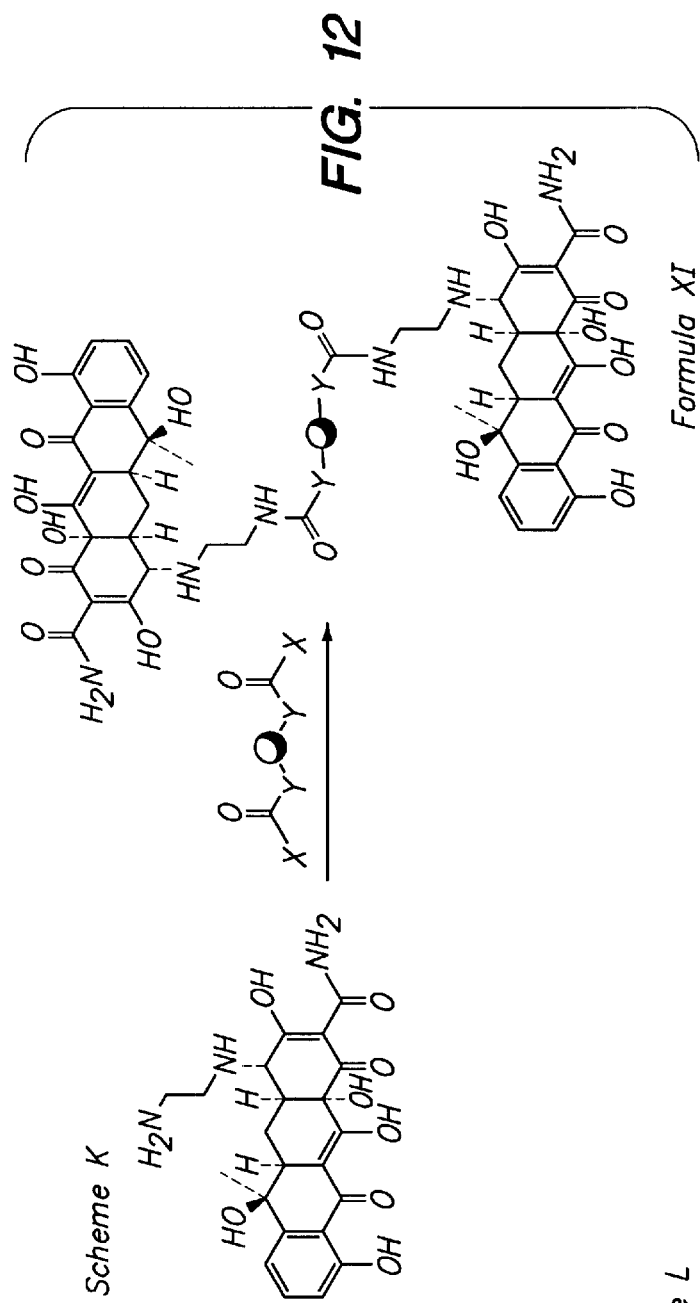
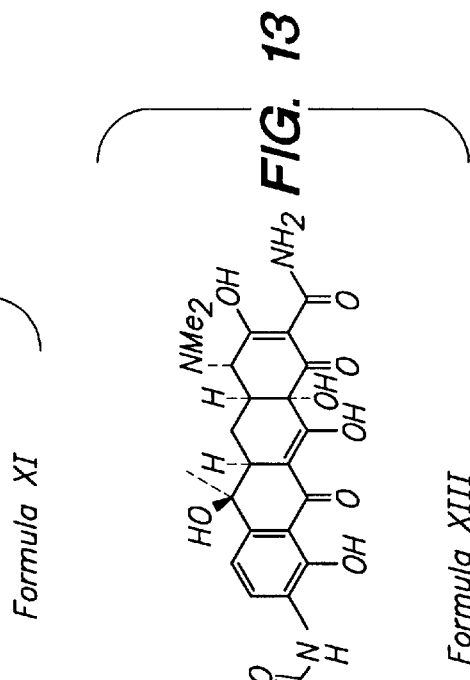
FIG. 12
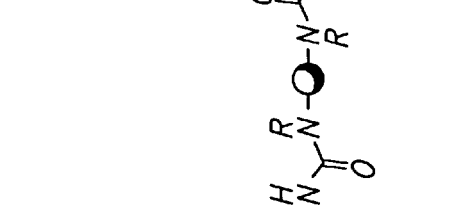
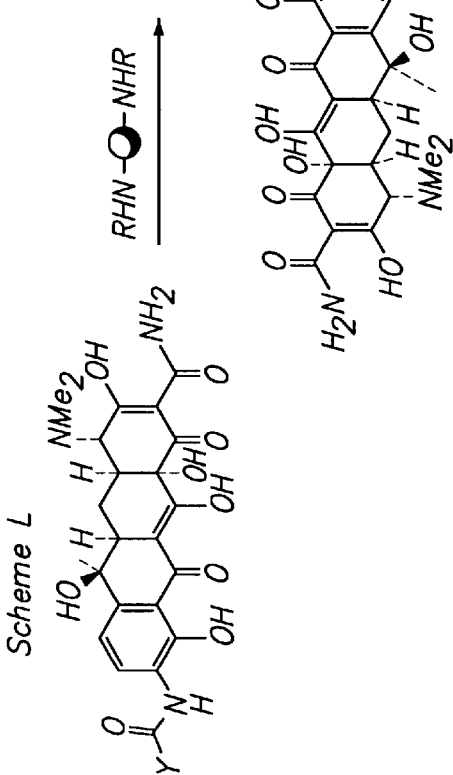
FIG. 13

Formula XV

Formula XXI

Scheme II

Formula XXXV

Scheme QQ

Formula XLIII    FIG. 42

Scheme WW

Formula XLIX

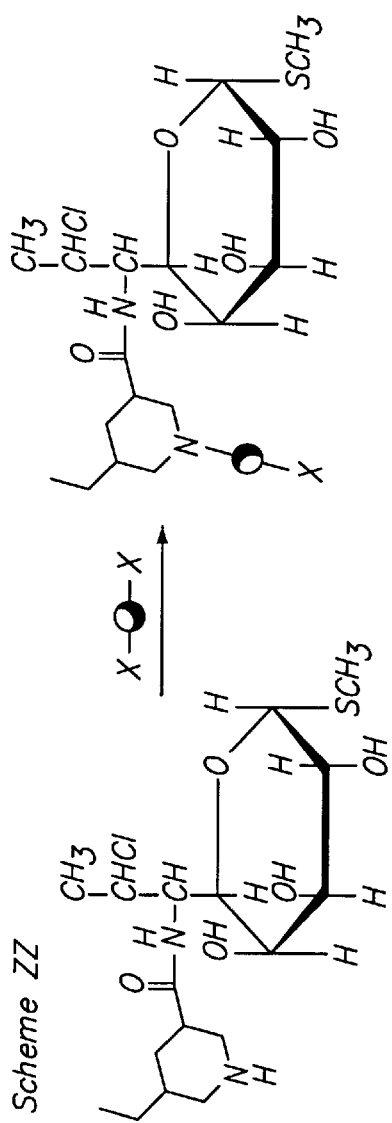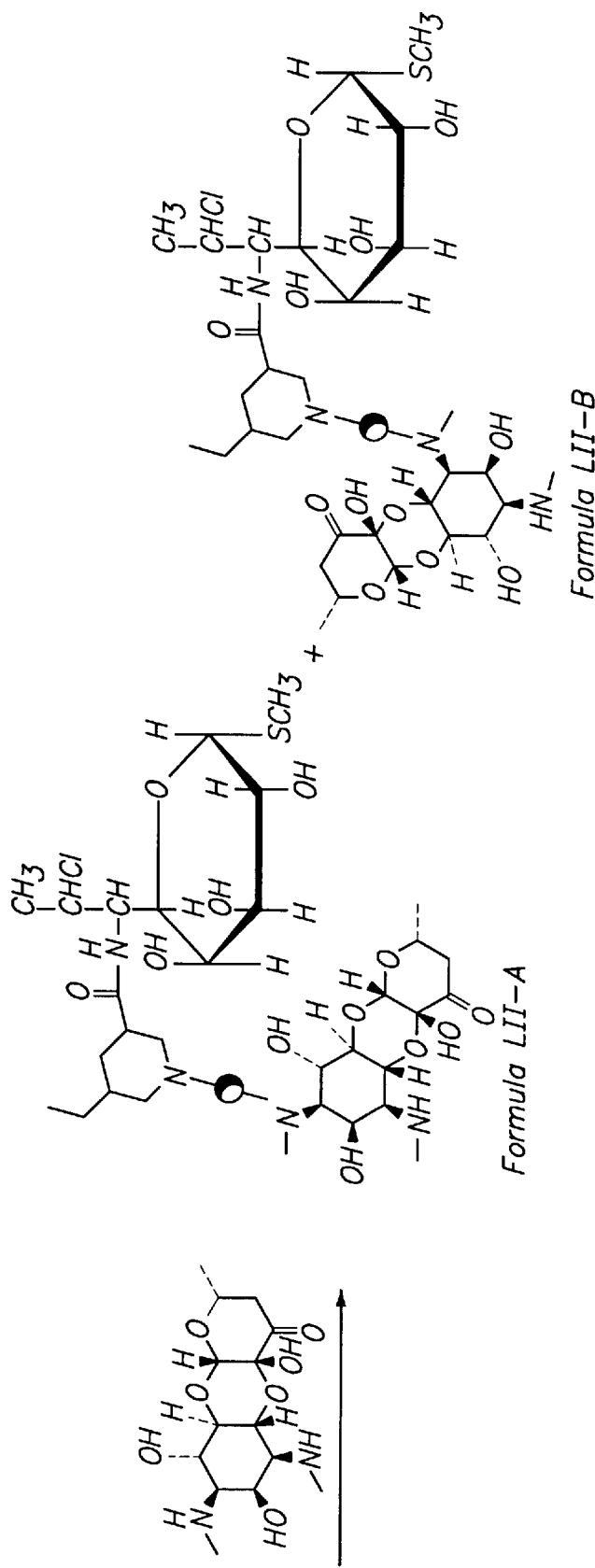
FIG. 51

Scheme AAA

Formula LIII-A

Formula LIII-A

FIG. 53  Formula LIV

FIG. 54 Scheme CCC  Formula LV

MULTIVALENT MACROLIDE ANTIBIOTICS

CROSS-REFERENCE TO RELATED APPLICATIONS

This application is related U.S. Provisional Patent Application Serial No. 60/088,448 filed Jun. 8, 1998 and No. 60/093,072 filed Jul. 16, 1998 both of which are incorporated herein by reference.

BACKGROUND OF THE INVENTION

1. Field of the Invention

This invention relates to novel multibinding compounds (agents) that are macrolide antibiotics, aminoglycosides, lincosamides, oxazolidinones, streptogramins, tetracyclines or other compounds which bind to bacterial ribosomal RNA or one or more proteins involved in ribosomal protein synthesis in the bacterium, and to pharmaceutical compositions comprising such compounds. The compounds are useful as antibacterial agents for treating a variety of bacterial infections.

2. State of the Art

Organisms generate polypeptides (proteins) in order to survive. Organisms that cannot generate proteins cannot maintain viability. Because the majority of genes encode proteins, "gene expression" is nearly synonymous with protein synthesis. Gene expression involves two steps—transcription and translation. Genes code for proteins using various codons (units of three nucleotides), such as start codons (which initiate translation), stop codons (which stop translation) and codons in between the start and stop codons which selectively code for the various amino acids.

Translation is the RNA directed synthesis of polypeptides. This process requires all three classes of RNA. The template for correct addition of individual amino acids is the mRNA, yet both tRNAs and rRNAs are involved in the process.

Prokaryotes and eukaryotes use ribosomes to generate proteins. Ribosomes are cytoplasmic organelles, and are large complexes of proteins and three (prokaryotes) or four (eukaryotes) rRNA (ribosonial ribonucleic acid) molecules called subunits made in the nucleolus. Ribosomes serve as the site of mRNA translation. Once the two (large and small) subunits are joined by the mRNA from the nucleus, the ribosome translates the mRNA into a specific sequence of amino acids, or a polypeptide chain.

In its inactive state, the ribosome exists as two subunits; a large subunit and a small subunit. When the small subunit encounters an mRNA, the process of translation of the mRNA to protein begins. There are two sites in the large subunit, for subsequent amino acid-charged tRNAs to bind to and thus be close enough to each other for the formation of a peptide bond. The A site accepts a new tRNA bearing an amino acid, and the P site bears the tRNA attached to the growing chain.

tRNA (transfer RNA) is a specific RNA molecule which acts as a translator between mRNA and protein. Each tRNA has a specific anticodon and acceptor site. Each tRNA also has a specific charger protein; this protein can only bind to that particular tRNA and attach the correct amino acid to the acceptor site. The energy to make this bond comes from ATP. These charger proteins are called aminoacyl tRNA synthetases. The tRNAs carry activated amino acids into the ribosome. The ribosome is associated with the mRNA ensuring correct access of activated tRNAs and containing the necessary enzymatic activities to catalyze peptide bond formation.

Protein synthesis proceeds from the N-terminus to the C-terminus of the protein. The ribosomes "read" the mRNA in the 5' to 3' direction. Active translation occurs on polyribosomes (also termed polysomes). This means that more than one ribosome can be bound to and translate a given mRNA at any one time. Chain elongation occurs by sequential addition of amino acids to the C-terminal end of the ribosome bound polypeptide. Translation proceeds in an ordered process. First accurate and efficient initiation occurs, then chain elongation and finally accurate and efficient termination must occur. All three of these processes require specific proteins, some of which are ribosome associated and some of which are separate from the ribosome, but may be temporarily associated with it.

Initiation of Translation

Before translation occurs, a ribosome must dissociate into its 30S and 50S subunits. A ternary complex termed the preinitiation complex is formed consisting of the initiator, GTP, eIF-2 and the 40S subunit. The mRNA is bound to the preinitiation complex.

Initiation of translation in both prokaryotes and eukaryotes requires a specific initiator tRNA (which includes methionine). The initiation of translation requires recognition of a start (AUG) codon.

Peptide bond formation is catalyzed by a 23S rRNA component of the 50S subunit (peptidyl transferase). Another important site for protein synthesis is the 16S rRNA component of the 30S subunit (the aminoacyl tRNA site). When protein synthesis is terminated, release factor proteins bind to the stop codons, GTP hydrolysis occurs, and peptidyl transferase activity is stimulated, causing release of the protein from the tRNA.

Elongation of the New Protein

After the first charged tRNA appears in the A site, the ribosome shifts so that the tRNA is in the P site. New charged tRNAs, corresponding to the codons of the mRNA, enter the A site, and a peptide bond is formed between the two amino acids. The first tRNA is now released and the ribosome shifts again so that a tRNA carrying two amino acids is now in the P site, and a new charged tRNA can bind to the A site. This process of elongation continues until the ribosome reaches a stop codon.

Elongation requires specific non-ribosomal proteins. Elongation of polypeptides occurs in a cyclic manner. At the end of one complete round of amino acid addition the A site will be empty and ready to accept the incoming aminoacyl-tRNA dictated by the next codon of the mRNA. This means that not only does the incoming amino acid need to be attached to the peptide chain but the ribosome must move down the mRNA to the next codon. Each incoming aminoacyl-tRNA is brought to the ribosome by an eEF-1a-GTP complex. When the correct tRNA is deposited into the A site the GTP is hydrolyzed and the eEF-1a-GDP complex dissociates. For additional translocation events to occur the GDP must be exchanged for GTP. This is carried out by eEF-1bg similarly to the GTP exchange that occurs with eIF-2 catalyzed by eIF-2B. The peptide attached to the tRNA in the P site is transferred to the amino group at the aminoacyl-tRNA in the A site. This reaction is catalyzed by peptidyltransferase in a process termed transpeptidation. The elongated peptide now resides on a tRNA in the A site. The A site needs to be freed in order to accept the next aminoacyl-tRNA. The process of moving the peptidyl-tRNA from the A site to the P site is termed, translocation. Translocation is catalyzed by eEF-2 coupled to GTP hydrolysis. In translocation, the ribosome is moved along the mRNA such that the next codon of the mRNA resides under the A site. Following translocation, eEF-2 is released from the ribosome and the cycle can start over again.

Termination of the Protein

When the ribosome reaches a stop codon, no aminoacyl tRNA binds to the empty A site. This signals the ribosomes to break into its large and small subunits, releasing the new protein and the mRNA. The protein may then undergo post-translational modifications. For example, it might be cleaved by a proteolytic (protein-cutting) enzyme at a specific place, have some of its amino acids altered, or become phosphorylated or glycosylated.

Protein Synthesis Inhibitors

In bacteria, if the ribosomal RNA is inactivated, for example, through binding of a ligand to the ribosomal RNA, protein synthesis is adversely affected and the bacteria will likely die. Many of the antibiotics, in particular, MLS antibiotics, used to treat bacterial infections function by inhibiting translation. Inhibition can be effected at all stages of translation, from initiation to elongation to termination. Many antibiotics are believed to primarily attach to the ribosomal RNA at the 16S and 23S ribosomal subunits and inhibit growth of bacteria by inhibiting protein synthesis.

Chloramphenicol inhibits prokaryotic peptidyl transferase. Streptomycin and neomycin inhibit prokaryotic peptide chain initiation, also induce mRNA misreading. Tetracycline inhibits prokaryotic aminoacyl-tRNA binding to the ribosome small subunit. Erythromycin inhibits prokaryotic translocation through the ribosome large subunit, and fusidic acid functions in a manner similar to erythromycin.

MLS antibiotics such as erythromycin have been used for years to treat various infections, for example, those caused by gram positive bacteria, gram negative bacteria and anaerobic bacteria. Many bacteria are becoming drug resistant. One theory of how the bacteria become drug resistant is that their ribosomal RNA mutates such that the antibiotics no longer bind as ligands to the RNA.

A number of macrolide antibiotics are orally bioavailable, but in contact with the gastrointestinal tract, degrade to some degree to form products which cause adverse side effects such as diarrhea. For this reason, many derivatives of naturally occurring macrolide antibiotics such as erythromycin are esterified at the 6-position to minimize formation of the degradation products following oral administration.

It would be advantageous to provide agents useful as antibiotics which have higher bioavailability, and are less subject to degradation and which have improved affinity for ribosomal RNA. The present invention provides such agents.

SUMMARY OF THE INVENTION

This invention is directed to novel multibinding compounds (agents) that are macrolide antibiotics, aminoglycosides, lincosamides, oxazolidinones, streptogramins, tetracyclines or other compounds which bind to ribosomal RNA and/or to one or more proteins involved in ribosomal protein synthesis in the bacterium. The multibinding compounds of this invention are useful as antibacterials, in particular, for gram positive, gram negative and anaerobic bacteria.

Accordingly, in one of its composition aspects, this invention provides a multibinding compound comprising from 2 to 10 ligands covalently attached to one or more linkers wherein each of said ligands independently comprises a macrolide antibiotic, aminoglycoside, lincosamide, oxazolidinone, streptogramin, tetracycline or other compound which binds to ribosomal RNA and/or to one or more proteins involved in ribosomal protein synthesis in the bacterium and adversely affects protein synthesis, and pharmaceutically-acceptable salts thereof.

In another of its composition aspects, this invention provides a multibinding compound of formula I:

$$(L)_p(X)_q \qquad\qquad I$$

wherein each L is independently a ligand comprising a macrolide antibiotic, aminoglycoside, lincosamide, oxazolidinone, streptogramin, tetracycline or other compound which binds to ribosomal RNA and/or to one or more proteins involved in ribosomal protein synthesis in the bacterium; each X is independently a linker; p is an integer of from 2 to 10; and q is an integer of from 1 to 20; and pharmaceutically-acceptable salts thereof.

Preferably, q is less than p in the multibinding compounds of this invention.

Preferably, each ligand, L, in the multibinding compound of formula I is independently selected from the group consisting of erythromycin and ester prodrugs/derivatives thereof, such as erythromycin stearate and erythromycin estolate; clarithromycin, roxythromycin, azithromycin, aureomycin, oleandomycin, sulfisoxazole, spiramycin, troleandomycin, josamycin, cytovaricin, linezolid, eperezolid, clindamycin [AntirobeR], lincomycin, quinupristin, dalfopristin (Synercid, Rhone-Poulenc Rorer), streptomycin, amikacin, gentamicin, kanamycin, neomycin, tobramycin, netilmicin, paromomycin, tetracycline, chlortetracycline, doxycycline, minocycline, declomycin, methacycline, spectinomycin, and oxytetracycline, and analogues thereof, which are well known to those of skill in the art. Examples of suitable analogues include alkylated, esterified, amidated, alkoxylated, sulfonated, carboxylated, halogenated, phosphorylated, thiolated and hydroxylated analogues.

In still another of its composition aspects, this invention provides a multibinding compound of formula II:

$$L'\text{—}X'\text{—}L' \qquad\qquad II$$

wherein each L' is independently a ligand comprising a macrolide antibiotic, aminoglycoside, lincosamide, oxazolidinone, streptogramin, tetracycline or other compound which binds to ribosomal RNA and/or to one or more proteins involved in ribosomal protein synthesis in the bacterium and X' is a linker; and pharmaceutically-acceptable salts thereof.

Preferably, in the multibinding compound of formula II, each ligand, L', is independently selected from the group consisting of macrolide antibiotics, oxazoldinones, lincosamides, streptogranims, tetracyclines and aminoglycosides. and X' is a linker; and pharmaceutically-acceptable salts thereof.

Preferably, in the above embodiments, each linker (i.e. , X, X' or X") independently has the formula:

$$\text{—}X^a\text{—}Z\text{—}(Y^a\text{—}Z)_m\text{—}Y^b\text{—}Z\text{—}X^a\text{—}$$

wherein m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of —C(O)NR'—, —NR'C(O)—, —NR'C(O)NR'—, —C(=NR')—NR'—, —NR'—C(=NR')—, —NR'—C(O)—O—, —N=C($X^a$)—NR'—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

In yet another of its composition aspects, this invention provides a pharmaceutical composition comprising a pharmaceutically acceptable carrier and an effective amount of a multibinding compound comprising from 2 to 10 ligands covalently attached to one or more linkers wherein each of said ligands independently comprises a macrolide antibiotic, aminoglycoside, lincosamide, oxazolidinone, streptogramin, tetracycline or other compound which binds to ribosomal RNA and/or to one or more proteins involved in ribosomal protein synthesis in the bacterium, and pharmaceutically-acceptable salts thereof.

This invention is also directed to pharmaceutical compositions comprising a pharmaceutically acceptable carrier and an effective amount of a multibinding compound of formula I or II.

The multibinding compounds of this invention are effective antibiotics. Accordingly, in one of its method aspects, this invention provides a method for treating bacterial infections.

When used to treat bacterial infections, for example, the method involves administering to a patient having a bacterial infection a pharmaceutical composition comprising a pharmaceutically-acceptable carrier and a therapeutically-effective amount of a multibinding compound comprising from 2 to 10 ligands covalently attached to one or more linkers wherein each of said ligands independently comprises a macrolide antibiotic, aminoglycoside, lincosamide, oxazolidinone, streptogramin, tetracycline or other compound which binds to ribosomal RNA and/or to one or more proteins involved in ribosomal protein synthesis in the bacterium; and pharmaceutically-acceptable salts thereof.

This invention is also directed to general synthetic methods for generating large libraries of diverse multimeric compounds which multimeric compounds are candidates for possessing multibinding properties with respect to ribosomal RNA and/or to one or more proteins involved in ribosomal protein synthesis in the bacterium. The diverse multimeric compound libraries provided by this invention are synthesized by combining a linker or linkers with a ligand or ligands to provide for a library of multimeric compounds wherein the linker and ligand each have complementary functional groups permitting covalent linkage. The library of linkers is preferably selected to have diverse properties such as valency, linker length, linker geometry and rigidity, hydrophilicity or hydrophobicity, amphiphilicity, acidity, basicity and polarization. The library of ligands is preferably selected to have diverse attachment points on the same ligand, different functional groups at the same site of otherwise the same ligand, and the like.

This invention is also directed to general synthetic methods for generating large libraries of diverse multimeric compounds which multimeric compounds are candidates for possessing multibinding properties with respect to bacterial ribosomal RNA and/or to one or more proteins involved in ribosomal protein synthesis in the bacterium. The diverse multimeric compound libraries provided by this invention are synthesized by combining a linker or linkers with a ligand or ligands to provide for a library of multimeric compounds wherein the linker and ligand each have complementary functional groups permitting covalent linkage. The library of linkers is preferably selected to have diverse properties such as valency, linker length, linker geometry and rigidity, hydrophilicity or hydrophobicity, amphiphilicity, acidity, basicity and polarizability and/or polarization. The library of ligands is preferably selected to have diverse attachment points on the same ligand, different functional groups at the same site of otherwise the same ligand, and the like.

This invention is also directed to libraries of diverse multimeric compounds which multimeric compounds are candidates for possessing multibinding properties with respect to bacterial ribosomal RNA and/or to one or more proteins involved in ribosomal protein synthesis in the bacterium. These libraries are prepared via the methods described above and permit the rapid and efficient evaluation of what molecular constraints impart multibinding properties to a ligand or a class of ligands targeting the bacterial ribosomal RNA and/or to one or more proteins involved in ribosomal protein synthesis in the bacterium.

Accordingly, in one of its method aspects, this invention is directed to a method for identifying multimeric ligand compounds possessing multibinding properties with respect to bacterial ribosomal RNA and/or to one or more proteins involved in ribosomal protein synthesis in the bacterium which method comprises:

(a) identifying a ligand or a mixture of ligands which bind to bacterial ribosomal RNA and/or to one or more proteins involved in ribosomal protein synthesis in the bacterium wherein each ligand contains at least one reactive functionality;

(b) identifying a library of linkers wherein each linker in said library comprises at least two functional groups having complementary reactivity to at least one of the reactive functional groups of the ligand;

(c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands; and (d) assaying the multimeric ligand compounds produced in (c) above to identify multimeric ligand compounds possessing multibinding properties.

In another of its method aspects, this invention is directed to a method for identifying multimeric ligand compounds possessing multibinding properties which method comprises:

(a) identifying a library of ligands which bind to bacterial ribosomal RNA and/or to one or more proteins involved in ribosomal protein synthesis in the bacterium wherein each ligand contains at least one reactive functionality;

(b) identifying a linker or mixture of linkers wherein each linker comprises at least two functional groups having complementary reactivity to at least one of the reactive functional groups of the ligand;

(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and (d) assaying the multimeric ligand compounds produced in (c) above to identify multimeric ligand compounds possessing multibinding properties.

The preparation of the multimeric ligand compound library is achieved by either the sequential or concurrent combination of the two or more stoichiometric equivalents of the ligands identified in (a) with the linkers identified in (b). Sequential addition is preferred when a mixture of different ligands is employed to ensure heteromeric or multimeric compounds are prepared. Concurrent addition of the ligands occurs when at least a portion of the multimer comounds prepared are homomultimeric compounds.

The assay protocols recited in (d) can be conducted on the multimeric ligand compound library produced in (c) above, or preferably, each member of the library is isolated by preparative liquid chromatography mass spectrometry (LCMS).

In one of its composition aspects, this invention is directed to a library of multimeric ligand compounds which may possess multivalent properties which library is prepared by the method comprising:

(a) identifying a ligand or a mixture of ligands which bind to bacterial ribosomal RNA and/or to one or more proteins involved in ribosomal protein synthesis in the bacterium wherein each ligand contains at least one reactive functionality;

(b) identifying a library of linkers wherein each linker in said library comprises at least two functional groups having complementary reactivity to at least one of the reactive functional groups of the ligand; and (c) preparing a multimeric ligand compound library by combining at least two stoichiometric equivalents of the ligand or mixture of ligands identified in (a) with the library of linkers identified in (b) under conditions wherein the complementary functional groups react to form a covalent linkage between said linker and at least two of said ligands.

In another of its composition aspects, this invention is directed to a library of multimeric ligand compounds which bind to bacterial ribosomal RNA and/or to one or more proteins involved in ribosomal protein synthesis in the bacterium which may possess multivalent properties which library is prepared by the method comprising:

(a) identifying a library of ligands which bind to bacterial ribosomal RNA and/or to one or more proteins involved in ribosomal protein synthesis in the bacterium wherein each ligand contains at least one reactive functionality;

(b) identifying a linker or mixture of linkers wherein each linker comprises at least two functional groups having complementary reactivity to at least one of the reactive functional groups of the ligand; and (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the library of linkers employed in either the methods or the library aspects of this invention is selected from the group comprising flexible linkers, rigid linkers, hydrophobic linkers, hydrophilic linkers, linkers of different geometry, acidic linkers, basic linkers, linkers of different polarizability and/or polarization and amphiphilic linkers. For example, in one embodiment, each of the linkers in the linker library may comprise linkers of different chain length and/or having different complementary reactive groups. Such linker lengths can preferably range from about 2 to 100 Å.

In another preferred embodiment, the ligand or mixture of ligands is selected to have reactive functionality at different sites on the ligands in order to provide for a range of orientations of said ligand on said multimeric ligand compounds. Such reactive functionality includes, by way of example, carboxylic acids, carboxylic acid halides, carboxyl esters, amines, halides, pseudohalides, isocyanates, vinyl unsaturation, ketones, aldehydes, thiols, alcohols, anhydrides, boronates and precursors thereof. It is understood, of course, that the reactive functionality on the ligand is selected to be complementary to at least one of the reactive groups on the linker so that a covalent linkage can be formed between the linker and the ligand.

In other embodiments, the multimeric; ligand compound is homomeric (i.e., each of the ligands is the same, although it may be attached at different points) or heteromeric (i.e., at least one of the ligands is different from the other ligands).

In addition to the combinatorial methods described herein, this invention provides for an iterative process for rationally evaluating what molecular constraints impart multibinding properties to a class of multimeric compounds or ligands targeting bacterial ribosomal RNA and/or to one or more proteins involved in ribosomal protein synthesis in the bacterium. Specifically, this method aspect is directed to a method for identifying multimeric ligand compounds possessing multibinding properties with respect to bacterial ribosomal RNA and/or to one or more proteins involved in ribosomal protein synthesis in the bacterium which method comprises:

(a) preparing a first collection or iteration of multimeric compounds which is prepared by contacting at least two stoichiometric equivalents of the ligand or mixture of ligands which target bacterial ribosomal RNA and/or to one or more proteins involved in ribosomal protein synthesis in the bacterium with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;

(b) assaying said first collection or iteration of multimeric compounds to assess which if any of said multimeric compounds possess multibinding properties;

(c) repeating the process of (a) and (b) above until at least one multimeric compound is found to possess multibinding properties;

(d) evaluating what molecular constraints imparted multibinding properties to the multimeric compound or compounds found in the first iteration recited in (a)–(c) above;

(e) creating a second collection or iteration of multimeric compounds which elaborates upon the particular molecular constraints imparting multibinding properties to the multimeric compound or compounds found in said first iteration;

(f) evaluating what molecular constraints imparted enhanced multibinding properties to tile multimeric compound or compounds found in the second collection or iteration recited in (e) above, (g) optionally repeating steps (e) and (f) to further elaborate upon said molecular constraints.

Preferably, steps (e) and (flare repeated at least two times, more preferably at from 2–50 times, even more preferably from 3 to 50 times, and still more preferably at least 5–50 times.

BRIEF DESCRIPTION OF THE DRAWINGS

FIGS. 2–20 are schematic illustrations of the preparation of compounds of formula I-XIX, respectively.

FIG. 51 is a schematic illustration of the preparation of compounds of formulas LII-A and LII-B.

DETAILED DESCRIPTION OF THE INVENTION

Figure 1:
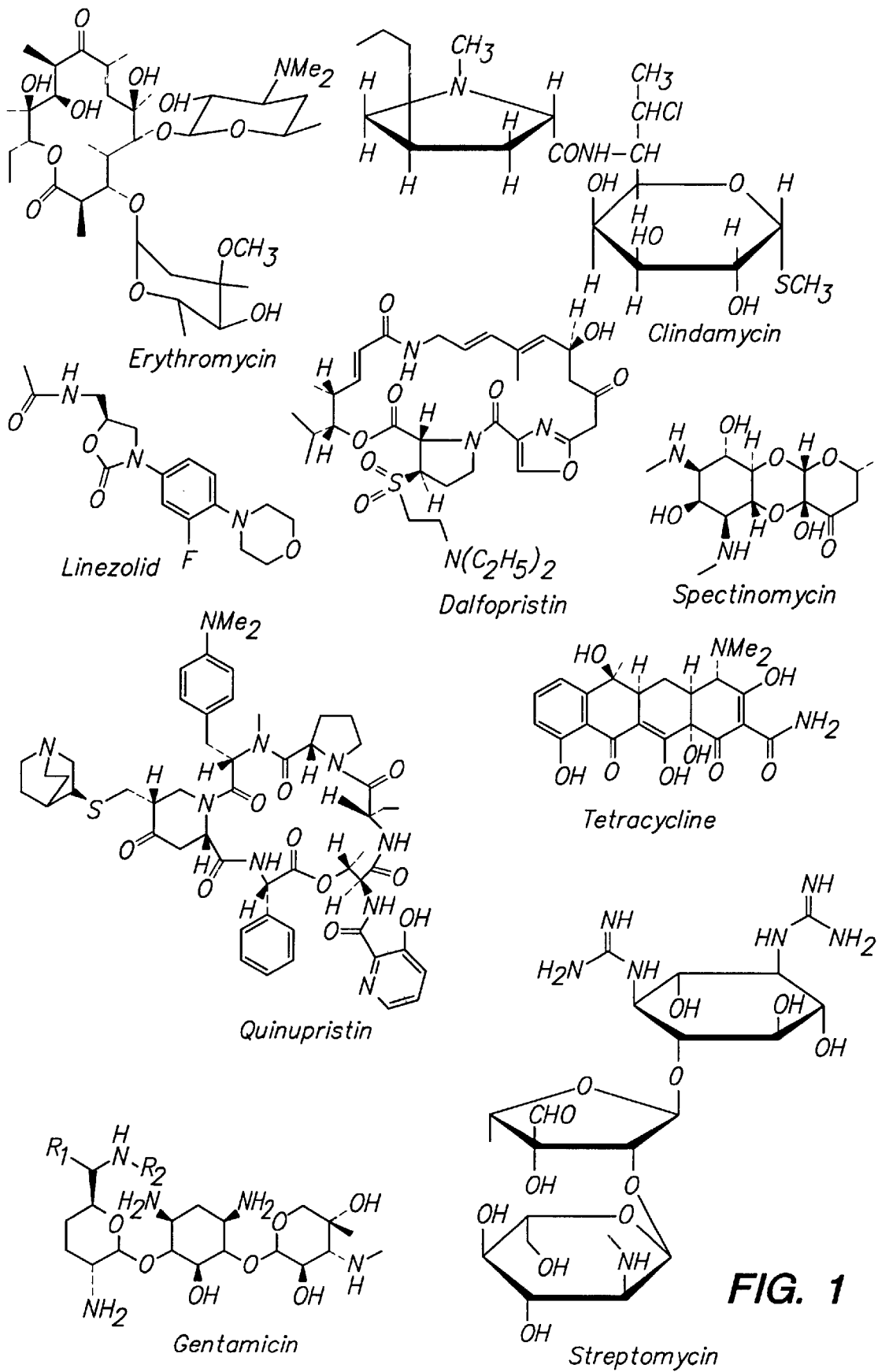
FIG. 1 is a schematic illustration of representative macrolide antibiotics, aminoglycosides and lincosamides, oxazolidinones, streptogramins, tetracycline which can be used to prepare the compounds of the present invention.

This invention is directed to multibinding compounds which are macrolide antibiotics, aminoglycosides, lincosamides, oxazolidinones, streptogramins, tetracyclines or other compounds which bind to bacterial ribosomal RNA and/or to one or more proteins involved in ribosomal protein synthesis in the bacterium, preferably in a manner which inhibits protein expression and results in an antibacterial activity, pharmaceutical compositions containing such compounds and methods of antibacterial treatment. When discussing such compounds, compositions or methods, the following terms have the following meanings unless otherwise indicated. Any undefined terms have their art recognized meanings.

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkylene" refers to a diradical of a branched or unbranched saturated hydrocarbon chain, preferably having from 1 to 40 carbon atoms, more preferably 1 to 10 carbon atoms and even more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—. cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, ti-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—$CH_2OCH_3$), ethylenemethoxy (—$CH_2CH_2OCH_3$), n-propylene-iso-propoxy (—$CH_2CH_2CH_2OCH(CH_3)_2$), methylene-t-butoxy (—$CH_2$—O—$C(CH_3)_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—$CH_2SCH_3$), ethylenethiomethoxy (—$CH_2CH_2SCH_3$), n-propylene-iso-thiopropoxy (—$CH_2CH_2CH_2SCH(CH_3)_2$), methylene-t-thiobutoxy (—$CH_2SC(CH_3)_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=$CH_2$), n-propenyl (—$CH_2$CH=$CH_2$), iso-propenyl (—$C(CH_3)$=$CH_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl —$SO_2$-aryl and —$SO_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —$CH_2$CH=CH— and —$C(CH_3)$=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—$CH_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—$CH_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3 -enyl and the like.

The term "substituted cycloalkenyl" refers to cycloalkenyl groups having from 1 to 5 substituents, and preferably 1 to 3' substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol. thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-S—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds, whether the isomers are those arising in the ligands, the linkers, or the multivalent constructs including the ligands and linkers.

The term "pharmaceutically-acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri (cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malicacid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

The term "protecting group" or "blocking group" refers to any group which when bound to one or more hydroxyl, thiol, amino or carboxyl groups of the compounds (including intermediates thereof) prevents reactions from occurring at these groups and which protecting group can be removed by conventional chemical or enzymatic steps to reestablish the hydroxyl, thiol, amino or carboxyl group. The particular removable blocking group employed is not critical and preferred removable hydroxyl blocking groups include conventional substituents such as allyl, benzyl, acetyl, chloroacetyl, thiobenzyl, benzylidene, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable thiol blocking groups include disulfide groups, acyl groups, benzyl groups, and the like.

Preferred removable amino blocking groups include conventional substituents such as t-butyoxycarbonyl (t-BOC), benzyloxycarbonyl (CBZ), fluotenylmethoxycarbonyl (FMOC), allyloxycarbonyl (ALOC), and the like which can be removed by conventional conditions compatible with the nature of the product.

Preferred carboxyl protecting groups include esters such as methyl, ethyl, propyl, t-butyl etc. which can be removed by mild conditions compatible with the nature of the product.

The term "optional" or "optionally" means that the subsequently described event, circumstance or substituent may or may not occur, and that the description includes instances where said event or circumstance occurs and instances where it does not.

The term "ligand" as used herein denotes a compound that binds to ribosomal RNA and/or to one or more proteins involved in ribosomal protein synthesis in the bacterium. The specific region or regions of the ligand that is (are) recognized by the enzyme is designated as the "ligand domain". A ligand may be either capable of binding to an enzyme by itself, or may require the presence of one or more non-ligand components for binding (e.g., $Ca^{+2}$, $Mg^{+2}$ or a water molecule is required for the binding of a ligand to various ligand binding sites).

Examples of ligands useful in this invention are described herein. General classes of compounds useful as ligands include macrolide antibiotics, oxazolidinones, lincosamides, streptogramins, tetracyclines and aminoglycosides. Examples of macrolide antibiotics include erythromycin and ester derivatives thereof, such as erythromycin stearate and erythromycin estolate; clarithromycin, roxythromycin, azithromycin, streptomycin, aureomycin, oleandomycin, sulfisoxazole, spiramycin, troleandomycin, josamycin and cytovaricin. Examples of oxazolidinones include linezolid and eperezolid. Examples of lincosamides include clindamycin [AntirobeR] and lincomycin. Examples of streptogramins include quinupristin and dalfopristin (Synercid, Rhone-Poulenc Rorer). Examples of aminoglycosides include streptomycin, amikacin, gentamicin, kanamycin, neomycin, tobramycin, netilmicin and paromomycin. Examples of tetracyclines include tetracycline, chlortetracycline, doxycycline, minocycline, declomycin, methacycline and oxytetracycline.

Those skilled in the art will appreciate that portions of the ligand structure that are not essential for specific molecular recognition and binding-activity may be varied substantially, replaced or substituted with unrelated structures (for example, with ancillary groups as defined below) and, in some cases, omitted entirely without affecting the binding interaction. The primary requirement for a ligand is that it has a ligand domain as defined above. It is understood that the term ligand is not intended to be limited to compounds known to be useful in binding to bacterial ribosomal RNA and/or to one or more proteins involved in ribosomal protein synthesis in the bacterium (e.g., known drugs). Those skilled in the art will understand that the term ligand can equally apply to a molecule that is not normally associated with bacterial ribosomal RNA binding properties. In addition, it should be noted that ligands that exhibit marginal activity or lack useful activity as monomers can be highly active as multivalent compounds because of the benefits conferred by multivalency.

The term "multibinding compound or agent" refers to a compound that is capable of multivalency, as defined below, and which has 2–10 ligands covalently bound to one or more linkers which may be the same or different. Multibinding compounds provide a biological and/or therapeutic effect greater than the aggregate of unlinked ligands equivalent thereto which are made available for binding. That is to say that the biological and/or therapeutic effect of the ligands attached to the multibinding compound is greater than that achieved by the same amount of unlinked ligands made available for binding to the ligand binding sites (receptors). The phrase "increased biological or therapeutic effect" includes, for example: increased affinity, increased selectivity for target, increased specificity for target, increased potency, increased efficacy, decreased toxicity, improved duration of activity or action, decreased side effects, increased therapeutic index, improved bioavailability, improved pharmacokinetics, improved activity spectrum, and the like. The multibinding compounds of this invention will exhibit at least one and preferably more than one of the above-mentioned effects.

The term "potency" refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay, in an appropriate animal model). The finding that the multibinding agent produces an equivalent biological or therapeutic effect at a lower concentration than the aggregate unlinked ligand is indicative of enhanced potency.

The term "univalency" as used herein refers to a single binding interaction between one ligand as defined herein with one ligand binding site as defined herein. It should be noted that a compound having multiple copies of a ligand (or ligands) exhibit univalency when only one ligand is interacting with a ligand binding site. Examples of univalent interactions are depicted below.

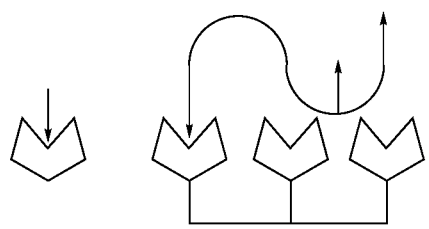

-continued

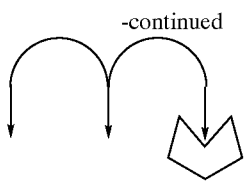

The term "multivalency" as used herein refers to the concurrent binding of from 2 to 10 linked ligands (which may be the same or different) and two or more corresponding receptors (ligand binding sites) on one or more bacterial ribosomes which may be the same or different.

For example, two ligands connected through a linker that bind concurrently to two ligand binding sites would be considered as bivalency; three ligands thus connected would be an example of trivalency. An example of trivalent binding, illustrating a multibinding compound bearing three ligands versus a monovalent binding interaction, is shown below:

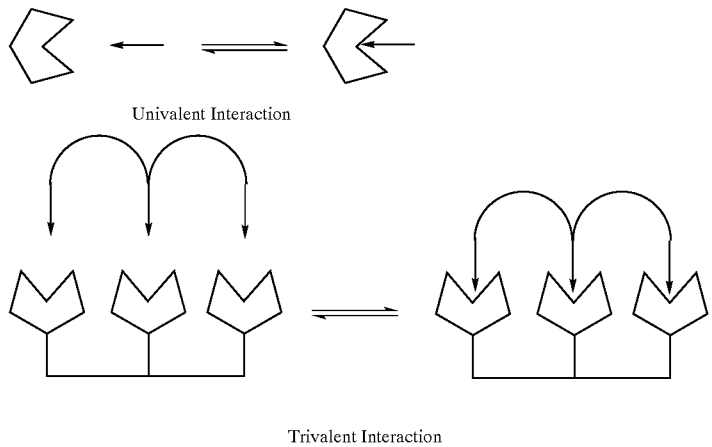

Univalent Interaction

Trivalent Interaction

It should be understood that all compounds that contain multiple copies of a ligand attached to a linker or to linkers do not necessarily exhibit the phenomena of multivalency, i.e., that the biological and/or therapeutic effect of the multibinding agent is greater than the sum of the aggregate of unlinked ligands made available for binding to the ligand binding site (receptor). For multivalency to occur, the ligands that are connected by a linker or linkers have to be presented to their ligand binding sites by the linker(s) in a specific manner in order to bring about the desired ligand-orienting result, and thus produce a multibinding event.

The term "selectivity" or "specificity" is a measure of the binding preferences of a ligand for different ligand binding sites (receptors). The selectivity of a ligand with respect to its target ligand binding site relative to another ligand binding site is given by the ratio of the respective values of $K_d$ (i.e., the dissociation constants for each ligand-receptor complex) or, in cases where a biological effect is observed below the $K_d$, the ratio of the respective $EC_{50}$'s (i.e., the concentrations that produce 50% of the maximum response for the ligand interacting with the two distinct ligand binding sites (receptors)).

The term "ligand binding site" denotes the site on the bacterial ribosomal RNA, which may be specific RNA and/or a site on one or more of the proteins involved in ribosomal protein synthesis in the bacterium that recognizes a ligand domain and provides a binding partner for the ligand. The ligand binding site may be defined by monomeric or multimeric structures.

It should be recognized that the ligand binding sites of the ribosome that participate in biological multivalent binding interactions are constrained to varying degrees by their intra- and inter-molecular associations (e.g., such macromolecular structures may be covalently joined to a single structure, noncovalently associated in a multimeric structure, embedded in a membrane or polymeric matrix, and so on) and therefore have less translational and rotational freedom than if the same structures were present as monomers in solution.

The term "inert organic solvent" means a solvent which is inert under the conditions of the reaction being described in conjunction therewith including, by way of example only, benzene, toluene, acetonitrile, tetrahydrofuran, dimethylformamide, chloroform, methylene chloride, diethyl ether, ethyl acetate, acetone, methylethyl ketone, methanol, ethanol, propanol, isopropanol, t-butanol, dioxane, pyridine, and the like. Unless specified to the contrary, the solvents used in the reactions described herein are inert solvents.

The term "treatment" refers to any treatment of a pathologic condition in a mammal, particularly a human, and includes:

(i) preventing the pathologic condition from occurring in a subject which may be predisposed to the condition but has not yet been diagnosed with the condition and, accordingly, the treatment constitutes prophylactic treatment for the disease condition;

(ii) inhibiting the pathologic condition, i.e., arresting its development;

(iii) relieving the pathologic condition, i.e., causing regression of the pathologic condition; or (iv) relieving the conditions mediated by the pathologic condition.

The term "pathologic condition which is modulated by treatment with a ligand" covers all disease states (i.e., pathologic conditions) which are generally acknowledged in the art to be usefully treated with a ligand for the bacterial ribosomal RNA and/or for one or more proteins involved in ribosomal protein synthesis in the bacterium, in general, and those disease states which have been found to be usefully treated by a specific multibinding compound of our invention. Such disease states include, by way of example only, the treatment of bacterial infections.

Examples of bacteria which can be treated with the compositions and methods described herein include gram-positive cocci, for example, staphylococci and streptococci, gram-positive rods such as corynebacteria and diphtheroids, bacilli, mycobacteria and Nocardia, gram-negative rods such as enteric gram-negative rods, Pseudomonas, curved gram-negative rods, parvobacteria and Haemophilus, gram-negative cocci such as Neisseria, obligate anaerobes such as Clostridium, non-sporing anaerobes, and unusual bacteria such as spirochaetes, rickettsia and chlamydia. Specific examples of bacterial diseases include chlamydia, gonorrhea, salmonellosis, shigellosis, tuberculosis, syphilis, bacterial pneumonia, bacterial sepsis, urinary tract infections, bacterial upper respiratory tract infections, otitis media, and lyme disease.

While not wishing to be bound to a particular theory, it is believed that the compounds described herein inhibit growth of bacteria by binding to their 16S or 23S ribosomal subunits, or to one or more proteins present on the bacterial ribosome, and inhibiting protein synthesis.

The term "therapeutically effective amount" refers to that amount of multibinding compound which is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "linker", identified where appropriate by the symbol X, X' or X", refers to a group or groups that covalently links from 2 to 10 ligands (as identified above) in a manner that provides for a compound capable of multi-valency. Among other features, the linker is a ligand-orienting entity that permits attachment of multiple copies of a ligand (which may be the same or different) thereto. In some cases, the linker may itself be biologically active. The term "linker" does not, however, extend to cover solid inert supports such as beads, glass particles, fibers. and the like. But it is understood that the multibinding compounds of this invention can be attached to a solid support if desired. For example, such attachment to solid supports can be made for use in separation and purification processes and similar applications.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits facile synthesis thereof. In one embodiment, the library of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members; preferably from 2 to $10^9$ members and still more preferably from 10 to $10^4$ members.

The term "multimeric compound" refers to compounds comprising from 2 to 10 ligands covalently connected through at least one linker which compounds may or may not possess multibinding properties (as defined herein).

The term "pseudohalide" refers to functional groups which react in displacement reactions in a manner similar to a halogen. Such functional groups include, by way of example, mesyl, tosyl, azido and cyano groups.

The extent to which multivalent binding is realized depends upon the efficiency with which the linker or linkers that joins the ligands presents these ligands to the array of available ligand binding sites. Beyond presenting these ligands for multivalent interactions with ligand binding sites, the linker or linkers spatially constrains these interactions to occur within dimensions defined by the linker or linkers. Thus, the structural features of the linker (valency, geometry, orientation, size, flexibility, chemical composition, etc.) are features of multibinding agents that play an important role in determining their activities.

The linkers used in this invention are selected to allow multivalent binding of ligands to the ligand binding sites of bacterial ribosomal RNA and/or of one or more proteins involved in ribosomal protein synthesis in the bacterium, wherever such sites are located on the receptor structure.

The ligands are covalently attached to the linker or linkers using conventional chemical techniques providing for covalent linkage of the ligand to the linker or linkers. Reaction chemistries resulting in such linkages are well known in the art and involve the use of complementary functional groups on the linker and ligand. Preferably, the complementary functional groups on the linker are selected relative to the functional groups available on the ligand for bonding or which can be introduced onto the ligand for bonding. Again, such complementary functional groups are well known in the art. For example, reaction between a carboxylic acid of either the linker or the ligand and a primary or secondary amine of the ligand or the linker in the presence of suitable, well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalently linking the ligand to the linker.

Table I below illustrates numerous complementary reactive groups and the resulting bonds formed by reaction therebetween.

TABLE I

Representative Complementary Binding Chemistries

| First Reactive Group | Second Reactive Group | Linkage |
|---|---|---|
| hydroxyl | isocyanate | urethane |
| amine | epoxide | β-hydroxyamine |
| sulfonyl halide | amine | sulfonamide |
| carboxyl | amine | amide |
| hydroxyl | alkyl/aryl halide | ether |
| aldehyde | amine/NaCNBH$_4$ | amine |
| ketone | amine/NaCNBH$_4$ | amine |
| amine | isocyanate | urea |

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

Suitable linkers and ligands are discussed more fully below.

At present, it is preferred that the multibinding agent is a bivalent compound, e.g., two ligands which are covalently linked to linker X.

Methodology

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines". By controlling the hydrophilicity/hydrophobicity, the ability of the compounds to cross the blood/brain barrier can be controlled. This can be important when one wishes to maximize or minimize CNS effects.

Examples of molecular structures in which the above bonding patterns could be employed as components of the linker are shown below.

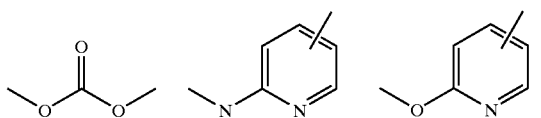

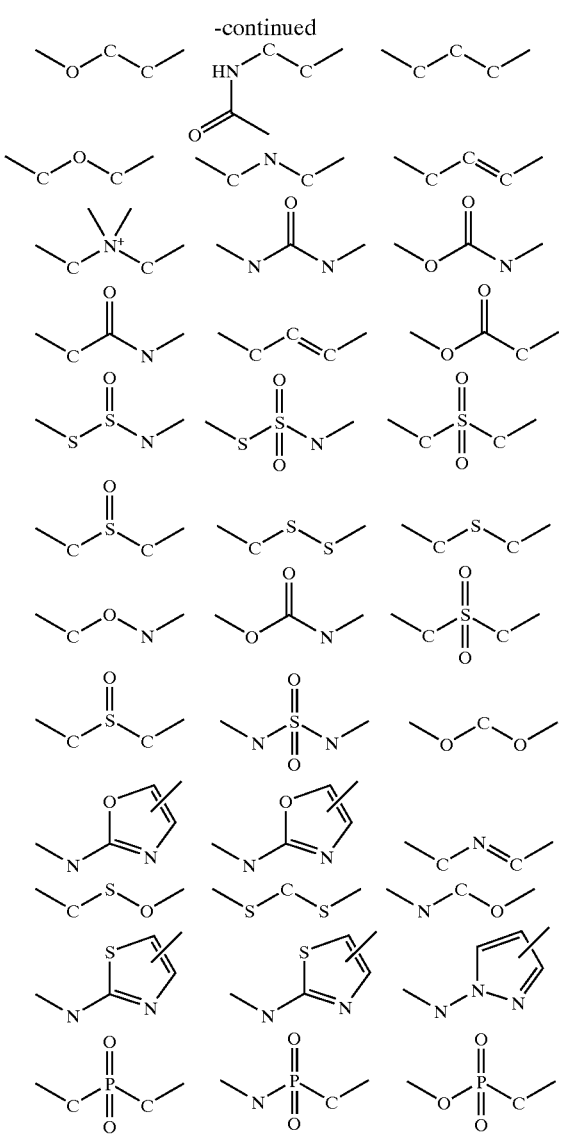

The identification of an appropriate framework geometry and size for ligand domain presentation are important steps in the construction of a multibinding compound with enhanced activity. Systematic spatial searching strategies can be used to aid in the identification of preferred frameworks through an iterative process. Numerous strategies are known to those skilled in the art of molecular design and can be used for preparing compounds of this invention.

It is to be noted that core structures other than those shown here can be used for determining the optimal framework display orientation of the ligands. The process may require the use of multiple copies of the same central core structure or combinations of different types of display cores.

The above-described process can be extended to trimers and compounds of higher valency.

Assays of each of the individual compounds of a collection generated as described above will lead to a subset of compounds with the desired enhanced activities (e.g., potency, selectivity, etc.). The analysis of this subset using a technique such as Ensemble Molecular Dynamics will provide a framework orientation that favors the properties desired. A wide diversity of linkers is commercially available (see, e.g., Available Chemical Directory (ACD)). Many of the linkers that are suitable for use in this invention fall into this category. Other can be readily synthesized by methods well known in the art and/or are described below.

Having selected a preferred framework geometry, the physical properties of the linker can be optimized by varying the chemical composition thereof. The composition of the linker can be varied in numerous ways to achieve the desired physical properties for the multibinding compound.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof.

Examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/hydrophilicity will be a polyether.

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (e.g., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, including deprotection of a carboxyl, hydroxyl, thiol or amino group by a change in pH, oxidation, reduction or other mechanisms known to those skilled in the art which result in removal of the protecting group, is within the scope of this invention.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that links the ligands in such a manner that they are presented to the enzyme for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

Figure 56:
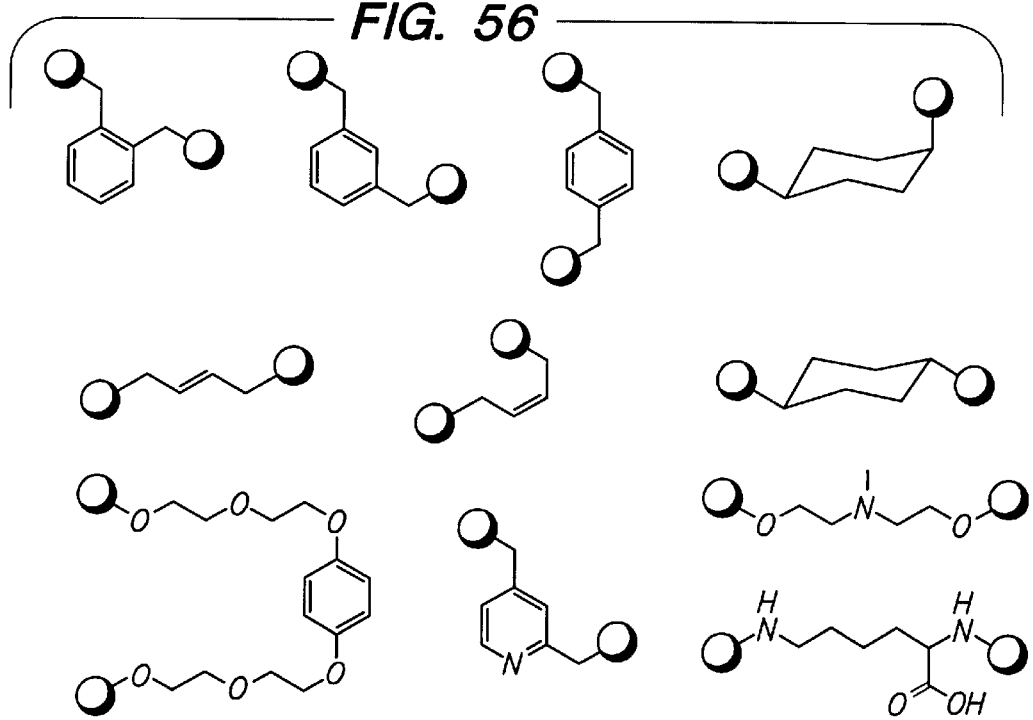
FIG. 56 illustrates examples of multibinding compounds comprising 2 ligands attached in different forms to a linker.
Figure 57:
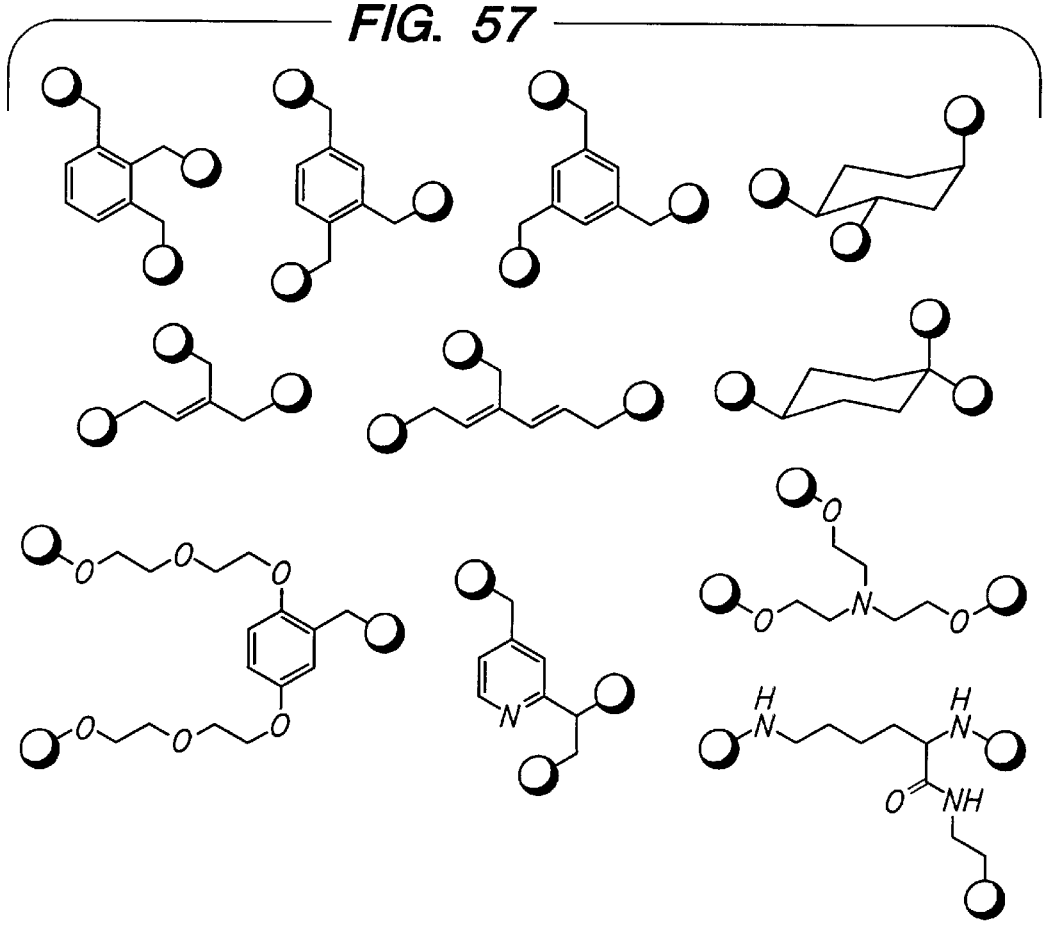
FIG. 57 illustrates examples of multibinding compounds comprising 3 ligands attached in different forms to a linker.
Figure 58:
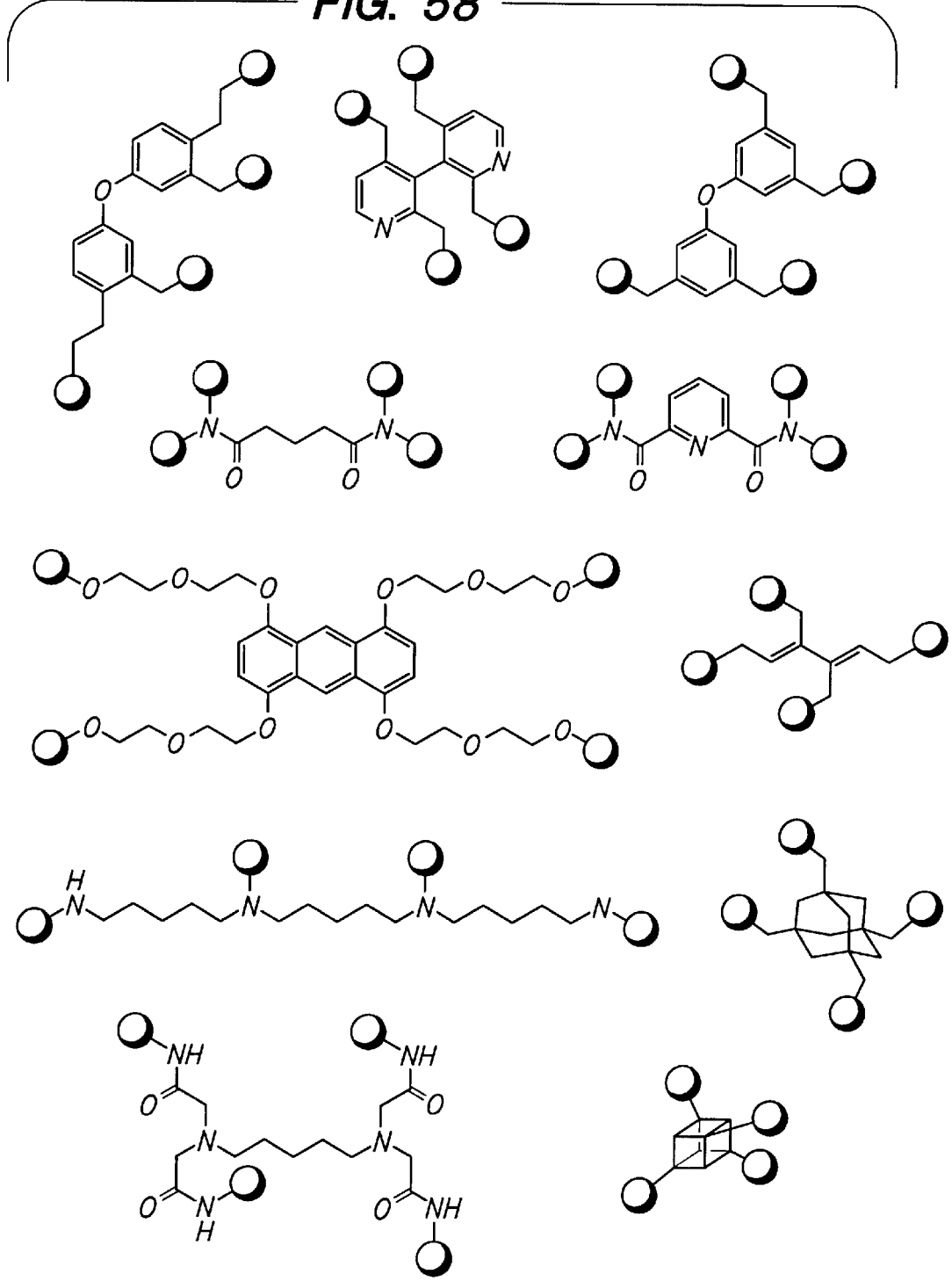
FIG. 58 illustrates examples of multibinding compounds comprising 4 ligands attached in different forms to a linker.

The simplest and most preferred multibinding compound is a bivalent compound which can be represented as L—X—L, where each L is independently a ligand which may be the same or different and each X is independently the linker. Examples of such bivalent compounds are provided in FIG. 56 where each shaded circle represents a ligand. A trivalent compound could also be represented in a linear fashion, i.e., as a sequence of repeated units L—X—L—X—L, in which L is a ligand and is the same or different at each occurrence, as can X. However, a trimer can also be a radial multibinding compound comprising three ligands attached to a central core, and thus represented as $(L)_3X$, where the linker X could include, for example, an aryl or cycloalkyl group. Illustrations of trivalent and tetravalent compounds of this invention are found in FIGS. 57 and 58, respectively, where again, the shaded circles represent ligands. Tetravalent compounds can be represented in a linear array, e.g.,

L—X—L—X—L—X—L in a branched array, e.g.,

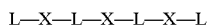

(a branched construct analogous to the isomers of butane— n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker.

Figure 59:
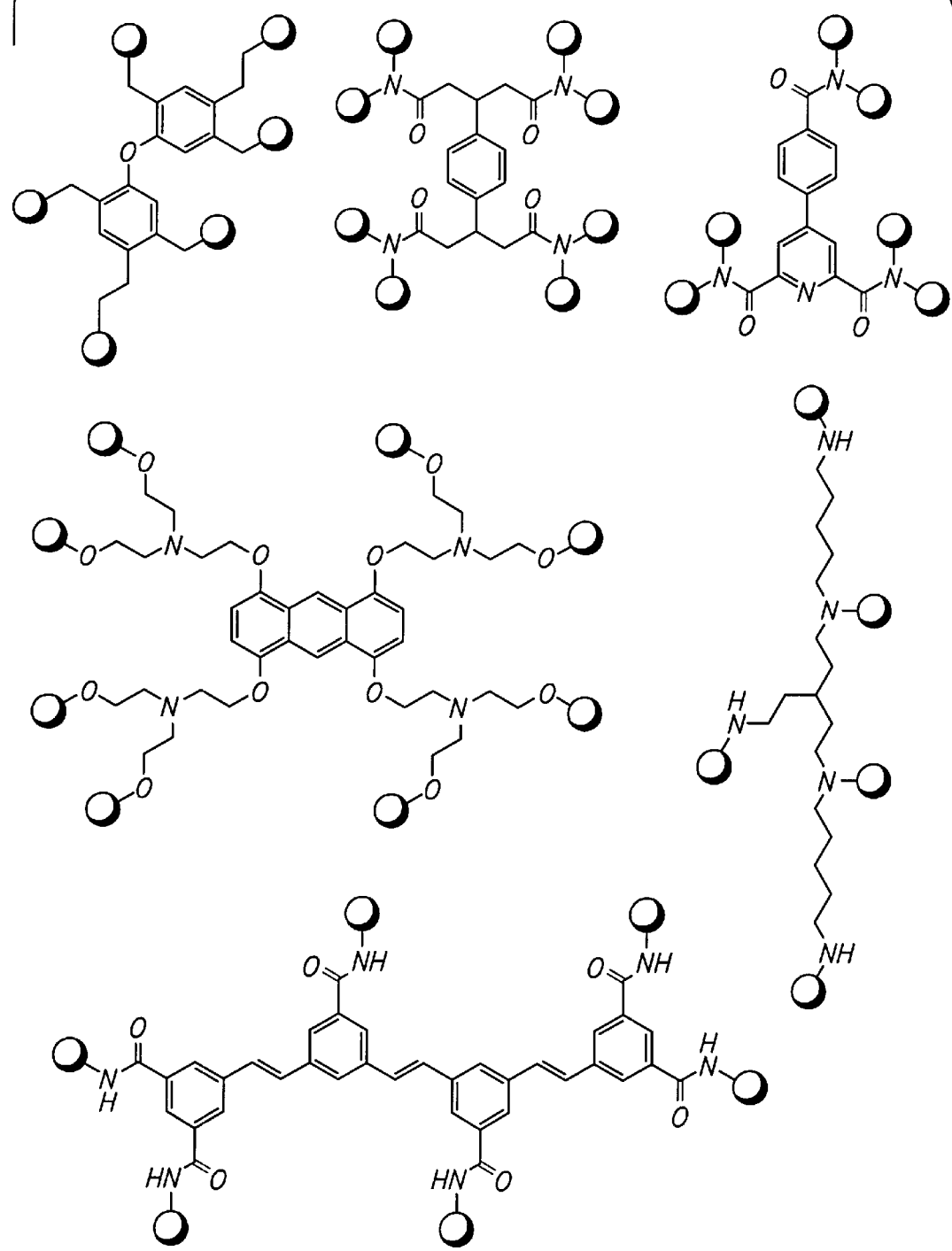
FIG. 59 illustrates examples of multibinding compounds comprising between 5 and 10 ligands attached in different forms to a linker.

The same considerations apply to higher multibinding compounds of this invention containing 5–10 ligands, as illustrated in FIG. 59. However, for multibinding agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

Certain of the above described compounds may alternatively be represented as cyclic chains of the form:

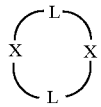

and variants thereof.

All of the above variations are intended to be within the scope of the invention defined by the formula $(L)_p(X)_q$.

With the foregoing in mind, a preferred linker may be represented by the following formula:

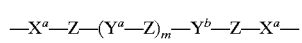

in which:

m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— or a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

$Y^a$ and $Y^b$ at each separate occurrence are selected from the group consisting of:

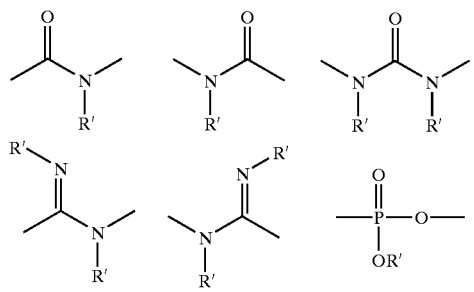

-continued

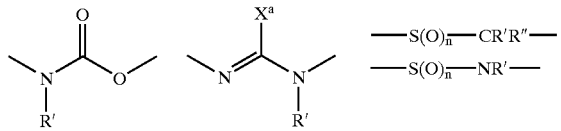

—S—S— or a covalent bond; in which:

n is 0, 1 or 2; and

R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

Additionally, the linker moiety can be optionally substituted at any atom therein by one or more alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic group.

In one embodiment of this invention, the linker (i.e., X, X' or X") is selected those shown in Table II:

TABLE II

Representative Linkers

Linker

—HN—(CH$_2$)$_2$—NH—C(O)—(CH$_2$)—C(O)—NH—(CH$_2$)$_2$—NH—
—HN—(CH$_2$)$_2$—NH—C(O)—(CH$_2$)$_2$—C(O)—NH—(CH$_2$)$_2$—NH—
—HN—(CH$_2$)$_2$—NH—C(O)—(CH$_2$)$_3$—C(O)—NH—(CH$_2$)$_2$—NH—
—HN—(CH$_2$)$_2$—NH—C(O)—(CH$_2$)$_4$—C(O)—NH—(CH$_2$)$_2$—NH—
—HN—(CH$_2$)$_2$—NH—C(O)—(CH$_2$)$_5$—C(O)—NH—(CH$_2$)$_2$—NH—
—HN—(CH$_2$)$_2$—NH—C(O)—(CH$_2$)$_6$—C(O)—NH—(CH$_2$)$_2$—NH—
—HN—(CH$_2$)$_2$—NH—C(O)—(CH$_2$)$_7$—C(O)—NH—(CH$_2$)$_2$—NH—
—HN—(CH$_2$)$_2$—NH—C(O)—(CH$_2$)$_8$—C(O)—NH—(CH$_2$)$_2$—NH—
—HN—(CH$_2$)$_2$—NH—C(O)—(CH$_2$)$_9$—C(O)—NH—(CH$_2$)$_2$—NH—
—HN—(CH$_2$)$_2$—NH—C(O)—(CH$_2$)$_{10}$—C(O)—NH—(CH$_2$)$_2$—NH—
—HN—(CH$_2$)$_2$—NH—C(O)—(CH$_2$)$_{11}$—C(O)—NH—(CH$_2$)$_2$—NH—
—HN—(CH$_2$)$_2$—NH—C(O)—(CH$_2$)$_{12}$—C(O)—NH—(CH$_2$)$_2$—NH—
—HN—(CH$_2$)$_2$—NH—C(O)—Z—C(O)—NH—(CH$_2$)$_2$—NH— where Z is 1,2-phenyl
—HN—(CH$_2$)$_2$—NH—C(O)—Z—C(O)—NH—(CH$_2$)$_2$—NH— where Z is 1,3-phenyl
—HN—(CH$_2$)$_2$—NH—C(O)—Z—C(O)—NH—(CH$_2$)$_2$—NH— where Z is 1,4-phenyl
—HN—(CH$_2$)$_2$—NH—C(O)—Z—O—Z—C(O)—NH—(CH$_2$)$_2$—NH— where Z is 1,4-phenyl
—HN—(CH$_2$)$_2$—NH—C(O)—(CH$_2$)$_2$—CH(NH—C(O)—(CH$_2$)$_8$—CH$_3$)—C(O)—NH—(CH$_2$)$_2$—NH—
—HN—(CH$_2$)$_2$—NH—C(O)—(CH$_2$)$_2$—O—(CH$_2$)$_2$—C(O)—NH—(CH$_2$)$_2$—NH—
—HN—(CH$_2$)$_2$—NH—C(O)—Z—C(O)—NH—(CH$_2$)$_2$—NH— where Z is 5-(n-octadecyloxy)-1,3-phenyl
—HN—(CH$_2$)$_2$—NH—C(O)—(CH$_2$)$_2$—CH(NH—C(O)—Z)—C(O)—NH—(CH$_2$)$_2$—NH— where Z is 4-biphenyl
—HN—(CH$_2$)$_2$—NH—C(O)—Z—C(O)—NH—(CH$_2$)$_2$—NH— where Z is 5-(n-butyloxy)-1,3-phenyl
—HN—(CH$_2$)$_2$—NH—C(O)—(CH$_2$)$_8$-trans-(CH=CH)—C(O)—NH—(CH$_2$)$_2$—NH—
—HN—(CH$_2$)$_2$—NH—C(O)—(CH$_2$)$_2$—CH(NH—C(O)—(CH$_2$)$_{12}$—CH$_3$)—C(O)—NH—(CH$_2$)$_2$—NH—
—HN—(CH$_2$)$_2$—NH—C(O)—(CH$_2$)$_2$—CH(NH—C(O)—Z)—C(O)—NH—(CH$_2$)$_2$—NH— where Z is 4-(n-octyl)-phenyl
—HN—(CH$_2$)—Z—O—(CH$_2$)$_6$—O—Z—(CH$_2$)—NH— where Z is 1,4-phenyl
—HN—(CH$_2$)$_2$—NH—C(O)—(CH$_2$)$_2$—NH—C(O)—(CH$_2$)$_3$—C(O)—NH—(CH$_2$)$_2$—C(O)—NH—(CH$_2$)$_2$—NH—
—HN—(CH$_2$)$_2$—NH—C(O)—(CH$_2$)$_2$—CH(NH—C(O)—Ph)—C(O)—NH—(CH$_2$)$_2$—NH—
—HN—(CH$_2$)$_2$—NH—C(O)—(CH$_2$)—N+((CH$_2$)$_9$—CH$_3$)(CH$_2$—C(O)—NH—(CH$_2$)$_2$—NH$_2$)—(CH$_2$)—C(O)—NH—(CH$_2$)$_2$—NH—
—HN—(CH$_2$)$_2$—NH—C(O)—(CH$_2$)—N((CH$_2$)$_9$—CH$_3$)—(CH$_2$)—C(O)—NH—(CH$_2$)$_2$—NH—
—HN—(CH$_2$)$_2$—NH—C(O)—(CH$_2$)$_2$—NH—

TABLE II-continued

Representative Linkers

Linker

C(O)—(CH$_2$)$_2$—NH—C(O)—(CH$_2$)$_3$—C(O)—NH—(CH$_2$)$_2$—C(O)—NH—(CH$_2$)$_2$—C(O)—NH—(CH$_2$)$_2$—NH—
—HN—(CH$_2$)$_2$—NH—C(O)—Z—C(O)—NH—(CH$_2$)$_2$—NH—
where Z is 5-hydroxy-1,3-phenyl In another embodiment of this invention, the linker (i.e., X, X' or X") has the formula:

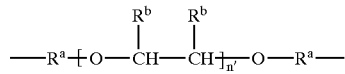

wherein each $R^a$ is independently selected from the group consisting of a covalent bond, alkylene, substituted alkylene and arylene;

each $R^b$ is independently selected from the group consisting of hydrogen, alkyl and substituted alkyl; and n' is an integer ranging from 1 to about 20.

In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

Ligands

Any compound which binds to bacterial ribosomal RNA and/or to one or more proteins involved in ribosomal protein synthesis in the bacterium, and preferably, which inhibits protein expression through such binding, can be used as a ligand to prepare the compounds described herein. Such ligands are well known to those of skill in the art.

Preferably, each ligand, L, in the multibinding compound of formula I is independently selected from a compound of the formulas shown in FIG. 1.

The ligands shown in FIG. 1 (and the precursors/synthons thereof are well-known in the art and can be readily prepared using art-recognized starting materials, reagents and reaction conditions. By way of illustration, the following patents and publications disclose compounds, intermediates and procedures useful in the preparation of ligands with the formulas shown in FIG. 1 or related compounds suitable for use in this invention:

Ahonkhai, V. I. et al., *In Vitro Activity of U-57930E, a New, Clindamycin Analog, Against Aerobic Gram-Positive Bacteria, Antimicrobial Agents and Chemotherapy*, 21(6):902–905 (1982).

Ballesta, J. P., et al., *Peptidyltransferase inhibitors: Structure-Activity Relationship Analysis by Chemical Modification*, Centro de Biologia Molecular, Chapter 44, pp 502–510, 199???. XAV PCT WO 95/07271 by Barbachyn, p 1–33

Barden, T. C., et al., *In Vitro Antibacterial Activity of 9-(Glycylamido) tetracycline Derivatives, J. Med. Chem.* 37(20):3205–3211 (1995).

Blackwood, R. K., et al., *Some Transformations of Tetracycline at the 4-Position, Can, J. Chem.* 43:1382–1388 (1965).

Brickner, S. J., et al., *Synthesis and Antibacterial Activity, of U-100592 and u-100766, Two Oxazolidinone Anti-* bacterial Agents for the Potential Treatment of Multidrug-Resistant Gram-Positive Bacterial Infections, J. Med. Chem., 39:673–679 (1986).

Cooperman, B. S. et al., Antibiotic Probes of Escherichia coli Ribosomal Peptidyltransferase, Roche Institute of Molecular Biology, Chapter 42, pp 491–501, 199???. XAV Cundliffe, Eric, Recognition Sites for Antibiotics within rRNA, Department of Biochemistry and Leicester Biocentre, LEI 7RH, UK, Chapter 41, pp 479–510, 199???.XAV Delaware, D. L., et al., Aminoglycoside Antibiotics (Dihydrostreptomycin Analogies), J. Antibiotics, XXXIX(2):251–258 (1986).

Herrinton, P. M., et al., Oxidation and Alkylation of Spectinomycin Derivatives; Synthesis of Trospectomycin from Spectinomycin, J. Org. Chem., 678–682 (1993).

Kirst, Ph.D., H. A., 2 Semi-synthetic derivatives of Erythromycin, Med. Chem., 30:57–88 (1993).

LemieuX, R. U., et al., The Chemistry of Streptomycin, J. Am. Chem. Soc. 52:337–385 (1947).

Mossa, J. S., et al., Streptomycin, Analytical Profiles of Drug Substances, 16:507, 531–535,587 (1987).

Rosenbrook, Jr., W., et al., Spectinomycin Modification, ACS Symposium, Series 125, 1980.

Spahn, C. M. T., et al., Throwing a spanner in the works: antibiotics and the translation apparatus, Mol. Med., 74:423–430 (1996).

Thomas, R. C., et al., Synthesis of Spectinomycin Analogs, ACS Symposium, Series 125, 121–130 (1980).

Tohma, S., et al., Ashimycins A and B, new streptomycin Analogues, J. Antibiotics. XLII(8):1205–1212 (1989).

Tucker, J. A., et al., Piperazinyl Oxazolidinone Antibacterial Agents Containing a pyridine, Diazene, or Triazene Heteroaromatic Ring, J. Med Chem., 41:3727–3735 (1988).

White, D. R., et al., The Synthesis of Trospectomycin (6'-n-Propylspectinomycin, U-63,366F) From Spectinomycin, Tetrahedron Letters, 30(12): 1469–1472 (1989).

Each of these patents and publications is incorporated herein by reference in its entirety to the same extent as if each individual patent or publication was specifically and individually indicated to be incorporated by reference in its entirety.

Drugs such as chloramphenicol, erythromycin, clarithromycin, azithromycin, dirithromycin, flurithromycin clindamycin, lincomycin, quinopristin, dalfopristin, streptogramins, linezolid, U-100480, U-101603, U-94901, U-101244, pristinamycin, MJ-347-81F4A, HMR-3647, L-708299, A-184656, L-708365, L-701677, lexithromycin, RU-64004, CP-227182, CP-426027, TEA-0769, CP-279107, RU-56006, RU-6652, RU-59616, L-744434, L-744433, L-740893, L-709936, leucomycin, A-1 79796, eperezolid, and U-100480 inhibit ribosomal protein biosynthesis through binding to the SOS ribosomal subunit. They can be used to treat Bacterial infections, generally, and, more specifically, Pneumocystis carinii infections.

Drugs such as tetracycline, chlortetracycline, oxytetracycline, demeclocycline, methacycline, doxycycline, minocycline, CL-331002, glycylcyclines, CL-331928, CL-344667, CL-329998 and PAM-MINO inhibit ribosomal protein biosynthesis through binding to the aminoacyl tRNA site on the 30S ribosomal unit. They can be used to treat bacterial infections, generally.

Drugs such as streptomycin, gentamicin, tobramycin, amikacin, netilimicin, kanamycin, neomycin, spectinomycin, dactimicin, paromomycin and trospectomycin inhibit ribosomal protein synthesis through binding to the 30S ribosomal unit. They can be used to treat bacterial infections, generally.

Drugs such as fusidic acid and purpuromycin inhibit protein synthesis through binding to soluble protein factors. They can be used to treat bacterial infections, generally.

Preparation of Multibinding Compounds

The multibinding compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, Protecting Groups in Organic Synthesis, Second Edition, Wiley, New York, 1991, and references cited therein.

Any compound which binds to bacterial ribosomal RNA and/or to one or more proteins present in the bacterial ribosome, arid, preferably, which inhibits or otherwise adversely affects protein expression, can be used as a ligand in this invention. As discussed in further detail below, numerous such compound are known in the art and any of these known compounds or derivatives thereof may be employed as ligands in this invention. Typically, a compound selected for use as a ligand will have at least one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures. The patents and publications set forth above provide numerous examples of suitably functionalized macrolide antibiotics, aminoglycosides, lincosamides, oxazolidinones, streptogramins, tetracycline and other compounds which bind to bacterial ribosomal RNA and/or to one or more proteins involved in ribosomal protein synthesis in the bacterium, and intermediates thereof, which may be used as ligands in this invention.

The ligands can be covalently attached to the linker through any available position on the ligands, provided that when the ligands are attached to the linker, at least one of the ligands retains its ability to bind to bacterial ribosomal RNA and/or to one or more proteins involved in ribosomal protein synthesis in the bacterium. Certain sites of attachment of the linker to the ligand are preferred based on known structure-activity relationships. Preferably, the linker is attached to a site on the ligand where structure-activity studies show that a wide variety of substituents are tolerated without loss of receptor activity.

It will be understood by those skilled in the art that the following methods may be used to prepare other multibinding compounds of this invention. Ligand precursors, for example, ligands containing a leaving group or a nucleophilic group, can be covalently linked to a linker precursor containing a nucleophilic group or a leaving group, using conventional reagents and conditions.

Figure 2:
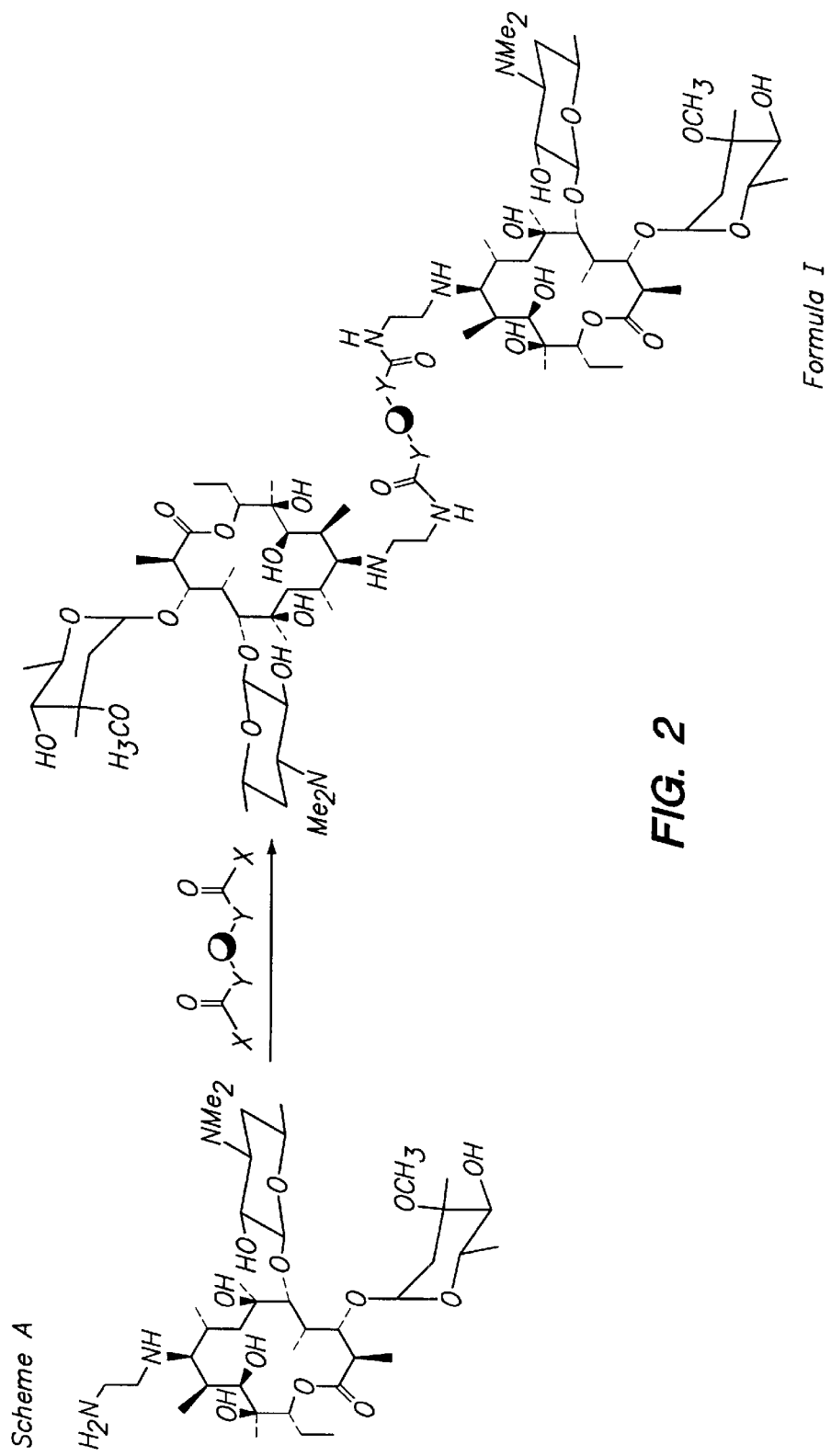

As shown in Scheme A (FIG. 2), the reaction product of erythromyclamine and Fmoc protected glycinal followed by reduction of the resulting imine and deprotection (compound 103) can be reacted with a diacid under routine amidation conditions to afford a ligand dimer.

Figure 3:
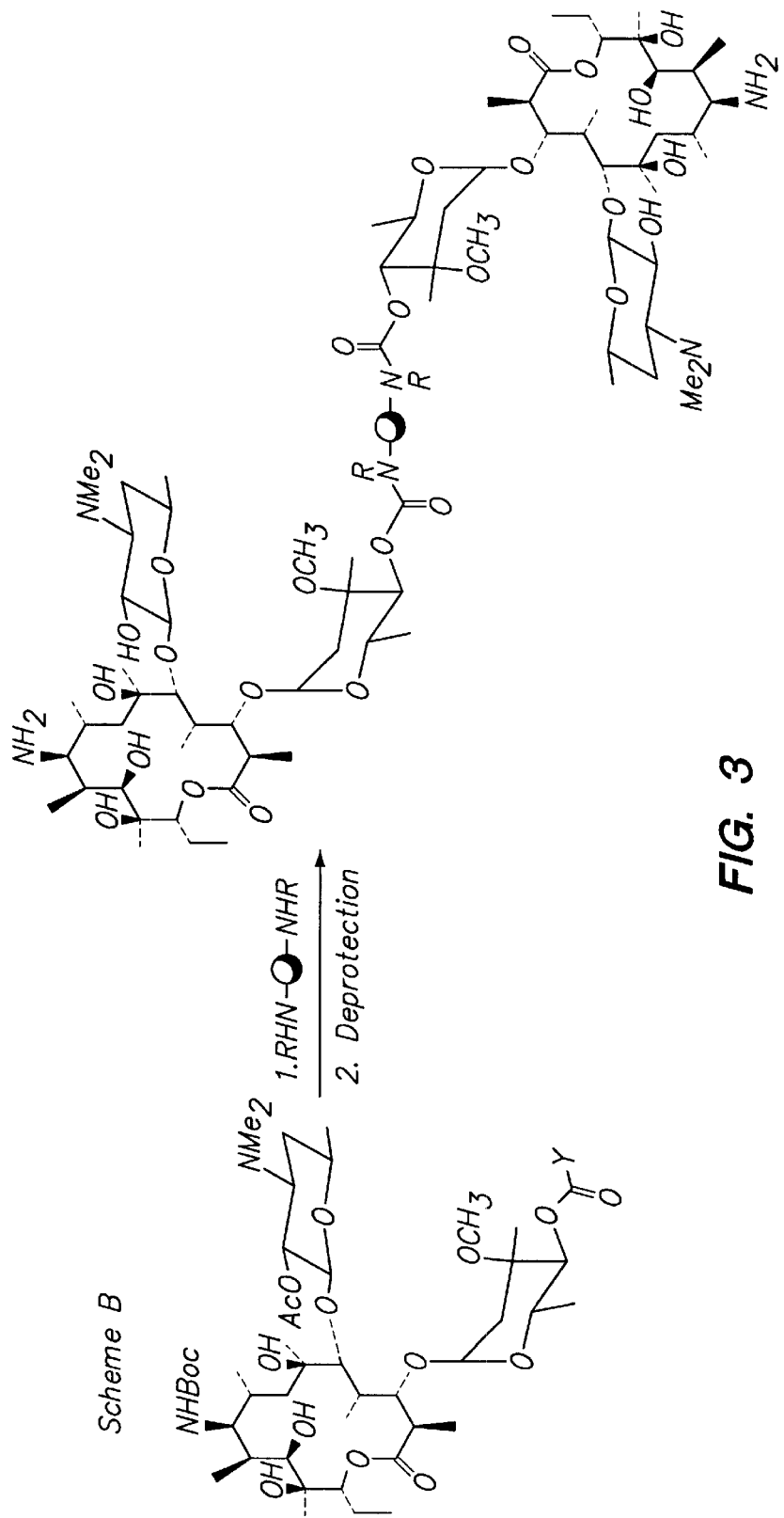

As shown in Scheme B (FIG. 3), the amine in erythromyclamine can be protected and a reactive hydroxy group reacted to form an imidazolide which can be reacted with a diamine to form a ligand dimer.

Figure 4:
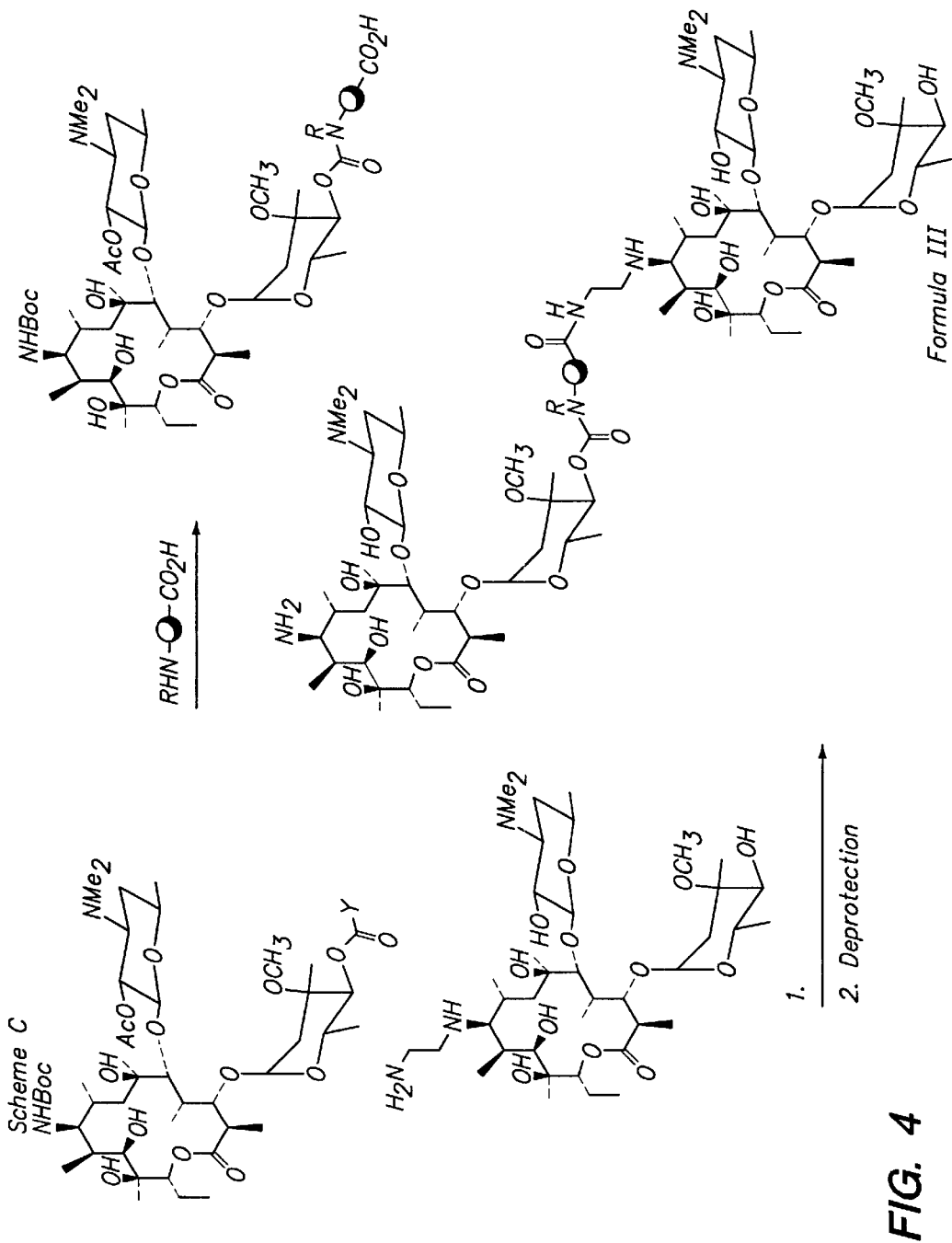

As shown in Scheme C (FIG. 4), an imidazolide can be reacted with an amino acid. The resulting compound has a carboxylic acid group which can be coupled with the free amine group in (103) using routine conditions.

Figures 5, 6:
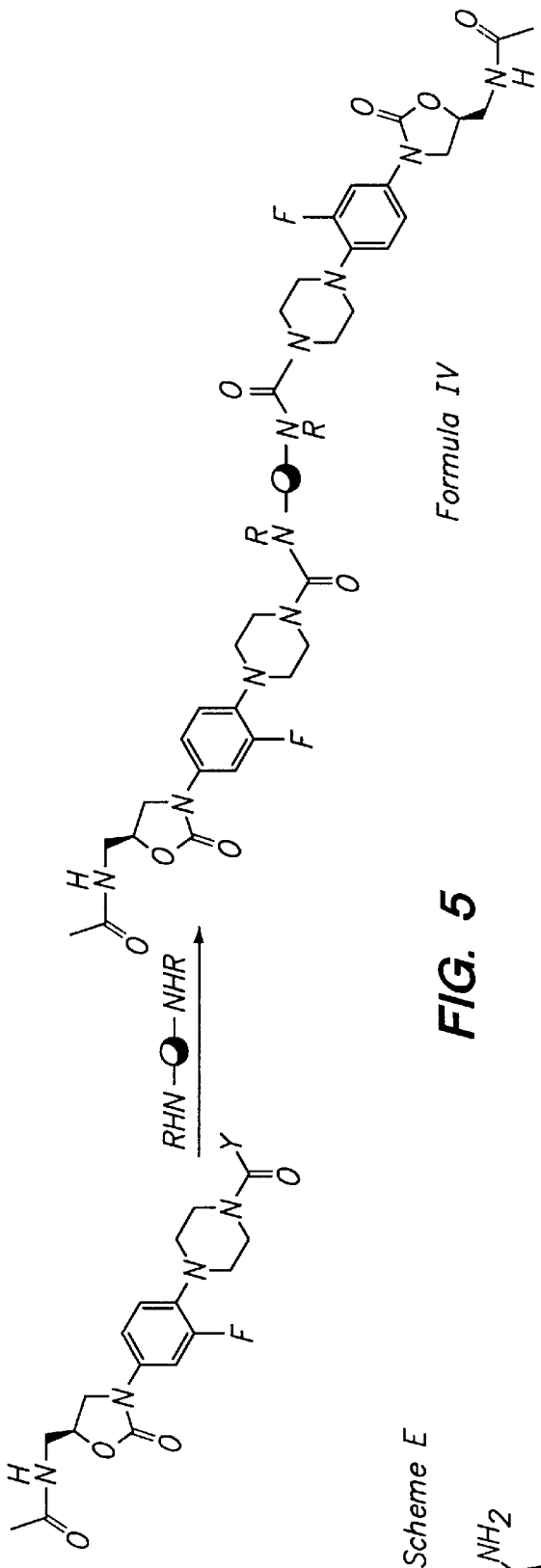

As shown in Scheme D (FIG. 5), an imidazolide can be reacted with two equivalents of an amine to form a diurea compound.

As shown in Scheme E (FIG. 6), two equivalents of an amine-containing compound can be reacted with a diacid such as adipic acid to form a di-amide.

As shown in Scheme F (FIG. 7), an imidazolide can be reacted with an amino acid to form a urea linkage, and the free carboxylic acid group from the amino acid can be coupled with an amine to form a ligand dimer.

Figure 9:
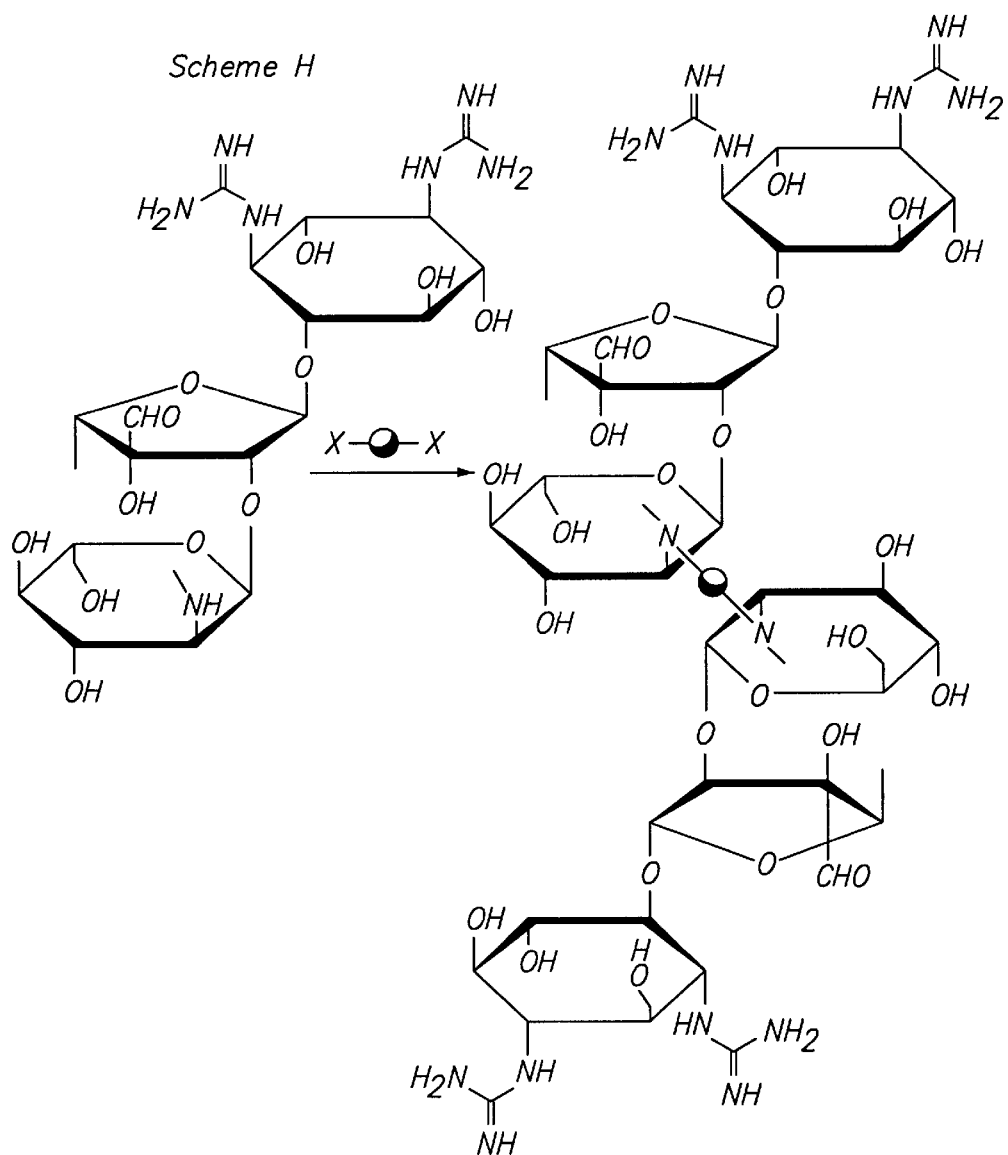

As shown in Scheme G (FIG. 8) and Scheme H (FIG. 9), two molecules containing amine groups can be reacted with a dibromide or a diacid to form the desired compound.

Figure 10:
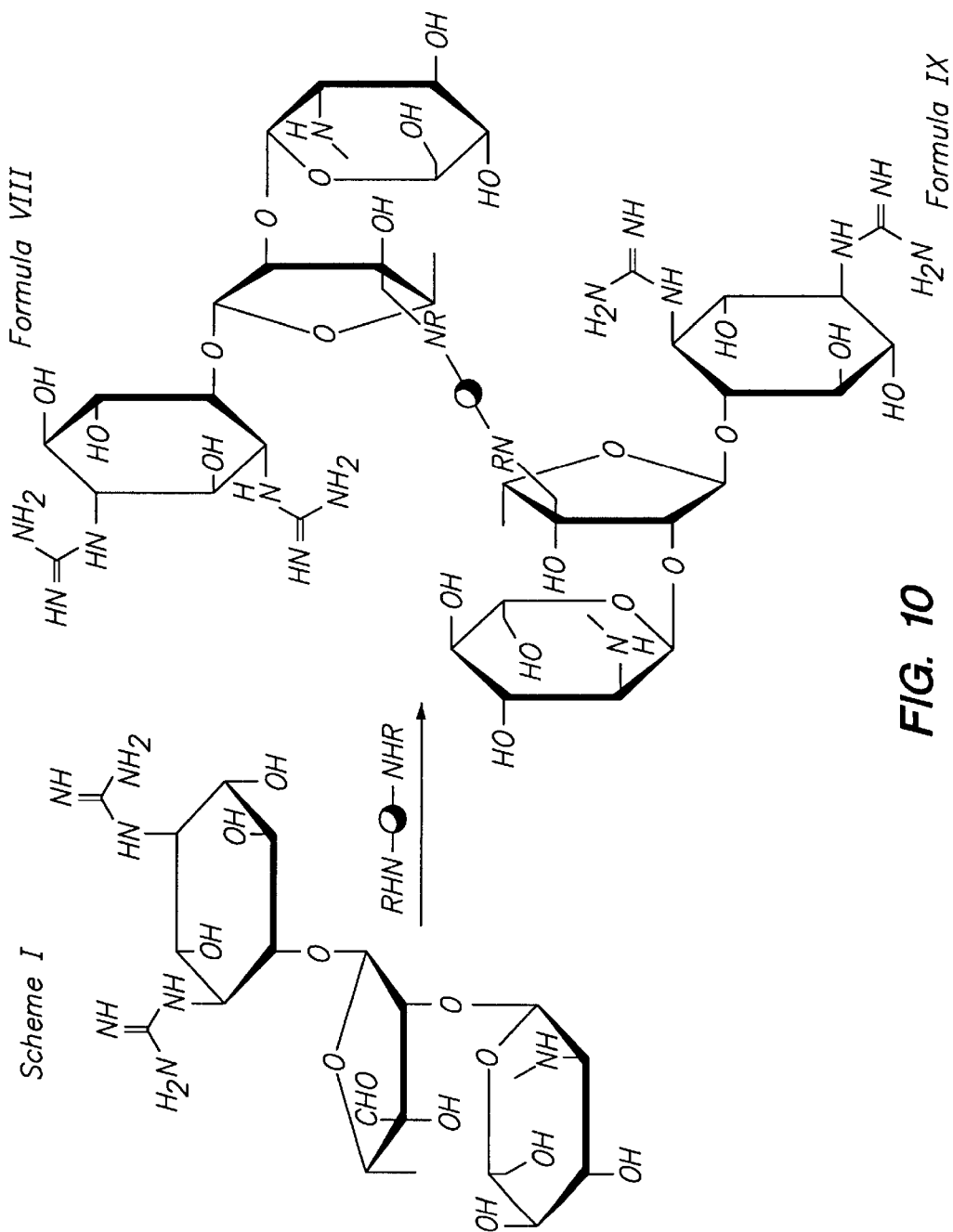

As shown in Scheme I (FIG. 10), two equivalents of a ligand containing an aldehyde group can be reacted with a linker containing two amine groups, and the resulting imine reduced to form a diamine.

Figure 11:
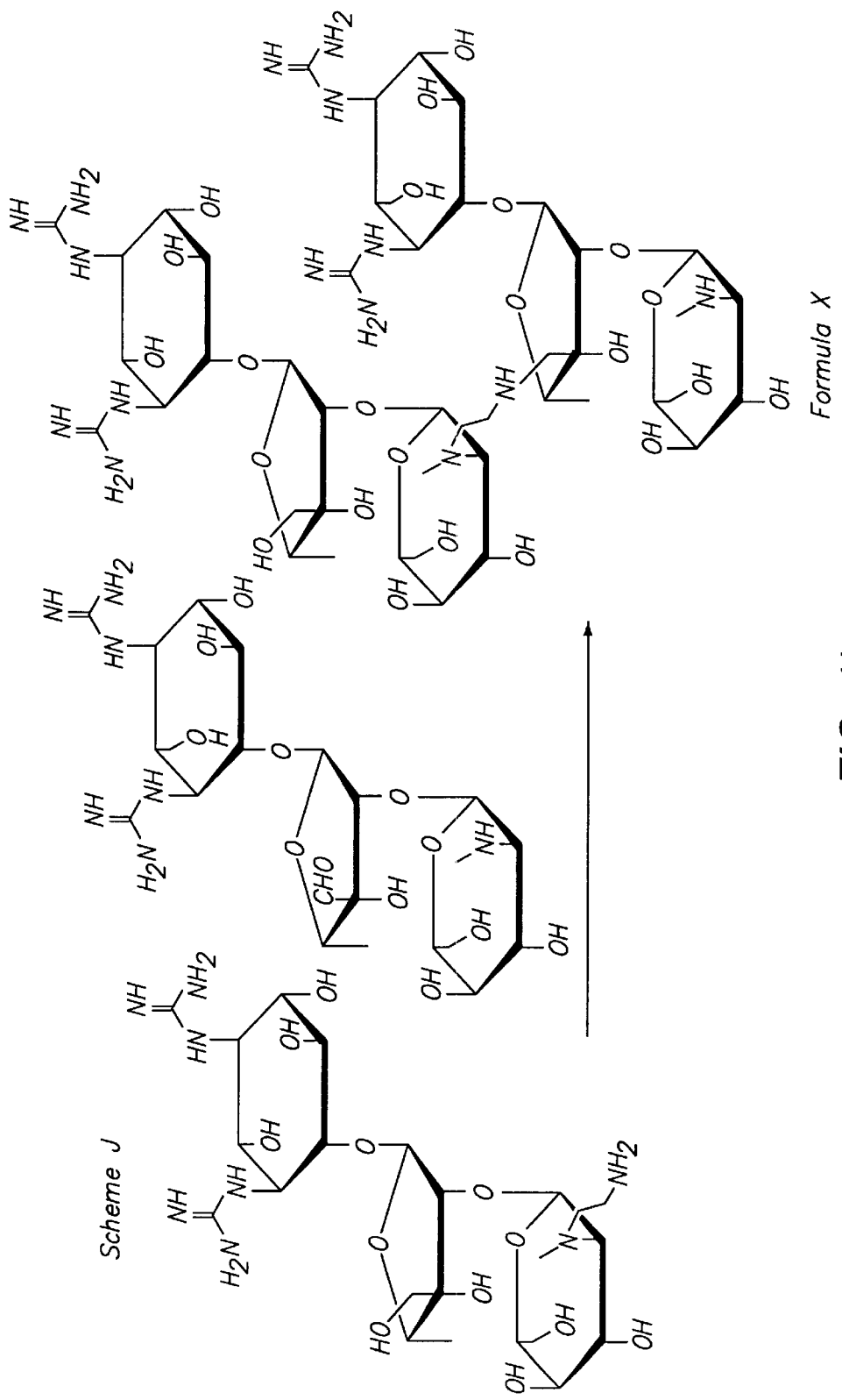

As shown in Scheme J (FIG. 11), a ligand containing an amine group can be reacted with a linker containing an aldehyde group, and the resulting imine reduced to form a diamine.

As shown in Scheme K (FIG. 12), a ligand containing a secondary amine can be reacted with an Fmoc protected glycine and the resulting amine deprotected to form a primary amine derivative. Two equivalents of the primary amine can be reacted with a diacid to form a ligand dimer.

As shown in Scheme L (FIG. 13), a ligand with an aromatic amine group can be reacted to form an imidazolide. Two equivalents of the imidazolide can be reactrd with a diamine to form a diurea compound.

Figure 14:
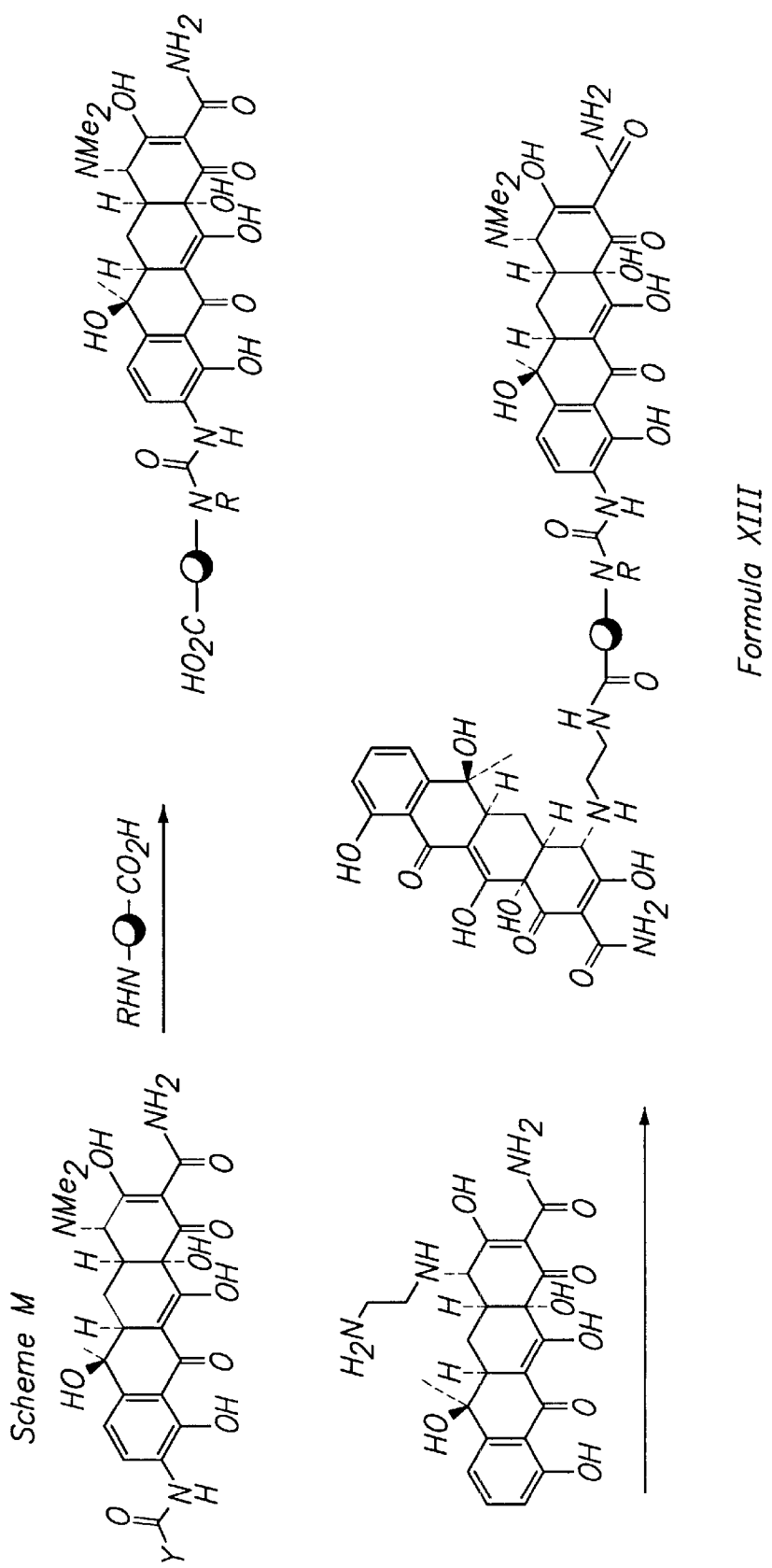

As shown in Scheme M (FIG. 14), the imidazolide from scheme L can be reacted with an amino acid to form an amide linkage, and the free carboxylic acid group reacted with an amine on a second ligand to create a dimer with mixed ligands.

Figure 15:
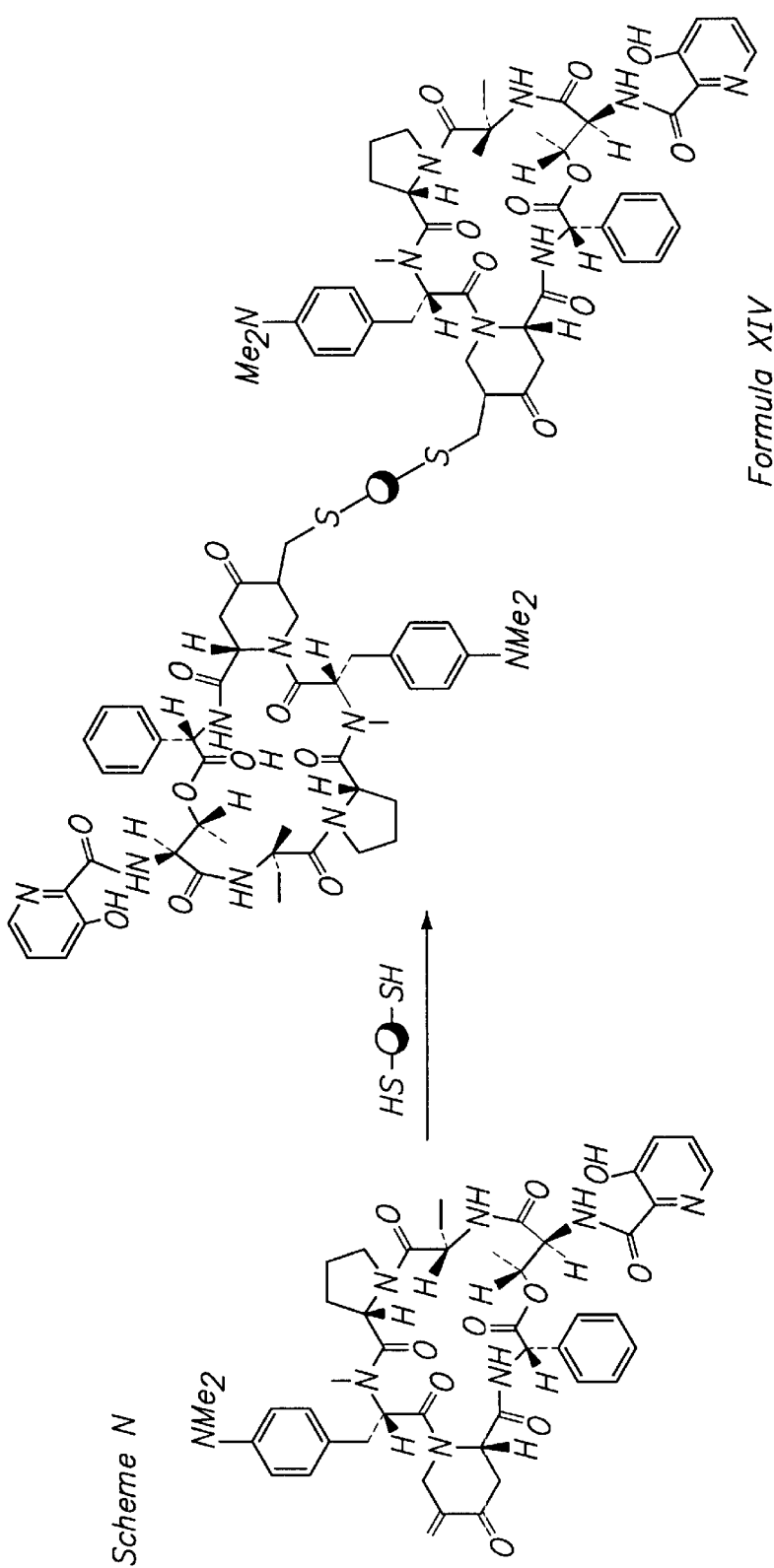

As shown in Scheme N (FIG. 15), two equivalents of a ligand with an alpha-beta unsaturated ketone moiety can be reacted with a dithiol to form the desired product after the thiols add across the double bond on the ligands.

Figure 16:
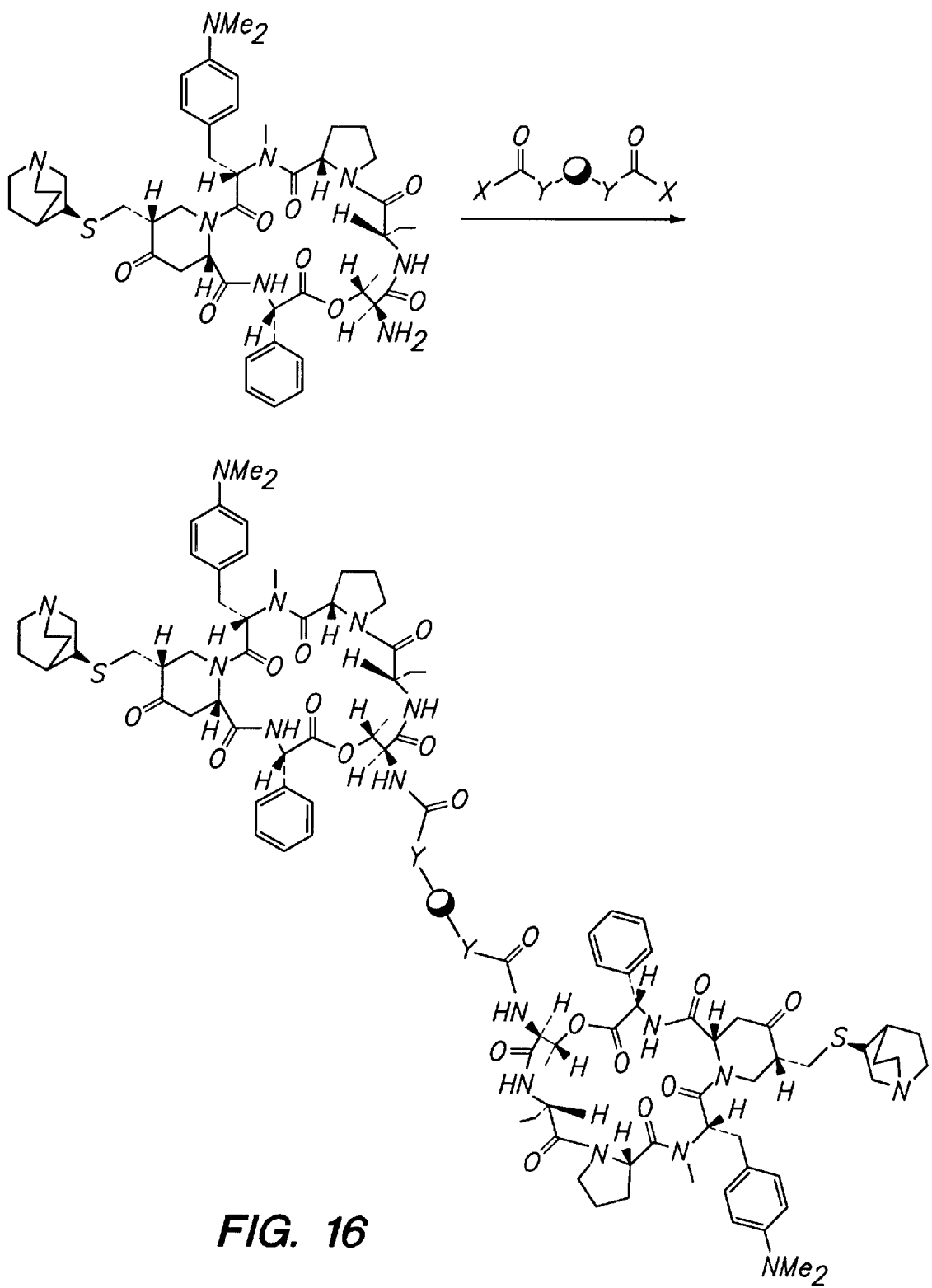

As shown in Scheme O (FIG. 16), two equivalents of a ligand with a primary amine group can be reacted with a diacid under appropriate conditions to form a di-amide reaction product.

Figure 17:
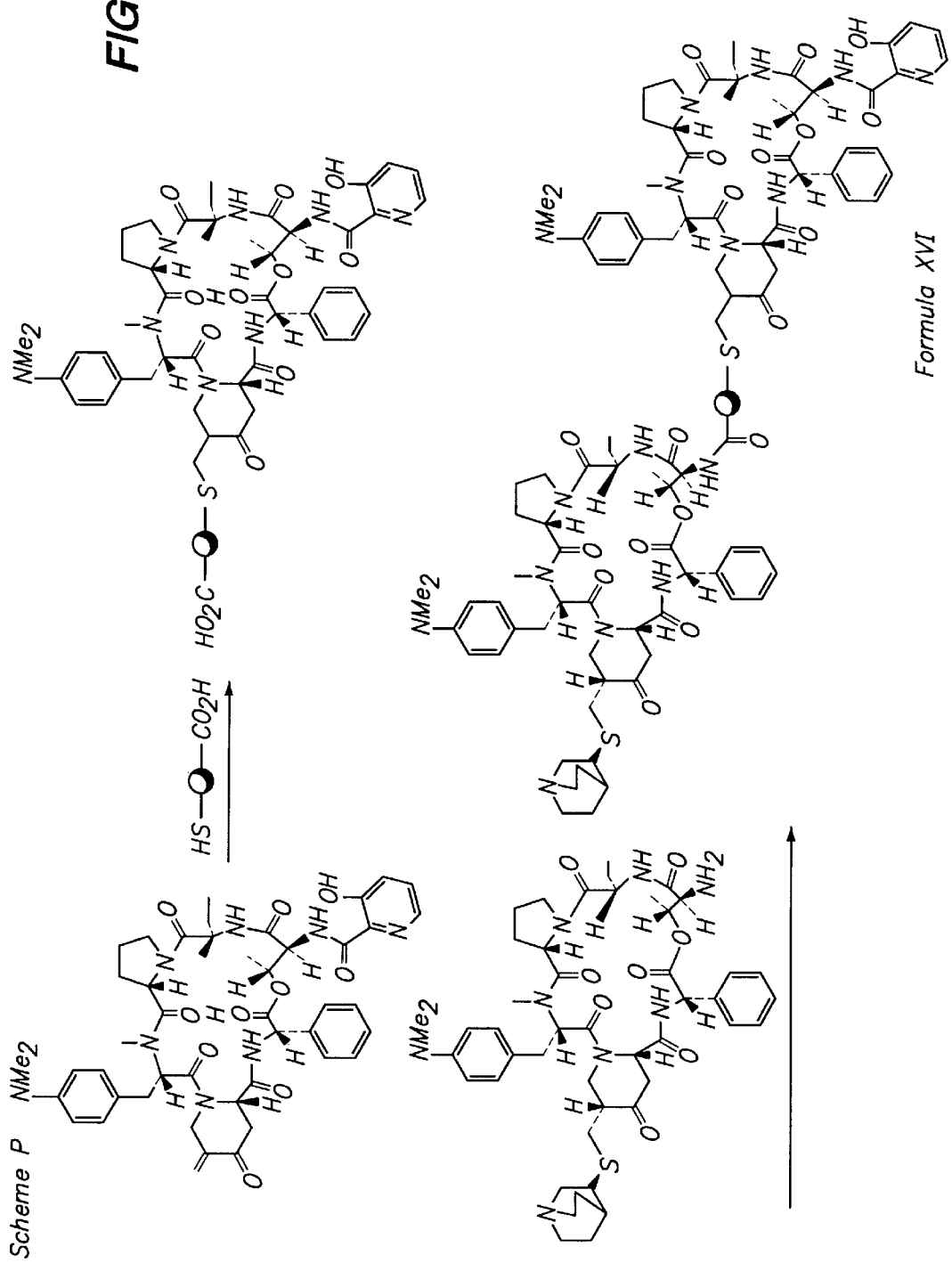

As shown in Scheme P (FIG. 17), one equivalent of a ligand with an alpha-beta unsaturated ketone can be reacted with a linker including a thiol group and a carboxylic acid group such that the thiol adds across the double bond. The free carboxylic acid is then free to react with an amine group on a second ligand to form a dimer.

Figure 18:
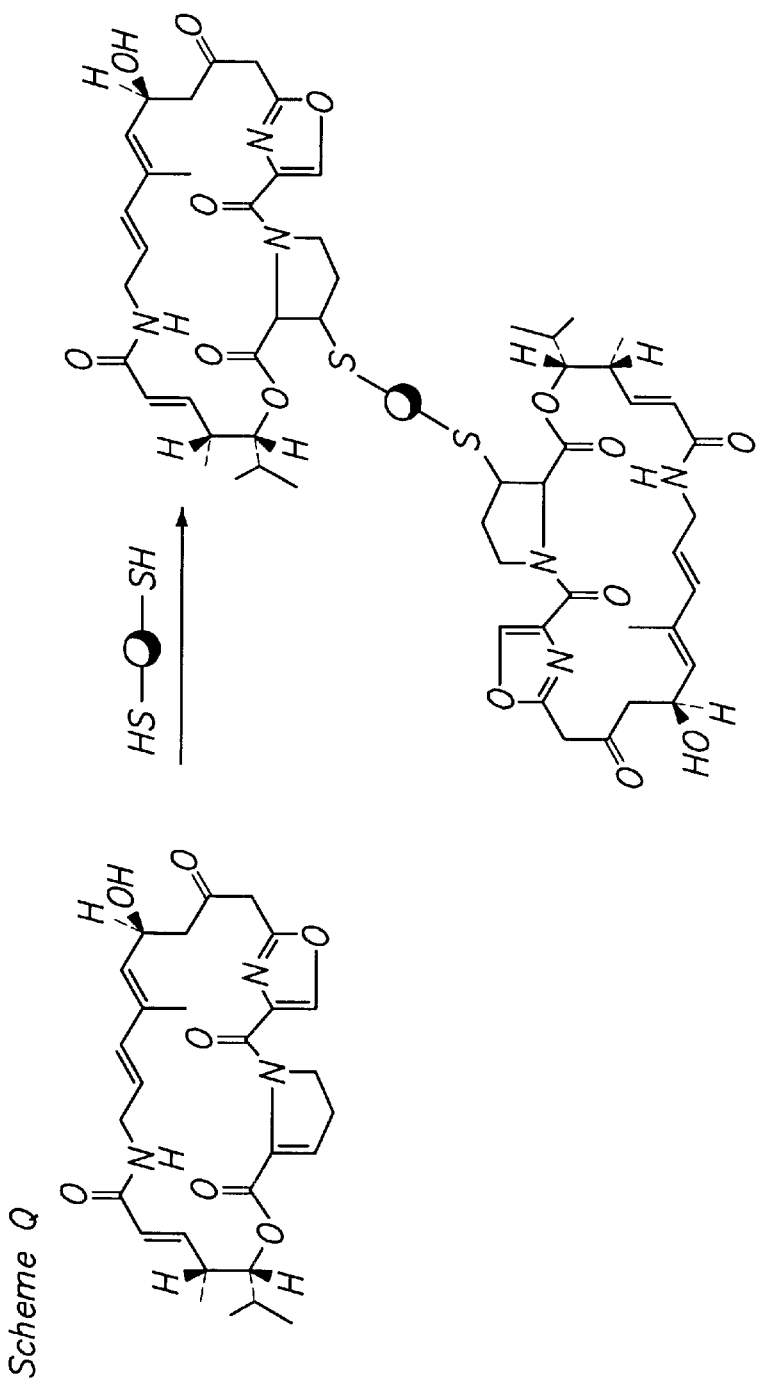

As shown in Scheme Q (FIG. 18), two equivalents of a ligand with an unsaturated ester linkage can also be reacted with a dithiol linker under conditions where the thiol groups add across the double bonds to form the desired product.

Figure 19:
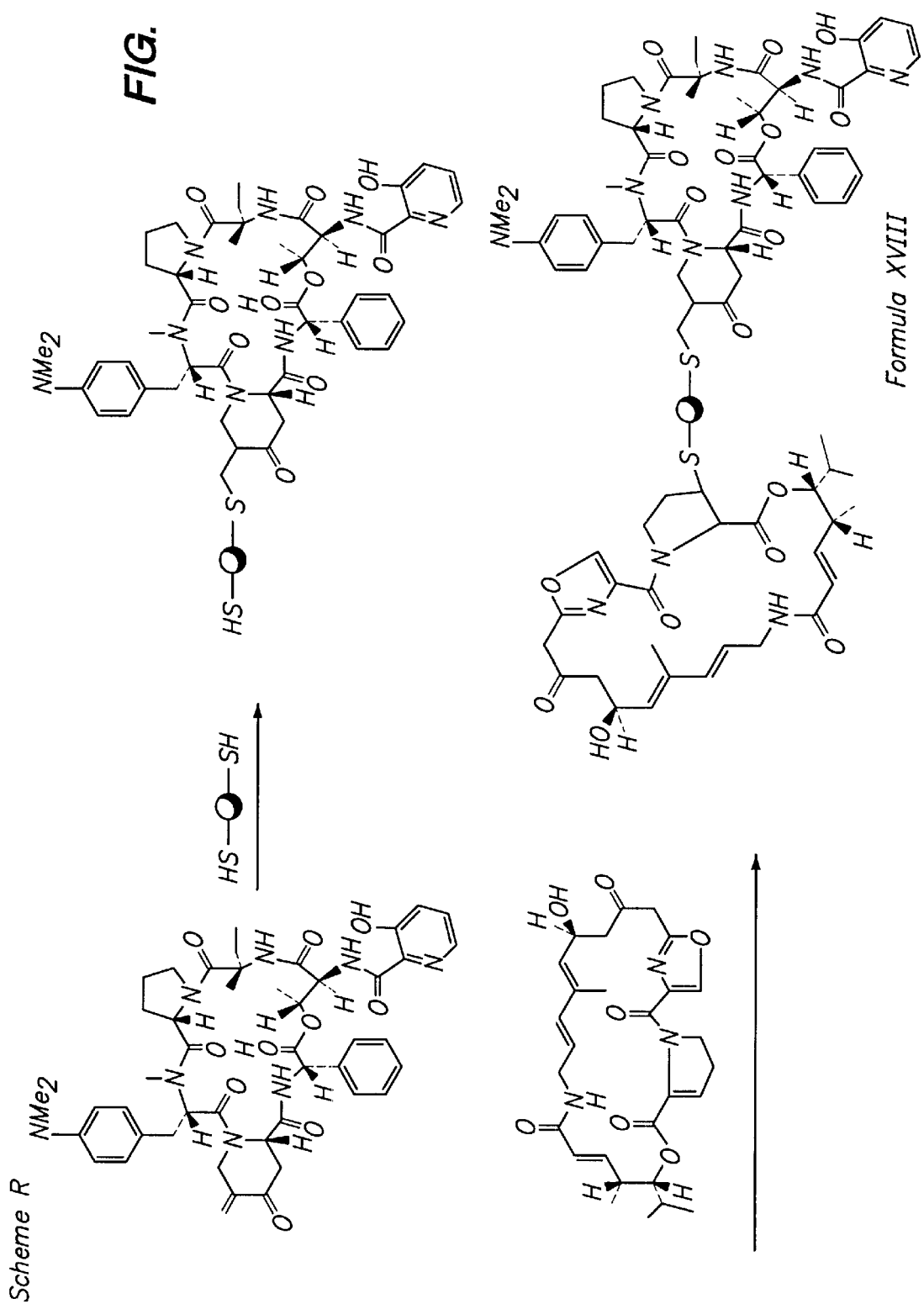

As shown in Scheme R (FIG. 19), one equivalent of a first ligand containing an alpha-beta unsaturated ketone and one equivalent of a dithiol can be reacted such that the resulting product includes a reactive thiol group, which can then be reacted with a second ligand containing an unsaturated ester moiety, to form a mixed dimer.

Figure 20:
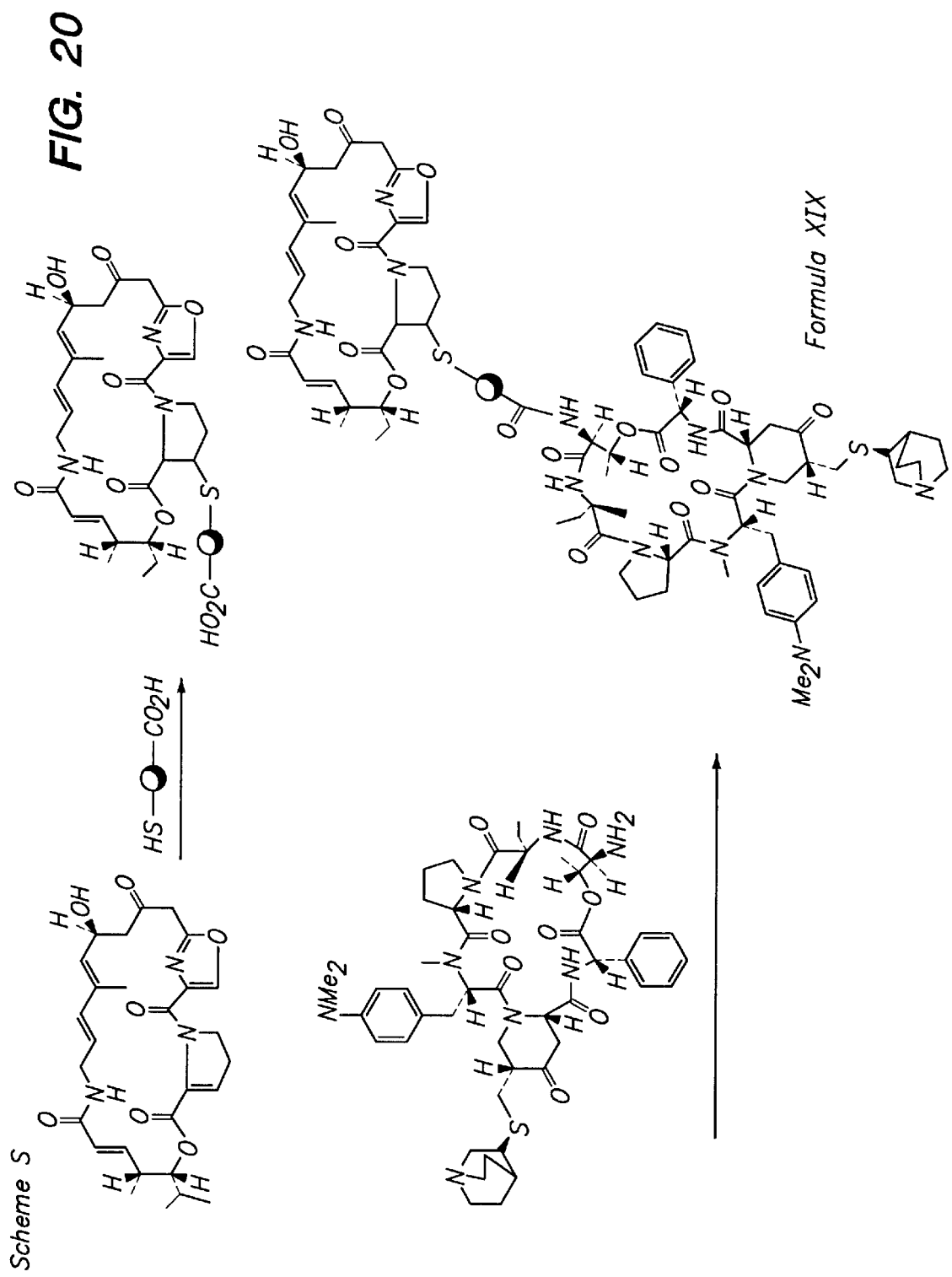

As shown in Scheme S (FIG. 20), one equivalent of a ligand containing an unsaturated ester moiety can be reacted with one equivalent of a linker including a thiol and a carboxylic acid moiety to form an intermediate containing a free carboxylic acid group. This carboxylic acid group can then be reacted with a free amine group on a second ligand to form a mixed dimer.

Figure 21:
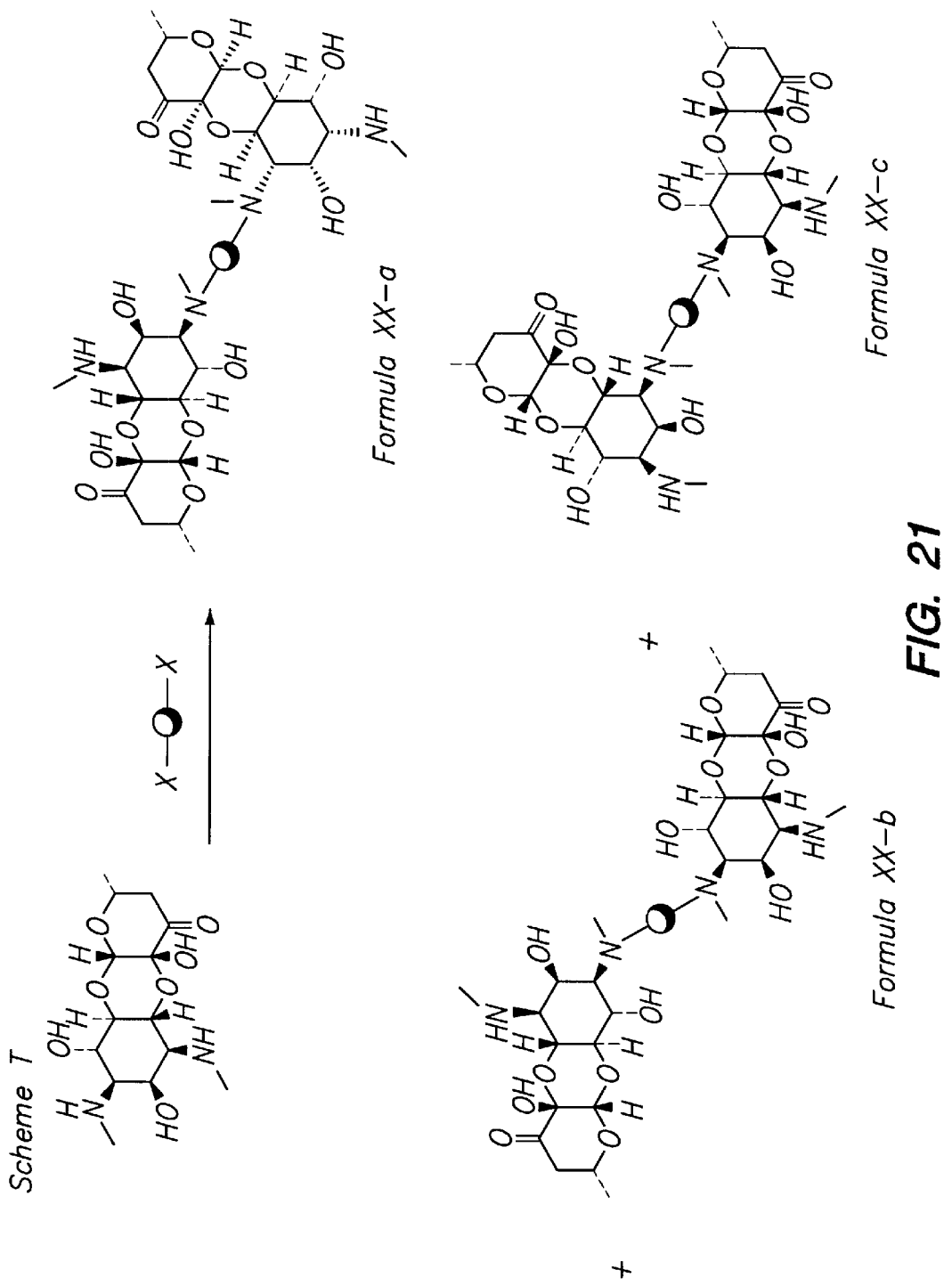
FIG. 21 is a schematic illustration of the preparation of compounds of formulas XXa, XXb and XXc.

As shown in Scheme T (FIG. 21), a ligand with more than one amine group can be reacted with a dihalide to form a mixture of dimers.

Figure 22:
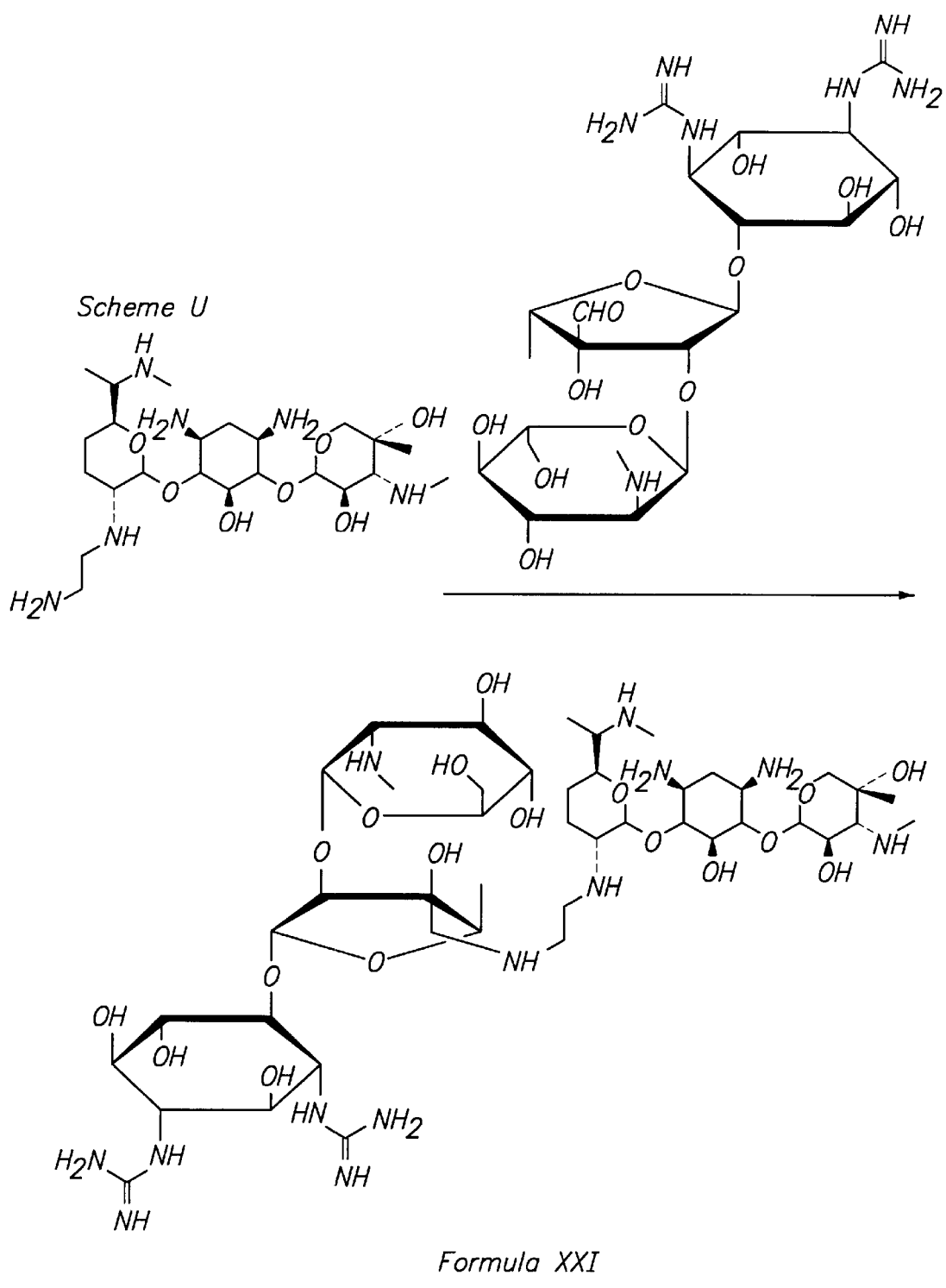
FIGS. 22–24, 24a, 25, 25a, and 26–37 are schematic illustrations of the preparation of compounds of formula XXI-XXXVIII, respectively.

As shown in Scheme U (FIG. 22), a ligand with a primary amine group and one or more additional secondary amine groups can be selectively reacted with an aldehyde group on a second ligand to form a dimer without the need for an intermediate linker molecule.

Figure 23:
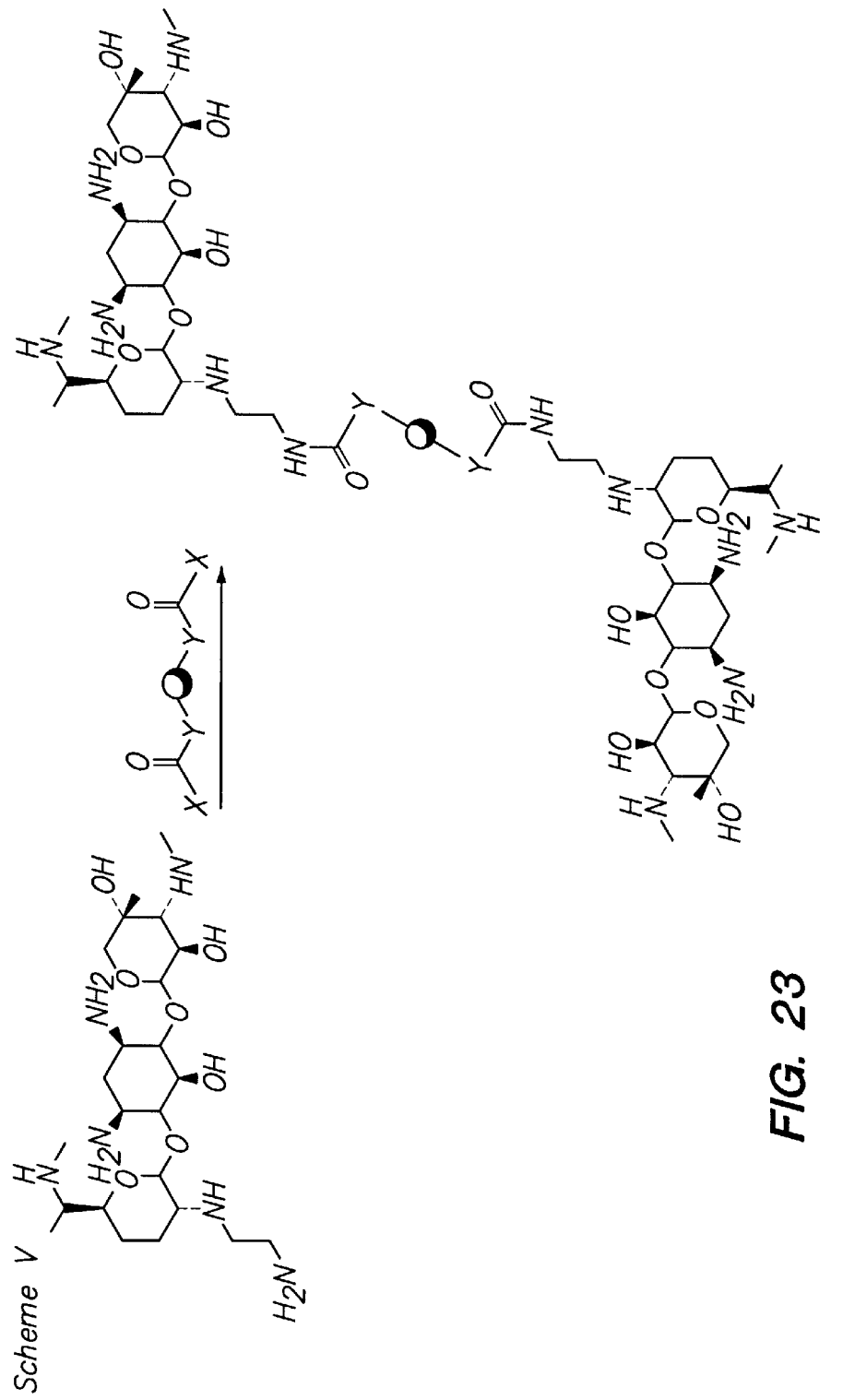

As shown in Scheme V (FIG. 23), a ligand with a primary amine group and one or more additional secondary amine groups can be selectively reacted with a linker molecule containing two acid groups to form a dimer.

Figure 24:
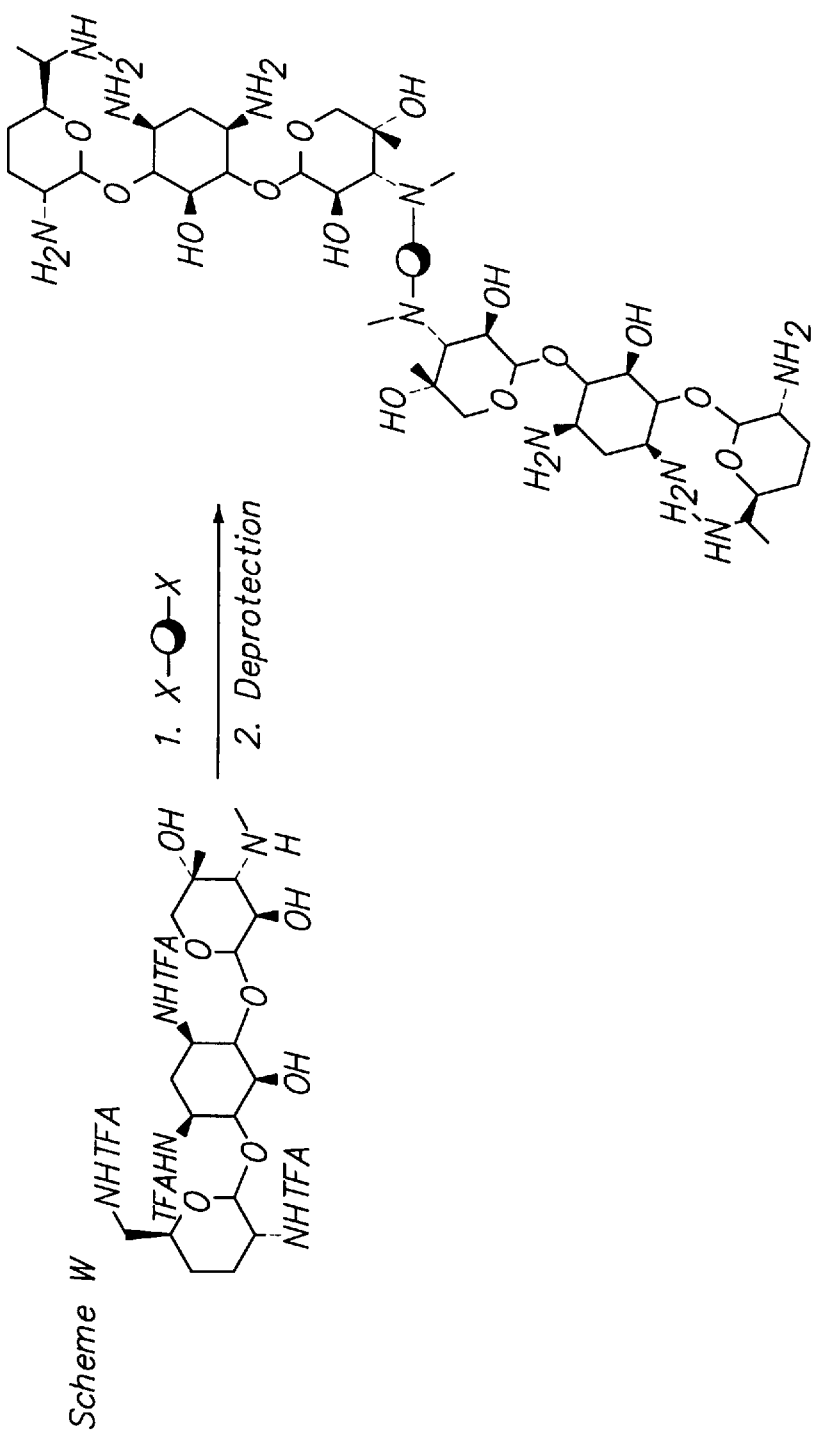

As shown in Scheme W (FIG. 24), a ligand with an unprotected amine group and one or more additional protected amine groups can be selectively reacted with a linker molecule with two bromo groups to form a dimer.

Figure 24A:
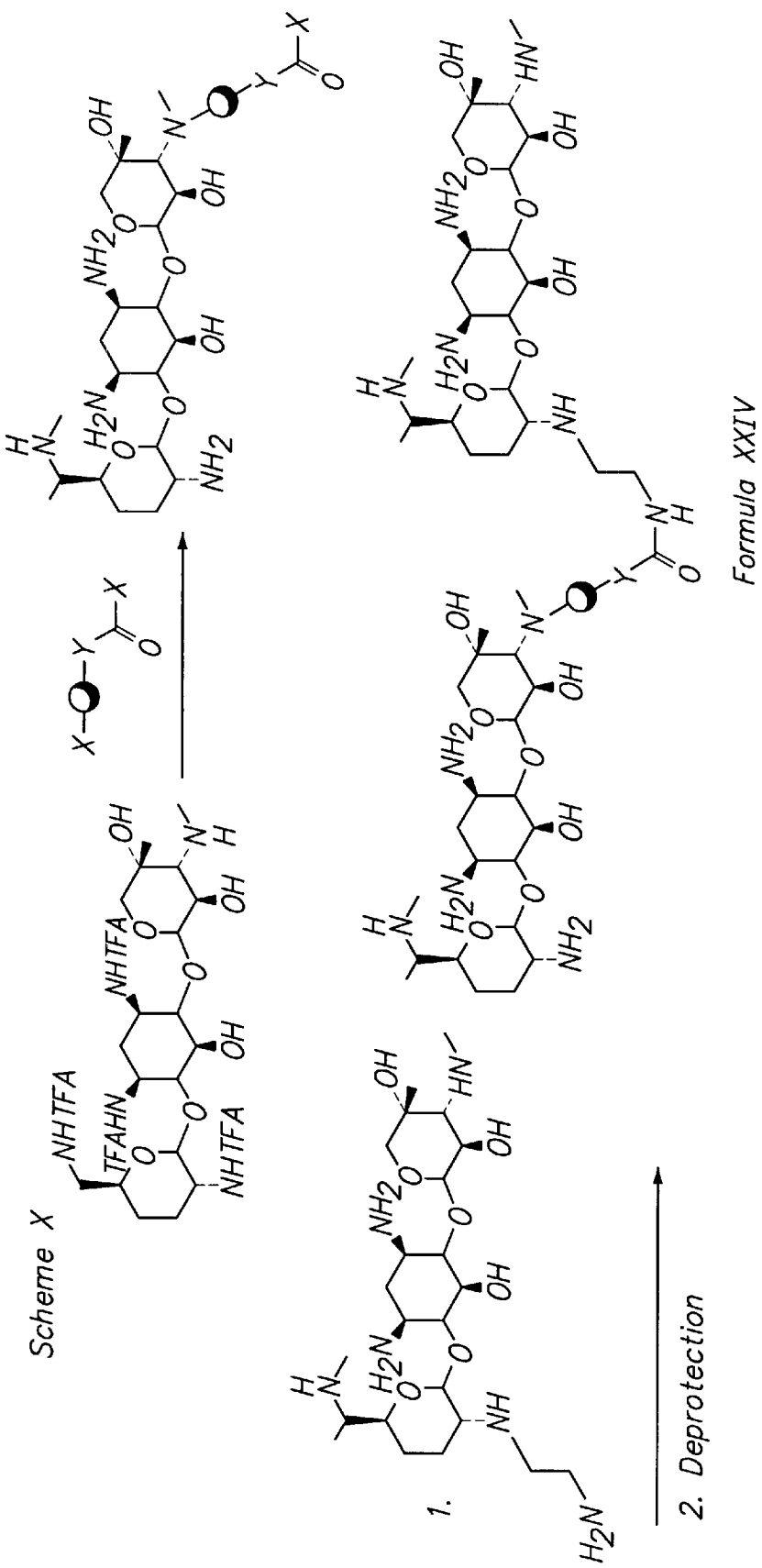

As shown in Scheme X (FIG. 24A), a ligand with an unprotected amine group and one or more additional protected amine groups can be selectively reacted with a linker molecule with a halide group and a carboxylic acid group to form an intermediate with a free carboxylic acid group, which can then be reacted with another ligand containing an amine group to form a mixed dimer.

Figure 25:
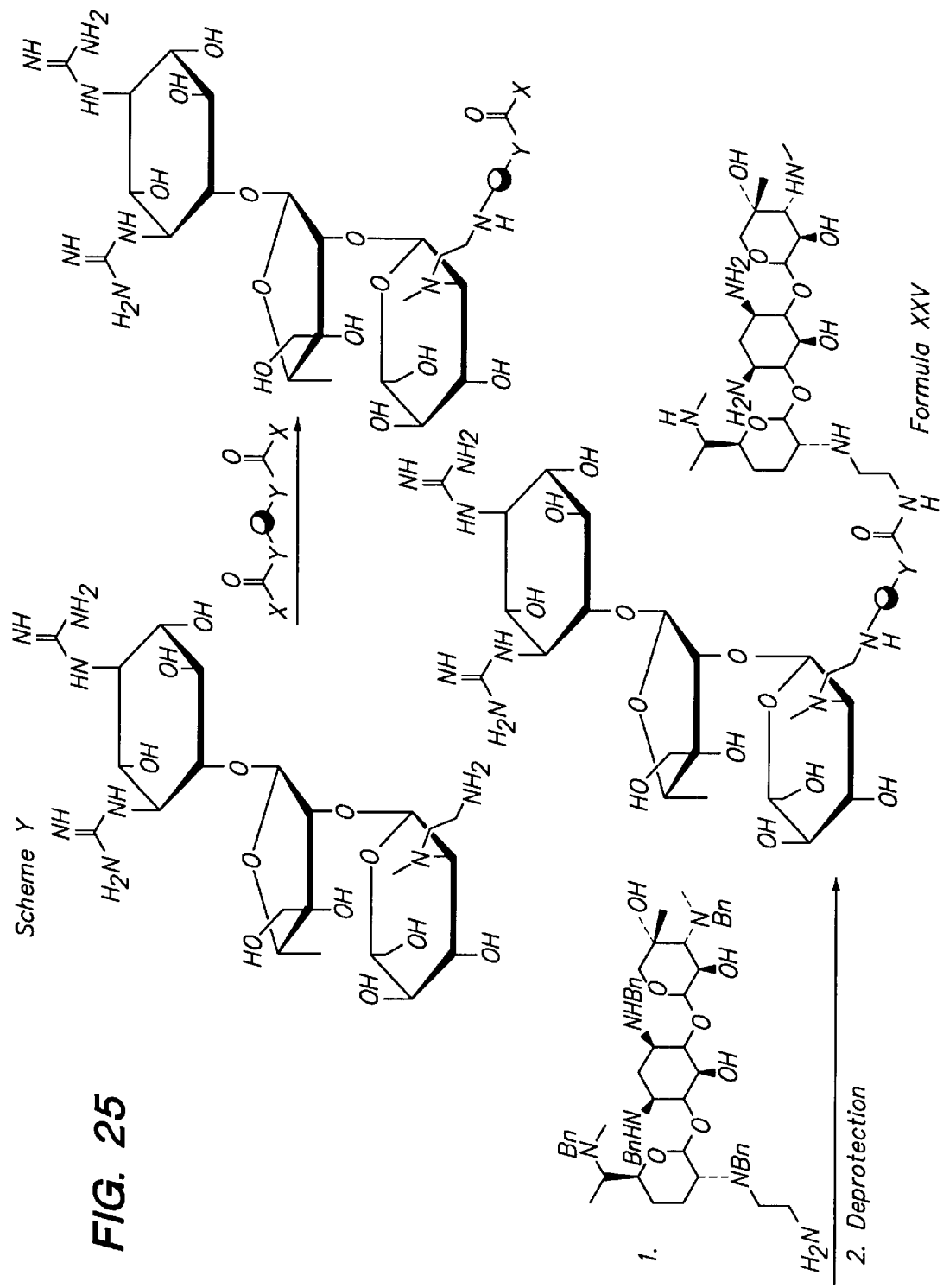

As shown in Scheme Y (FIG. 25), one equivalent of a ligand with an amine group can be reacted with one equivalent of a linker with two acid groups to form an intermediate with a free carboxylic acid group. This intermediate can be reacted with a second ligand which includes an unprotected amine group and one or more additional protected amine groups to form a mixed dimer.

Figure 25A:
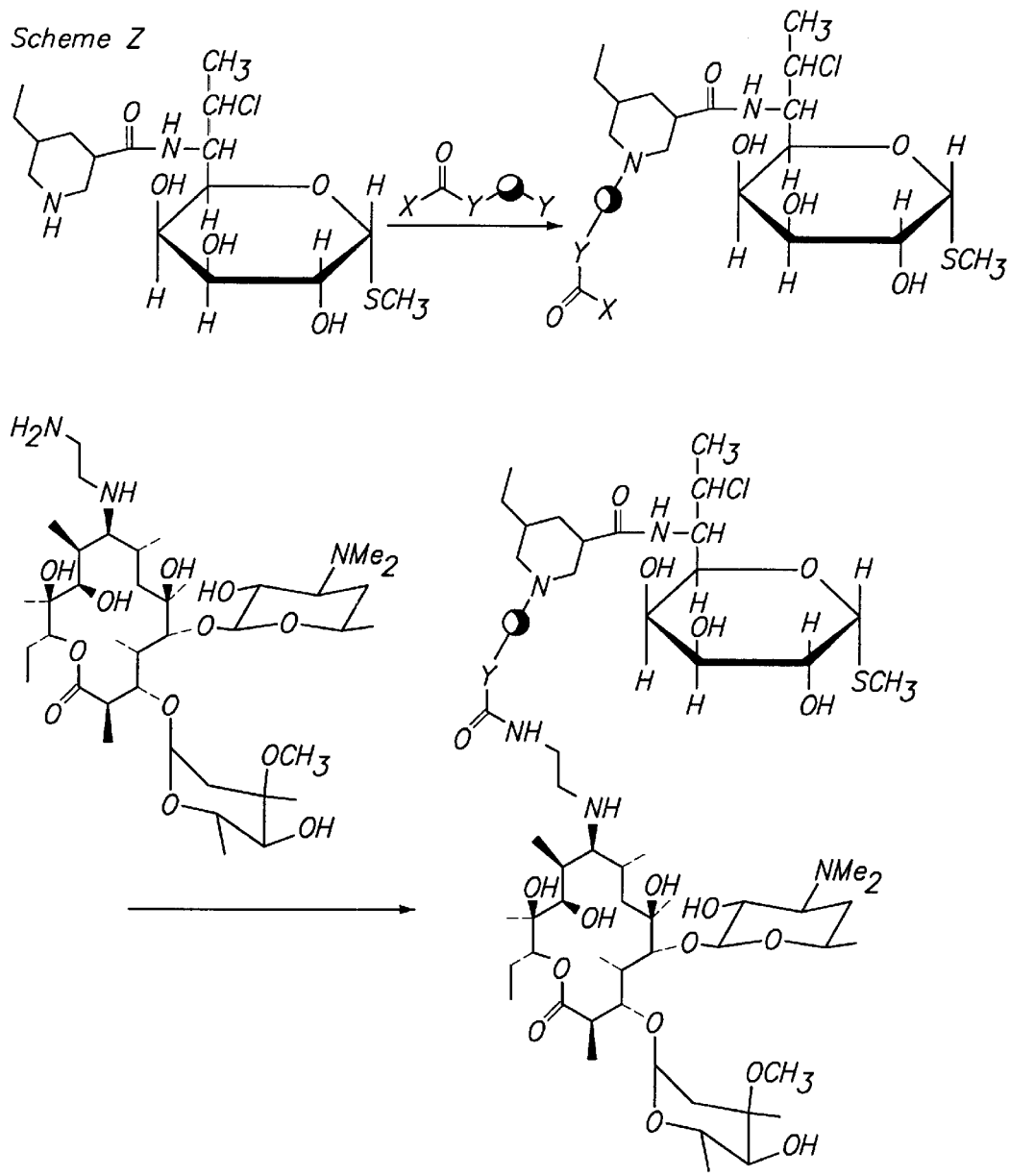

As shown in Scheme Z (FIG. 25A), a ligand with a secondary amine group can be reacted with a linker molecule containing a halide and a carboxylic acid group to form an intermediate with a free carboxylic acid group. The intermediate can then be reacted with a second ligand with a free amine group to form a mixed dimer.

Figure 26:
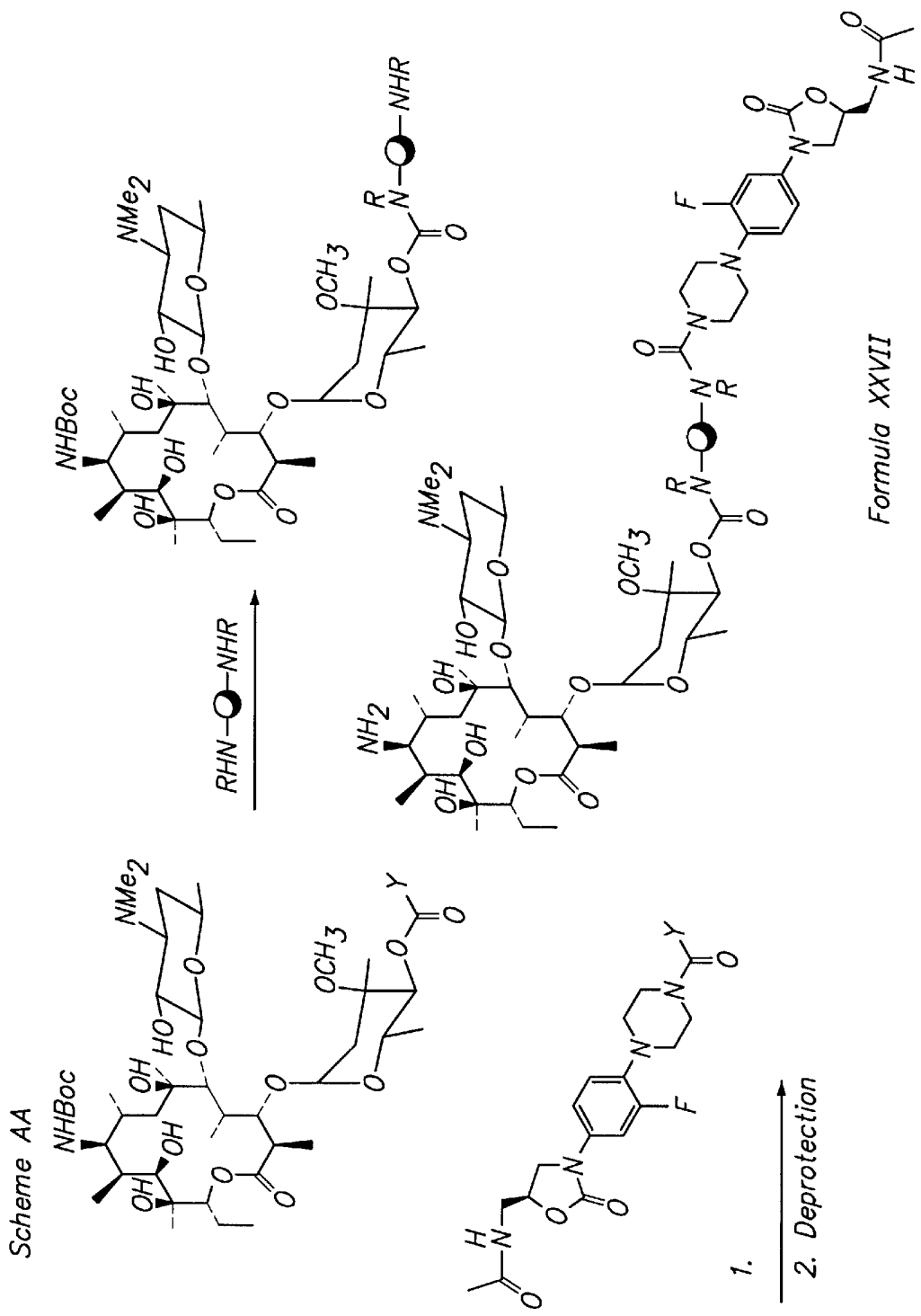

As shown in Scheme AA (FIG. 26), one equivalent of a ligand containing an imidazolide group (and in FIG. 26, a protected amine group) can be reacted with one equivalent of a linker molecule with two amine groups to form an intermediate with a free amine group. This intermediate can be reacted with a second ligand with an imidazolide group to form a mixed dimer (in FIG. 26, the protected amine group was is then deprotected).

Figure 27:
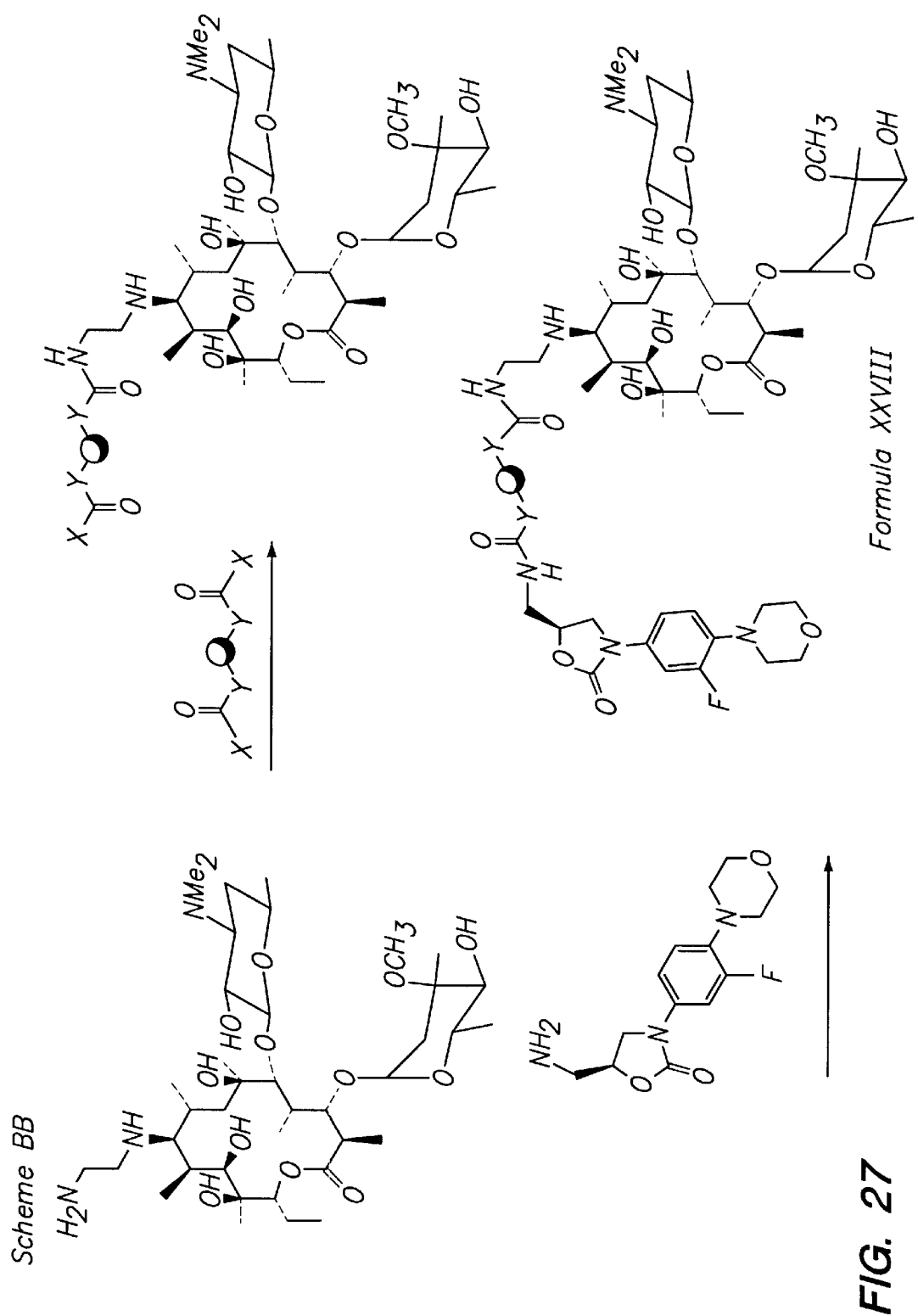

As shown in Scheme BB (FIG. 27), one equivalent of a ligand with a free primary amine group can be reacted with one equivalent of a diacid to form an intermediate with a free carboxylic acid group. This intermediate can be reacted with a second ligand with a free amine group to form a mixed dimer.

Figure 28:
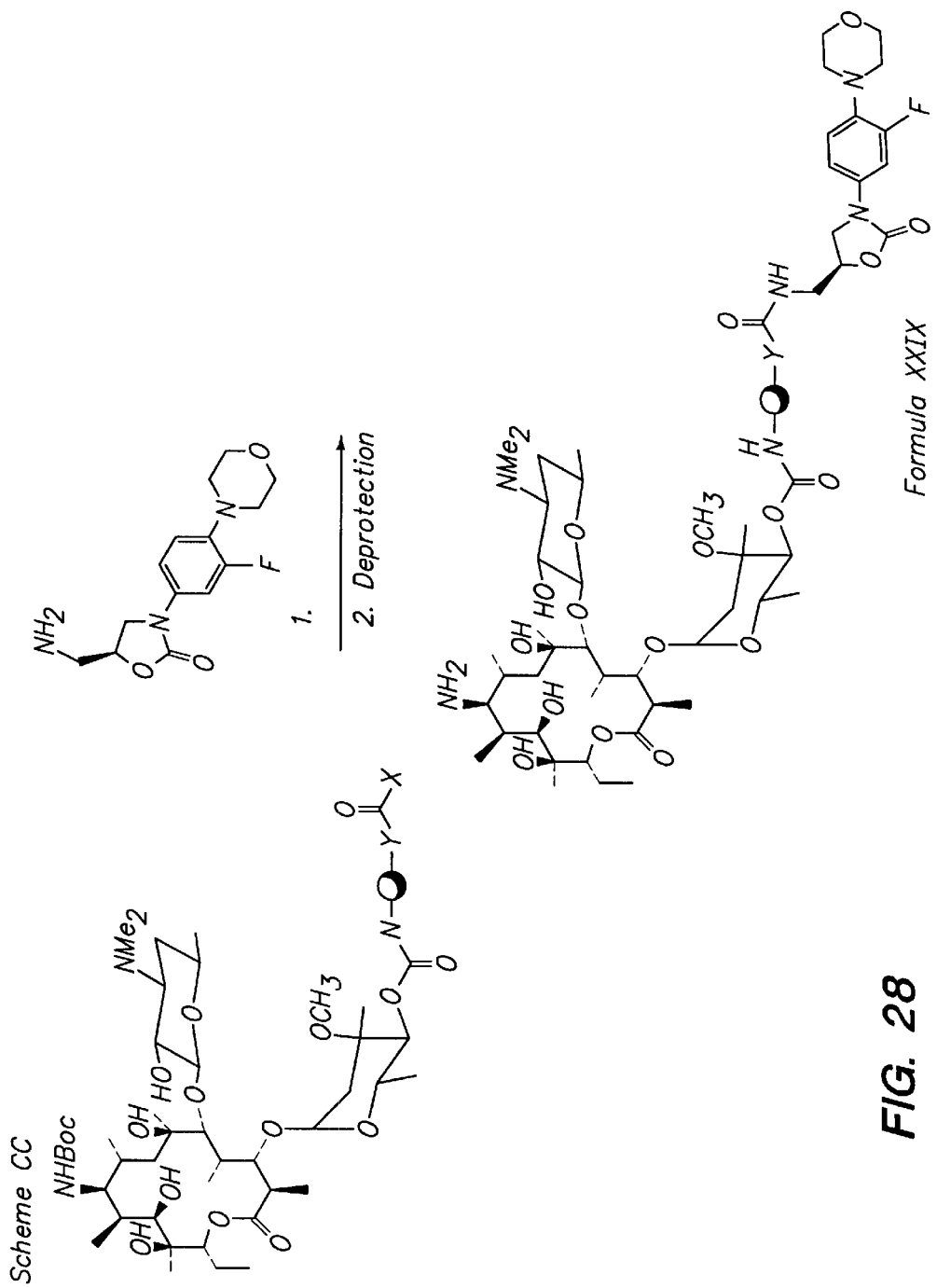

As shown in Scheme CC (FIG. 28), an intermediate ligand/dimer which includes a urethane group and a free carboxylic acid group can be reacted with a second ligand containing a free amine group to form mixed dimer.

Figure 29:
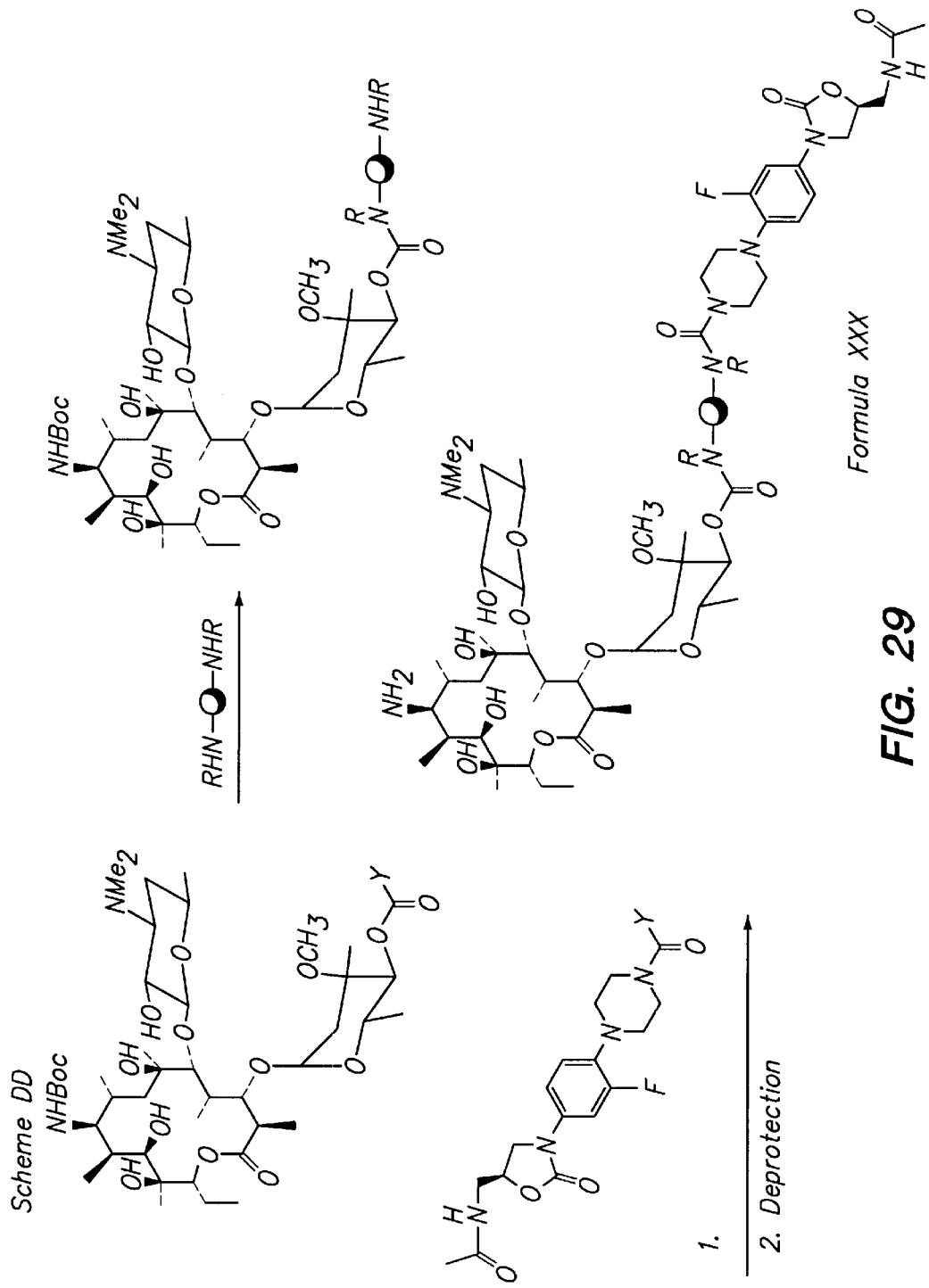

As shown in Scheme DD (FIG. 29), one equivalent of a ligand with an imidazolide or other activated carboxylic acid group can be reacted with one equivalent of a linker with two amine groups to form an intermediate with a free amine group. This intermediate can be reacted with a second ligand with an imidazolide or other activated carboxylic acid group to form a mixed dimer.

Figure 30:
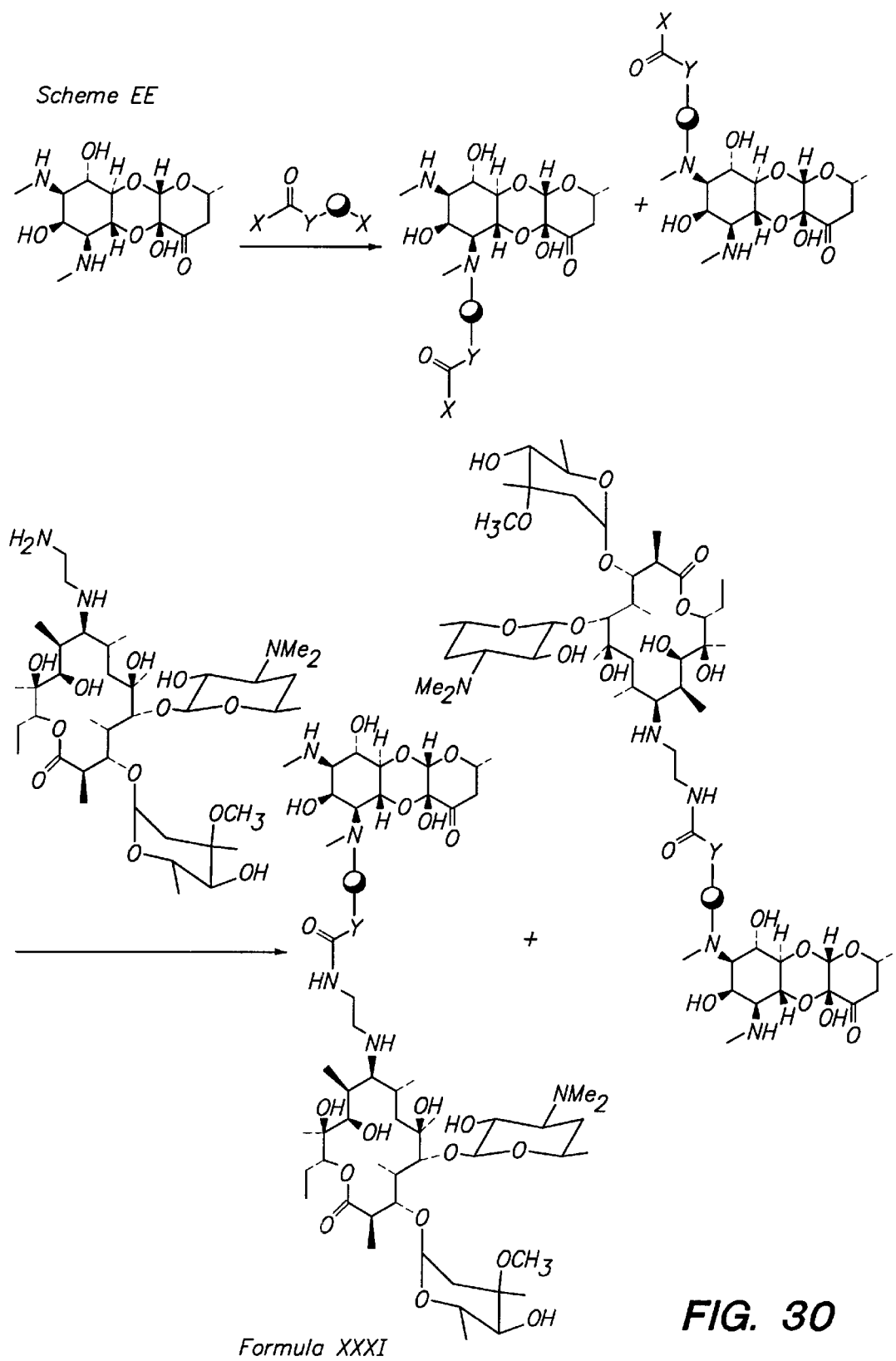

As shown in Scheme EE (FIG. 30), one equivalent of a ligand with two free amine groups can be reacted with a linker with a halide and a carboxylic acid group to form a mixture of intermediates with a free carboxylic acid group. These intermediates can then be reacted with a second ligand with a free amine group to form a mixture of ligand dimers.

Figure 31:
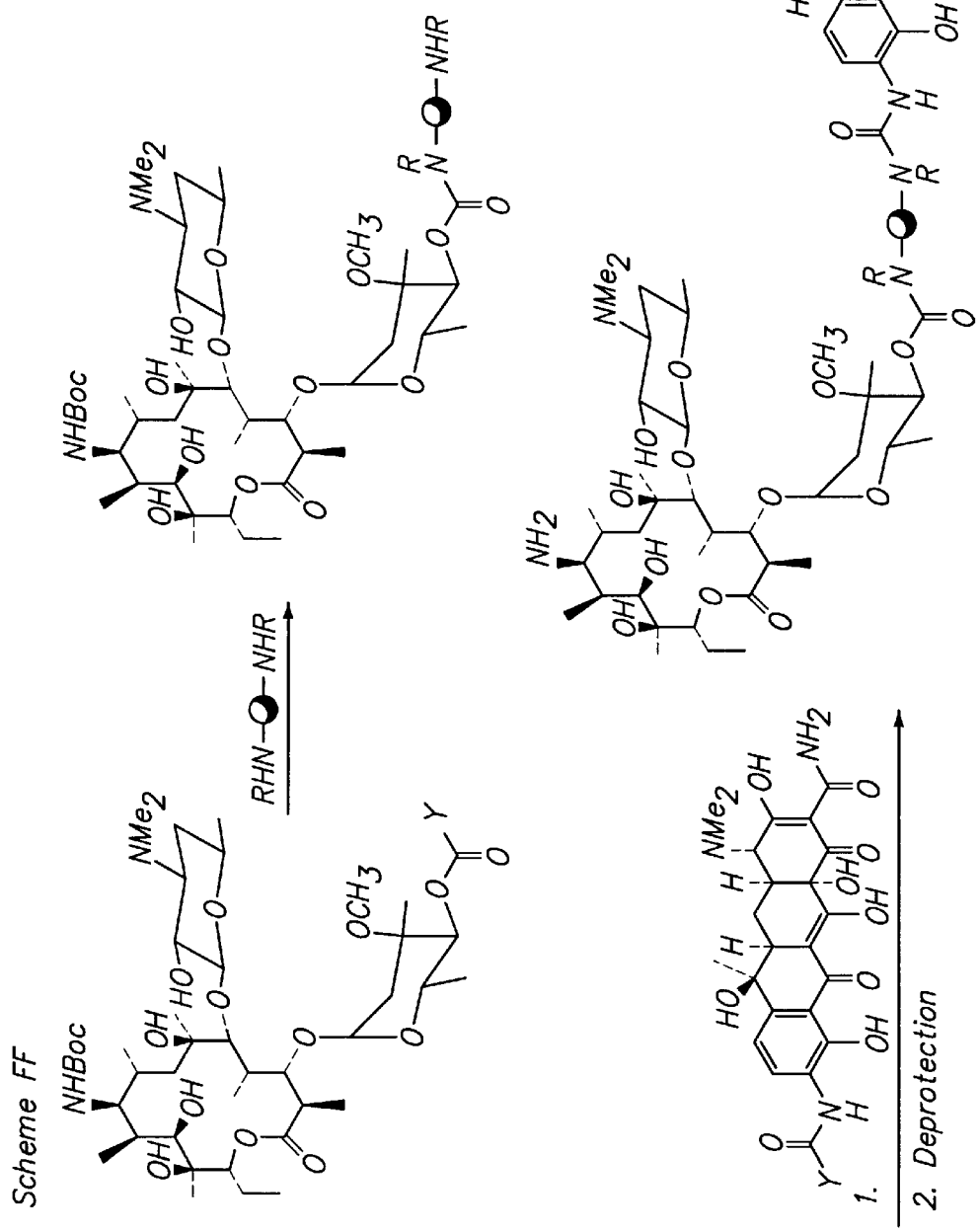

As shown in Scheme FF (FIG. 31), one equivalent of a ligand with an imidazolide or other activated carboxylic acid group can be reacted with one equivalent of a linker with two amine groups to form an intermediate with a free amine group, which can be reacted with a second ligand with an imidazolide or other activated carboxylic acid group to form a mixed dimer.

Figure 32:
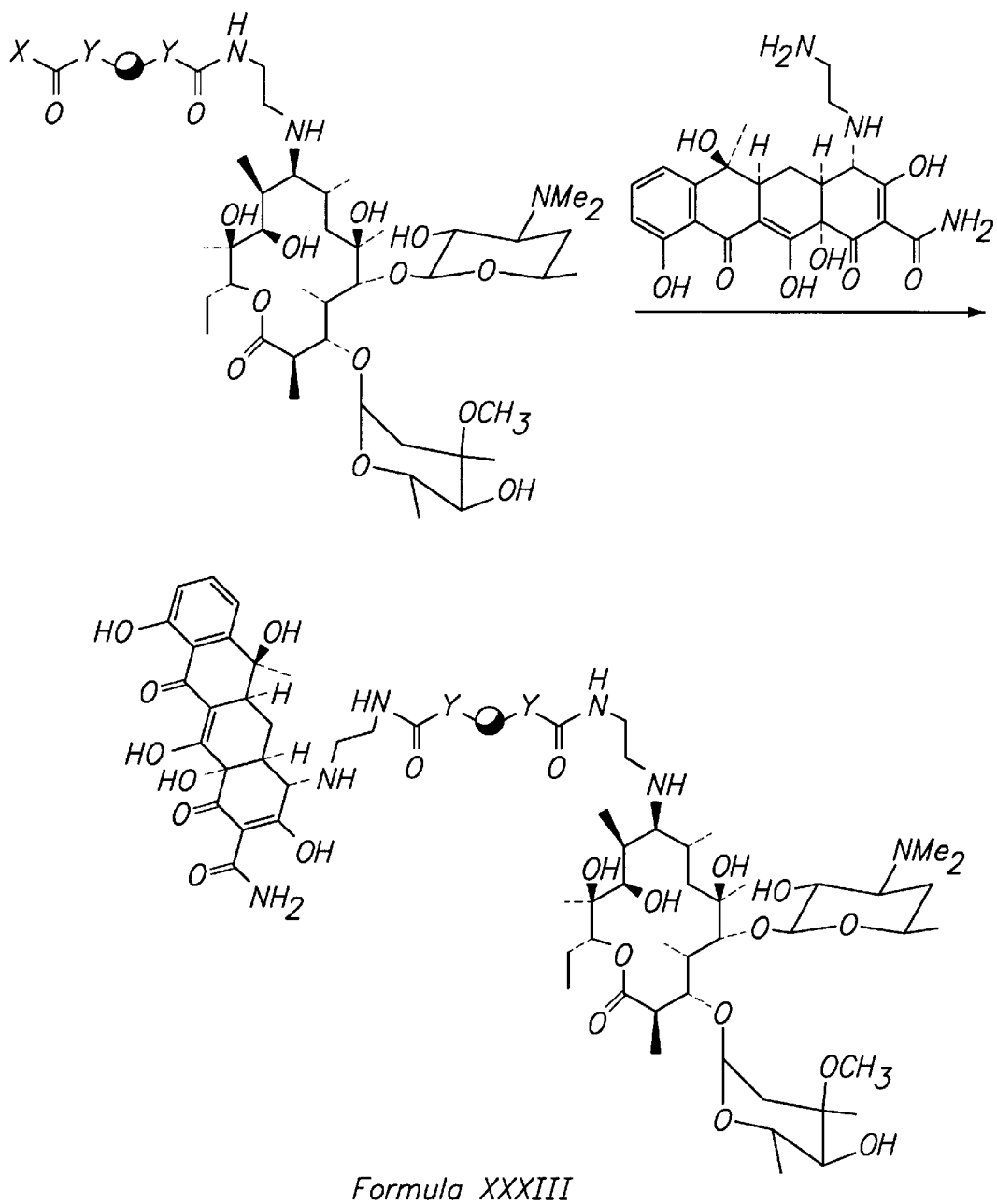

As shown in Scheme GG (FIG. 32), an intermediate formed by reacting a first ligand containing an amine group with a diacid can be reacted with a second ligand with a free amine group to form a mixed dimer.

Figure 33:
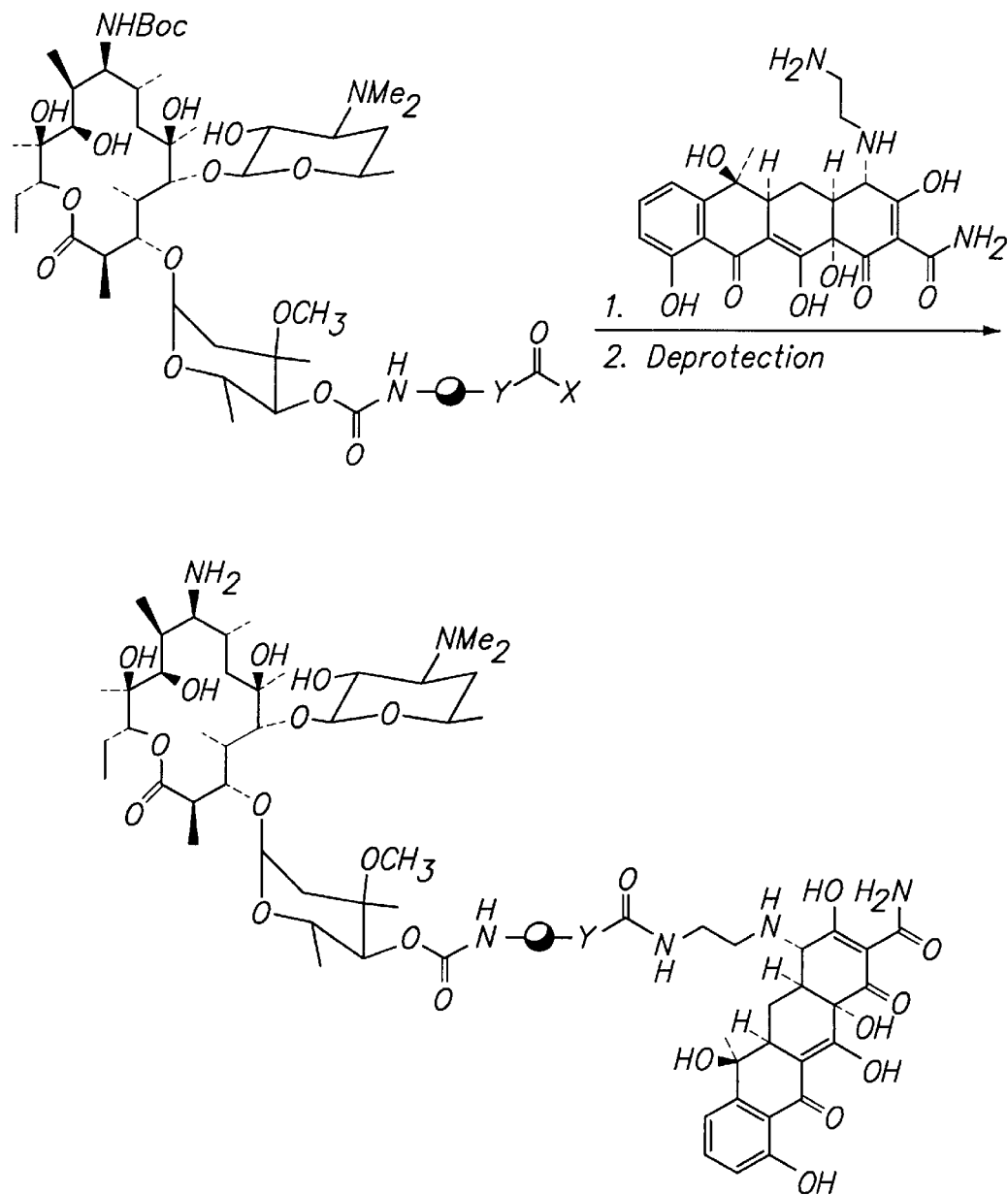

As shown in Scheme HH (FIG. 33), an intermediate formed by reacting a first ligand containing an imidazolide group with a linker containing an amine group and a carboxylic acid can be reacted with a second ligand with a free amine group to form a mixed dimer.

Figure 34:
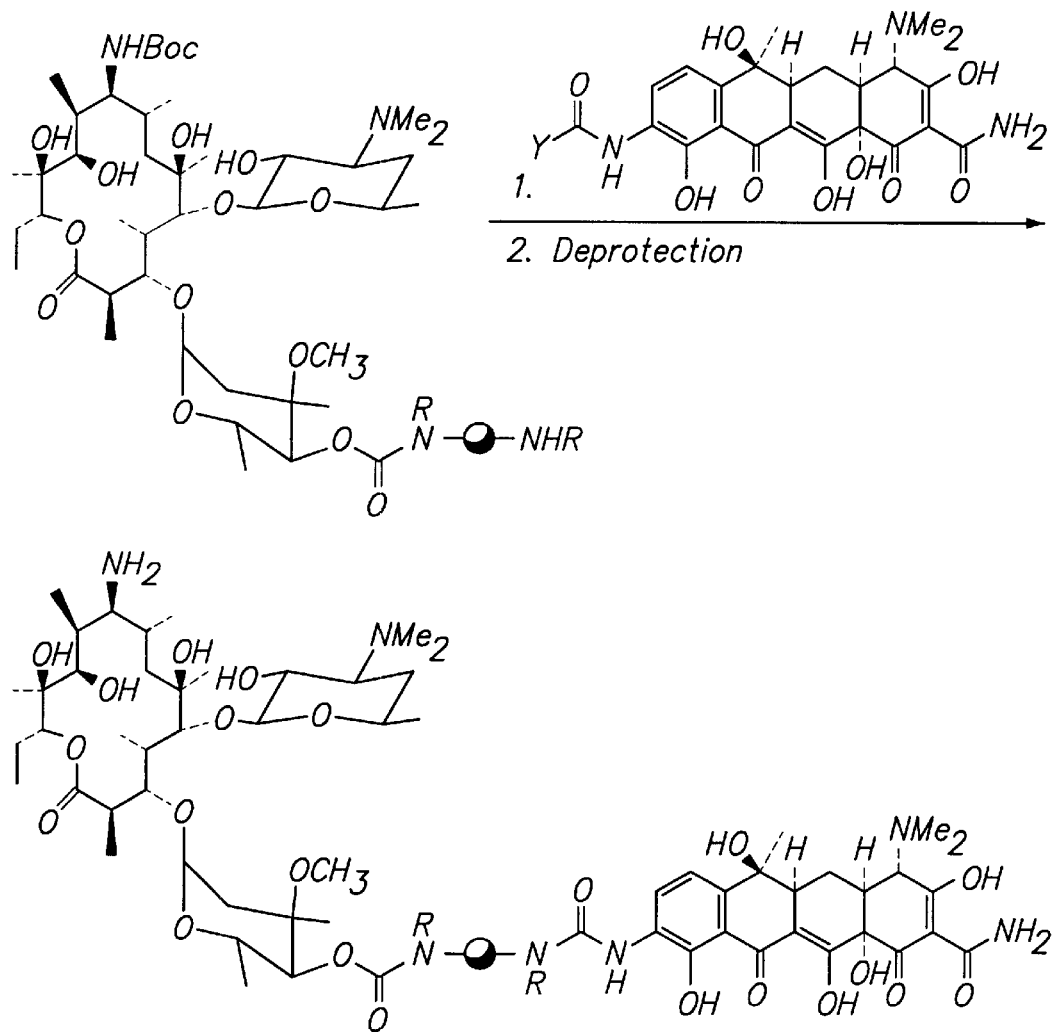

As shown in Scheme II (FIG. 34), an intermediate formed by reacting a ligand containing an imidiazolide or other activated carboxylic acid group with a linker with two amine groups can be reacted with a second ligand with an imidiazolide or other activated carboxylic acid group to form a mixed dimer.

Figure 35:
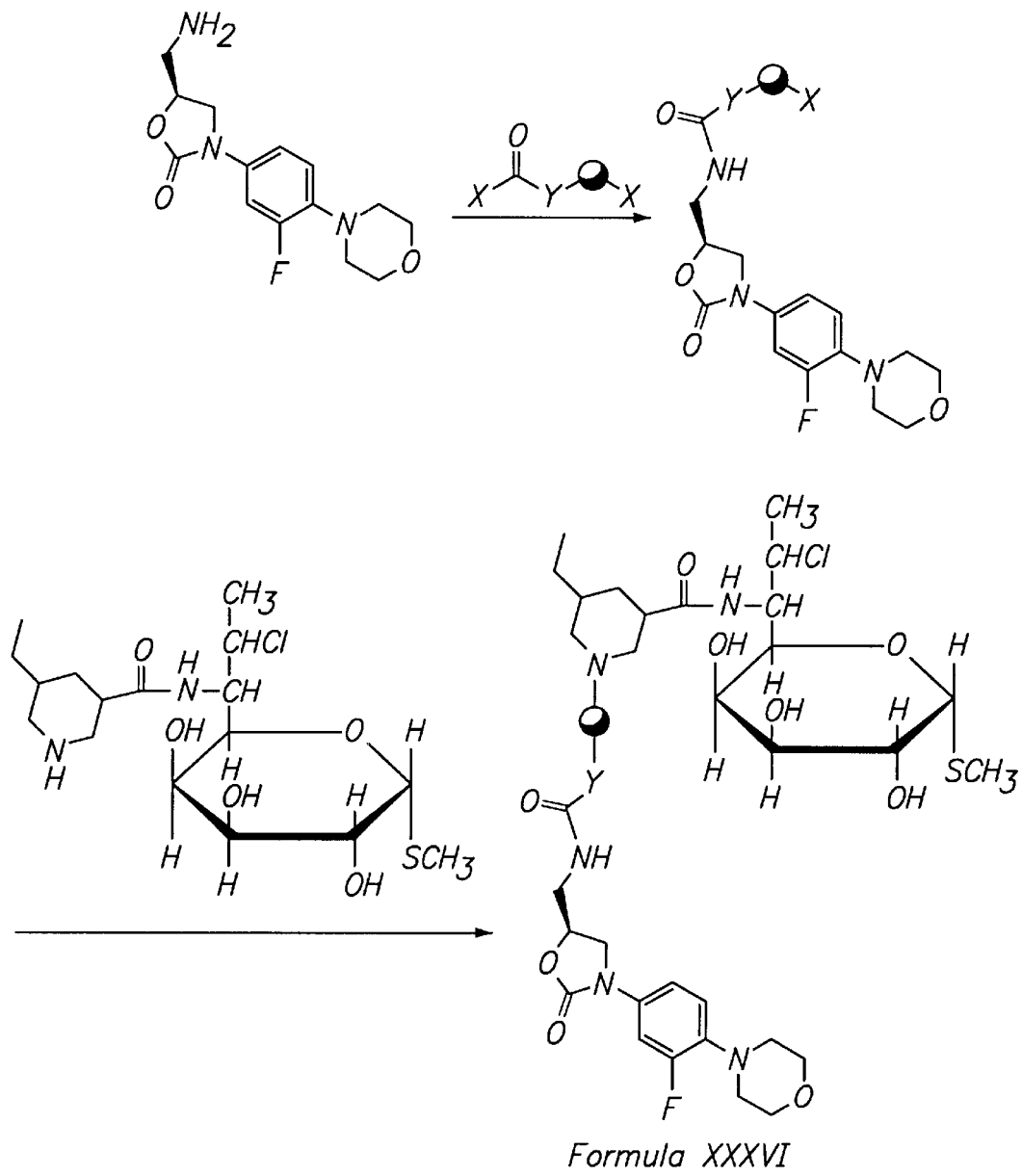

As shown in Scheme JJ (FIG. 35), a ligand with an amine group can be reacted with a linker with a halide and a carboxylic acid group to form an intermediate with a free halide group. This intermediate can be reacted with a second ligand with a free amine group to form a mixed dimer.

Figure 36:
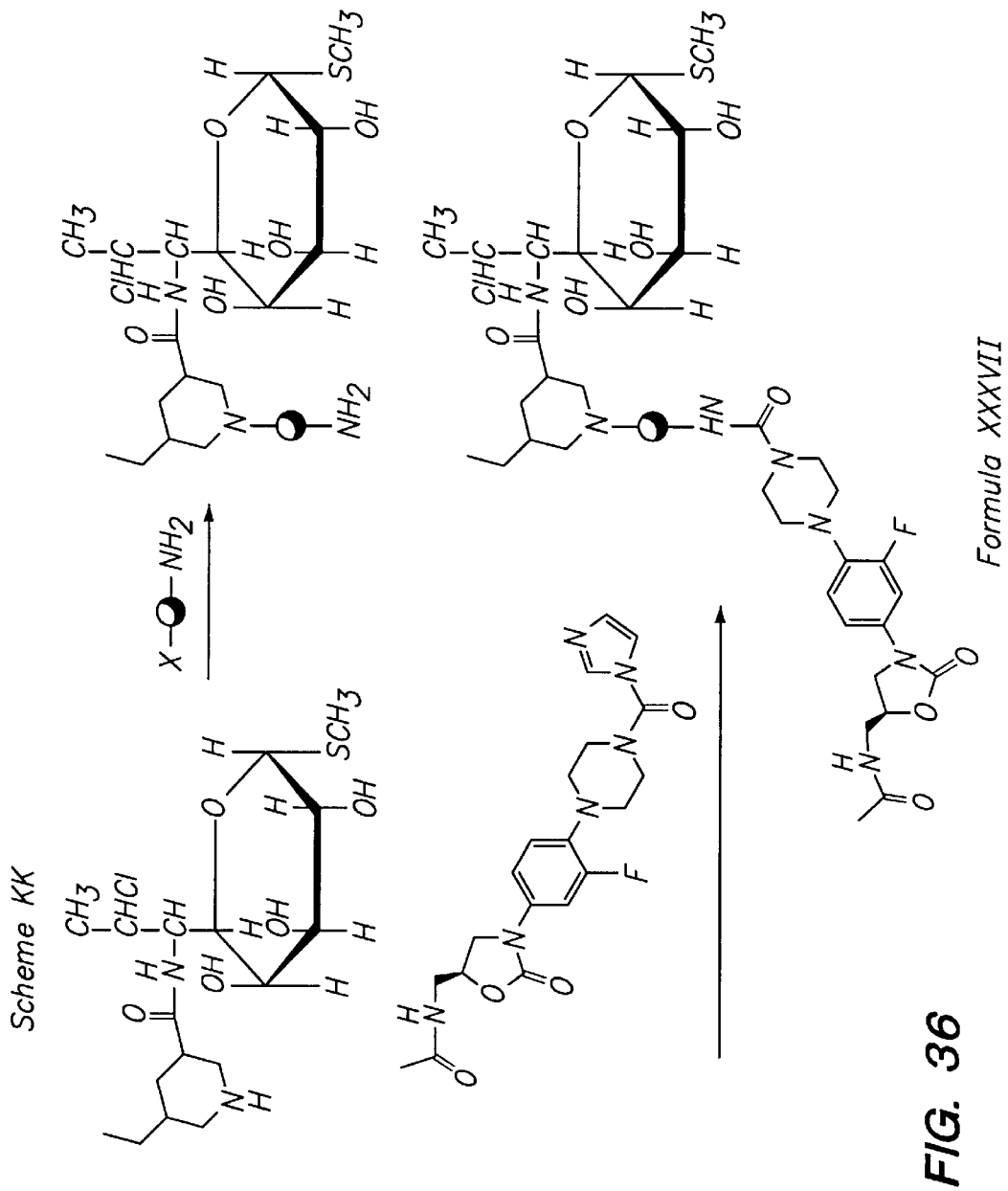

As shown in Scheme KK (FIG. 36), a ligand with an imidazolide or other active carboxylic acid group can be reacted with a linker with a primary amine group and a halide group to form an intermediate with a halide group. The halide group can be reacted with an amine on a second ligand to form a mixed dimer.

Figure 37:
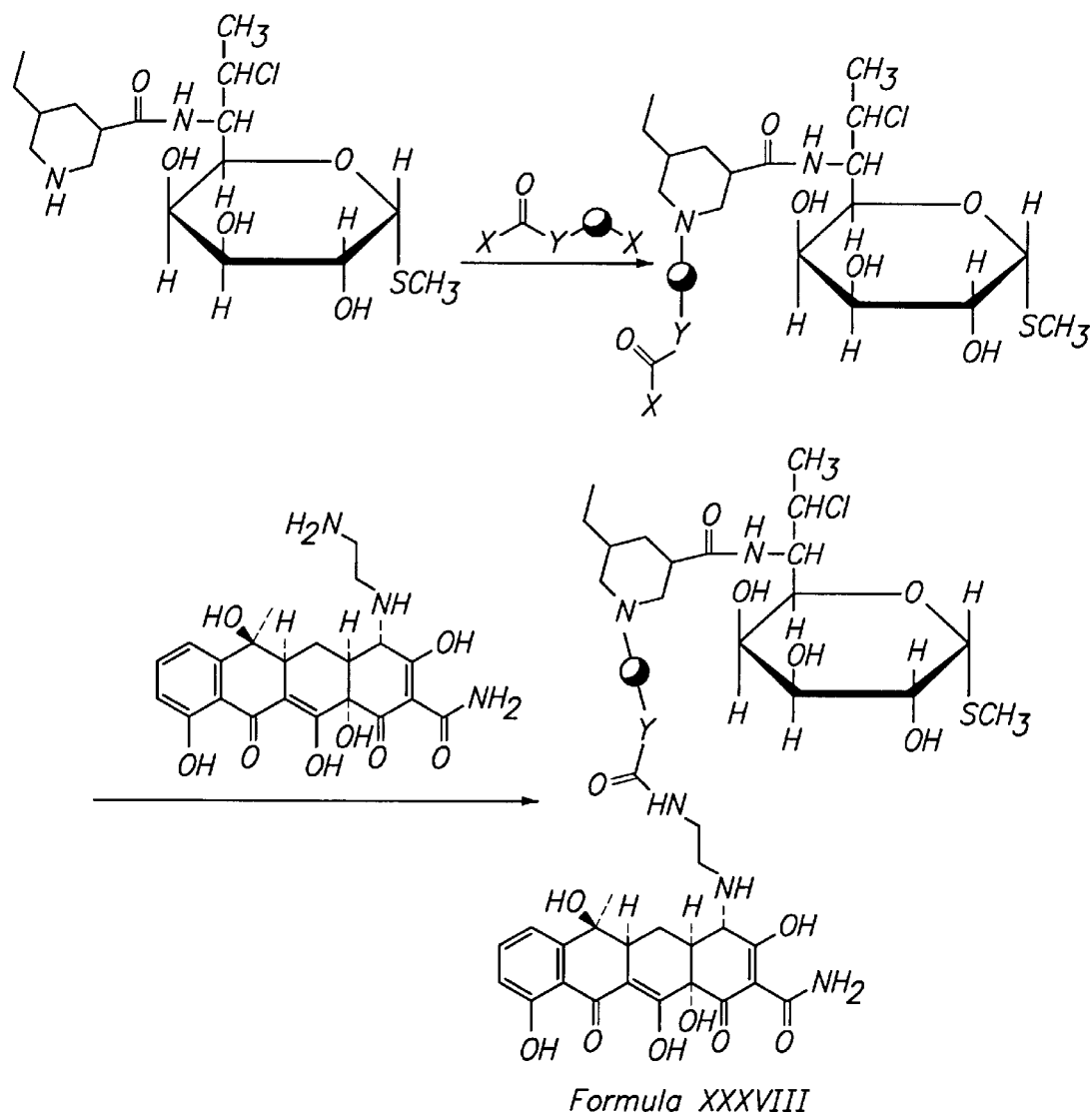

As shown in Scheme LL (FIG. 37), a ligand with a secondary amine group can be reacted with a linker with a halide group and a carboxylic acid group to form an intermediate with a free carboxylic acid group. This intermediate can be reacted with a second ligand with a free amine group to form a mixed dimer.

Figure 38:
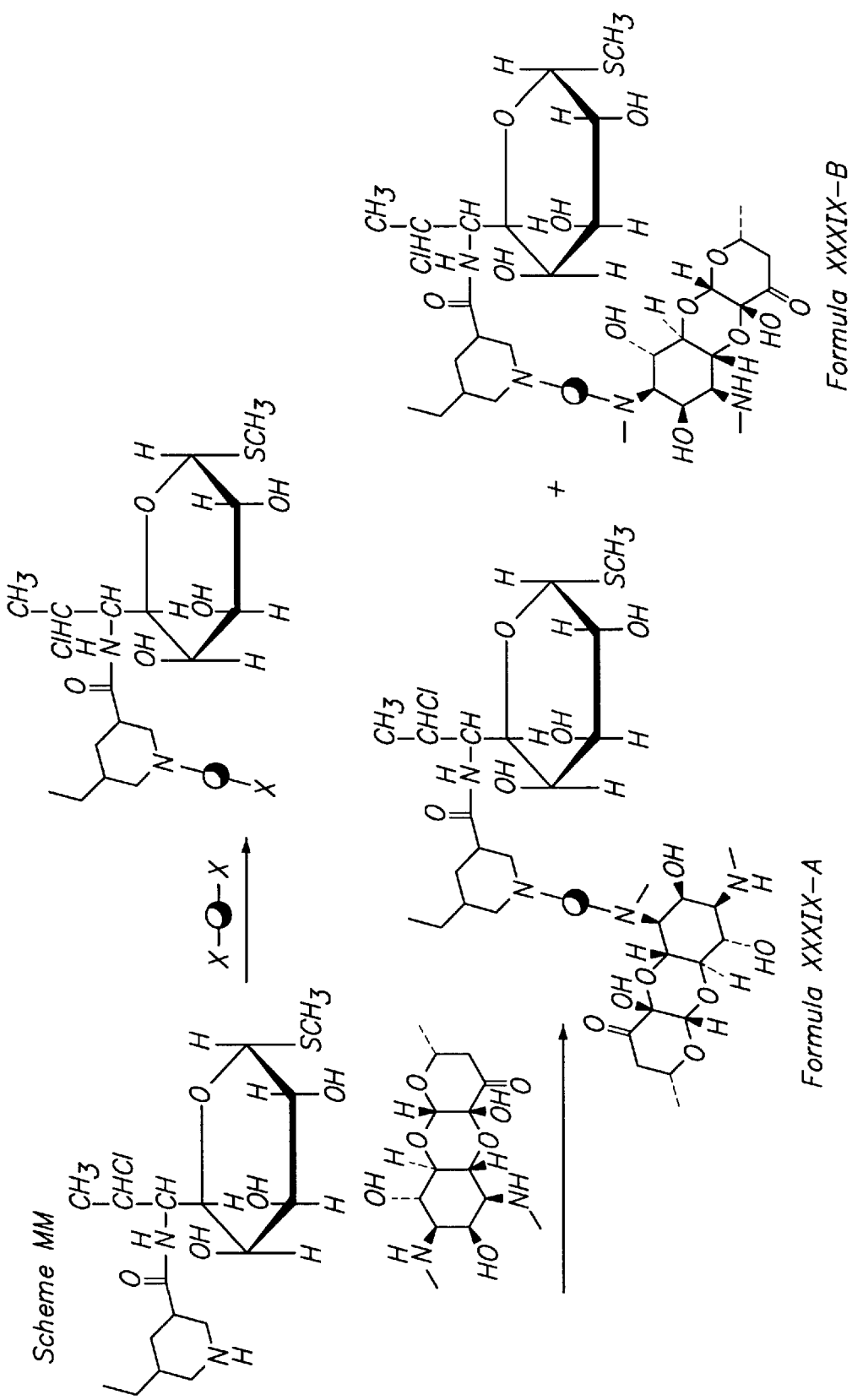
FIG. 38 is a schematic illustration of the preparation of compounds of formulas XXXIX-A and XXXIX-B.

As shown in Scheme MM (FIG. 38), one equivalent of a ligand with a secondary amine group can be reacted with one equivalent of a dihalide linker to form an intermediate which has a halide group. This intermediate can be reacted with a second ligand with two free amino groups to form a mixture of mixed dimers.

Figure 39:
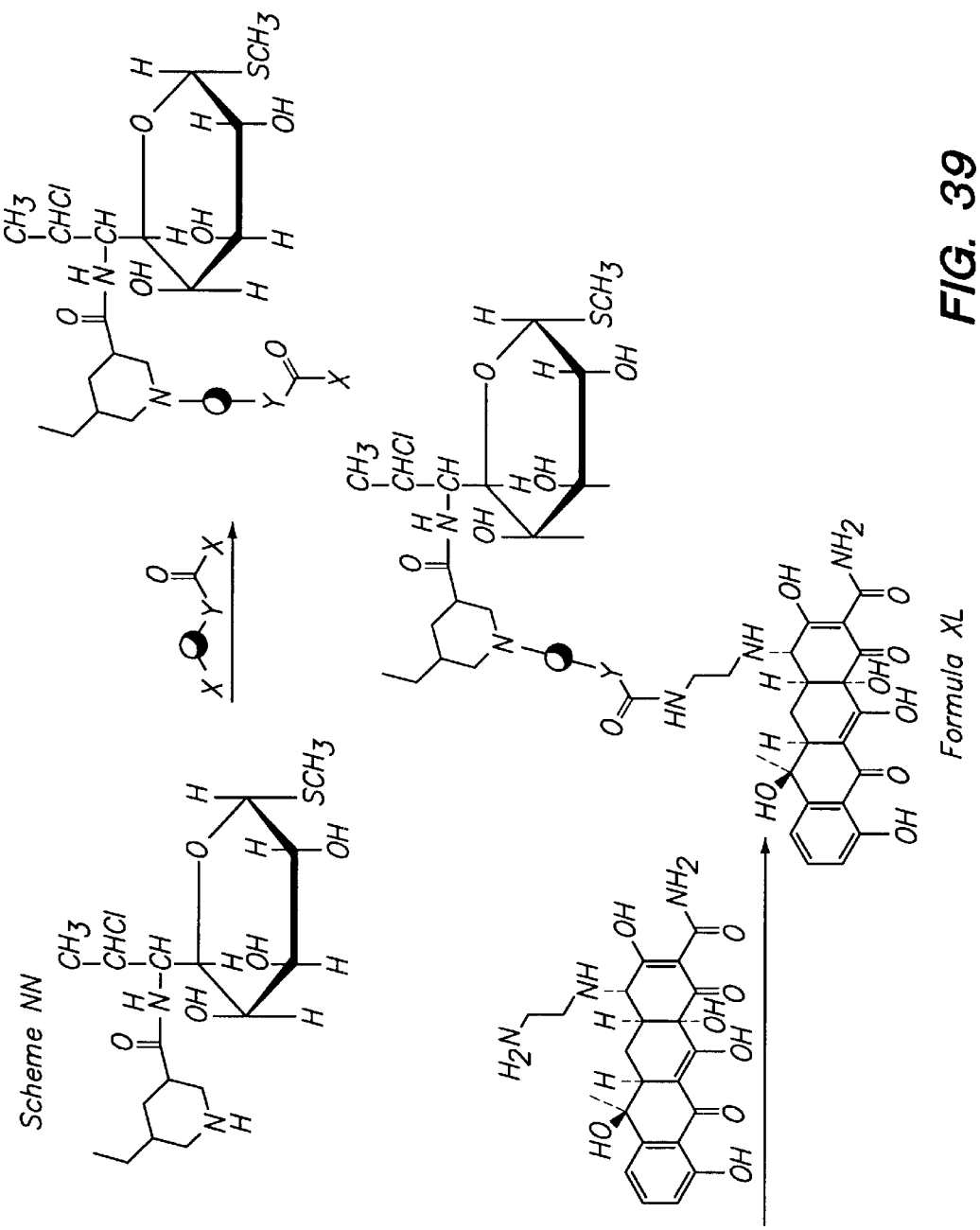
FIGS. 39–49 are schematic illustrations of the preparation of compounds of formula XL-L.

As shown in Scheme NN (FIG. 39), one equivalent of a ligand with a secondary amine group can be reacted with a linker with a halide group and a carboxylic acid group to form an intermediate which has a free carboxylic acid group. This intermediate can be reacted with a second ligand with an amine group to form a mixed dimer.

Figure 40:
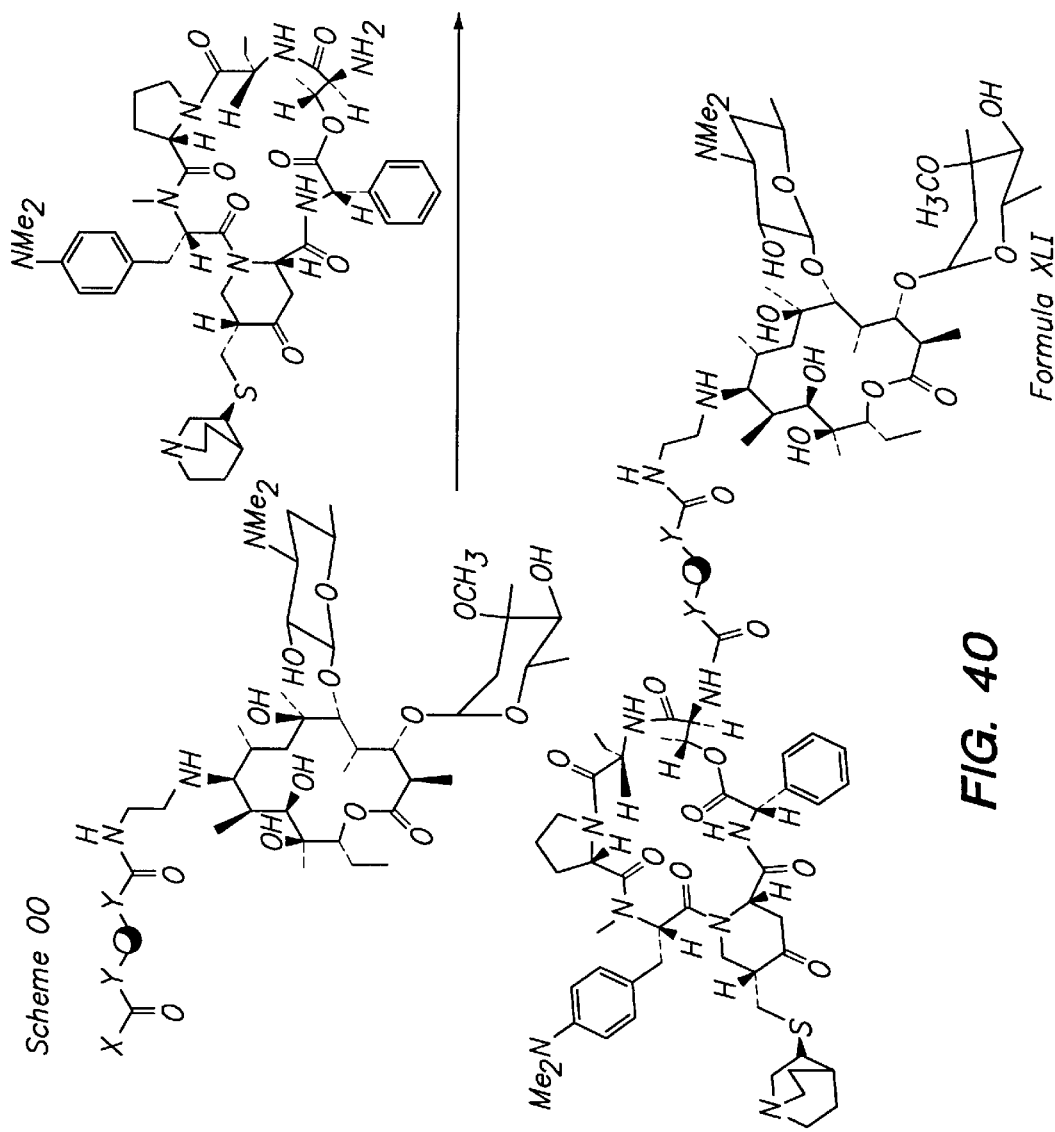

As shown in Scheme OO (FIG. 40), an intermediate formed from a ligand containing an amine group and a linker with two carboxylic acid groups can be reacted with a second ligand with an amine group to form a mixed dimer.

Figure 41:
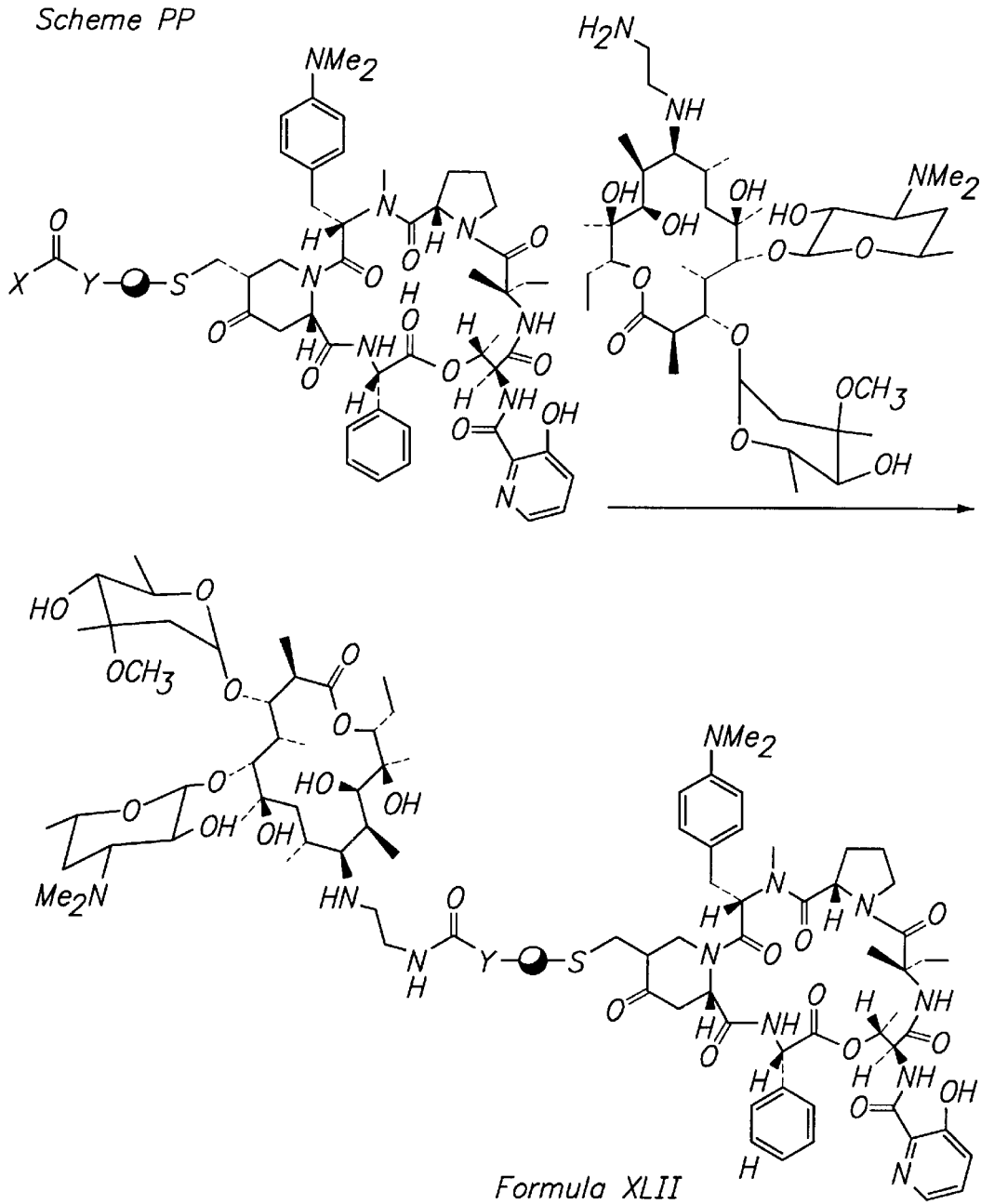

As shown in Scheme PP (FIG. 41), an intermediate formed by reacting a ligand containing an unsaturated ketone group with a linker with a thiol and a carboxylic acid group can be reacted with one equivalent of a second ligand with an amine group to form a mixed dimer.

Figure 42:
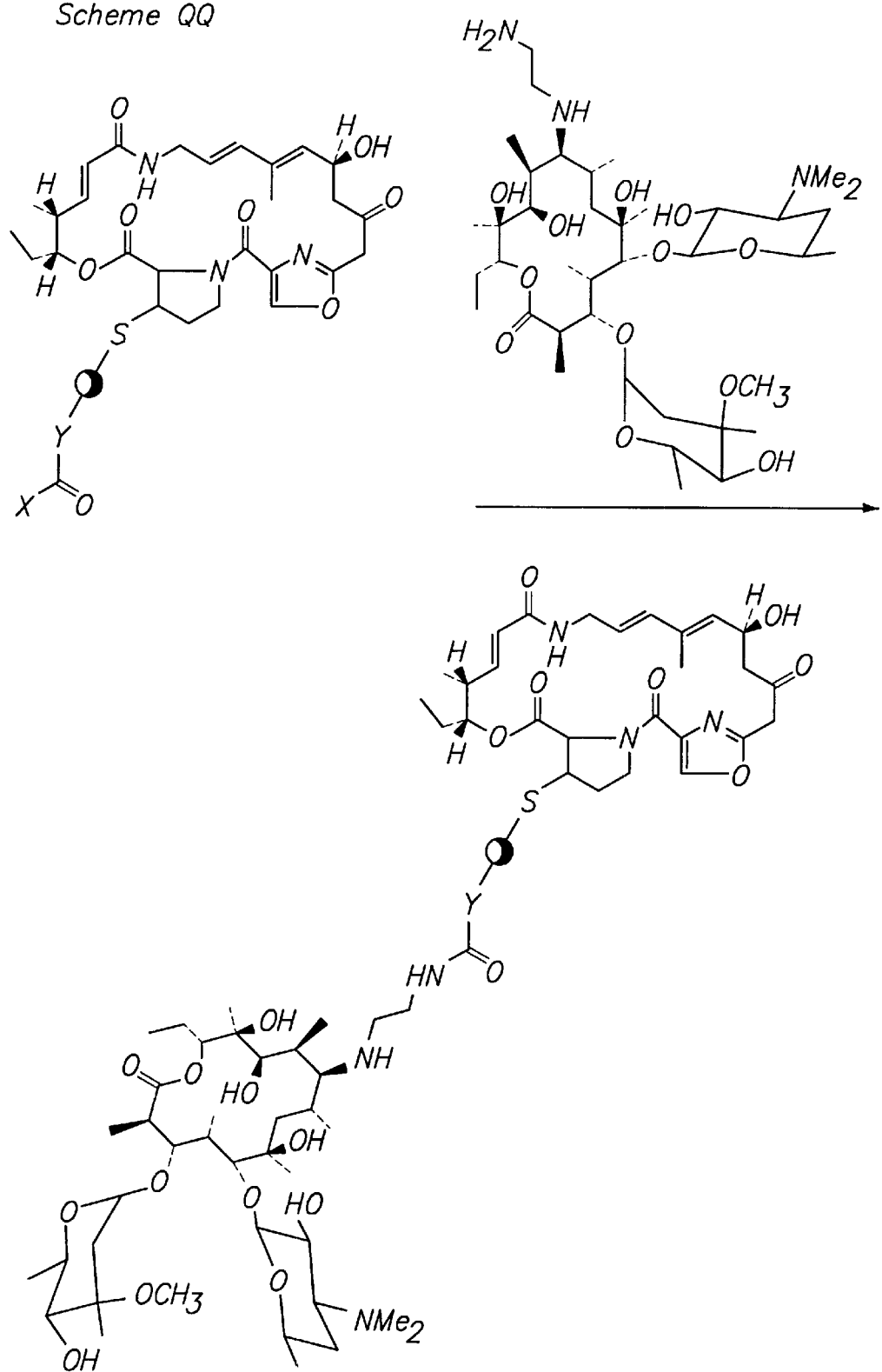

As shown in Scheme QQ (FIG. 42), an intermediate formed by reacting a ligand containing an unsaturated ester group with a linker with a thiol and a carboxylic acid group can be reacted with one equivalent of a second ligand with an amine group to form a mixed dimer.

Figure 43:
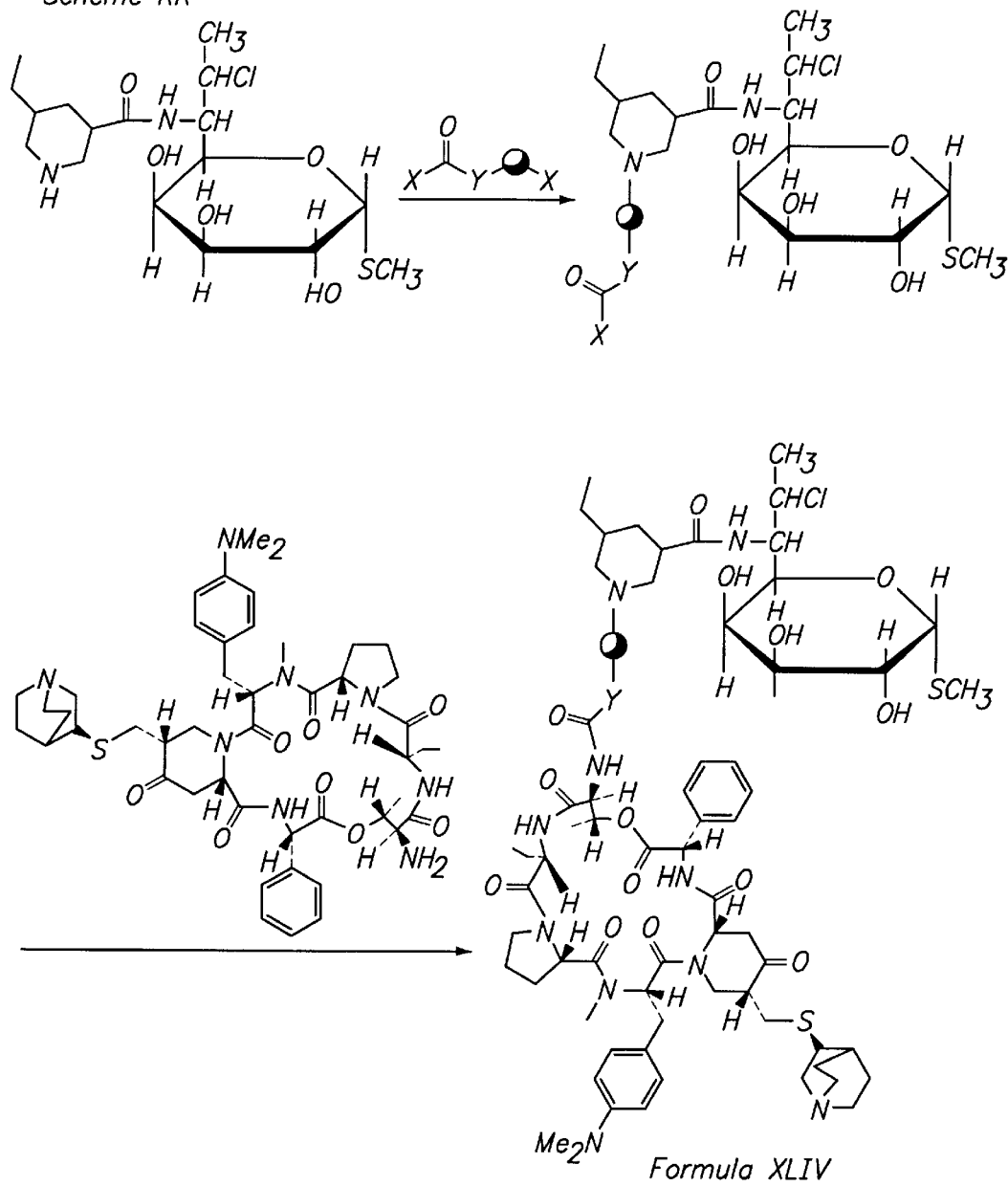

As shown in Scheme RR (FIG. 43), one equivalent of an intermediate formed by reacting a ligand with a secondary amine group with a linker with a halide group and a carboxylic acid group can be reacted with a second ligand with an amine group to form a mixed dimer.

Figure 44:
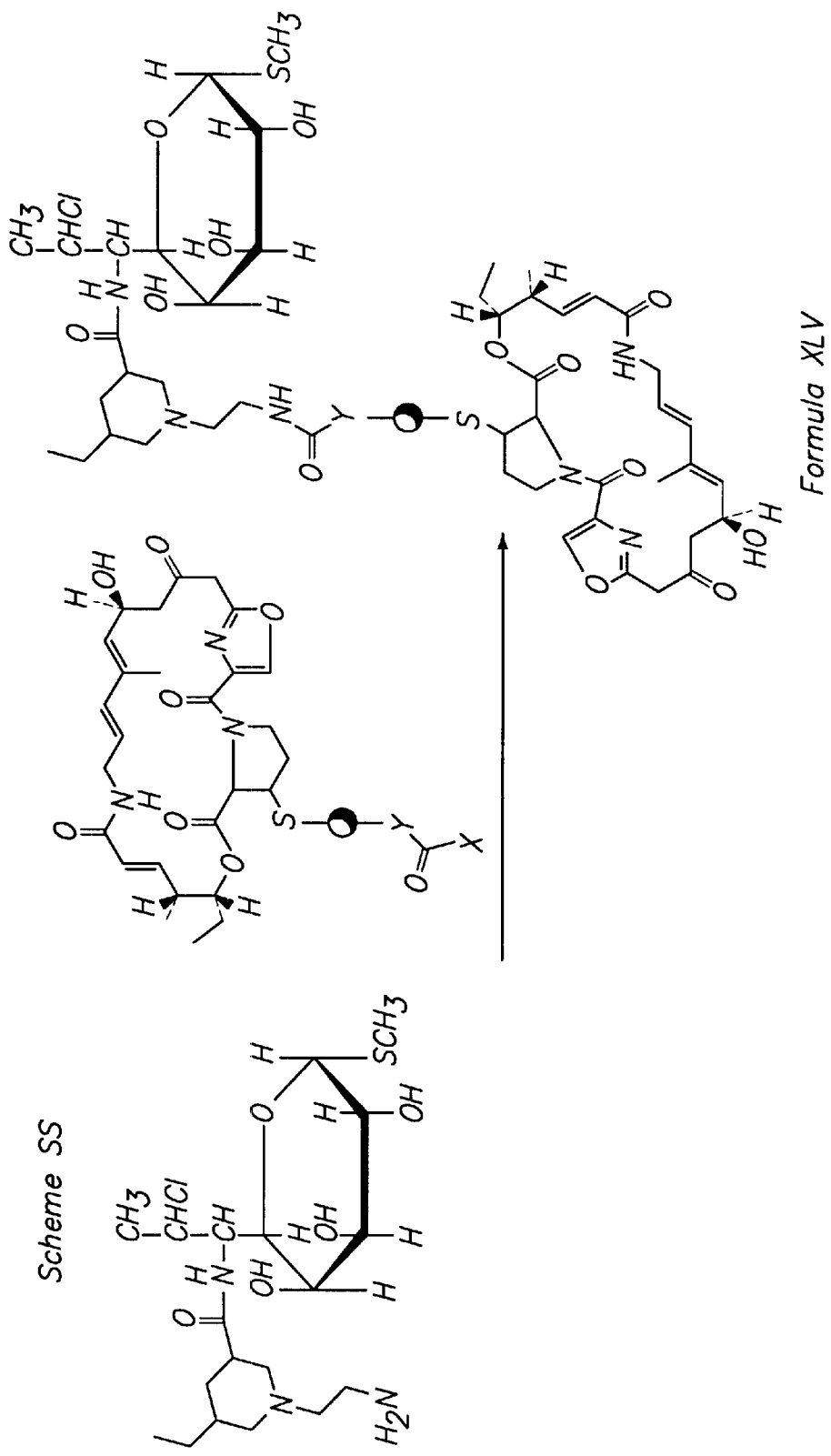

As shown in Scheme SS (FIG. 44), a ligand with a primary amine group can be reacted with an intermediate formed by reacting a linker containing a thiol group and a carboxylic acid group with a ligand with an unsaturated ester group to form a mixed dimer.

Figure 45:
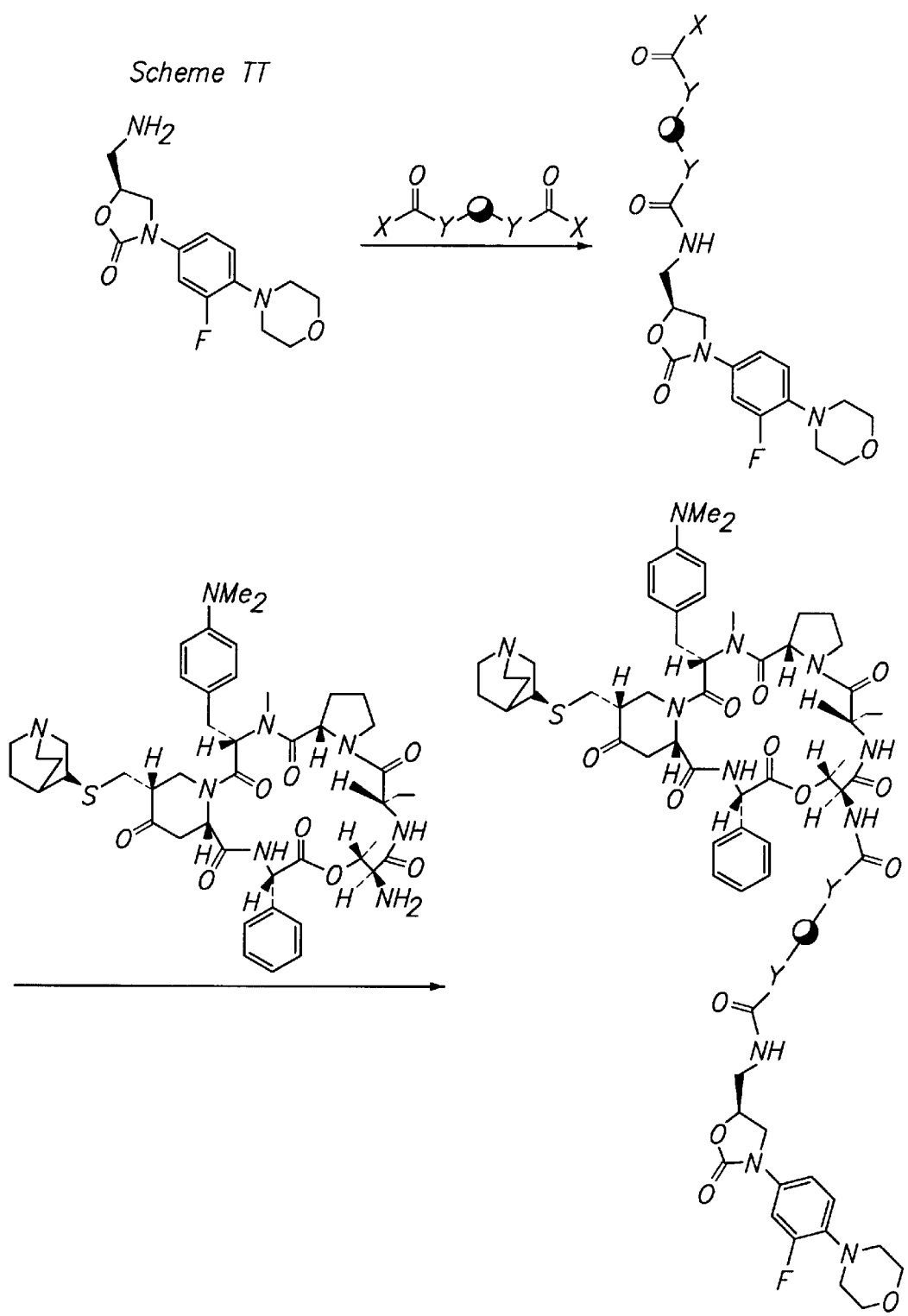

As shown in Scheme TT (FIG. 45), one equivalent of a ligand with an amine group can be reacted with one equivalent of a linker with two carboxylic acid groups to form an intermediate with a free carboxylic acid group, which can be reacted with a second ligand with an amine group to form a mixed dimer.

Figure 46:
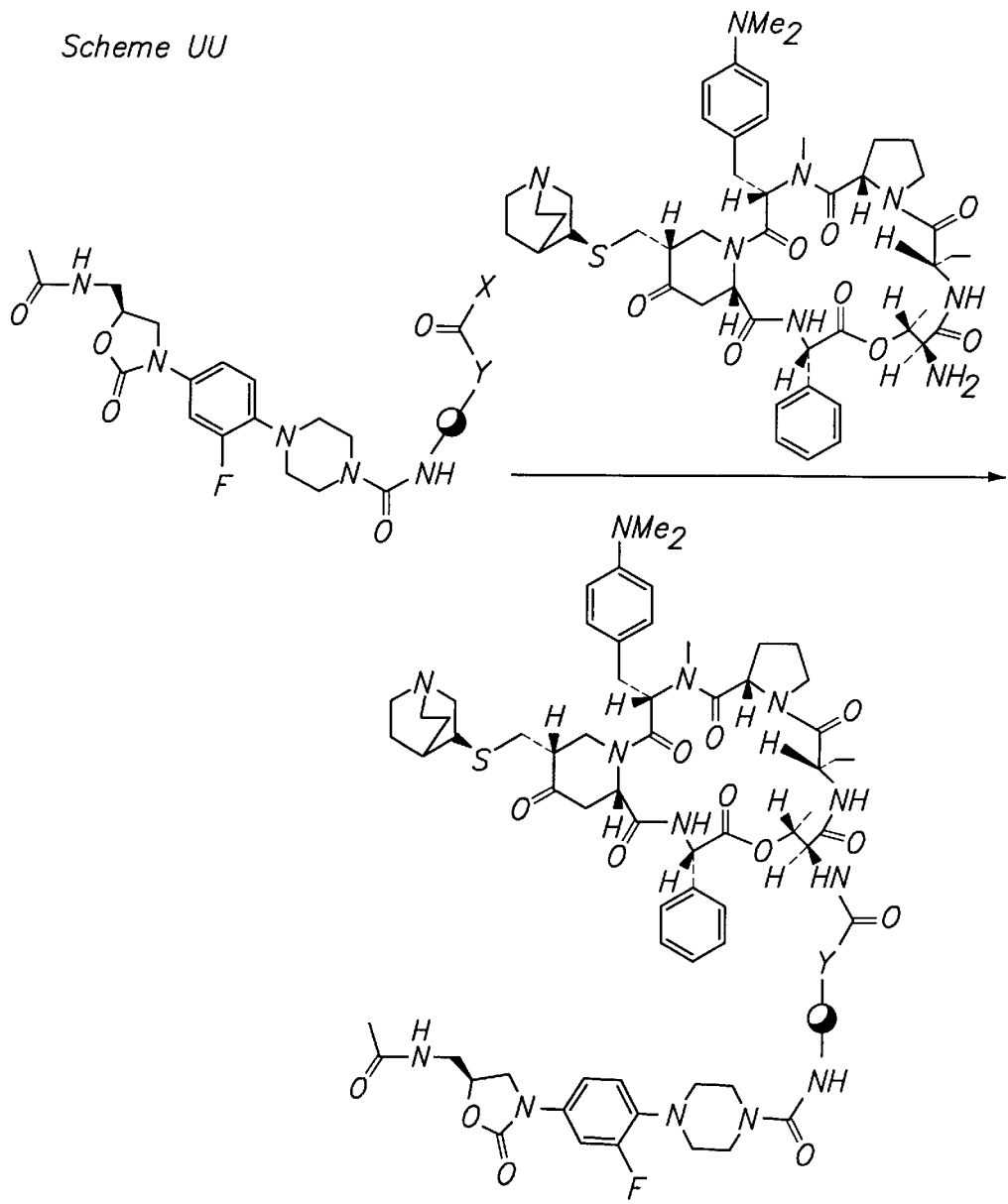

As shown in Scheme UU (FIG. 46), an intermediate formed by reacting a ligand containing an imidazolide group with a linker molecule containing an amine group and a carboxylic acid group can be reacted with a second ligand with a free amine group to form a mixed dimer.

Figure 47:
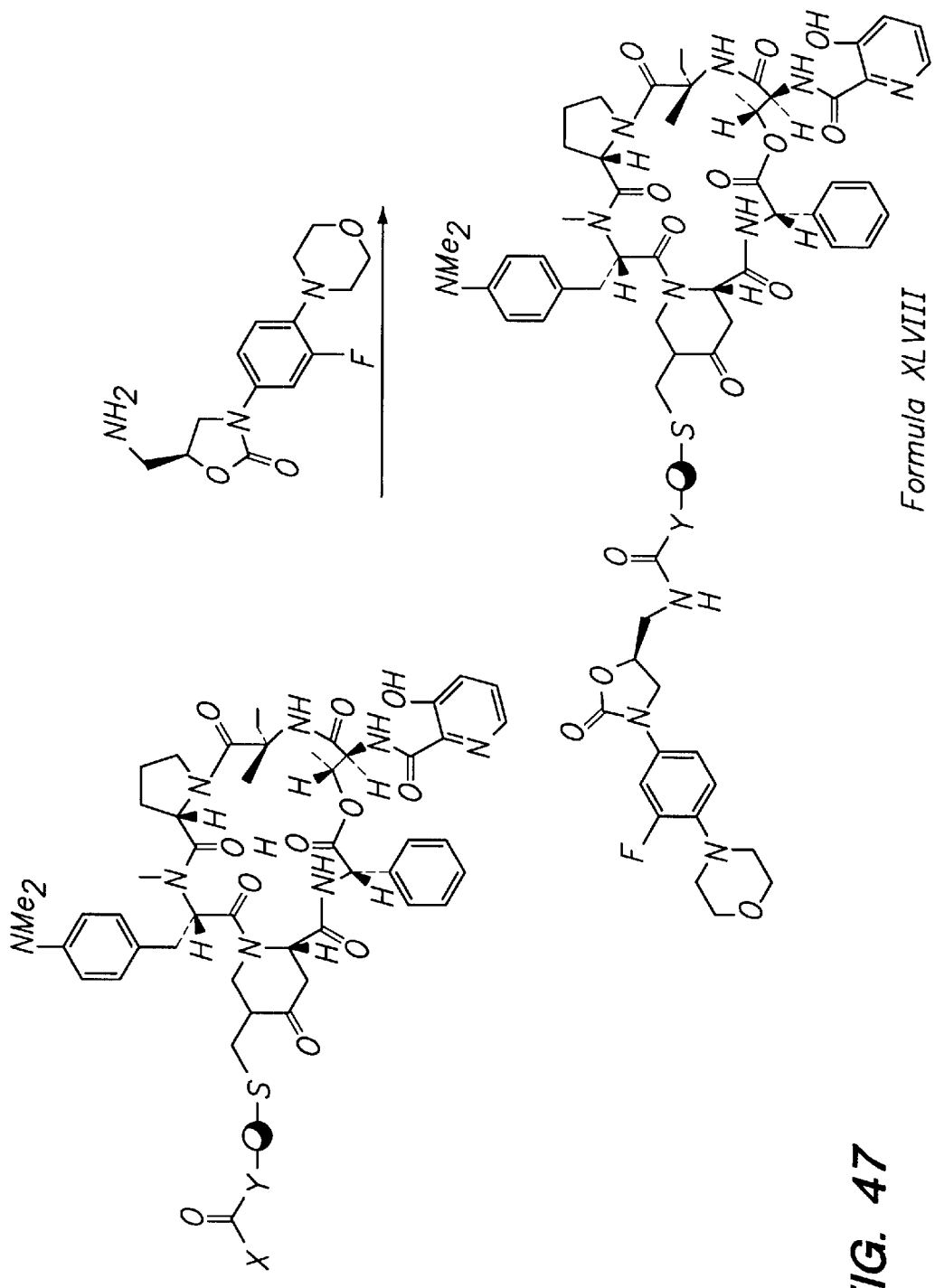
Figure 48:
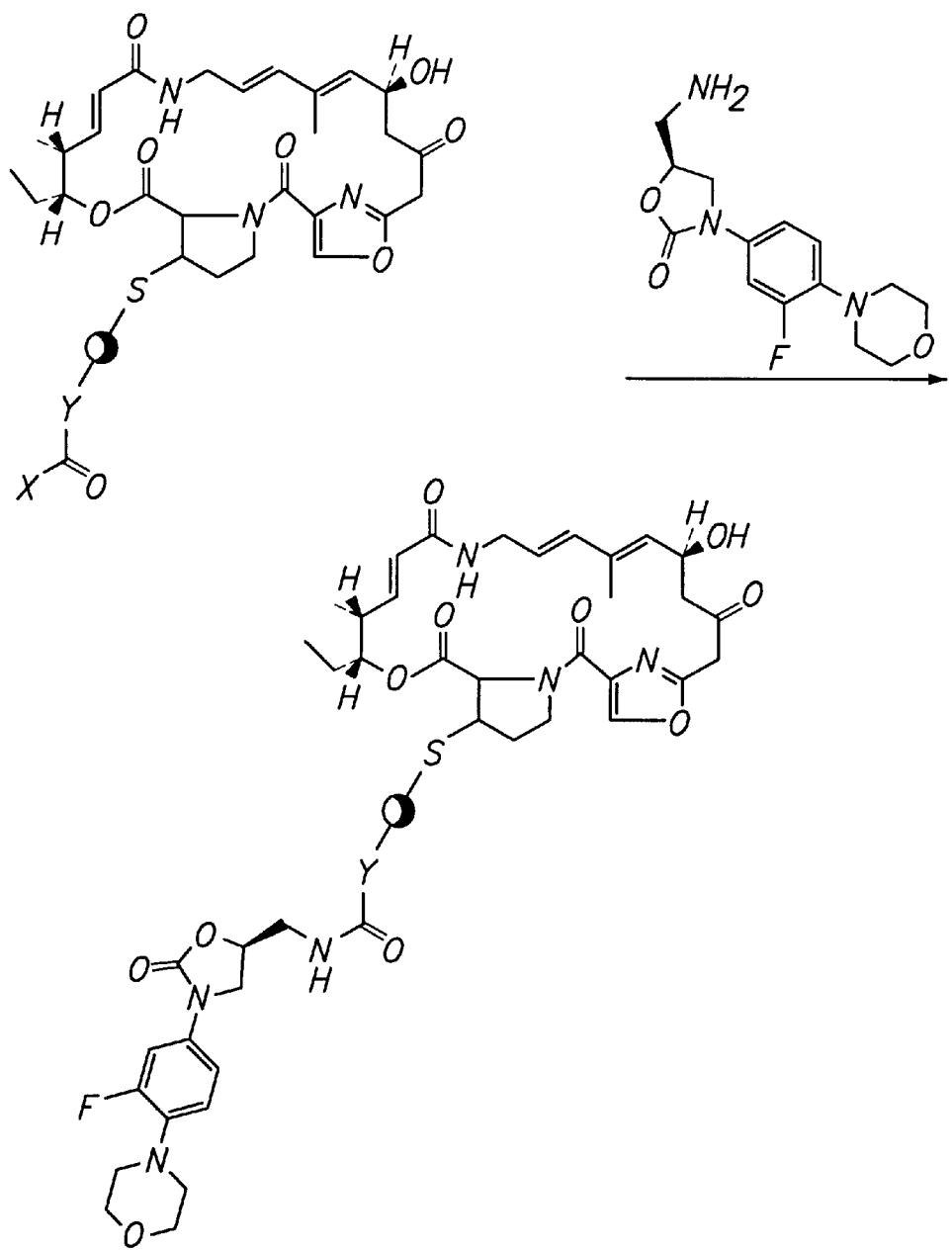

As shown in Scheme VV (FIG. 47) and Scheme WW (FIG. 48), an intermediate formed by reacting a ligand containing an unsaturated ester group with a linker containing a thiol and a carboxylic acid group can be reacted with a second ligand with an amine group to form a mixed dimer.

Figure 49:
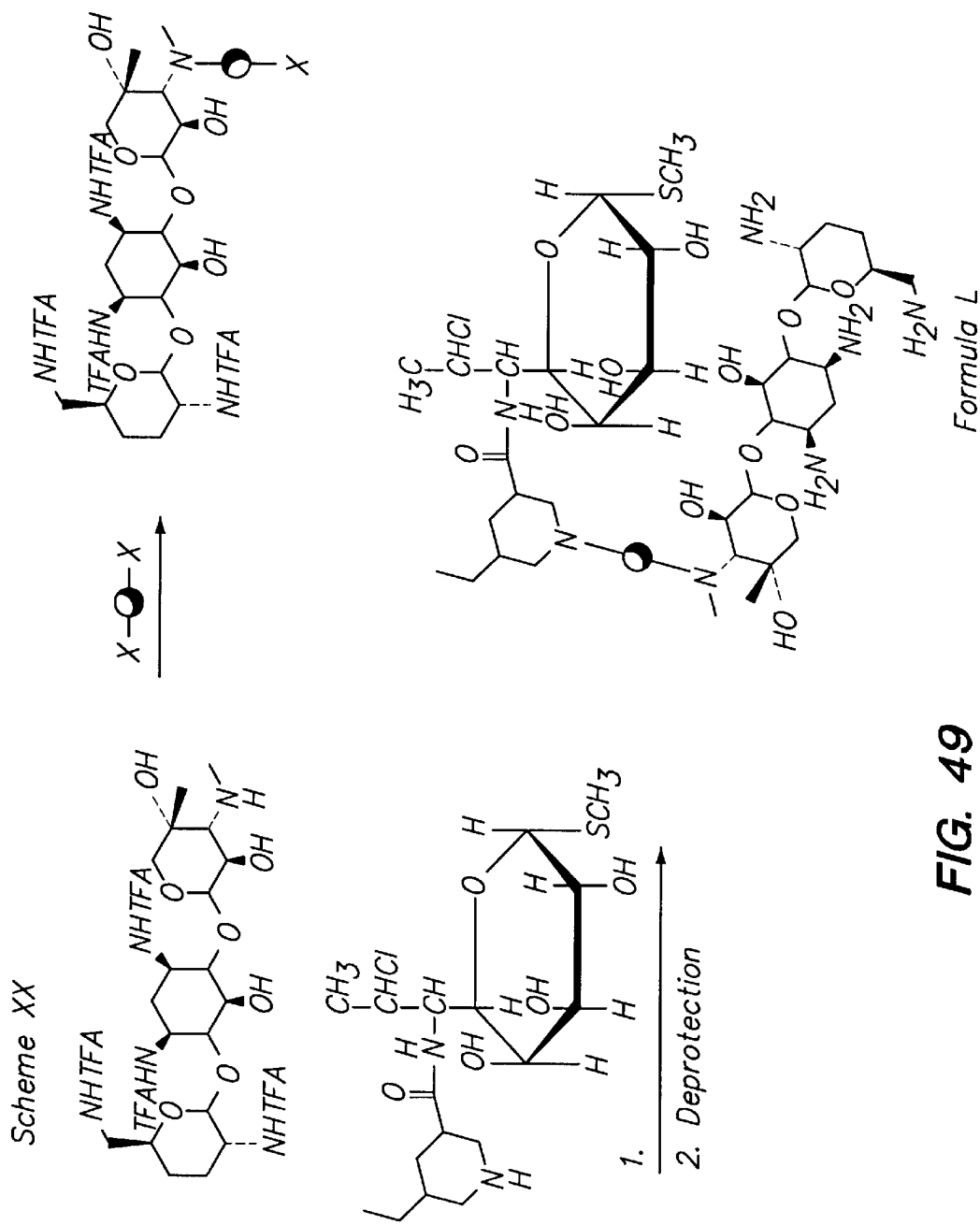

As shown in Scheme XX (FIG. 49), an intermediate formed by reacting a ligand containing an unprotected amine group (and, as shown in the figure, four protected amine groups) with a linker containing two halide groups can be reacted with a ligand containing an amine group to form a mixed dimer. The protected amine groups can then be deprotected.

Figure 50:
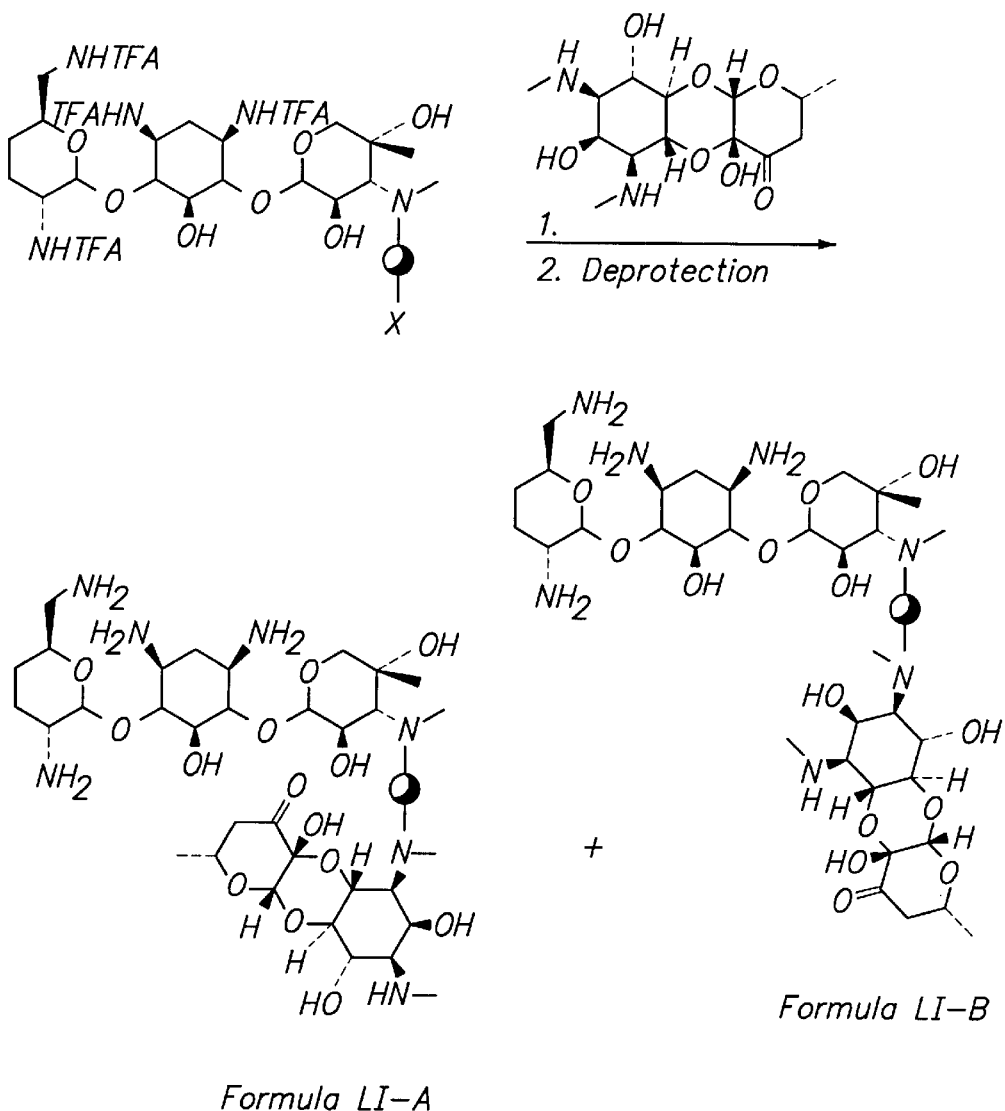
FIG. 50 is a schematic illustration of the preparation of compounds of formulas LI-A and LI-B.

As shown in Scheme YY (FIG. 50), a first ligand containing an unprotected amine group can be reacted with a dihalide linker to form an intermediate with a free halide group. This intermediate can be reacted with a ligand with two unprotected amine groups to form a mixture of mixed dimers. The protected amine groups can then be deprotected.

As shown in Scheme ZZ (FIG. 51), one equivalent of a ligand with an amine group can be reacted with one equivalent of a dihalide to form an intermediate with a free halide group. This intermediate can be reacted with a second ligand with two free amine groups to form a mixture of mixed dimers.

Figure 52:
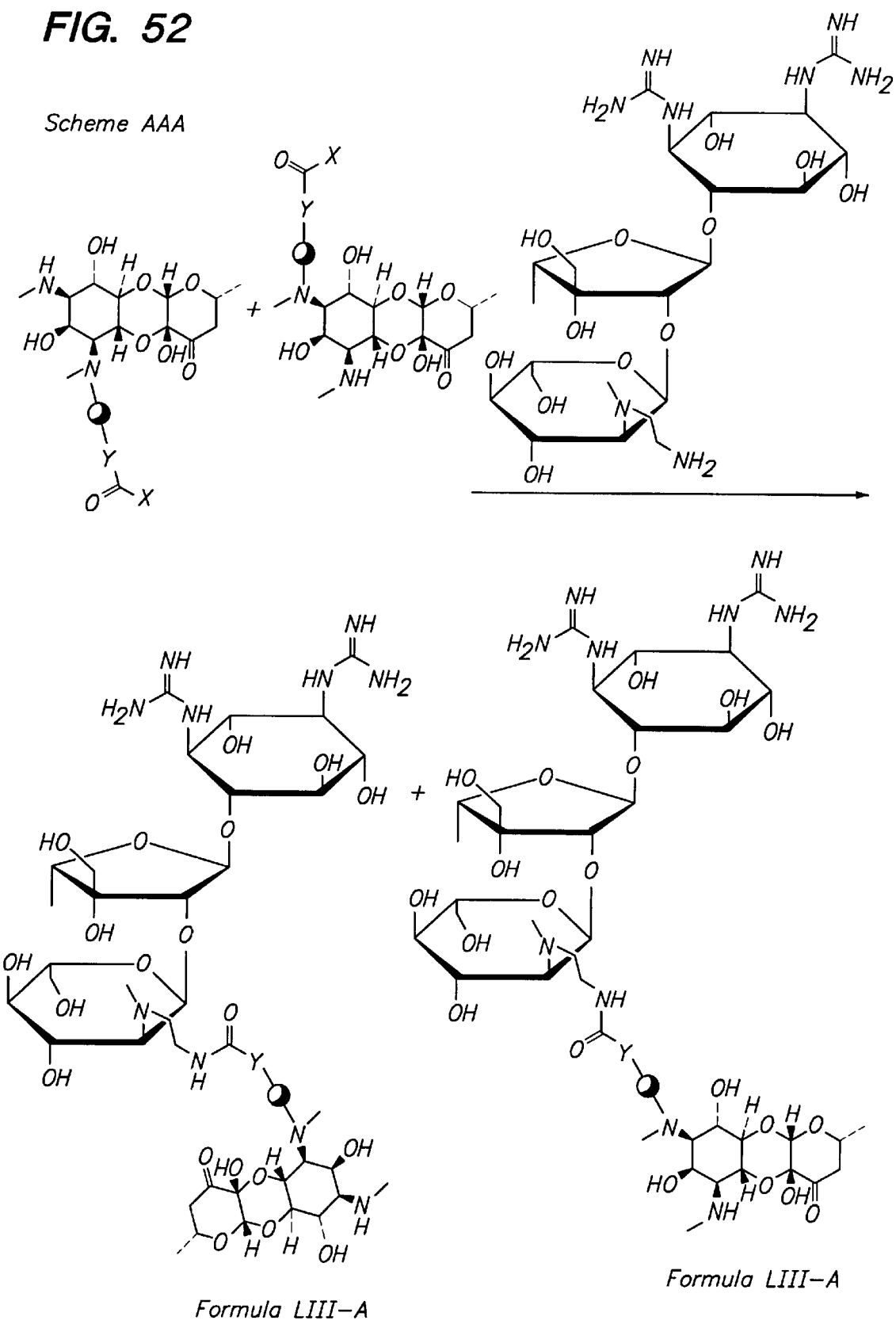
FIG. 52 is a schematic illustration of the preparation of compounds of formula LIII-A and LIII-B.

As shown in Scheme AAA (FIG. 52), two intermediates formed by reacting one equivalent of a ligand with two secondary amine groups with one equivalent of a linker with a halide and a carboxylic acid group are reacted with a second ligand containing a primary amine group to form a mixture of mixed dimers.

Figure 53:
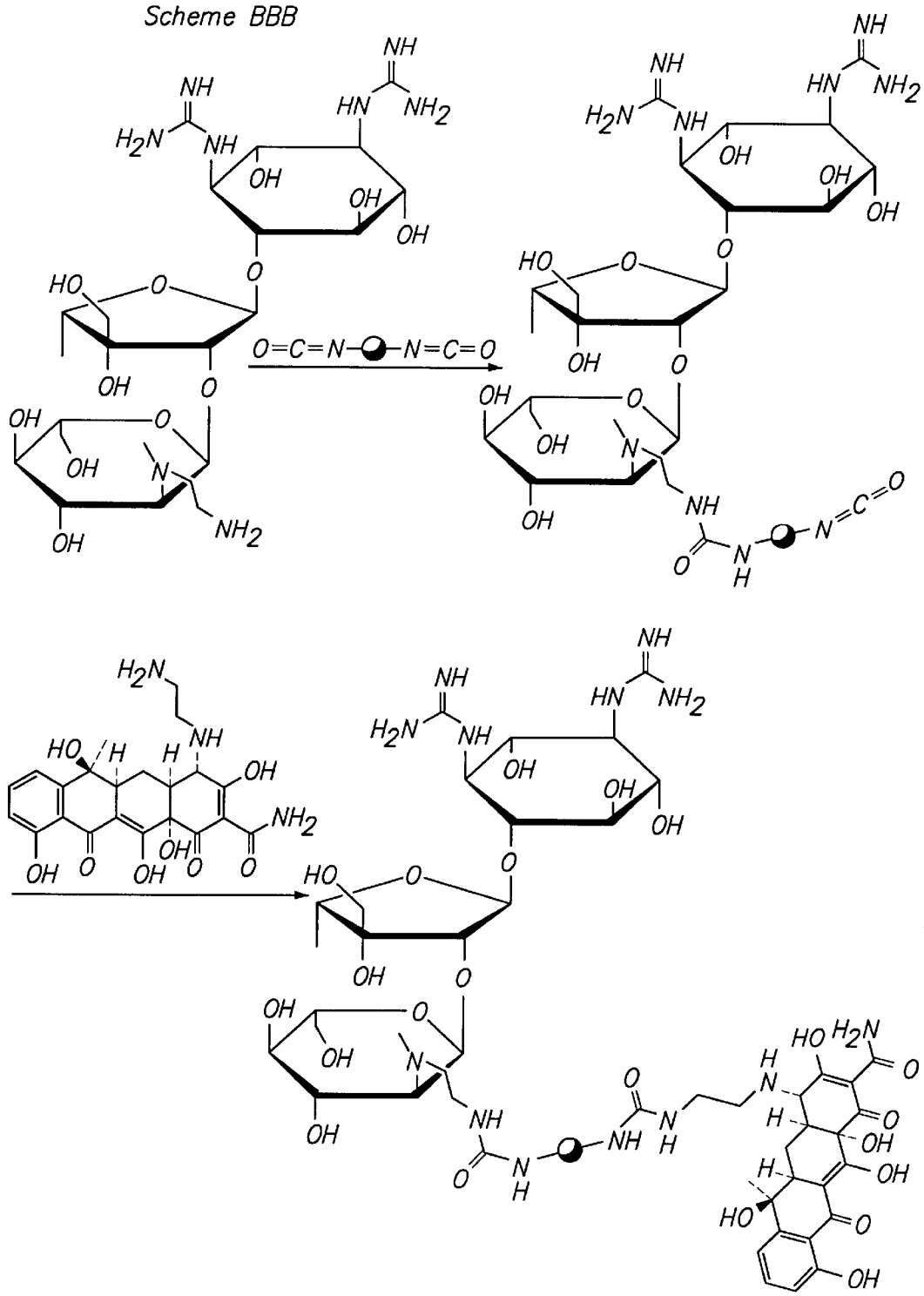
FIGS. 53–55 are schematic illustrations of the preparation of compounds of formula LIV-LVI.

As shown in Scheme BBB (FIG. 53), one equivalent of a first ligand containing an amine group can be reacted with one equivalent of a linker molecule with two isocyanate groups to form an intermediate with a urea linkage and a free isocyanate group. This intermediate can be reacted with a second ligand with an amine group to form a mixed dimer with two urea linkages.

Figure 54:
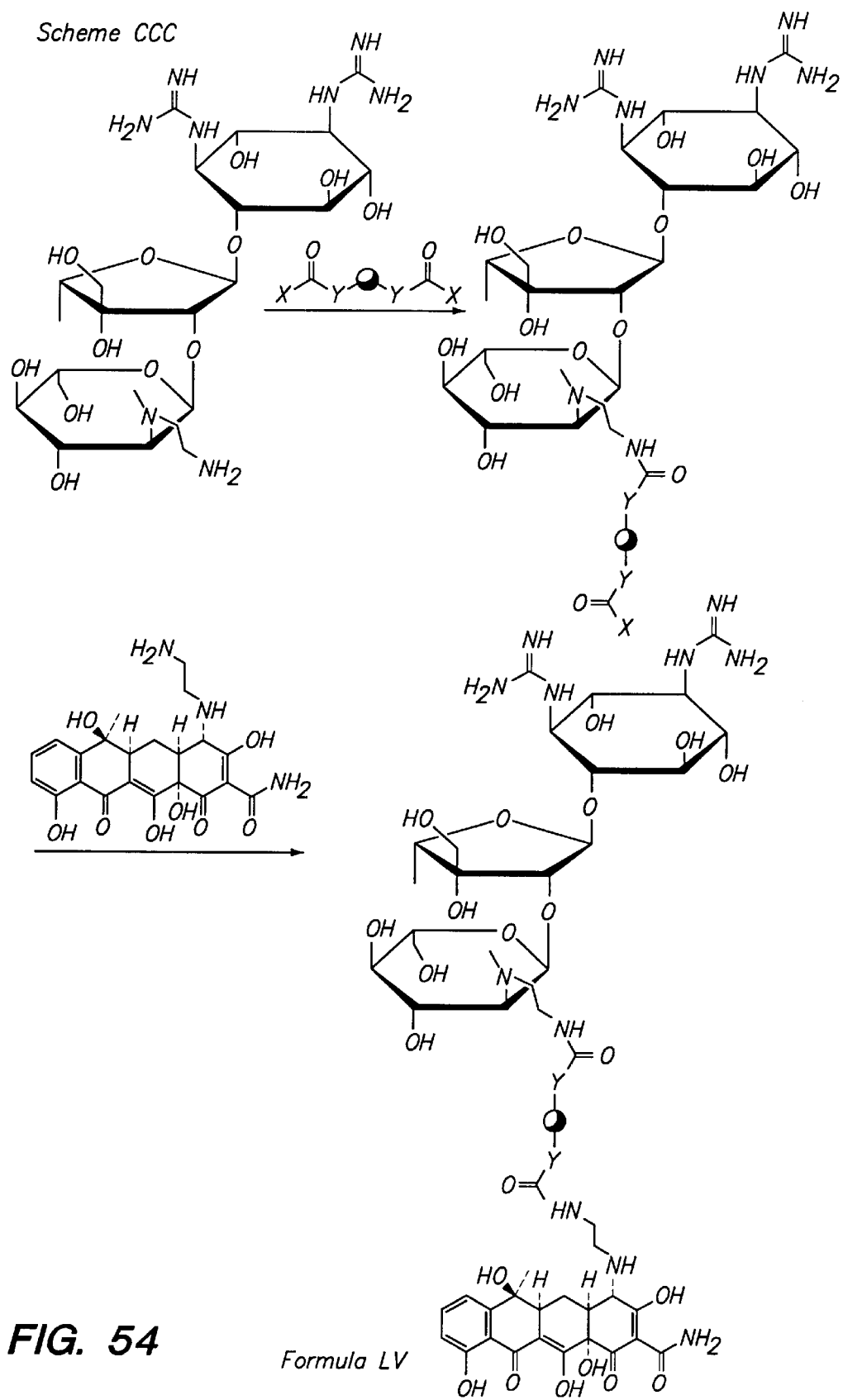

As shown in Scheme CCC (FIG. 54), a ligand with an amine group can be coupled with a linker with two carboxylic acid groups to form an intermediate with a free carboxylic acid group. This intermediate can be reacted with a second ligand with an amine group to form a mixed dimer.

Figure 55:
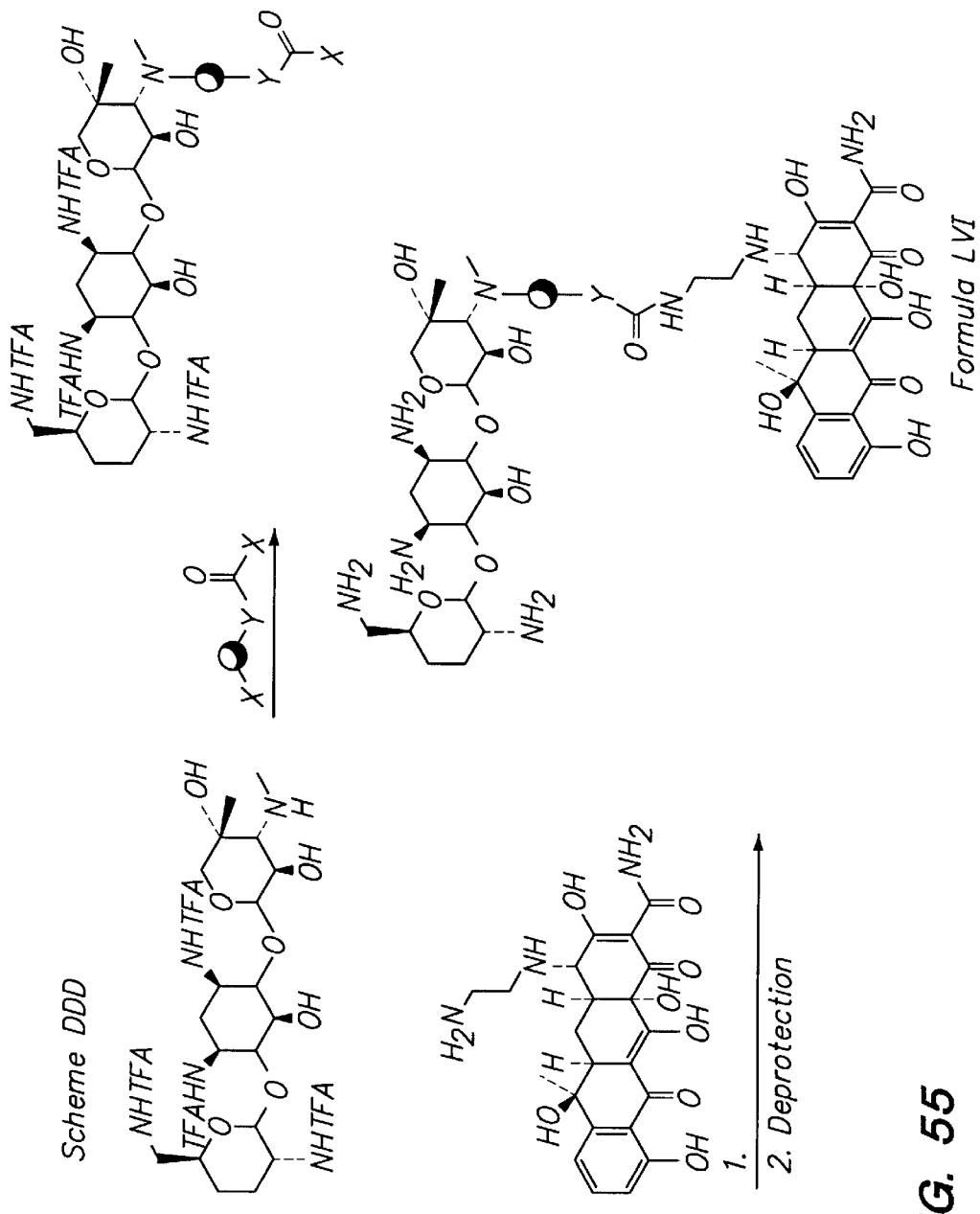

As shown in Scheme DDD (FIG. 55), a ligand with an amine group can be reacted with a linker containing a halide group and a carboxylic acid group to form an intermediate with a free carboxylic acid group. This intermediate can be reacted with a second ligand with an amine group to form a mixed dimer.

In each of the above reaction schemes, a particular antibiotic or combination thereof is listed. However, it is intended that these schemes are applicable to other ligands with similar reactive groups.

Other methods are well known to those of skill in the art for coupling molecules such as the ligands described herein with the linker molecules described herein. For example, two equivalents of ligand precursor with a halide, tosylate, or other leaving group, can be readily coupled to a linker precursor containing two nucleophilic groups, for example, phenoxide groups, to form a dimer. The leaving group employed in this reaction may be any conventional leaving group including, by way of example, a halogen such as chloro, bromo or iodo, or a sulfonate group such as tosyl, mesyl and the like. When the nucleophilic group is a phenol, any base which effectively deprotonates the phenolic hydroxyl group may be used, including, by way of illustration, sodium carbonate, potassium carbonate, cesium carbonate, sodium hydride, sodium hydroxide, potassium hydroxide, sodium ethoxide, triethylamine, diisopropylethylamine and the like. Nucleophilic substitution reactions are typically conducted in an inert diluent, such as tetrahydrofiran, N,N-dimethylformamide, N,N-dimethylacetamide, acetone, 2-butanone, 1-methyl-2-pyrrolidinone and the like. After the reaction is complete, the dimer is typically isolated using conventional procedures, such as extraction, filtration, chromatography and the like.

By way of further illustration, dimers with a hydrophilic linker can be formed using a ligand precursor containing nucleophilic groups and a polyoxyethylene containing leaving groups, for example, poly(oxyethylene)dibromide (where the number of oxyethylene units is typically an integer from 1 to about 20). In this reaction, two molar equivalents of the ligand precursor are reacted with one molar equivalent of the poly(oxyethylene) dibromide in the presence of excess potassium carbonate to afford a dimer. This reaction is typically conducted in N,N-dimethylformamide at a temperature ranging from about 25° C. to about 100° C. for about 6 to about 48 hours.

Alternatively, the linker connecting the ligands may be prepared in several steps. Specifically, a ligand precursor can first be coupled to an "adapter", i.e., a bifunctional group having a leaving group at one end and another functional group at the other end which allows the adapter to be coupled to a intermediate linker group. In some cases, the functional group used to couple to the intermediate linker is temporarily masked with a protecting group ("PG"). Representative examples of adapters include, by way of illustration, tert-butyl bromoacetate, 1-Fmoc-2-bromoethylamine, 1-trityl-2-bromoethanethiol, 4-iodobenzyl bromide, propargyl bromide and the like. After the ligand precursor is coupled to the adapter and the protecting group is removed from the adapter's functional group (if a protecting group is present) to form an intermediate, two molar equivalents of the intermediate are then coupled with an intermediate linker to form a dimer.

Ligand precursors can be coupled with adapters which include both leaving groups and protecting groups to form protected intermediates. The leaving group employed in this reaction may be any conventional leaving group including, by way of example, a halogen such as chloro, bromo or iodo, or a sulfonate group such as tosyl, mesyl and the like. Similarly, any conventional protecting group may be employed including, by way of example, esters such as the methyl, tert-butyl, benzyl ("Bn") and 9-fluorenylmethyl ("Fm") esters.

Protected intermediates can then be deprotected using conventional procedures and reagents to afford deprotected intermediates. For example, tert-butyl esters are readily hydrolyzed with 95% trifluoroacetic acid in dichloromethane; methyl esters can be hydrolyzed with lithium hydroxide in tetrahydrofuran/water; benzyl esters can be removed by hydrogenolysis in the presence of a catalyst, such as palladium on carbon; and 9-fluorenylmethyl esters are readily cleaved using 20% piperidine in DMF. If desired, other well-known protecting groups and deprotecting procedures may be employed in these reactions to form deprotected intermediates.

Similarly, ligand precursors having an adapter with an amine functional group can be prepared. Ligand precursors can be coupled with adapters which include leaving groups and protected amine groups to afford protected intermediates. The leaving group employed in this reaction may be any conventional leaving group. Similarly, any conventional amine protecting group may be employed including, by way of example, trityl, tert-butoxycarbonyl ("Boc"), benzyloxycarbonyl ("CBZ") and 9-fluorenylmethoxy-carbonyl ("Fmoc"). After coupling the adapter to the ligand precursor, the resulting protected intermediate is deprotected to afford a ligand precursor including an amine group using conventional procedures and reagents. For example, a trityl group is readily removed using hydrogen chloride in acetone; a Boc group is removed using 95% trifluoroacetic acid in dichloromethane; a CBZ group can be removed by hydrogenolysis in the presence of a catalyst, such as palladium on carbon; and a 9-fluorenylmethoxycarbonyl group is readily cleaved using 20% piperidine in DMF to afford the deblocked amine. Other well-known amine protecting groups and deprotecting procedures may be employed in these reactions to form amine-containing intermediates and related compounds.

Ligand precursors having an adapter, for example, one including a free carboxylic acid group or a free amine group, can be readily coupled to intermediate linkers having complementary functional groups to form multibinding compounds as described herein. For example, when one component includes a carboxylic acid group, and the other includes an amine group, the coupling reaction typically employs a conventional peptide coupling reagent and is conducted under conventional coupling reaction conditions, typically in the presence of a trialkylamine, such as ethyldiisopropylamine. Suitable coupling reagents for use in this reaction include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), O-(7-azabenzotriazol-1-yl)-N, N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, may be employed in this reaction. Typically, this coupling reaction is conducted at a temperature ranging from about 0° C. to about 60° C. for about 1 to about 72 hours in an inert diluent, such as THF, to afford the dimer.

The multibinding compounds described herein can also be prepared using a wide variety of other synthetic reactions and reagents. For example, ligand precursors having aryliodide, carboxylic acid, amine and boronic acid functional groups can be prepared. Hydroxymethyl pyrrole can be readily coupled under Mitsunobu reaction conditions to various phenols to provide, after deprotection, functionalized intermediates. The Mitsunobu reaction is typically conducted by reacting hydroxymethyl pyrrole and the appropriate phenol using diethyl azodicarboxylate (DEAD) and triphenylphosphine at ambient temperature for about 48 hours. Deprotection, if necessary, using conventional procedures and reagents then affords the functionalized intermediates.

The functionalized intermediates can be employed in the synthesis of multibinding compounds. For example, aryliodide intermediates can be coupled with bis-boronic acid linkers to provide dimers. Typically, this reaction is conducted by contacting two molar equivalents of the aryliodide and one molar equivalent of the bis-boronic acid in the presence of tetrakis(triphenylphosphine)palladium(0), sodium carbonate and water in refluxing toluene.

Aryliodide intermediates can also be coupled with acrylate intermediates or alkyne intermediate to afford dimers. These reactions are typically conducted by contacting two molar equivalents of aryliodide intermediates with one molar equivalent of either acrylates or alkynes in the presence of dichlorobis(triphenylphosphine)palladium (II), copper (I) iodide and diisopropylethylamine in N,N-dimethylformamide to afford the respective dimers.

As will be readily apparent to those of ordinary skill in the art, the synthetic procedures described herein or those known in the art may be readily modified to afford a wide variety of compounds within the scope of this invention.

Combinatorial Libraries

The methods described herein lend themselves to combinatorial approaches for identifying multimeric compounds which possess multibinding properties.

Specifically, factors such as the proper juxtaposition of the individual ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters. that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of Ligand(s)

A single ligand or set of ligands is (are) selected for incorporation into the libraries of candidate multibinding compounds which library is directed against a particular biological target or targets, i.e., binding to bacterial ribosomal RNA and/or to one or more proteins involved in ribosomal protein synthesis in the bacterium, preferably in a manner which inhibits or otherwise adversely affects protein expression. The only requirement for the ligands chosen is that they are capable of interacting with the selected target (s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, log P, etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of Ligand Attachment Points and Linking Chemistry

Several points are chosen on each ligand at which to attach the ligand to the linker. The selected points on the ligand/linker for attachment are functionalized to contain complementary reactive functional groups. This permits probing the effects of presenting the ligands to their target binding site(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a ligand bound to its target allows one to identify one or more sites where linker attachment will not preclude the ligand/target interaction. Alternatively, evaluation of ligand/target binding by nuclear magnetic resonance will permit the identification of sites non-essential for ligand/target binding. See, for example, Fesik, et al., U.S. Pat. No. 5,891,643, the disclosure of which is incorporated herein by reference in its entirety. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a ligand bound to its target, and then consider modifying this ligand by attaching to it a second copy of the same ligand with a linker which allows the second ligand to interact with the same target at sites proximal to the first binding site, which include elements of the target that are not part of the formal ligand binding site and/or elements of the matrix surrounding the formal binding site, such as the membrane. Here, the most favorable orientation for interaction of the second ligand molecule may be achieved by attaching it to the linker at a position which abrogates activity of the ligand at the first binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heteromeric constructs bearing two different ligands that bind to common or different targets.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically innocuous under typical chemical and physiological conditions, and compatible with a large number of available linkers. Amide bonds, ethers, amines, carbamates, ureas, and sulfonamides are but a few examples of preferred linkages.

Linker Selection

In the library of linkers employed to generate the library of candidate multibinding compounds, the selection of linkers employed in this library of linkers takes into consideration the following factors:

Valency: In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small, molecules.

Linker Length: Linkers are chosen in a range of lengths to allow the spanning of a range of inter-ligand distances that encompass the distance preferable for a given divalent interaction. In some instances the preferred distance can be estimated rather precisely from high-resolution structural information of targets. In other instances where high-resolution structural information is not available, one can make use of simple models to estimate the maximum distance between binding sites either on adjacent receptors or at different locations on the same receptor. In situations where two binding sites are present on the same target (or target subunit for multisubunit targets), preferred linker distances are 2–20 Å, with more preferred linker distances of 3–12 Å. In situations where two binding sites reside on separate target sites, preferred linker distances are 20–100 Å, with more preferred distances of 30–70 Å.

Linker Geometry and Rigidity: The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties: The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups: Linker chemical functional groups are selected to be compatible with the chemistry chosen to connect linkers to the ligands and to impart the range of physical properties sufficient to span initial examination of this parameter.

Combinatorial Synthesis

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters for a particular target. For example, an array generated from two ligands, one which has two attachment points (A1, A2) and one which has three attachment points (B1, B2, B3) joined in all possible combinations provide for at least 15 possible combinations of multibinding compounds:

| A1-A1 | A1-A2 | A1-B1 | A1-B2 | A1-B3 | A2-A2 | A2-B1 | A2-B2 |
| A2-B3 | B1-B1 | B1-B2 | B1-B3 | B2-B2 | B2-B3 | B3-B3 | |

When each of these combinations is joined by 10 different linkers, a library of 150 candidate multibinding compounds results.

Given the combinatorial nature of the library, common chemistries are preferably used to join the reactive functionalies on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of the Library

Various methods are used to characterize the properties and activities of the candidate multibinding compounds in the library to determine which compounds possess multibinding properties. Physical constants such as solubility under various solvent conditions and log D/c log D values can be determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, can also be determined. Pharmacological data, including oral absorption, everted gut penetration, other pharmacokinetic parameters and efficacy data can be determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libaries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up Synthesis and Analysis of Additional Libraries

Based on the information obtained through analysis of the initial library, an optional component of the process is to ascertain one or more promising multibinding "lead" compounds as defined by particular relative ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantages towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| Representative Complementary Binding Chemisties | | |
|---|---|---|
| First Reactive Group | Second Reactive Group | Linkage |
| hydroxyl | isocyanate | urethane |
| amine | epoxide | β-hydroxyamine |
| sulfonyl halide | amine | sulfonamide |
| carboxyl acid | amine | amide |
| hydroxyl | alkyl/aryl halide | ether |
| aldehyde | amine(+ reducing agent) | amine |
| ketone | amine(+ reducing agent) | amine |
| amine | isocyanate | urea |

Exemplary linkers include the following linkers identified as X-1 through X-418 as set forth below:

Diacids

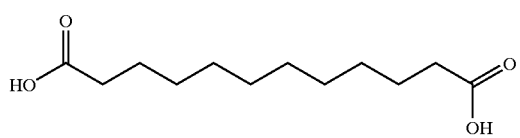

X-1

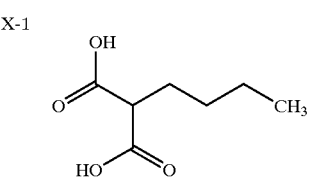

X-2

-continued
X-3
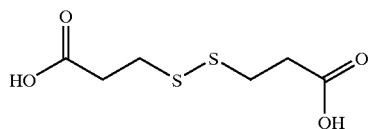
X-4
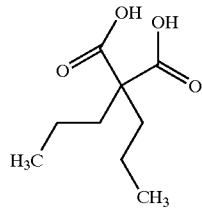
X-5
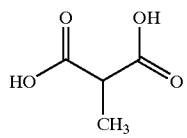
X-6
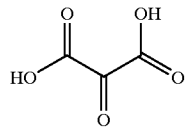
X-7
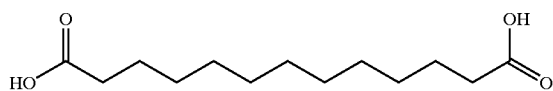
X-8
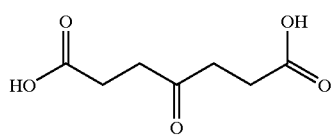
X-9
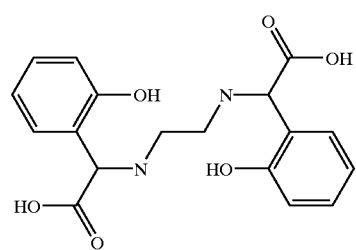
X-10
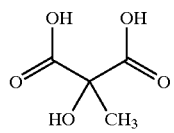
X-11
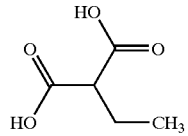
X-12
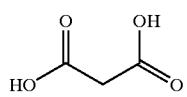
X-13
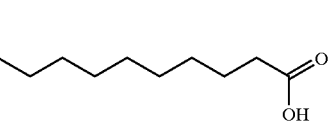
X-14
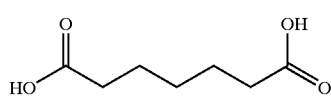
X-15
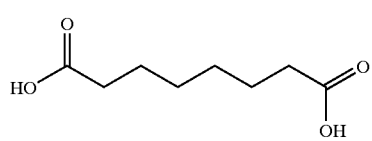
X-16
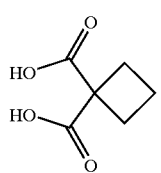
X-17
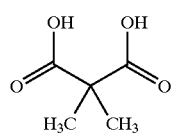
X-18
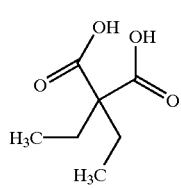
X-19
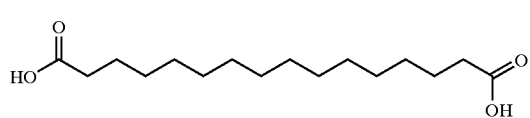

-continued
X-20
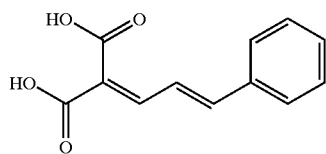
X-21
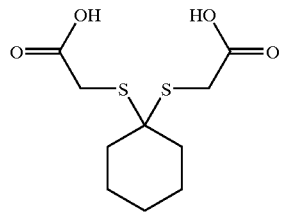
X-22
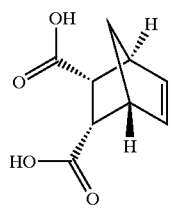
X-23
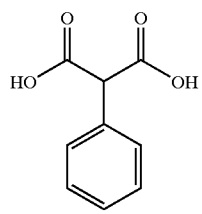
X-24
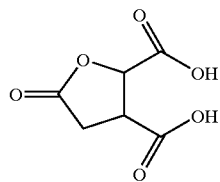
X-25
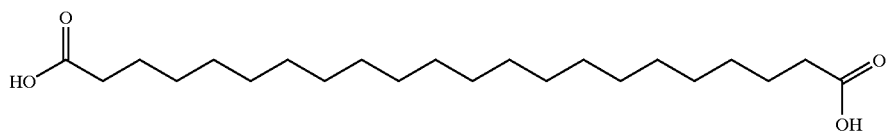
X-26
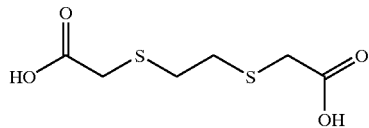
X-27
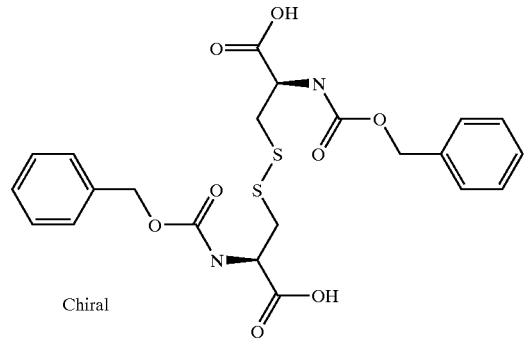
Chiral
X-28
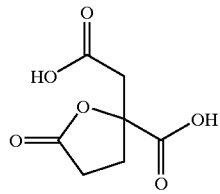
X-29
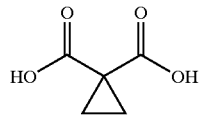
X-30
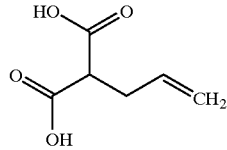
X-31
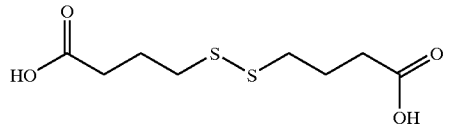

-continued
X-32
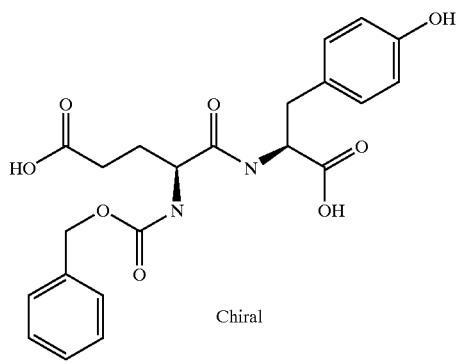
Chiral
X-33
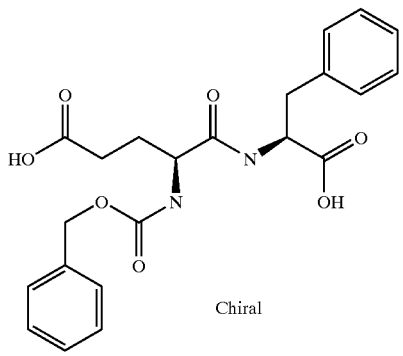
Chiral
X-34
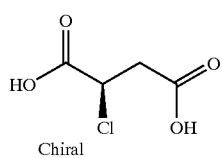
Chiral
X-35
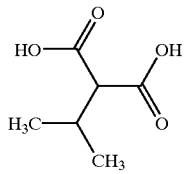
X-36
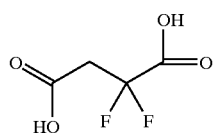
X-37
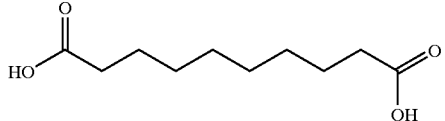
X-38
X-39
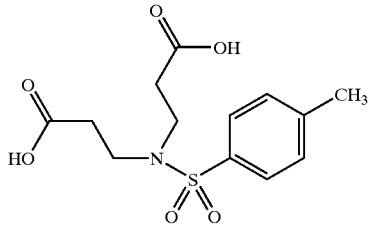
X-40
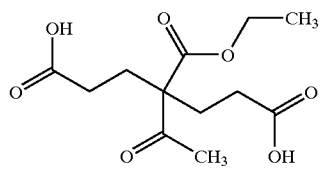
X-41
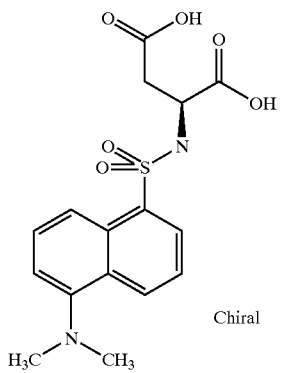
Chiral
X-42
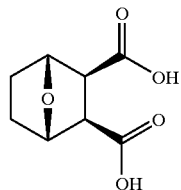
X-43
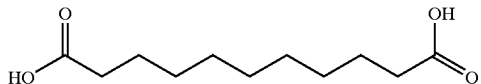

-continued
X-44 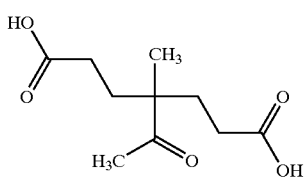
X-45 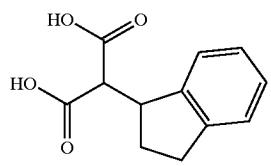
X-46 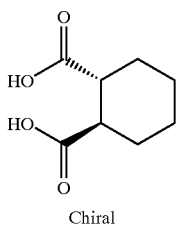
X-47 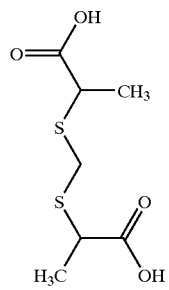
X-48 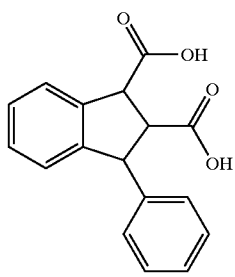
X-49 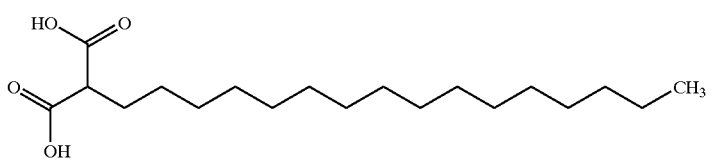
X-50 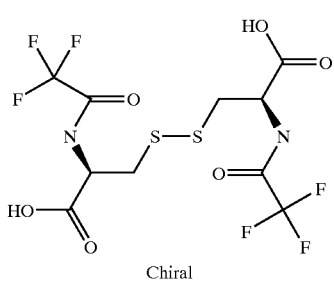
X-51 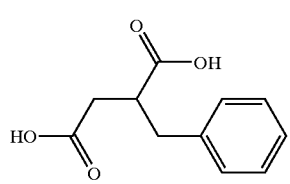
X-52 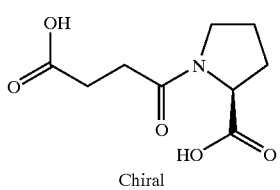
X-53 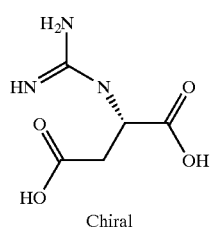
X-54 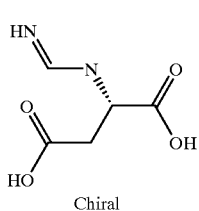
X-55 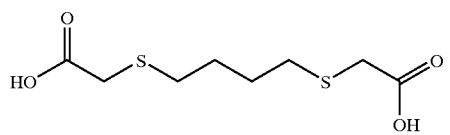

53
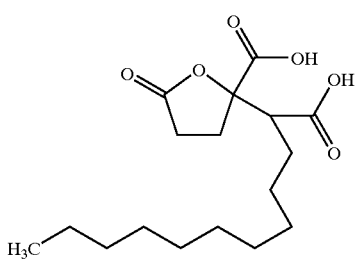
X-56
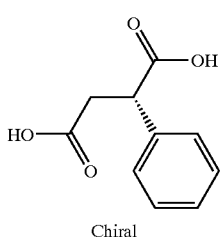
Chiral
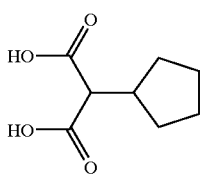
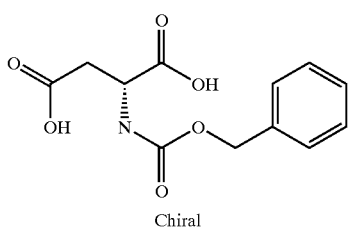
Chiral
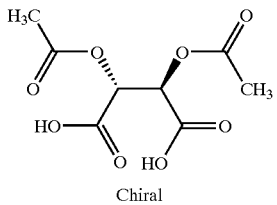
Chiral
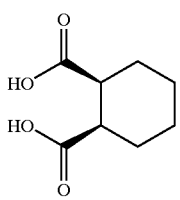
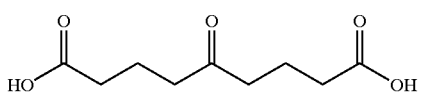
54
-continued
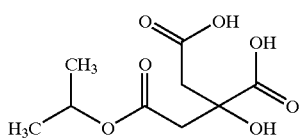
X-57
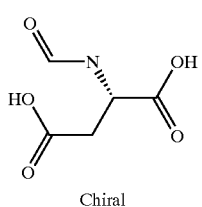
X-58  Chiral  X-59
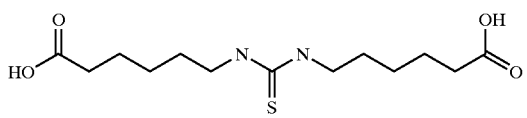
X-60  X-61
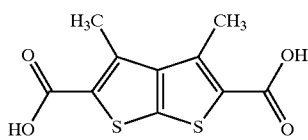
X-62  X-63
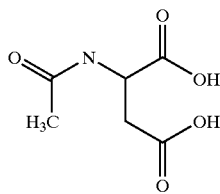
X-64  X-65
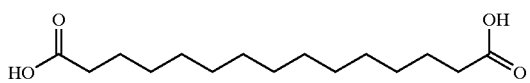
X-66  X-67
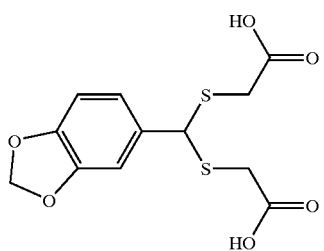
X-68  X-69

-continued
X-70
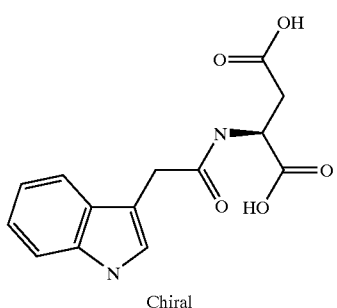
Chiral
X-71
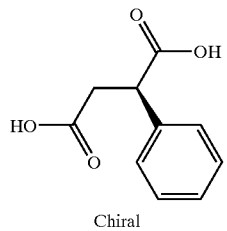
Chiral
X-72
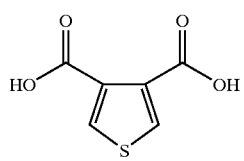
X-73
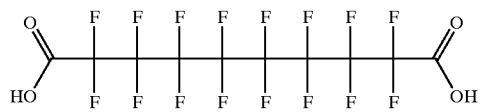
X-74
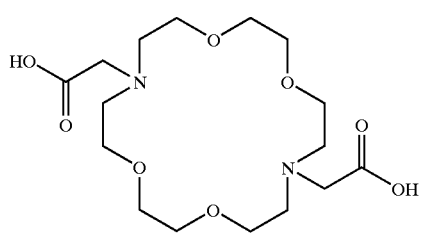
X-75
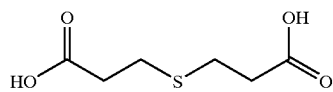
X-76
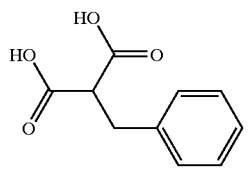
X-77
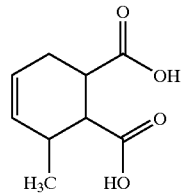
X-78
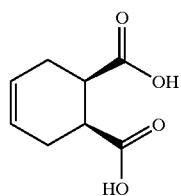
X-79
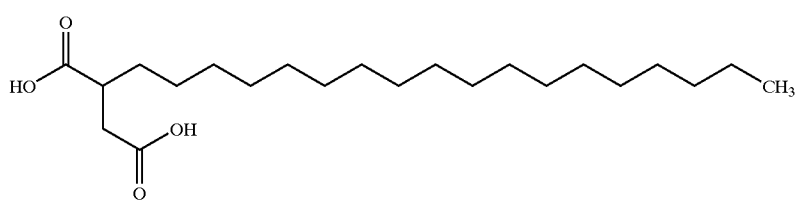
X-80
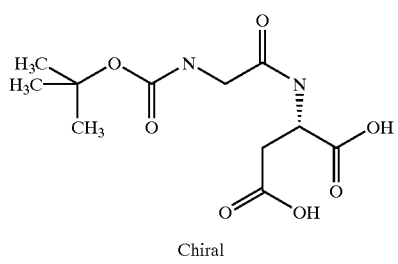
Chiral
X-81
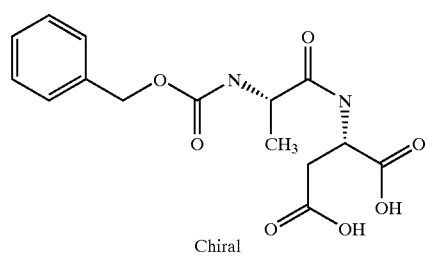
Chiral -continued
X-81
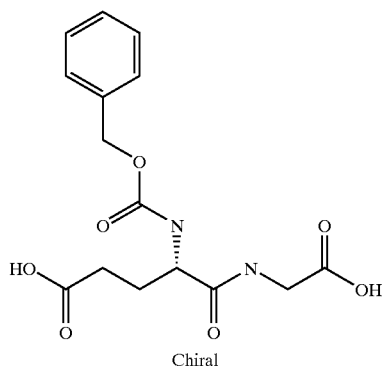
X-82
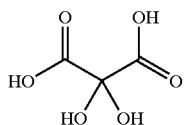
X-83
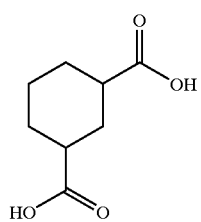
X-84
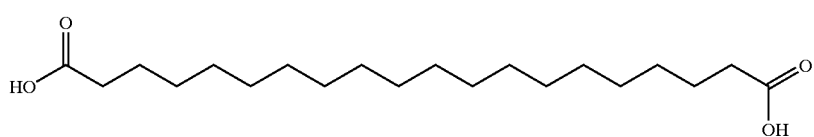
X-85
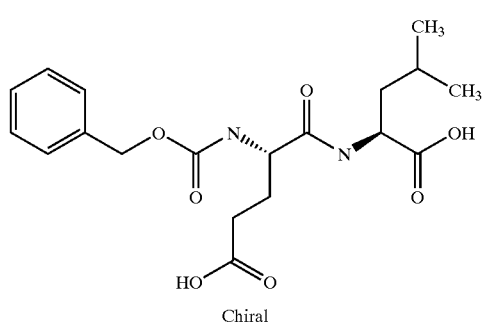
X-86
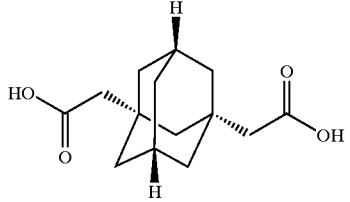
X-87
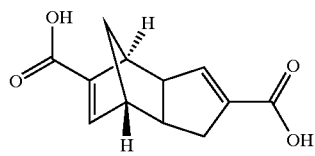
X-88
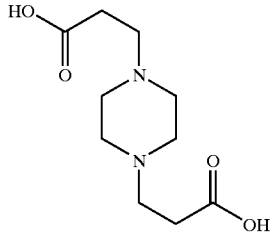
X-89
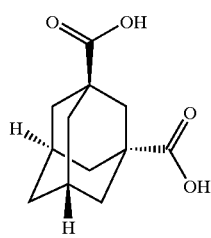
X-90

-continued
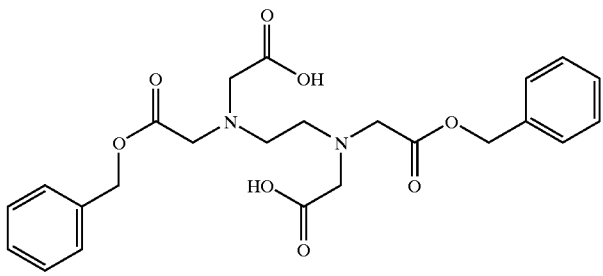
X-91
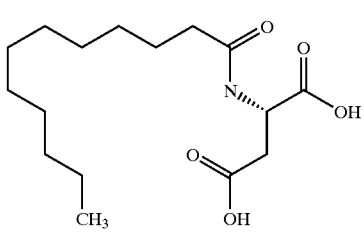
X-92
Chiral
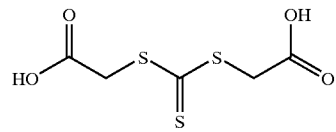
X-93
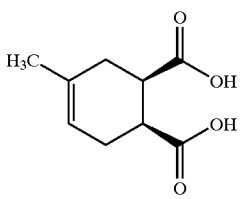
X-94
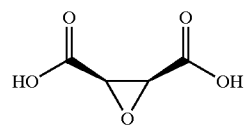
X-95
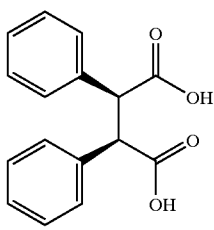
X-96
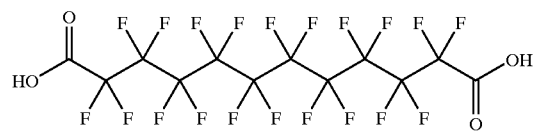
X-97
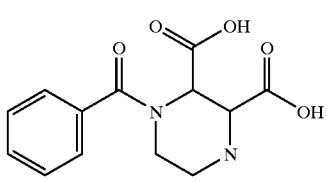
X-98
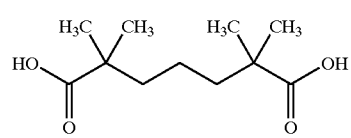
X-99
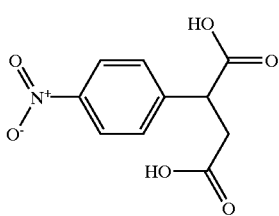
X-100
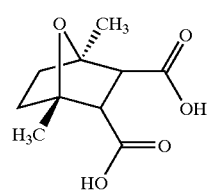
X-101
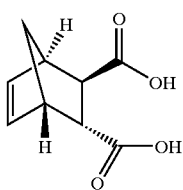
X-102
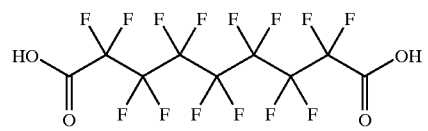
X-103

-continued
X-104 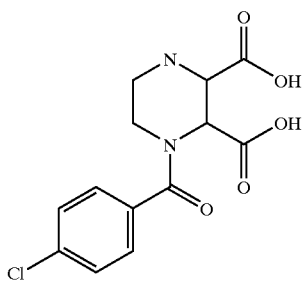
X-105 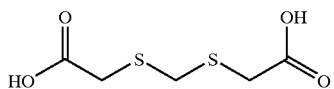
X-106 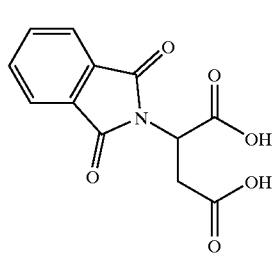
X-107 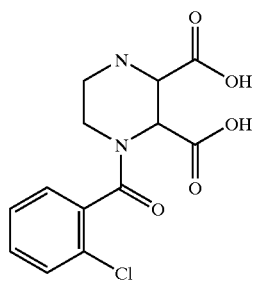
X-108 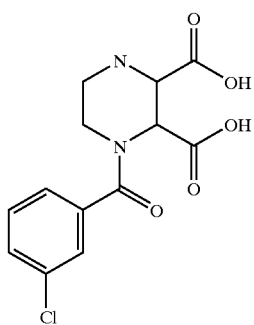
X-109 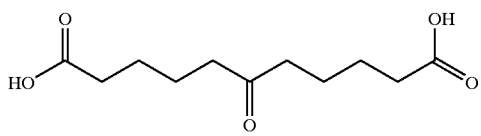
X-110 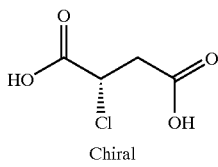
X-111 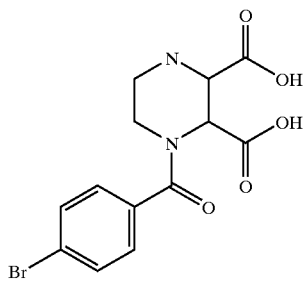
X-112 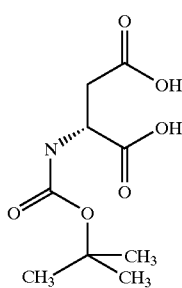
X-113 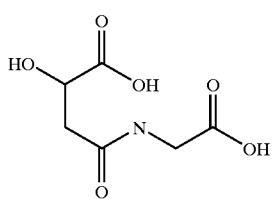

-continued
X-114 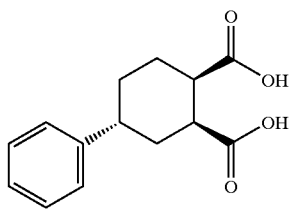
X-115 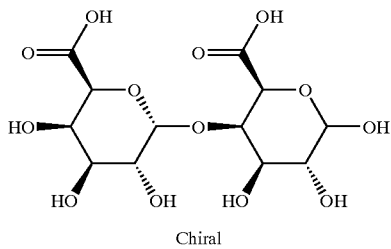
Chiral
X-116 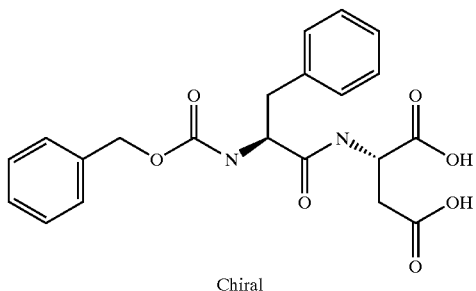
Chiral
X-117 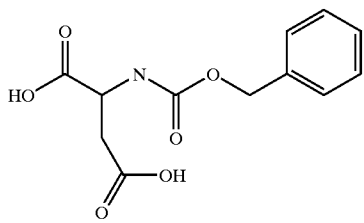
X-118 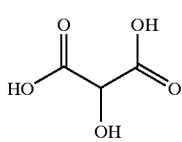
X-119 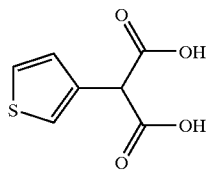
X-120 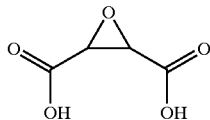
X-121 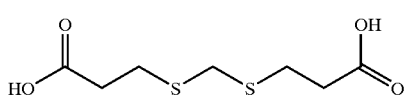
X-122 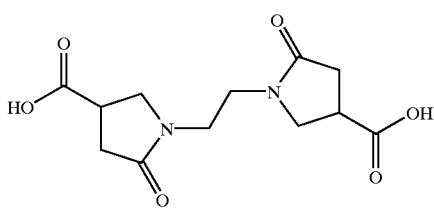
X-123 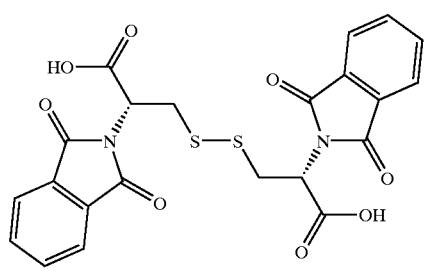
Chiral
X-124 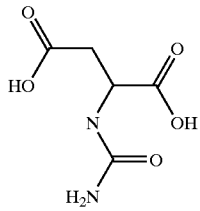
X-125

X-126
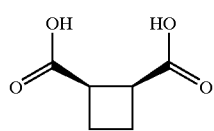
X-127
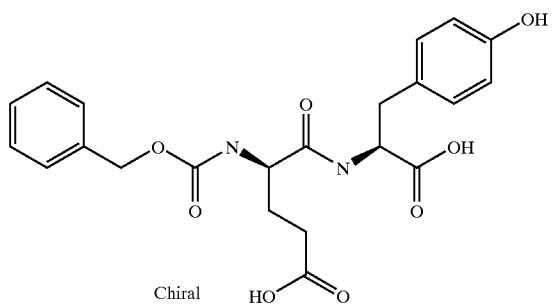
Chiral
X-128
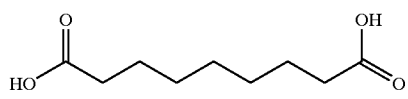
X-129
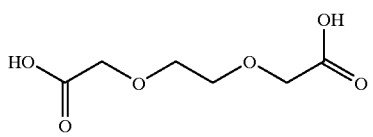
X-130
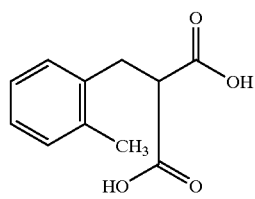
X-131
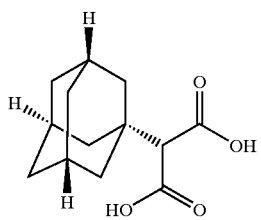
X-132
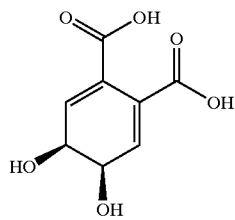
Disulfonyl Halides
X-133
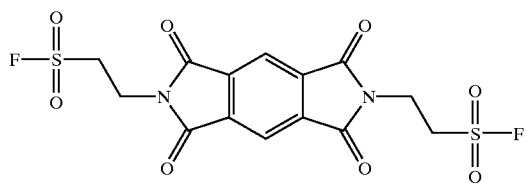
X-134
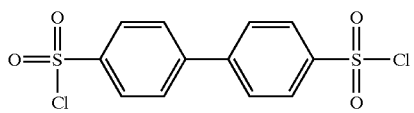
X-135
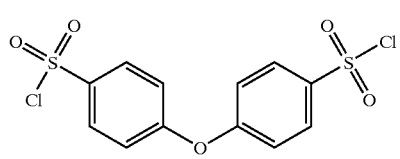
X-136
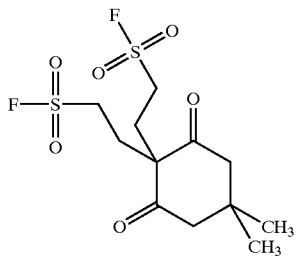
X-137
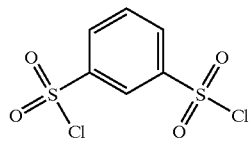
X-138
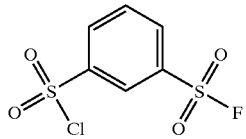

-continued
X-139 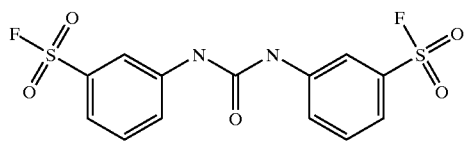 X-140 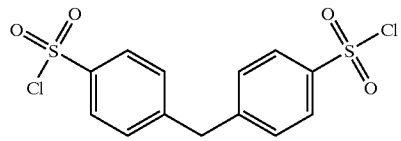
X-141 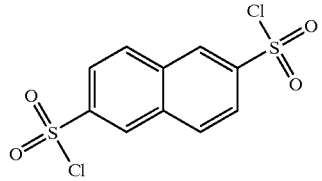 X-142 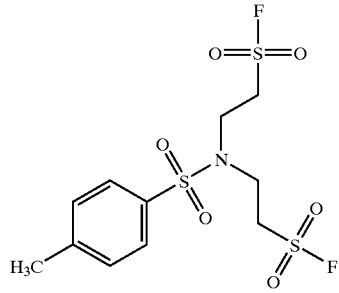
X-143 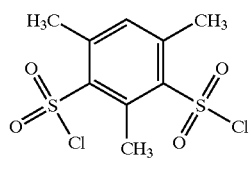 X-144 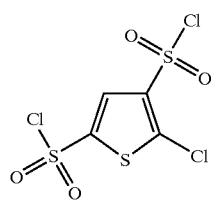
X-145 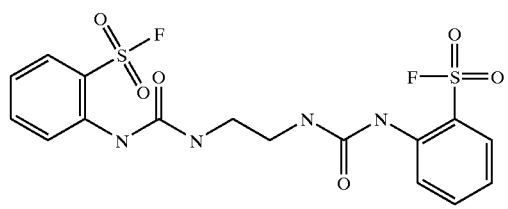 X-146 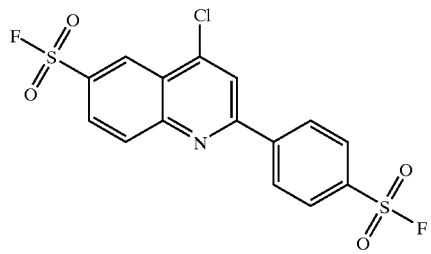
X-147 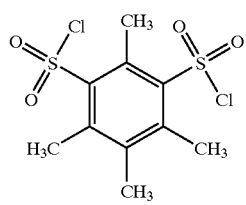 X-148 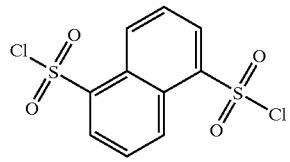
X-149 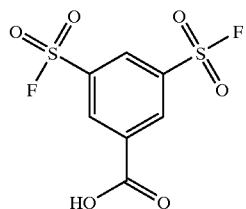 X-150 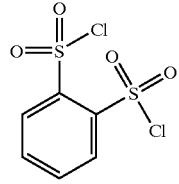
X-151 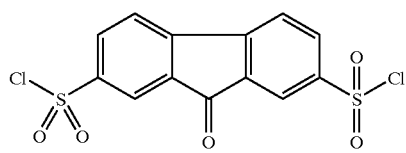 X-152 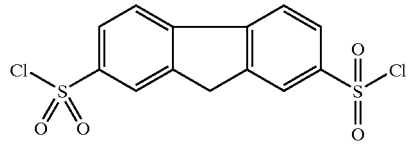
Dialdehydes -continued
X-153
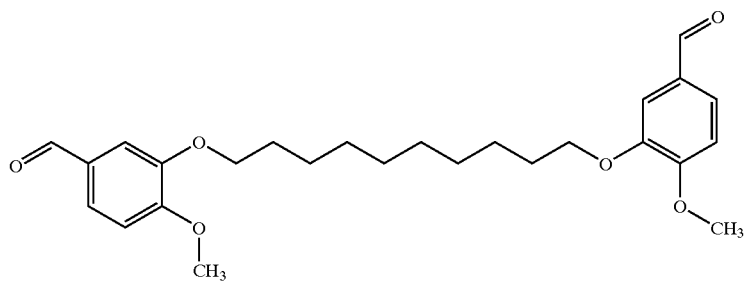
X-154
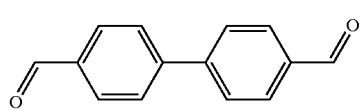
X-155
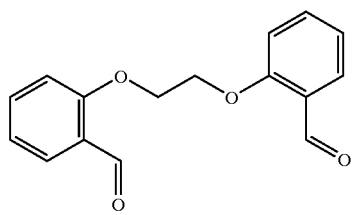
X-156
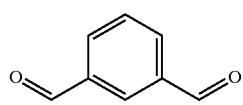
X-157
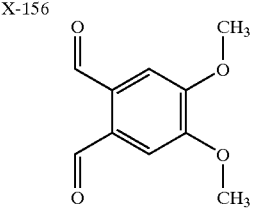
X-158
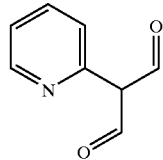
X-159
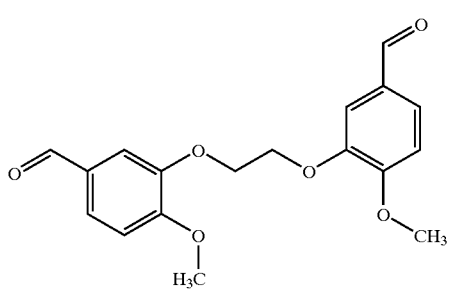
X-160
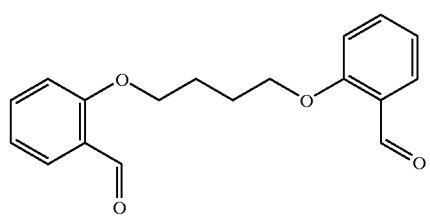
X-161
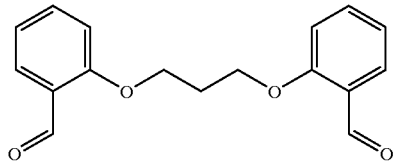
X-162
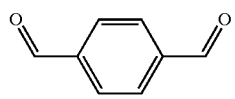
X-163
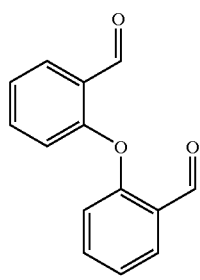

X-164 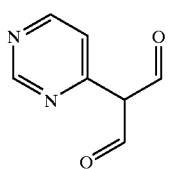
X-165 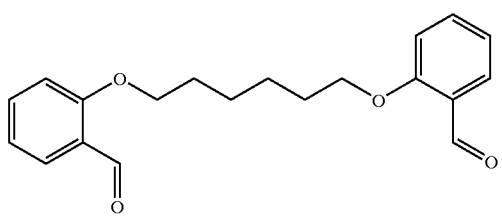
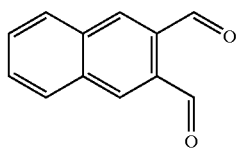
X-166 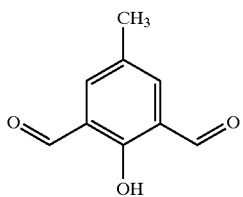
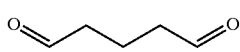
X-167 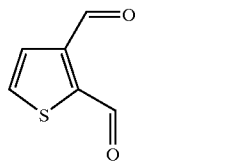
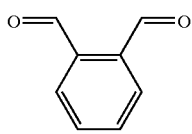
X-168 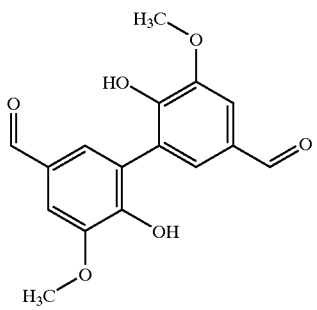
X-169
X-170
X-171
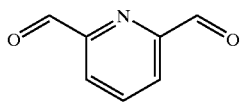
X-172 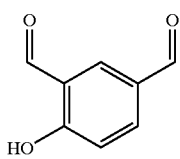
X-173
X-174
Dihalides
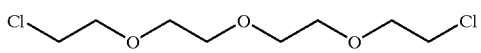
X-175 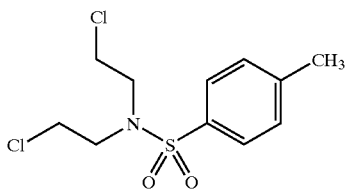
X-176
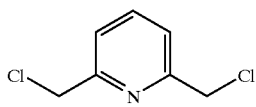
X-177 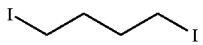
X-178
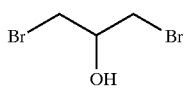
X-179 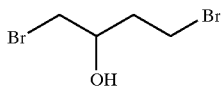
X-180

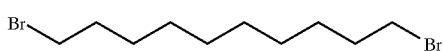
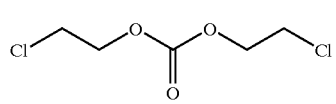 X-181
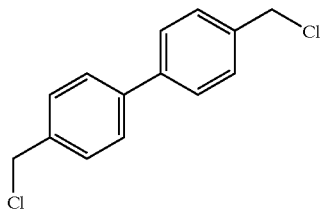
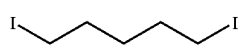 X-183
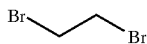
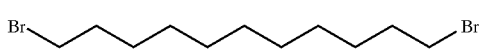
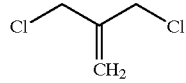 X-185
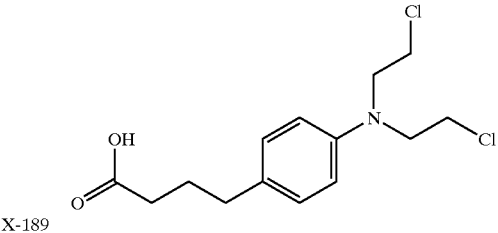 X-187
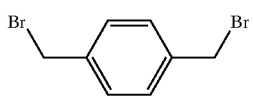
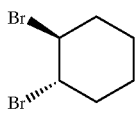
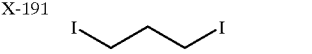 X-191
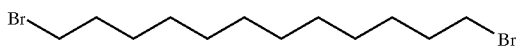
X-193
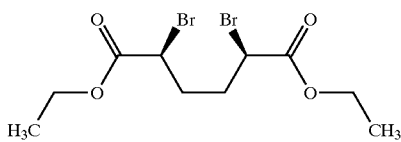
X-194
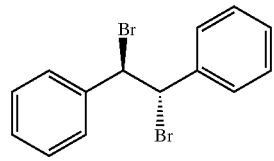 X-195
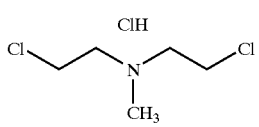
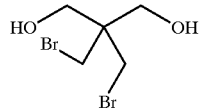 X-196
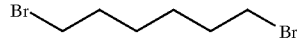 X-198
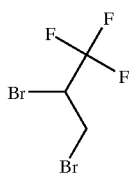
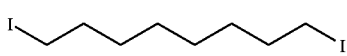
X-200
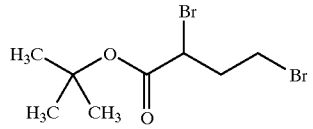 X-201

-continued
X-202 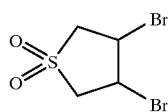
X-203 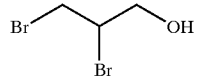
X-204 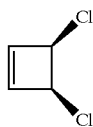
X-205 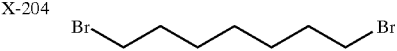
X-206 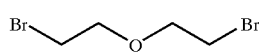
X-207 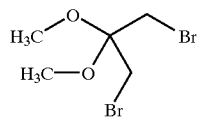
X-208 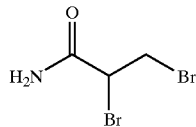
X-209 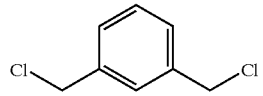
X-210 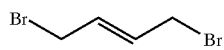
X-211 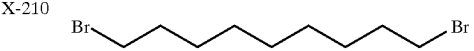
X-212 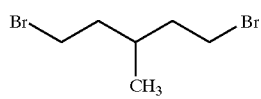
X-213 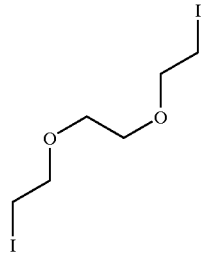
X-214 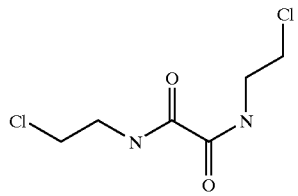
Diisocyanates
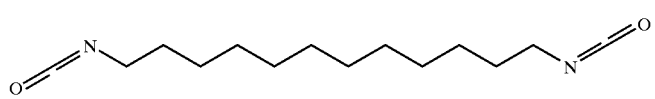
X-215
X-216 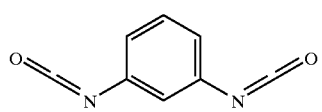
X-217 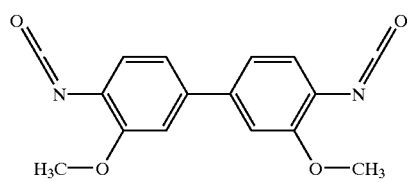

-continued
X-218
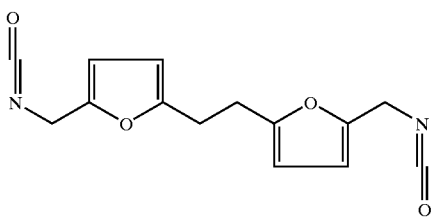
X-219
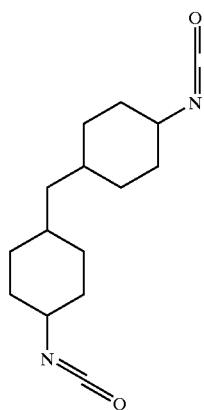
X-220
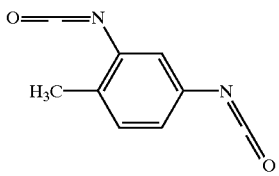
X-221
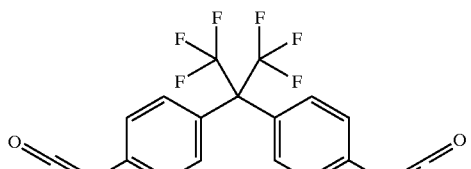
X-222
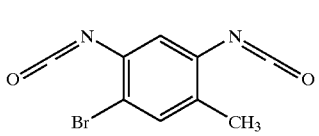
X-223
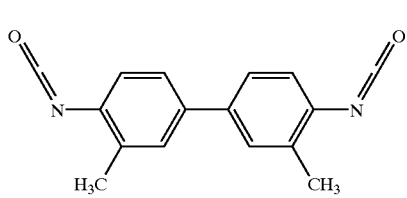
X-224
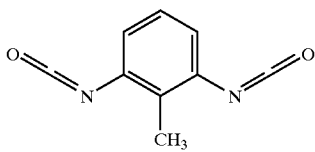
X-225
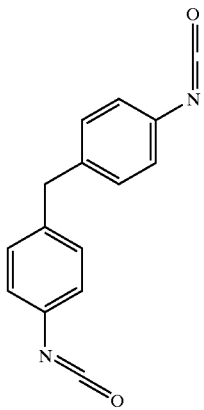
X-226
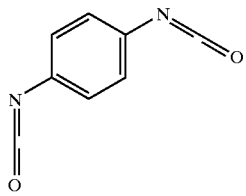
X-227
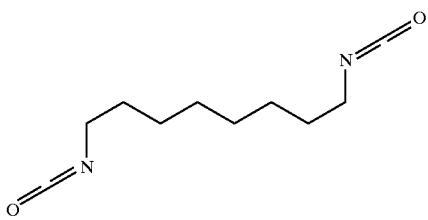
X-228
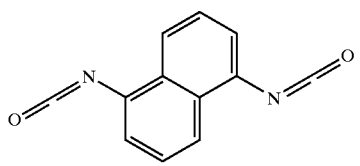

-continued
X-229 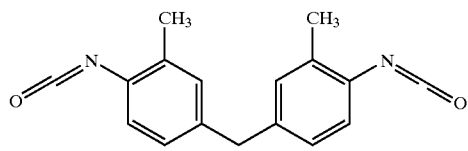
X-230 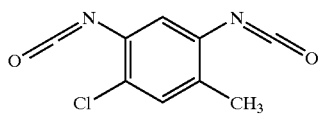
X-231 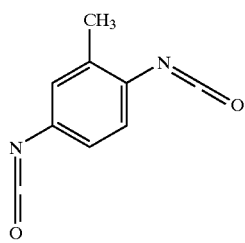
X-232 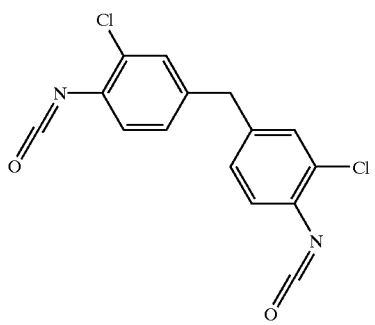
X-233 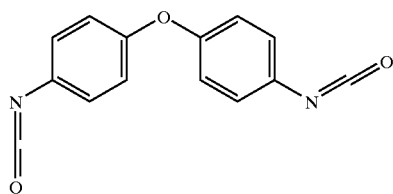
X-234 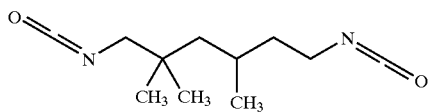
X-235 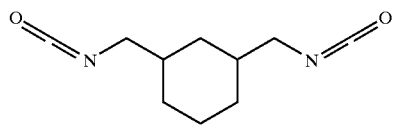
X-236 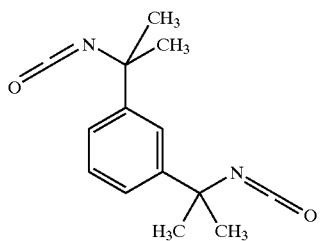
X-237 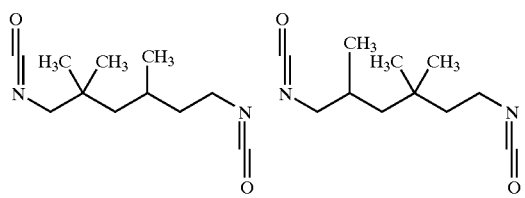
X-238 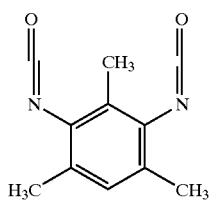
X-239 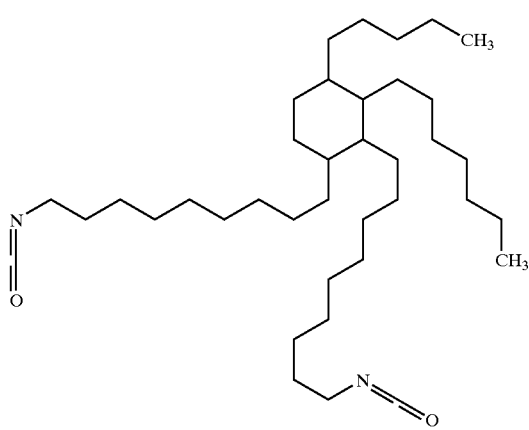
X-240 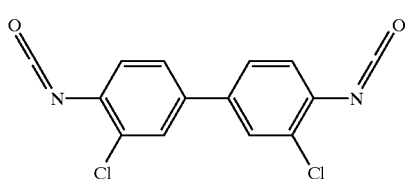

-continued
X-241 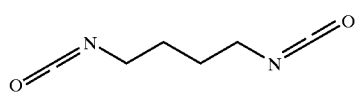
X-242 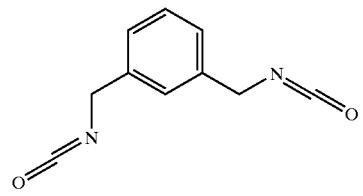
X-243 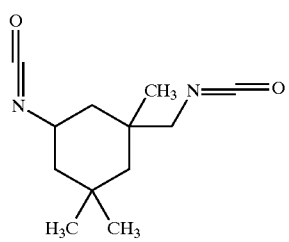
X-244 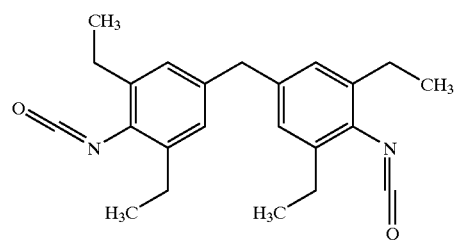
X-245 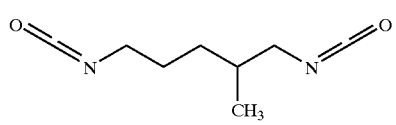
X-246 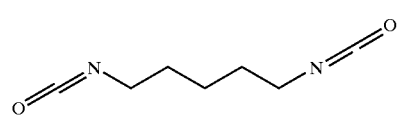
X-247 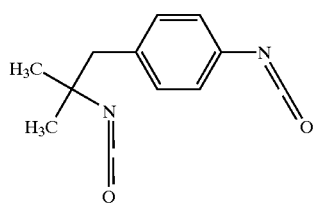
X-248 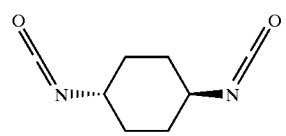
Diamines
X-249 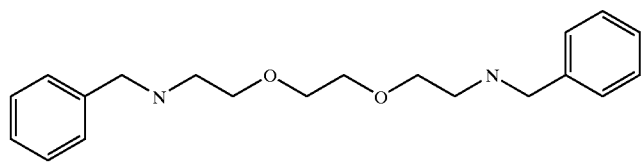
X-250 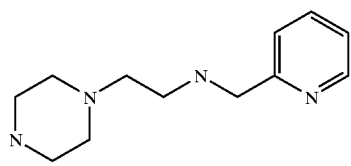
X-251 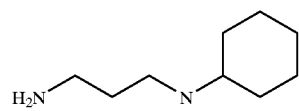
X-252 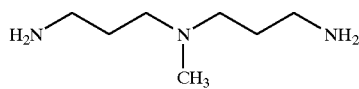
X-253
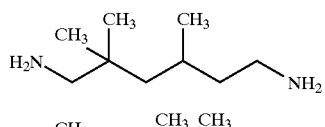
X-254 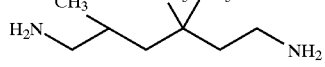
X-256 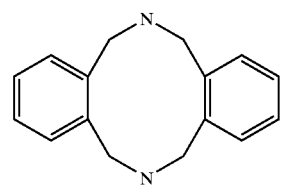
X-255 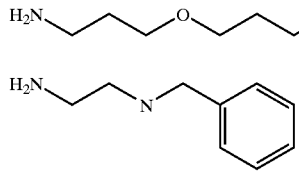
X-257
X-258 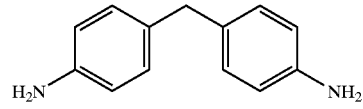

-continued
X-259
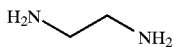
X-260
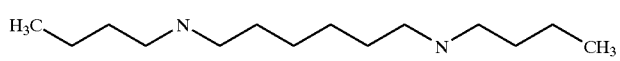
X-261
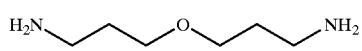
X-262
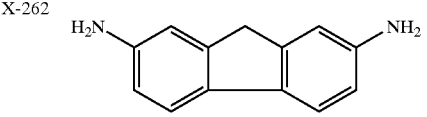
X-263
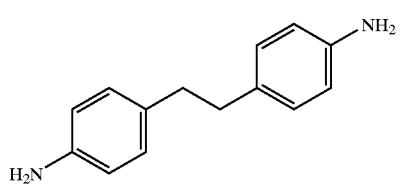
X-264
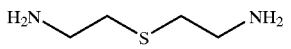
X-265
X-266
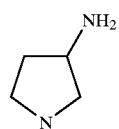
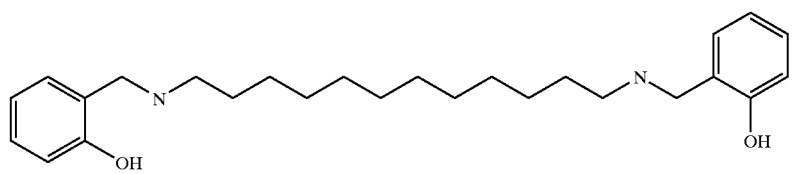
X-267
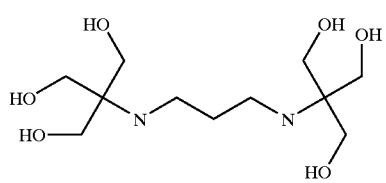
X-268
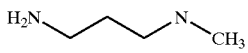
X-269
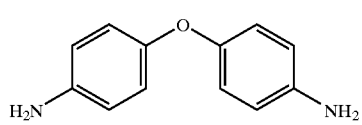
X-270
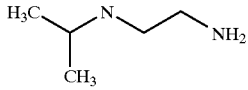
X-271
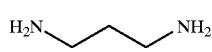
X-272
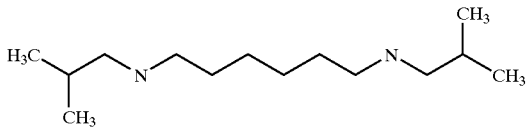
X-273
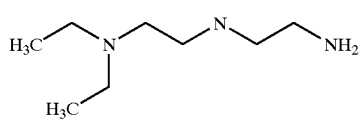
X-274
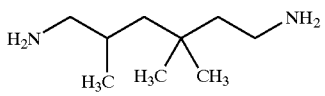
X-275

-continued
X-276
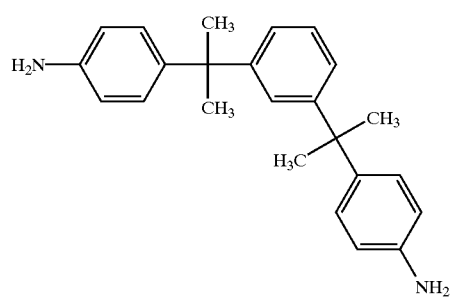
X-277
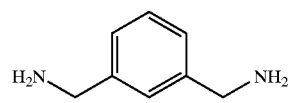
X-278
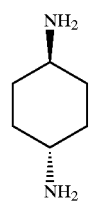
X-279
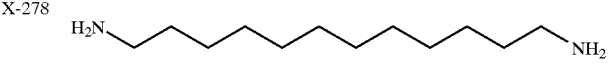
X-280
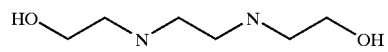
X-281
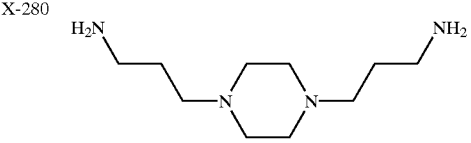
X-282
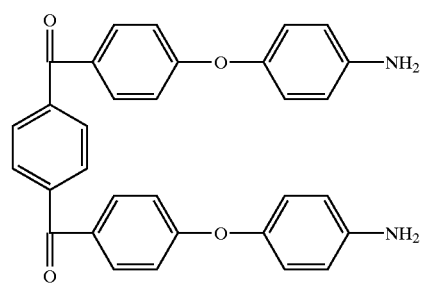
X-283
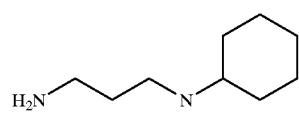
X-284
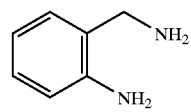
X-285
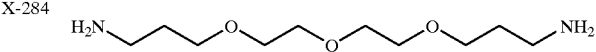
X-286
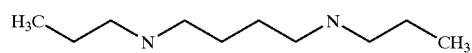
X-287
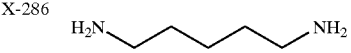
X-288
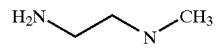
X-289
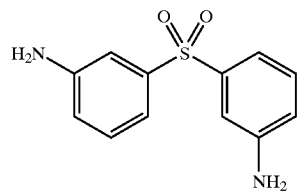
X-290
X-291
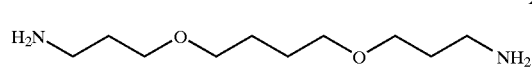
X-292
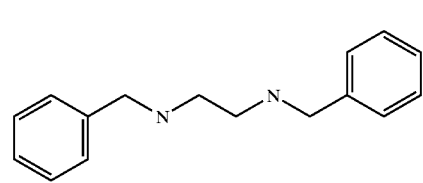
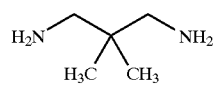

-continued
X-292 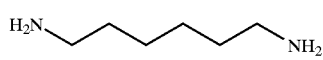
X-293 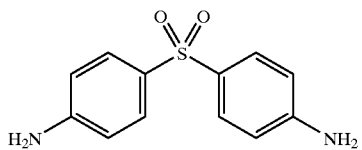 X-294
X-294 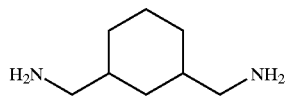
X-295 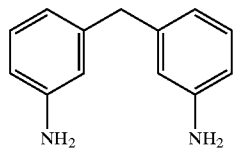 X-296
X-296 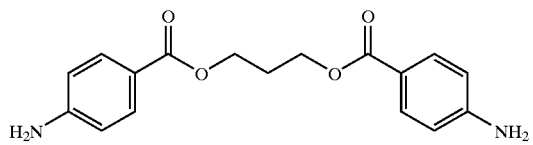
X-297 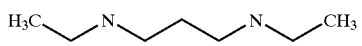 X-298
X-298 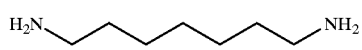
X-299 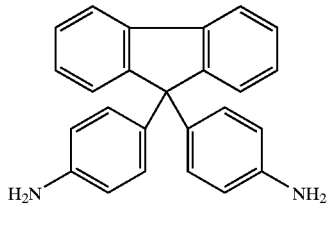 X-300
X-300 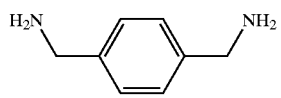
X-301 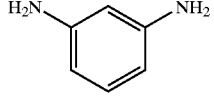 X-302
X-303 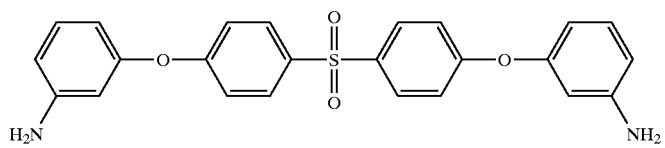
X-304 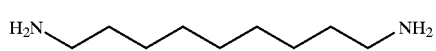
X-304 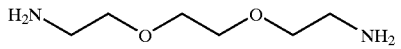 X-305
X-306 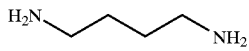 X-307
X-306 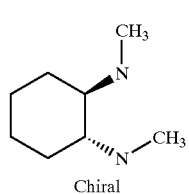
Chiral
X-308 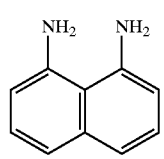
X-309 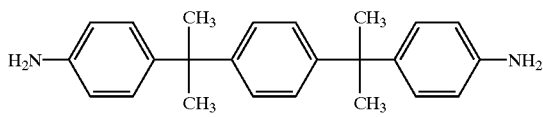
X-310 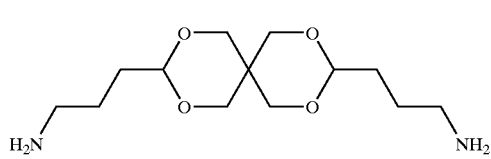
X-311 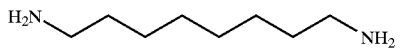

-continued
X-312 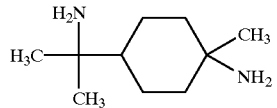 X-313
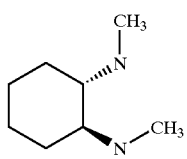
X-314 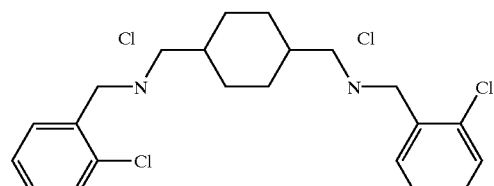 X-315
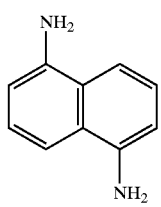
X-316 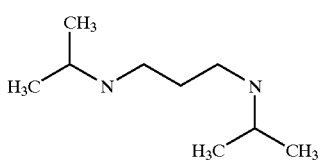 X-317
X-318 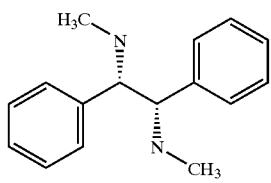 X-319
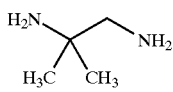
Chiral
X-320 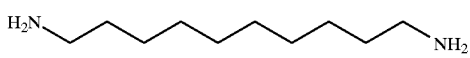 X-321
X-322 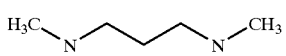 X-323
X-324 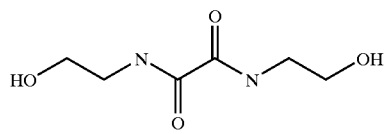 X-325
Diols
X-326
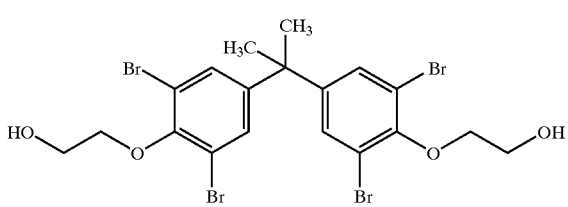
X-327 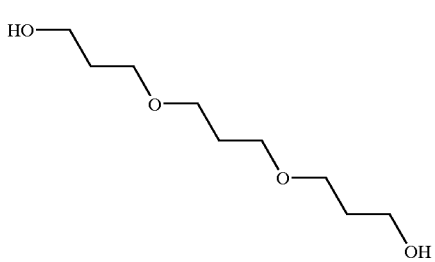 X-328

-continued

X-329

X-330

X-331

X-332

X-333

X-334

X-335

X-336

X-337

X-338

X-339

X-340

X-341

X-342

X-343

X-344

-continued

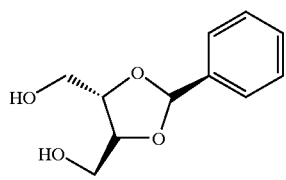
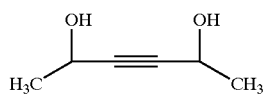
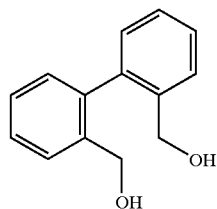
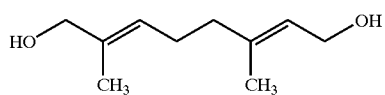
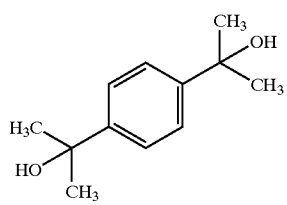
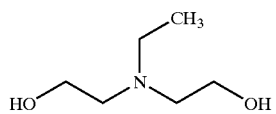
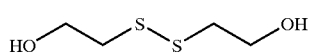
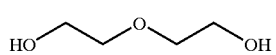
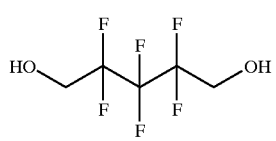
Dithiols
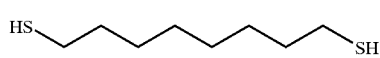
-continued
X-369     X-370
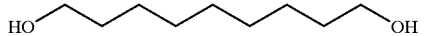
X-371     X-372
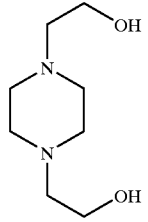
X-373     X-374
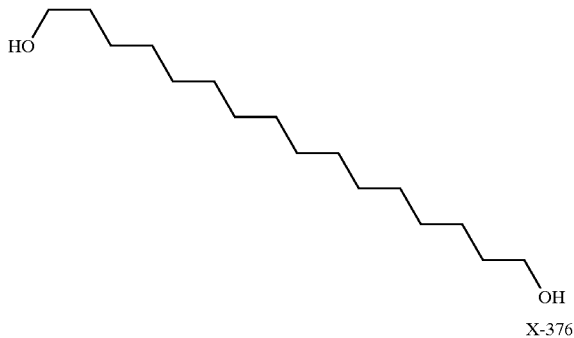
X-375     X-376
X-377     X-378
X-379     X-380
X-381     X-382
X-383     X-384
X-385
X-386     X-387

-continued
X-388 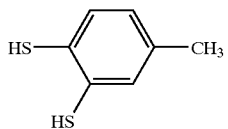 X-389
X-390 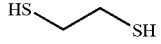 X-391
X-392 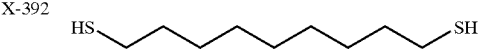 X-=393
X-394 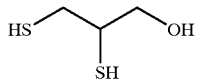 X-395
X-396 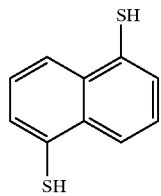 X-397
X-398 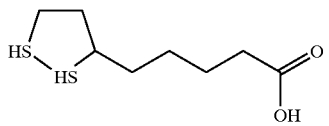 X-399
X-400 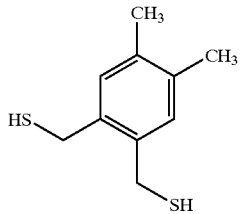 X-401
X-402  X-403
X-404 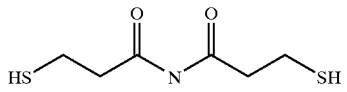 X-405
X-406  X-407
X-408 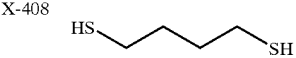 X-409
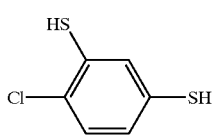
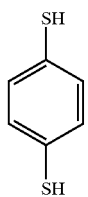
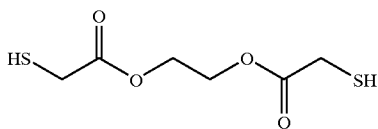
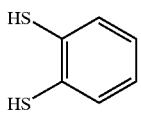
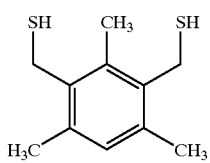
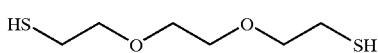
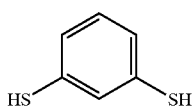
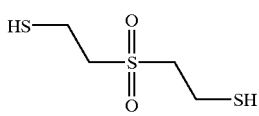
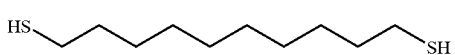
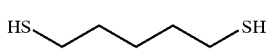

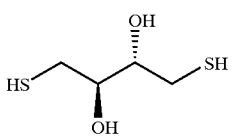
X-410

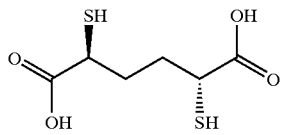
X-411

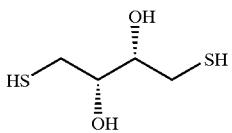

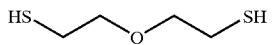
X-412                                X-413

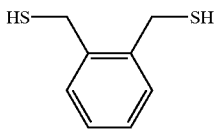
X-414

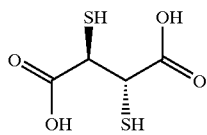
X-415

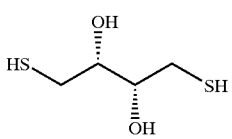

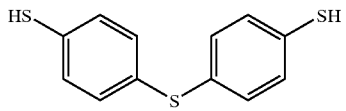
X-416                                X-417

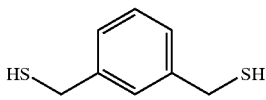
Chiral

X-418

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose; dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 1 g, more usually about 1 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example I
Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2
A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3
A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4
Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5
Capsules, each containing 40 mg of medicament are made as follows:

| Ingredient | Quantity (mg/capsule) |
|---|---|
| Active Ingredient | 40.0 mg |
| Starch | 109.0 mg |

-continued

Formulation Example 5
Capsules, each containing 40 mg of medicament are made as follows:

| Ingredient | Quantity (mg/capsule) |
|---|---|
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6
Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7
Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8
A formulation may be prepared as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9
A formulation may be prepared as follows:

| Ingredient | Quantity |
|---|---|
| Active Ingredient | 5.0 mg |
| Corn Oil | 1.0 mL |

Formulation Example 10
A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Other suitable formulations for use in the present invention can be found in *Remington's Pharmaceutical Sciences*, Mace Publishing Company, Philadelphia, Pa., 17th ed. (1985).

Utility

The multibinding compounds of this invention are macrolide antibiotics, aminoglycosides, lincosamides, oxazolidinones, streptogramins, tetracycline or other compounds which are known to bind bacterial ribosomal RNA and/or one or more proteins involved in ribosomal protein synthesis in the bacterium. Accordingly, the multibinding compounds and pharmaceutical compositions of this invention are useful in the treatment and prevention of bacterial infections.

Examples of bacterial infections which can be treated using the compounds described herein include gram positive, gram negative and anaerobic bacterial infections.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like.

In therapeutic applications, compositions are administered to a patient already suffering from a bacterial infection.

Amounts effective for this use will depend on the judgment of the attending clinician depending upon factors such as the degree or severity of the disorder in the patient, the age, weight and general condition of the patient, and the like. The pharmaceutical compositions of this invention may contain more than one compound of the present invention.

As noted above, the compounds administered to a patient are in the form of pharmaceutical compositions described above which can be administered by a variety of routes including oral, rectal, transdermal, subcutaneous, intravenous, intramuscular, etc. These compounds are effective as both injectable and oral deliverable pharmaceutical compositions. Such compositions are prepared in a manner well known in the pharmaceutical art and comprise at least one active compound.

The multibinding compounds of this invention can also be administered in the form of pro-drugs, i.e., as derivatives which are converted into a biologically active compound in vivo. Such pro-drugs will typically include compounds in which, for example, a carboxylic acid group, a hydroxyl group or a thiol group is converted to a biologically liable group, such as an ester, lactone or thioester group which will hydrolyze in vivo to reinstate the respective group.

The compounds can be assayed to identify which of the multimeric ligand compounds possess multibinding properties. First, one identifies a ligand or mixture of ligands which each contain at least one reactive functionality and a library of linkers which each include at least two functional groups having complementary reactivity to at least one of the reactive functional groups of the ligand. Next one prepares a multimeric ligand compound library by combining at least two stoichiometric equivalents of the ligand or mixture of ligands with the library of linkers under conditions wherein the complementary functional groups react to form a covalent linkage between the linker and at least two of the ligands. The multimeric ligand compounds produced in the library can be assayed to identify multimeric ligand compounds which possess multibinding properties. The method can also be performed using a library of ligands and a linker or mixture of linkers.

The preparation of the multimeric ligand compound library can be achieved by either the sequential or concurrent combination of the two or more stoichiometric equivalents of the ligands with the linkers. The multimeric ligand compounds can be dimeric, for example, homodimeric or heteromeric. A heteromeric ligand compound library can be prepared by sequentially adding a first and second ligand.

Each member of the multimeric ligand compound library can be isolated from the library, for example, by preparative liquid chromatography mass spectrometry (LCMS). The linker or linkers can be flexible linkers, rigid linkers, hydrophobic linkers, hydrophilic linkers, linkers of different geometry, acidic linkers, basic linkers, linkers of different polarizability and/or polarization or amphiphilic linkers. The linkers can include linkers of different chain lengths and/or which have different complementary reactive groups. In one embodiment, the linkers are selected to have different linker lengths ranging from about 2 to 100 Å. The ligand or mixture of ligands can have reactive functionality at different sites on the ligands. The reactive functionality can be, for example, carboxylic acids, carboxylic acid halides, carboxyl esters, amines, halides, pseudohalides, isocyanates, vinyl unsaturation, ketones, aldehydes, thiols, alcohols, anhydrides, boronates, and precursors thereof, as long as the reactive functionality on the ligand is complementary to at least one of the reactive groups on the linker so that a covalent linkage can be formed between the linker and the ligand.

A library of multimeric ligand compounds can thus be formed which possesses multivalent properties.

Multimeric ligand compounds possessing multibinding properties can be identified in an iterative method by preparing a first collection or iteration of multimeric compounds by contacting at least two stoichiometric equivalents of the ligand or mixture of ligands which target bacterial ribosomal RNA and/or one or more proteins involved in ribosomal protein synthesis in the bacterium with a linker or mixture of linkers, where the ligand or mixture of ligands includes at least one reactive functionality and the linker or mixture of linkers includes at least two functional groups having complementary reactivity to at least one of the reactive functional groups of the ligand. The ligand(s) and linker(s) are reacted under conditions which form a covalent linkage between the linker and at least two of the ligands. The first collection or iteration of multimeric compounds can be assayed to assess which if any of the compounds possess multibinding properties. The process can be repeated until at least one multimeric compound is found to possess multibinding properties. By evaluating the particular molecular constraints which are imparted or are consistent with imparting multibinding properties to the multimeric compound or compounds in the first iteration, a second collection or iteration of multimeric compounds which elaborates upon the particular molecular constraints can be assayed, and the steps optionally repeated to further elaborate upon said molecular constraints. For example, the steps can be repeated from between 2 and 50 times, more preferably, between 5 and 50 times.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| Å | = | Angstroms |
| cm | = | centimeter |
| DCC | = | dicyclohexyl carbodiimide |
| DMF | = | N,N-dimethylformamide |
| DMSO | = | dimethylsulfoxide |
| EDTA | = | ethylenediaminetetraacetic acid |
| g | = | gram |
| HPLC | = | high performance liquid chromatography |
| MEM | = | minimal essential medium |
| mg | = | milligram |
| MIC | = | minimum inhibitory concentration |
| min | = | minute |
| mL | = | milliliter |
| mm | = | millimeter |
| mmol | = | millimol |
| N | = | normal |
| THF | = | tetrahydrofuran |
| µL | = | microliters |
| µm | = | microns |

ANALYTICAL EXAMPLES

Example 1

Binding Test

Methods for performing affinity labeling studies, for example, with chloramphenicol, are known to those of skill in the art. See, for example, Cooperman, "Functional sites on the E. coli ribosome as defined by affinity labeling," p. 531–554 (1980), Chambliss et al., in *Ribosomes-Structure, Function and Genetics*, University Park Press, Baltimore; Cooperman, Affinity labeling of ribosomes, *Methods Enzymol.*, 164:341–361 (1988); and Jaynes et al., *Biochemistry*, 17:561–569 (1978). Such methods can be used to determine the binding of the compounds of the present invention to various positions on ribosomal RNA and/or to proteins involved in bacterial protein synthesis.

BIOLOGICAL EXAMPLES

Example 1

Determination of Antibacterial Activity
In Vitro Determination of Antibacterial Activity Bacteria are obtained and phenotyped based on their sensitivity to different antibiotics including those that interfere with ribosomal protein synthesis. Minimal inhibitory concentrations (MICs) are measured in a microdilution broth procedure under NCCLS guidelines. The compounds are serially diluted into Mueller-Hinton broth in 96-well microtiter plates. Overnight cultures of bacterial strains are diluted based on absorbance at 600 nm so that the final concentration in each well was $5 \times 10^5$ cfu/ml. Plates are returned to a 35° C. incubator. The following day (or 24 hours in the case of Enterococci strains), MICs are determined by visual inspection of the plates.

Bacterial strains which may be tested in this model include, but are not limited to, those described herein. Growth conditions may be modified as necessary for each particular strain. Growing conditions and growth media for the strains described herein are known in the art.

Determination of Kill Time

Experiments to determine the time required to kill the bacteria are conducted. These experiments are conducted with both staphylococcus and enterococcus strains.

Briefly, several colonies are selected from an agar plate and grown at 35° C. under constant agitation until a turbidity of approximately $1.5 \times 10^8$ CFU/ml is achieved. The sample is diluted to about $6 \times 10^6$ CFU/ml and incubated at 35° C. under constant agitation. At various times, aliquots are removed and five ten-fold serial dilutions are performed. The pour plate method is used to determine the number of colony forming units (CFUs).

In Vivo Determination of Antibacterial Activity
Acute tolerability studies in mice In these studies, the compounds to be evaluated are administered either intravenously or subcutaneously and observed for 5–15 minutes. If there are no adverse effects, the dose is increased in a second group of mice. This dose incrementation continues until mortality occurs, or the dose is maximized. Generally, dosing begins at 20 mg/kg and increases by 20 mg/kg each time until the maximum tolerated dose (MTD) is achieved.

Bioavailability studies, in mice

Mice are administered the compound to be evaluated either intravenously or subcutaneously at a therapeutic dose (in general, approximately 50 mg/kg). Groups of animals are placed in metabolic cages so that urine and feces may be collected for analysis. Groups of animals (n=3) are sacrificed at various times (10 min, 1 hour and 4 hours). Blood is collected by cardiac puncture and the following organs are harvested: lung, liver, heart, brain, kidney, and spleen. Tissues were weighed and prepared for HPLC analysis. HPLC analysis on the tissue homogenates and fluids is used to determine the concentration of the compound. Metabolic products resulting from changes to the compound are also determined.

Mouse septecemia model

In this model, an appropriately virulent strain of bacteria (most commonly *S. aureus*, or *E. faecalis* or *E. faecium*) is administered intraperitoneally to mice (N=5 to 10 mice per group). The bacteria was combined with hog gastric mucin to enhance virulence. The dose of bacteria (normally $10^5$–$10^7$) is that which is sufficient to induce mortality in all of the mice over a three day period. One hour after the bacteria is administered, the compound to be evaluated is administered in a single dose, either IV or subcutaneously. Each dose is administered to groups of 5 to 10 mice, at doses that typically range from a maximum of about 20 mg/kg to a minimum of less than 1 mg/kg. A positive control (normally β-lactam with β-lactam sensitive strains) is administered in each experiment. The dose at which approximately 50% of the animals are saved is calculated from the results.

Neutropenic thigh model

In this model, antibacterial activity of the compound to be evaluated is evaluated against an appropriately virulent strain of bacteria (most commonly *S. aureus*). Mice are initially rendered neutropenic by administration of cyclophosphamide at 200 mg/kg on day 0 and day 2. On day 4, they are infected in the left anterior thigh by an IM injection of a single dose of bacteria. The mice are administered the compound one hour after the administration of bacteria. At various later times (normally 1, 2.5, 4 and 24 hours) the mice are sacrificed (3 per time point). The thigh is excised, homogenized and the number of CFUs (colony forming units) is determined by plating. Blood is also plated to determine the CFUs in the blood.

Pharmacokinetic studies

The rate at which the compound to be evaluated is removed from the blood can be determined in either rats or mice. In rats, the test animals are cannulated in the jugular vein. A compound is administered via tail vein injection, and at various time points (normally 5, 15, 30, 60 minutes and 2, 4, 6 and 24 hours) blood is withdrawn from the cannula. In mice, a compound is also administered via tail vein injection, and at various time points. Blood is normally obtained by cardiac puncture. The concentration of the remaining compound is determined by HPLC.

PREPARATIVE EXAMPLES

Example 1

Preparation of (113), a Compound of Formula I via Scheme A

Erythromyclamine (100) (10 mmol) is slurried in methanol:anhydrous dimethylformamide, stirred at room temperature, and treated sequentially with diisopropylethyl amine (20 mmol) and Fmoc glycinal (101) (10 mmol) (prepared as described by Salvi et al. *Tetrahedron Lett.* 1994, 35, 1181–1184). After 2 hours the reaction mixture is cooled in an ice water bath and treated further with sodium cyanoborohydride (4.0 mmol) and trifluoroacetic acid (30 mmol). After 2 additional hours the crude product is concentrated under reduced pressure and fractionated by reverse-phase HPLC to afford the desired product (102).

The above product (102) is then dissolved in anhydrous dimethylformamide (10 mL), stirred at room temperature and treated with excess piperidine (1.0 mL). After one hour the crude products are concentrated under reduced pressure and fractionated by reverse-phase HPLC to afford the desired product (103).

Succinic acid (104) (2.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated diacid is treated with compound (103) (4.0 mmol) and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

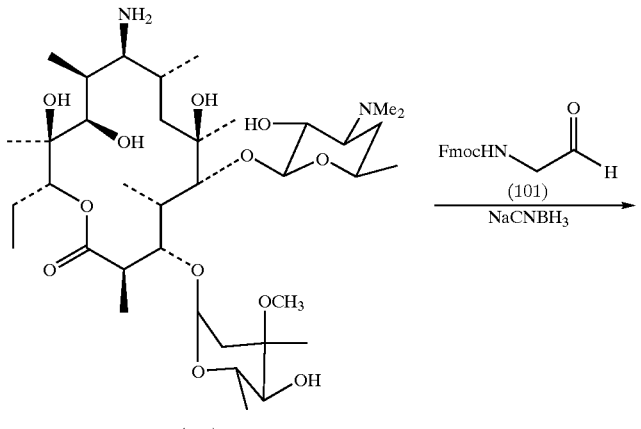
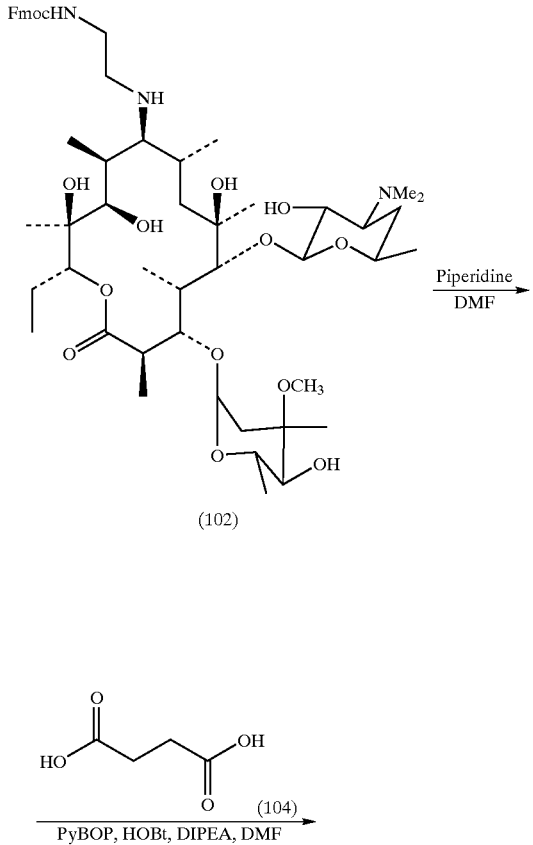
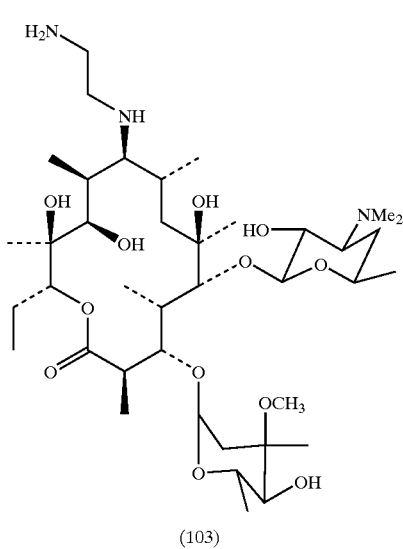
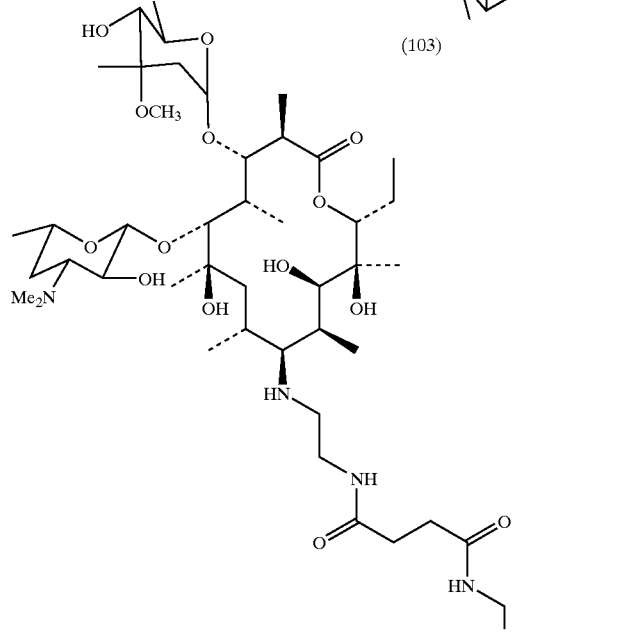

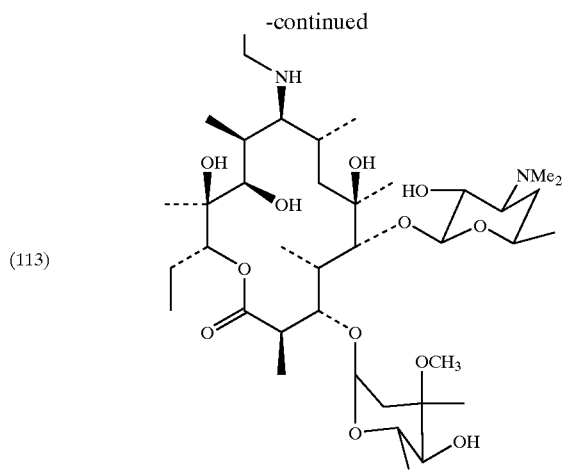

(113)

Example 2

Preparation of (108), a Compound of Formula II via Scheme B

Erythromyclamine (100) (34.0 mmol) is dissolved in THF under a nitrogen atmosphere. Di-tert-butyl dicarbonate (Boc$_2$O) (68.0 mmol) dissolved in dichloromethane is added dropwise to the stirred solution. The course of the reaction is followed by TLC and stirring is continued at room temperature until the reaction is judged complete. The reaction mixture is evaporated giving a precipitate that is collected by filtration. The precipitate is rinsed with ether to afford the desired product, which is treated with acetic anhydride in dichloromethane and purified by silica gel chromatography. The product (10 mmol) is then dissolved in toluene, stirred in an ice/water bath, and treated sequentially with K$_2$CO$_3$ (100 mmol) and carbonyldiimidazole (10 mmol). The ice bath is removed and the reaction mixture is allowed to warm to room temperature. The imidazolide (105) thus produced is used without further manipulation in the coupling reactions described below.

1,4-Diaminobutane (106) (2.0 mmol) is dissolved in toluene/DMF, stirred at room temperature, and treated sequentially with diisopropylethyl amine (4.0 mmol) and imidazolide (105) (4.0 mmol) prepared above. After 2 hours, volatiles are removed under vacuum and the crude product is purified by silica gel chromatography to afford the desired product (107).

Compound (107) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at refux for 1 hour. Volatiles are removed under vacuum and the crude is fractionated by reverse-phase HPLC to afford the title product after lyopholization of the appropriate fractions.

The chemistry is detailed below in the following reaction scheme:

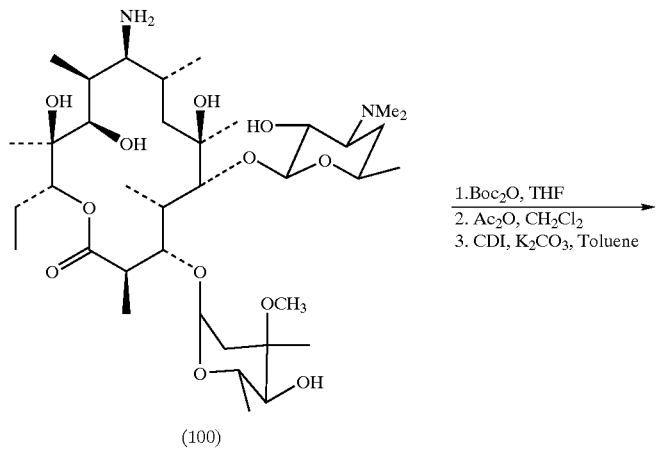

1. Boc$_2$O, THF
2. Ac$_2$O, CH$_2$Cl$_2$
3. CDI, K$_2$CO$_3$, Toluene (100)

-continued
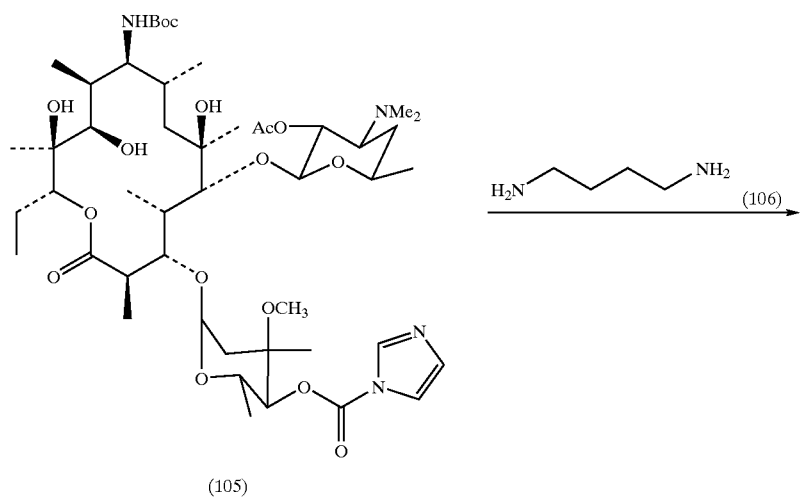
(105)
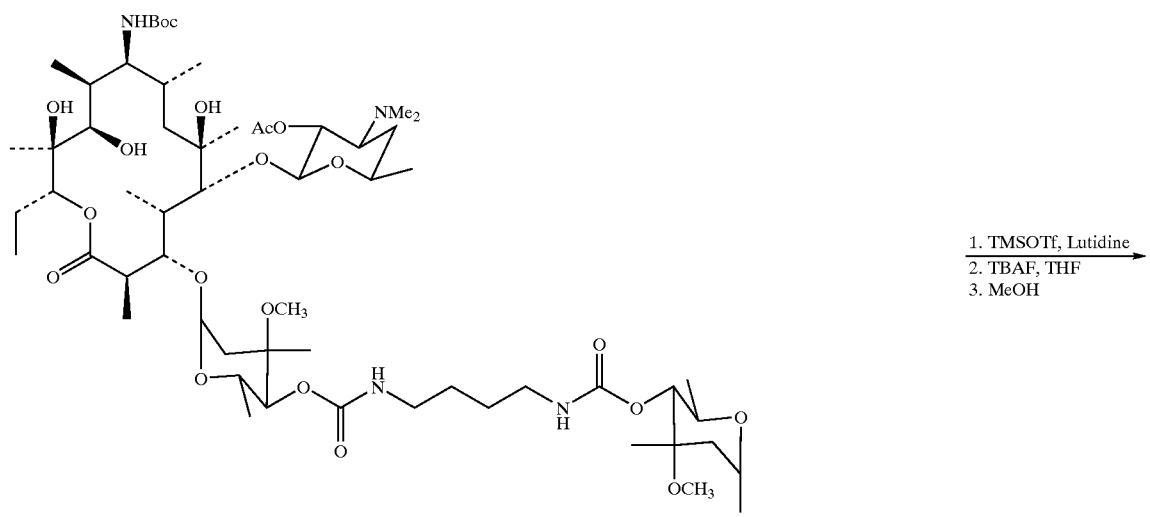
1. TMSOTf, Lutidine
2. TBAF, THF
3. MeOH
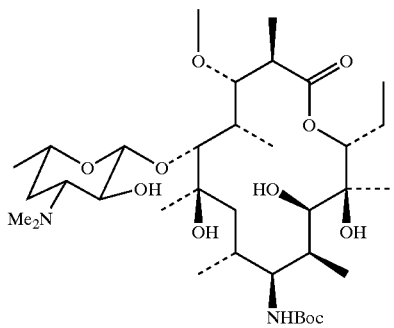
(107)

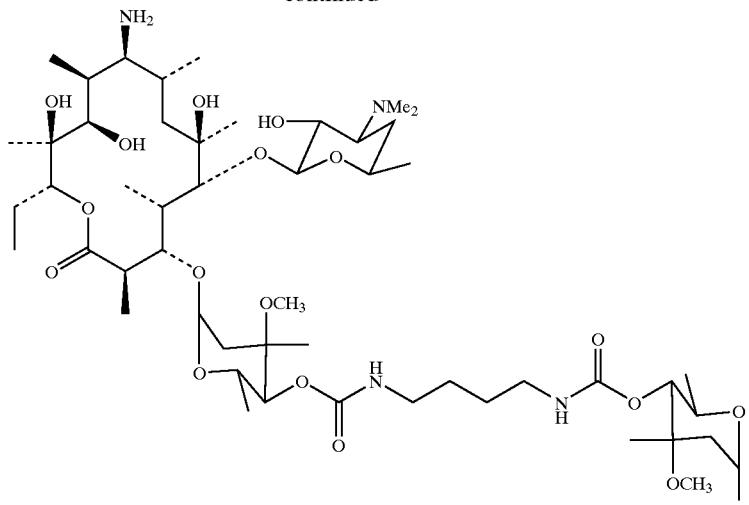

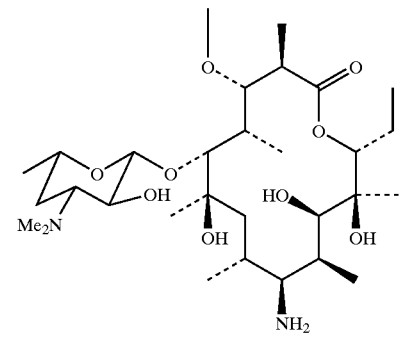

(108)

Example 3

Preparation of (112), a Compound of Formula III via Scheme C

A solution of (105) (6 mmol), prepared as described in Example 2, and 6-aminocaproic acid (109) (6 mmol) in DMF. The course of the reaction is followed by thin layer chromatography. When reaction has occurred, the reaction mixture is concentrated under reduced pressure to give the crude product. The desired compound (110) is obtained by purification of the crude product by use of HPLC.

Compound (110) (4.0 mmol) is dissolved in 10 mL anhydrous dimethylformamide and treated sequentially with compound (103) (4.0 mmol), hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the crude is fractionated by reverse-phase HPLC to afford the desired product (111) after lyopholization of the appropriate fractions.

Compound (111) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction followed by TLC. When judged complete, the mixture is diluted two-fold with methanol and heated at reflux for 1 hour. Volatiles are removed under vacuum and the crude is fractionated by reverse-phase HPLC to afford the title product after lyopholization of the appropriate fractions.

The chemistry is detailed below in the following reaction scheme:

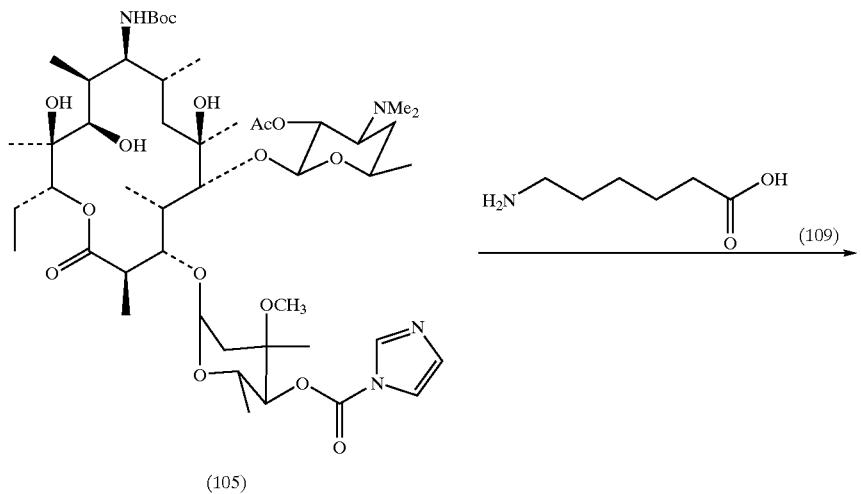
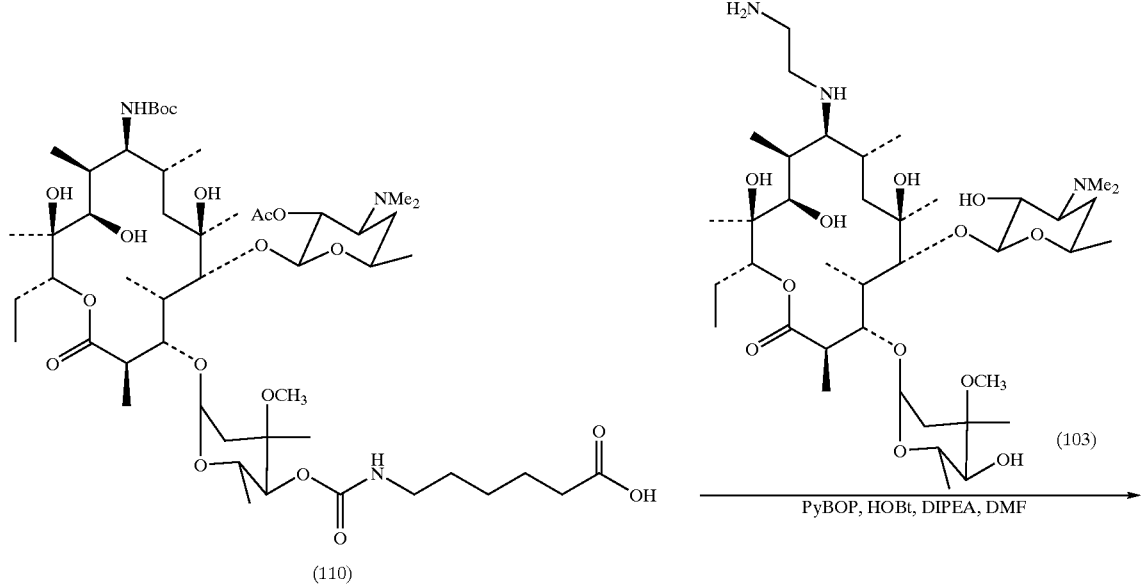
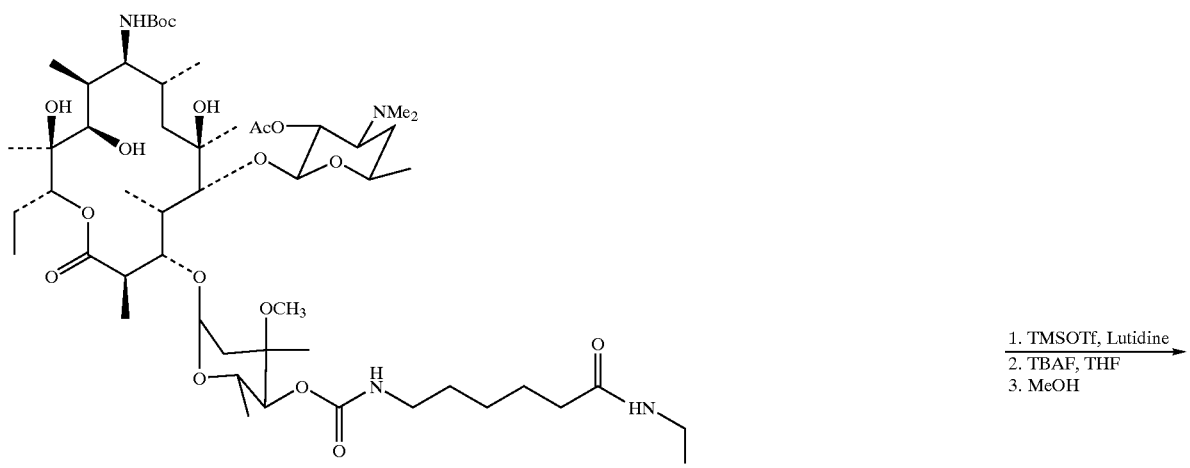

-continued

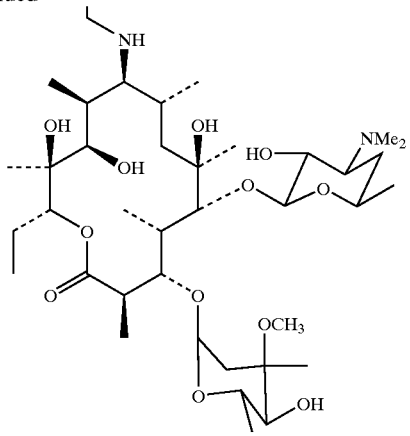

(111)

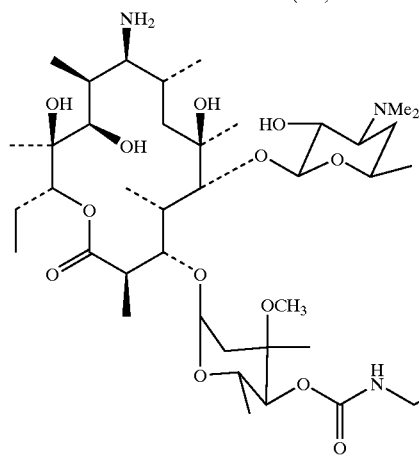

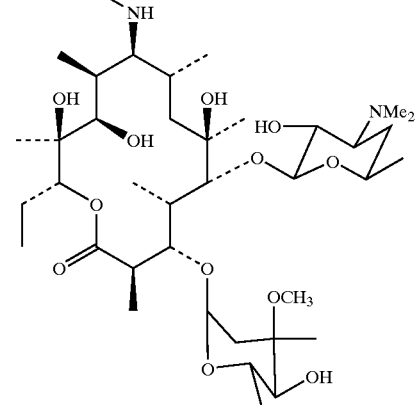

(112)

Example 4

Preparation of (203), a Compound of Formula IV via Scheme D

Compound (201) (1.0 mmol) is dissolved in toluene, stirred in an ice/water bath, and treated sequentially with $K_2CO_3$ (10 mmol) and carbonyldiimidazole (1.0 mmol). The ice bath is removed and the reaction mixture is allowed to warm to room temperature. The imidazolide (202) thus produced is used without further manipulation in the coupling reactions described below.

A solution of (202) (1.0 mmol) in toluene/DMF with 1,4-diaminobutane (106) (0.5 mmol) is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by silica gel chromatography to afford the title product.

Compound (201) is reported in J. Med. Chem. 1998, 41, 3727–3735.

The chemistry is detailed below in the following reaction scheme:

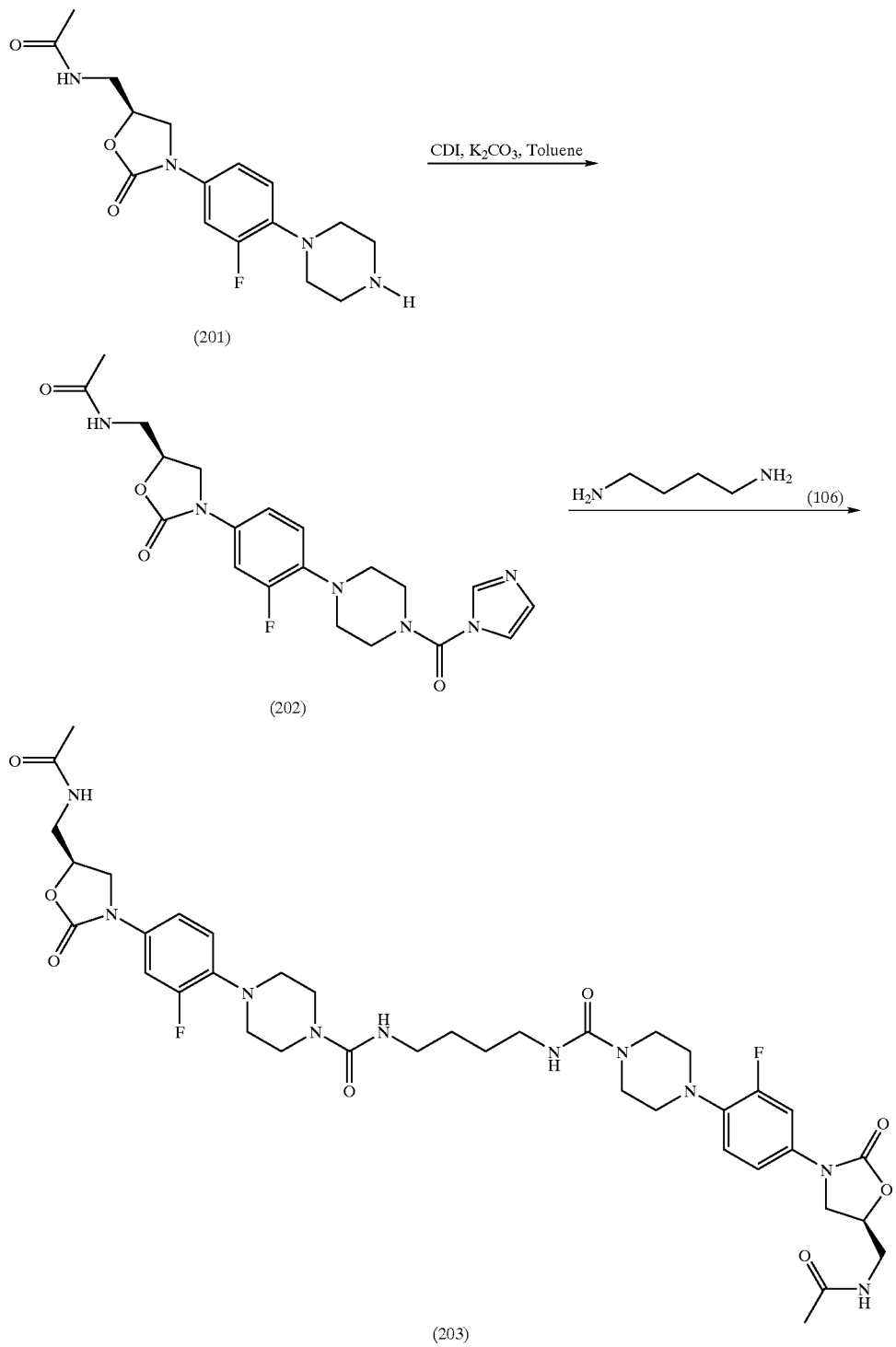

Example 5

Preparation of (206), a Compound of Formula V via Scheme E

Adipic acid (205) (2.0 mmol) is dissolved in 10 mL anhydrous dimethylformamide and treated sequentially with compound (204) (4.0 mmol), hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the product is purified by silica gel chromatography to afford the title product.

Compound (204) is reported in J. Med. Chem. 1996, 49, 673–679.

The chemistry is detailed below in the following reaction scheme:

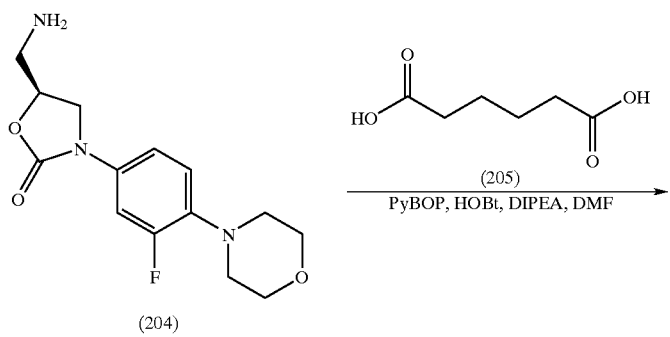

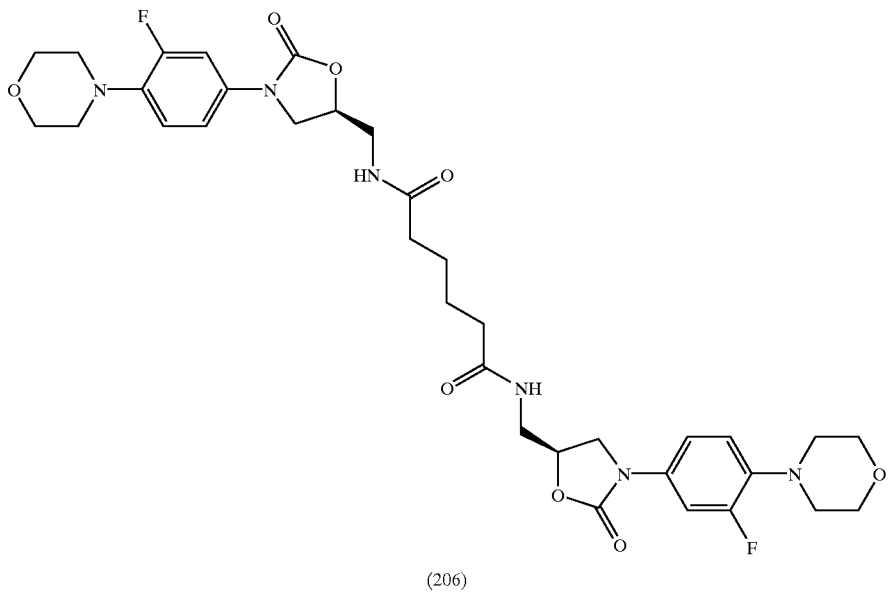

Example 6

Preparation of (208), a Compound of Formula VI via Scheme F

A solution of (202) (6 mmol), prepared as described in Example 4, and 6-aminocaproic acid (109) (6 mmol) in toluene/DMF is prepared under argon in a flask equipped with magnetic stirrer and drying tube. The course of the reaction is followed by thin layer chromatography. When reaction has occurred, the reaction solution is diluted with ethyl acetate and washed with aqueous HCl and then water. The organic layer is dried $Na_2SO_4$), filtered and concentrated under reduced pressure to give the crude product. The desired compound (207) is obtained by purification of the crude product by use of HPLC, Compound (207) (4.0 mmol) is dissolved in 10 mL anhydrous dimethylformamide and treated sequentially with compound (204) (4.0 mmol), hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the crude is fractionated by reverse-phase HPLC to afford the title product after lyopholization of the appropriate fractions.

Compound (204) is reported in J. Med. Chem. 1996, 49, 673–679.

The chemistry is detailed below in the following reaction scheme:

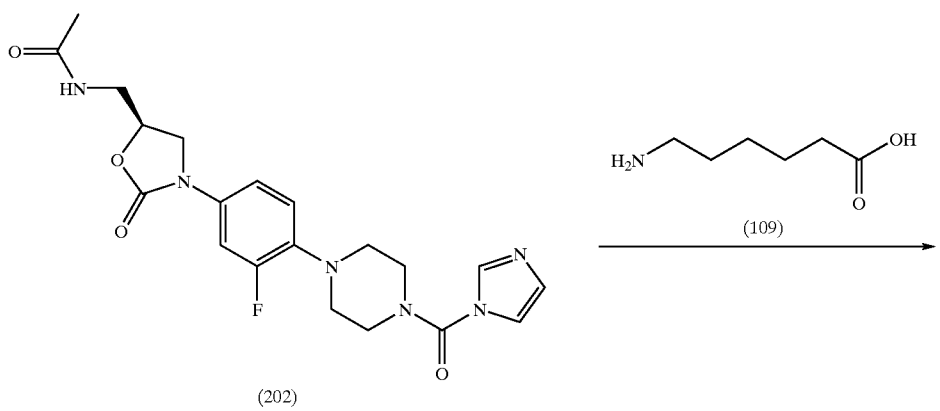

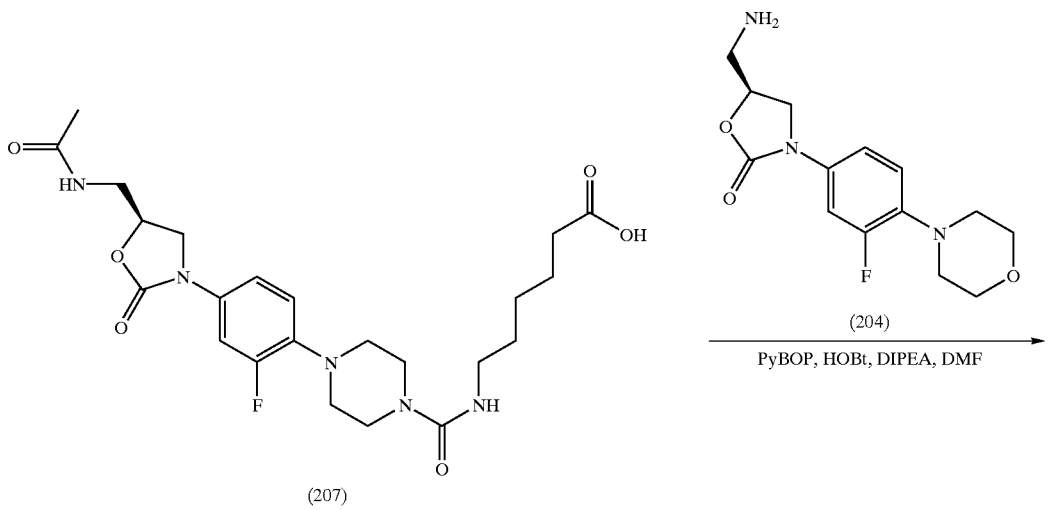

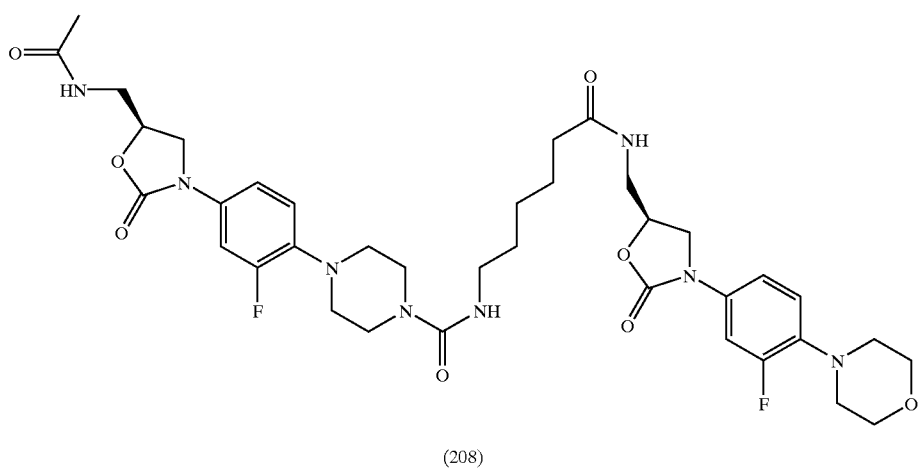

Example 7

Preparation of (303), a Compound of Formula VII via Scheme G

A solution of 20 mmols of compound (301) in DMF with 10 mmols of 1,6-dibromohexane (302) and 40 mmols of potassium carbonate is heated as necessary and the reaction followed by TLC. When reaction has occurred, the reaction mixture is concentrated under reduced pressure to give the crude product, which is fractionated by reverse-phase HPLC to afford the title product after lyopholization of the appropriate fractions.

Compound (301) is U-57930E and is reported in *Antimicrobial Agents Chemother,* 21:902–905 (1982).

The chemistry is detailed below in the following reaction scheme:

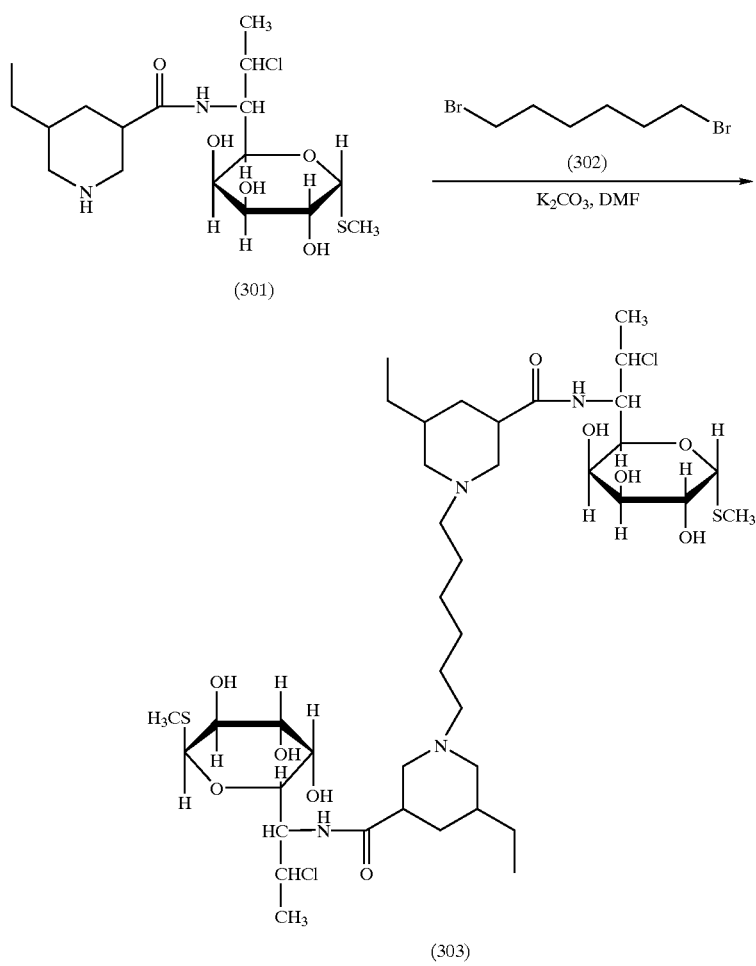

Example 8

Preparation of (403), a Compound of Formula VIII via Scheme H

A solution of 20 mmols of Streptomycin (401) in DMF with 10 mmols of 1,4-dibromobutane (402) and 40 mmols of potassium carbonate is heated as necessary and the reaction followed by TLC. When reaction has occurred, the reaction mixture is concentrated under reduced pressure to give the crude product, which is fractionated by reverse-phase HPLC to afford the title product after lyopholization of the appropriate fractions.

The chemistry is detailed below in the following reaction scheme:

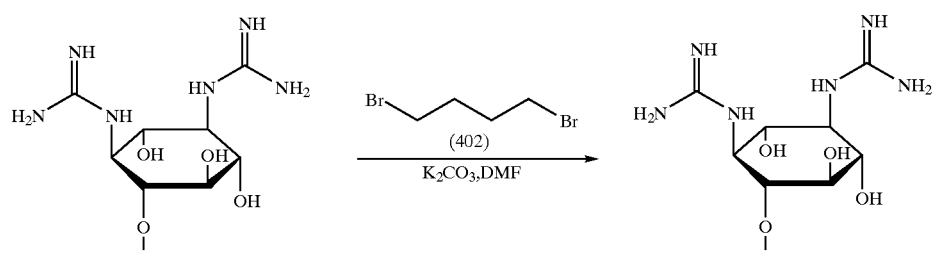

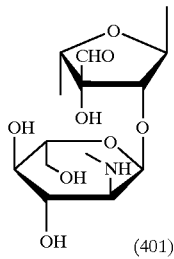

(401)

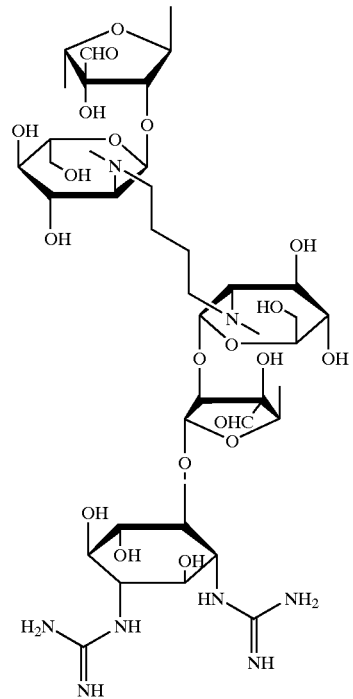

(403)

Example 9

Preparation of (404), a Compound of Formula VIII via Scheme H

Adipic acid (205) (2.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated diacid is treated with Streptomycin (401) (4.0 mmol) and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

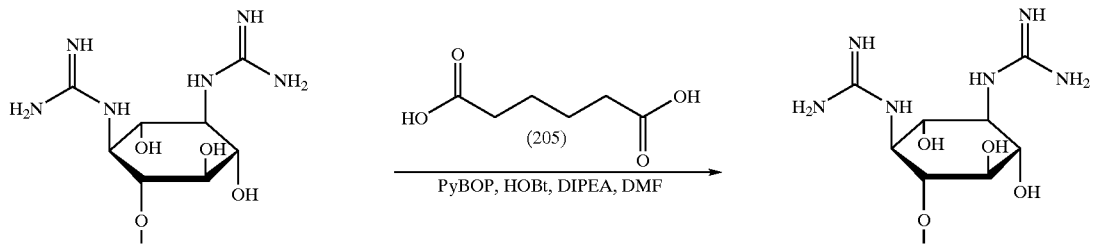

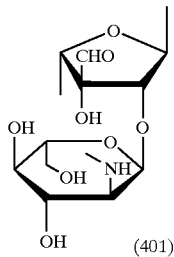

(401)

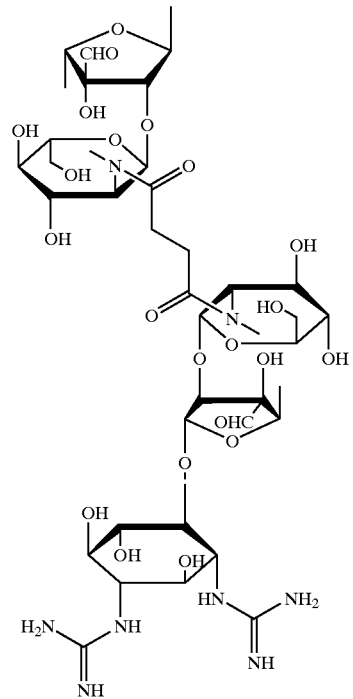

(404)

Example 10

Preparation of (406), a Compound of Formula IX via Scheme I 1,4-Diaminobutane (106) (10 mmol) is slurried in methanol:anhydrous dimethylformamide, stirred at room temperature and treated sequentially with diisopropylethyl amine (20 mmol) and Streptomycin (401) (20 mmol). After 2 hours the reaction mixture is cooled in an ice eater bath and treated further with sodium cyanoborohydride (4.0 mmol) and trifluoroacetic acid (30 mmol) After 2 additional hours the crude product is precipitated by dropwise addition to a ten-fold volume of acetonitrile, and then fractionated by reverse-phase HPLC to afford the title product.

The chemistry is detailed below in the following reaction scheme:

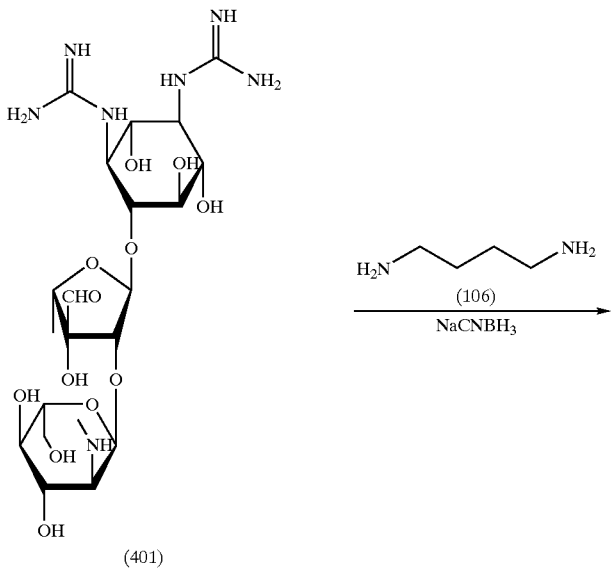

-continued

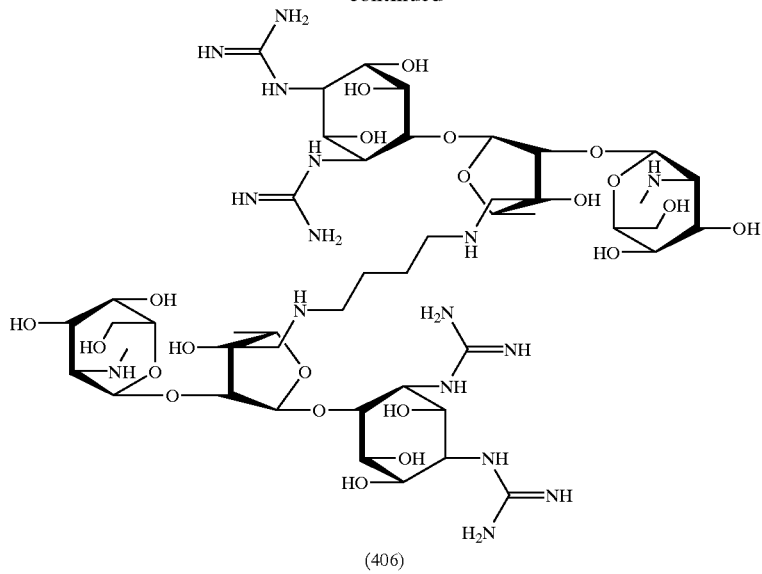

(406)

Example 11

Preparation of (409), a Compound of Formula X via Scheme J

Streptomycin (401) (10 mmol) is slurried in methanol:anhydrous dimethylformamide, stirred at room temperature, and treated sequentially with diisopropylethyl amine (20 mmol) and Fmoc glycinal (101) (10 mmol) (prepared as described by Salvi et al. Tetrahedron Lett. 1994, 35, 1181–1184). After 2 hours the reaction mixture is cooled in an ice water bath and treated further with sodium cyanoborohydride (4.0 mmol) and trifluoroacetic acid (30 mmol). After 2 additional hours the crude product is precipitated by dropwise addition to a ten-fold volume of acetonitrile, and then fractionated by reverse-phase HPLC to afford the desired product (407).

The above product (407) is then dissolved in anhydrous dimethylformamide (10 mL), stirred at room temperature and treated with excess piperidine (1.0 mL). After one hour the crude products are precipitated by dropwise addition to 100 mL acetonitrile with vigorous stirring. The crude products are fractionated by reverse-phase HPLC to afford the desired product (408).

Compound (408) (20 mmol) is slurried in methanol:anhydrous dimethylformamide, stirred at room temperature, and treated sequentially with diisopropylethyl amine (20 mmol) and Streptomycin (401) (20 mmol). After 2 hours the reaction mixture is cooled in an ice water bath and treated further with sodium cyanoborohydride (4.0 mmol) and trifluoroacetic acid (30 mmol). After 2 additional hours the crude product is precipitated by dropwise addition to a ten-fold volume of acetonitrile, and then fractionated by reverse-phase HPLC to afford the title product.

The chemistry is detailed below in the following reaction scheme:

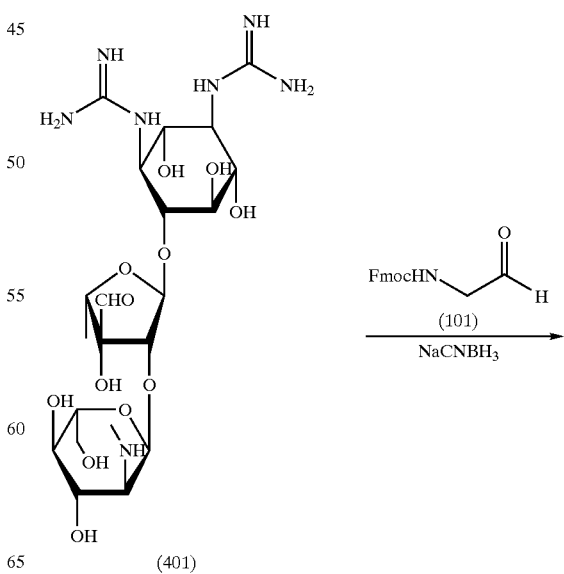

-continued

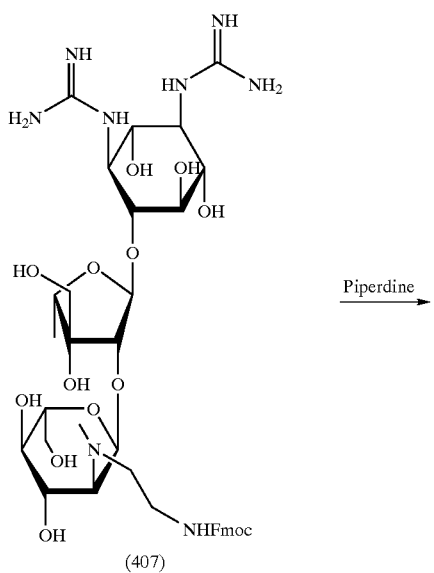

(407)

→ Piperdine

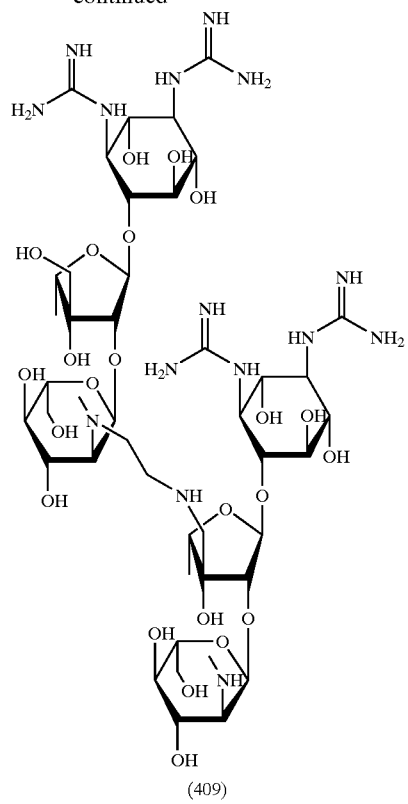

(409)

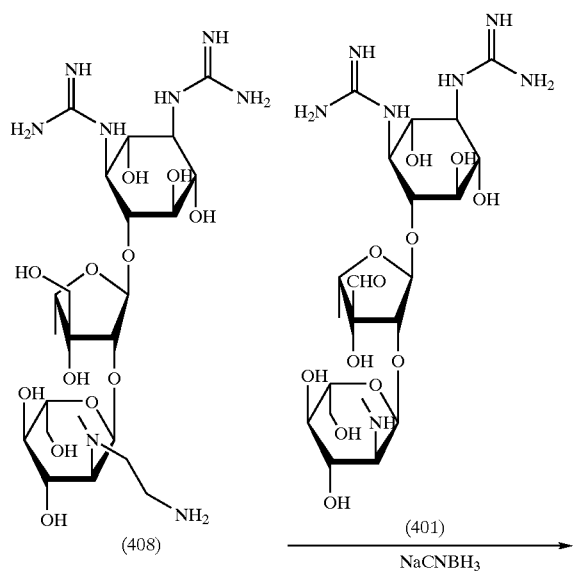

(408) + (401) →NaCNBH₃

Example 12
Preparation of (504), a Compound of Formula XI via Scheme K

Tetracycline (501) (10 mmol) is slurried in methanol:anhydrous dimethylformamide, stirred at room temperature, and treated sequentially with diisopropylethyl amine (20 mmol) and Fmoc glycinal (101) (10 mmol) (prepared as described by Salvi et al. *Tetrahedron Lett.* 1994, 35, 1181–1184). After 2 hours the reaction mixture is cooled in an ice water bath and treated further with sodium cyanoborohydride (4.0 mmol) and trifluoroacetic acid (30 mmol). After 2 additional hours the crude product is concentrated under reduced pressure and then fractionated by reverse-phase HPLC to afford the desired product (502).

The above product (502) is then dissolved in anhydrous dimethylformamide (10 mL), stirred at room temperature and treated with excess piperidine (1.0 mL). After one hour the crude product is concentrated under reduced pressure and then fractionated by reverse-phase HPLC to afford the desired product (503).

Adipic acid (205) (2.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated diacid is treated with compound (503) (4.0 mmol) and the coupling reaction mixture is stirred overnight at room temperature. Volatiles are removed under vacuum and the crude is fractionated by reverse-phase HPLC to afford the title product after lyopholization of the appropriate fractions.

Compound (501) is reported in Can. J. Chem. 1965, 43, 1382–1388; CAS 1771-31-9, 53864-51-0

The chemistry is detailed below in the following reaction scheme:

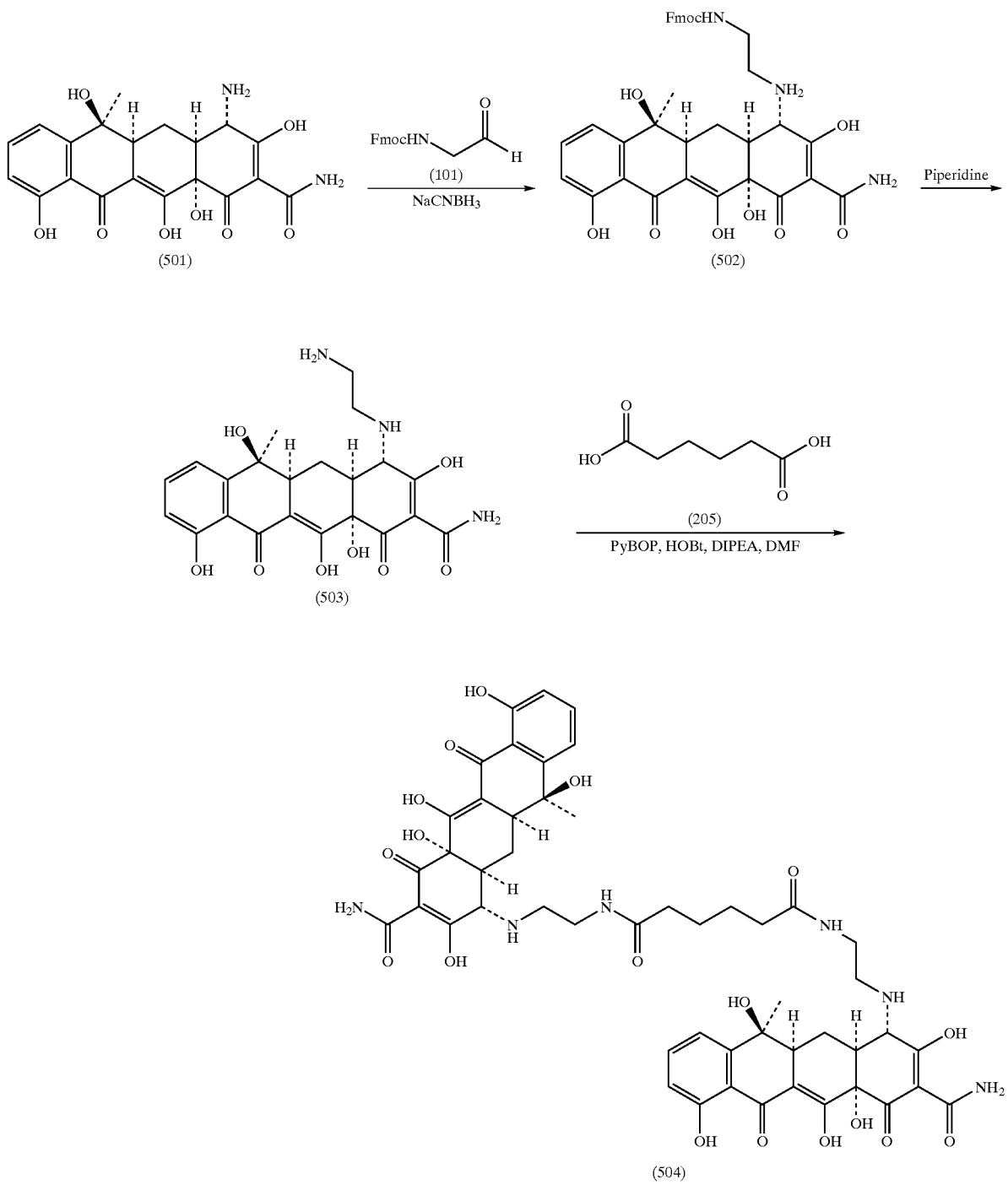

Example 13

Preparation of (507), a Compound of Formula XII via Scheme L

Compound (505) (1.0 mmol) is dissolved in toluene, stirred in an ice/water bath, and treated sequentially with $K_2CO_3$ (10 mmol) and carbonyldiimidazole (1.0 mmol). The ice bath is removed and the reaction mixture is allowed to warm to room temperature. The imidazolide (506) thus produced is used without further manipulation in the coupling reactions described below.

A solution of (506) (1.0 mmol) in toluene/DMF with 1,4-diaminobutane (106) (0.5 mmol) is heated as necessary in a sealed vessel and the reaction followed by TLC. When judged complete, volatiles are removed under vacuum and the crude is fractionated by reverse-phase HPLC to afford the title product after lyopholization of the appropriate fractions.

Compound (505) is reported in J. Med. Chem. 1994, 37, 3205–3211.

The chemistry is detailed below in the following reaction scheme:

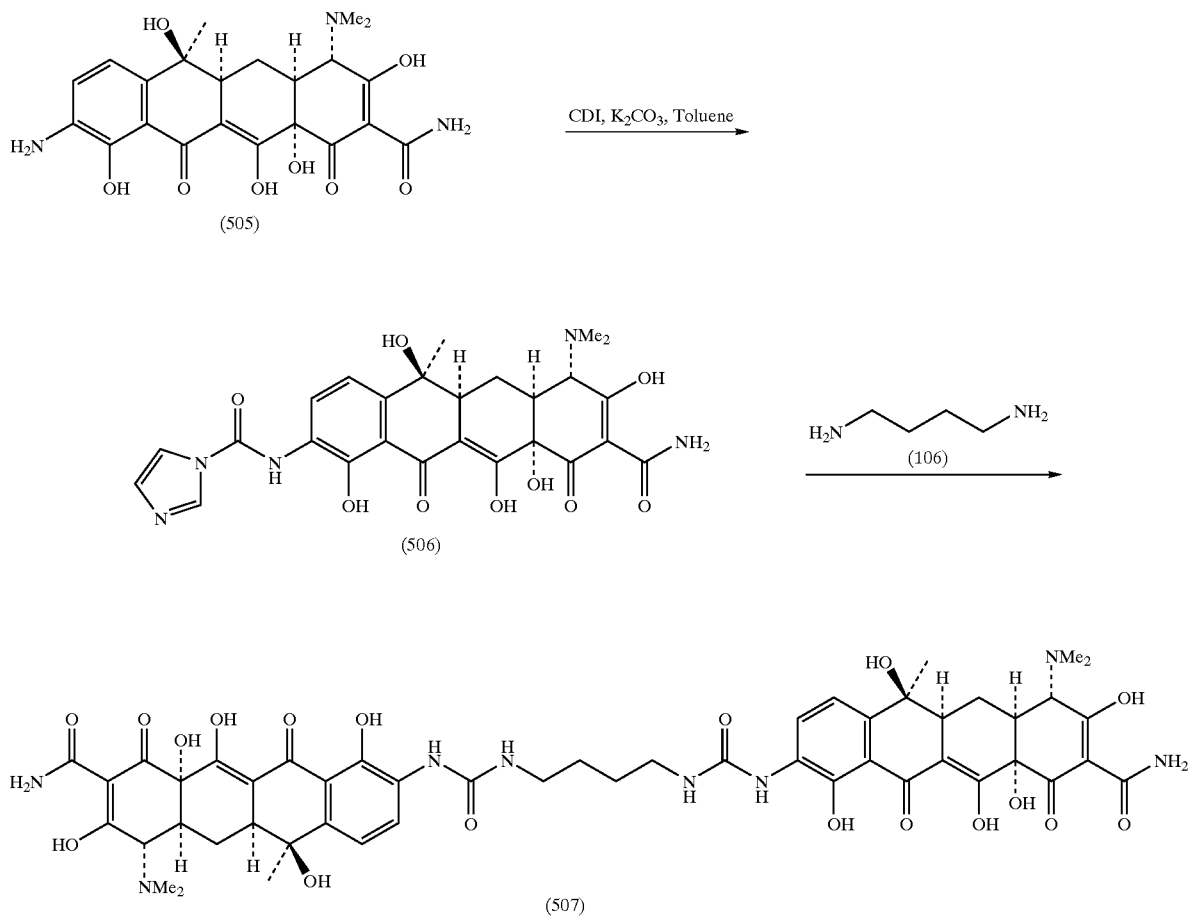

Example 14

Preparation of (509), a Compound of Formula XIII via Scheme M

A solution of (506) (6 mmol), prepared as described in Example 13, in toluene/DMF with 6-aminocaproic acid (109) (6 mmol) is heated as necessary in a sealed vessel and the reaction followed by TLC. When judged complete, volatiles are removed under vacuum and the crude is fractionated by reverse-phase HPLC to afford the desired product (508) after lyopholization of the appropriate fractions.

Compound (508) (4.0 mmol) is dissolved in 10 mL anhydrous dimethylformamide and treated with compound (503) (4.0 mmol), prepared as described in Example 12, hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

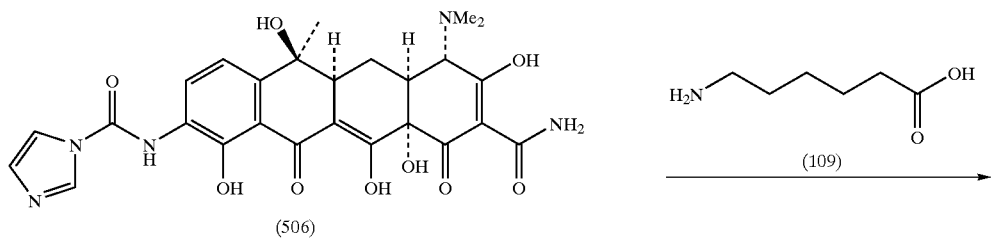

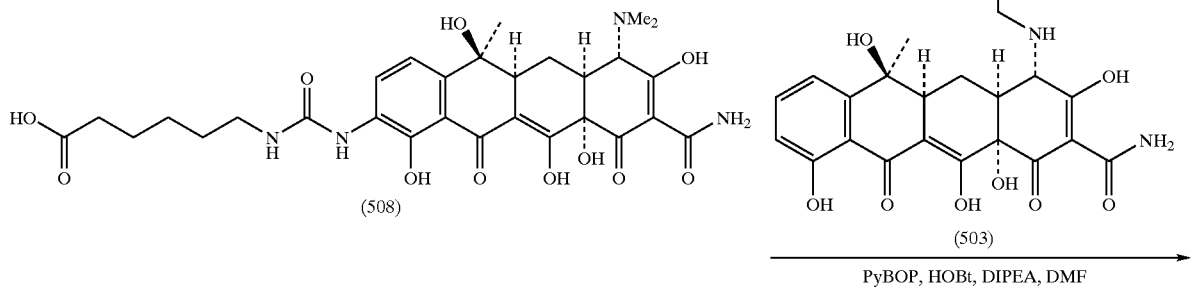

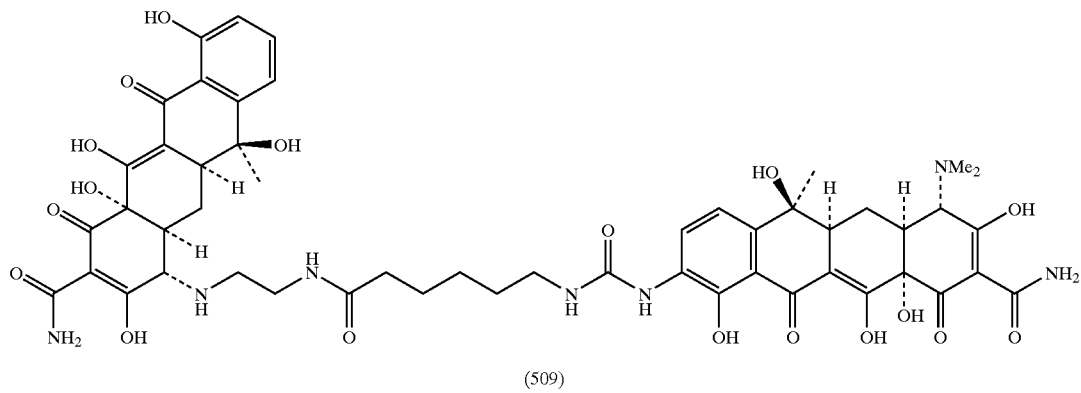

Example 15

Preparation of (605), a Compound of Formula XIV via Scheme N

Pristinamycin I (601) (10 mmol) is dissolved in MeOH, stirred at room temperature and treated sequentially with formalin (11 mmol), morpholine (11 mmol) and methanesulfonic acid (1 mmol), and then heated to 40° C. for 8 hours. The reaction mixture is partitioned between saturated sodium bicarbonate solution and ethyl acetate. The organic phase is dried over anhydrous sodium sulfate, and volatiles removed under reduced pressure to afford crude morpholine adduct (602) which is used without further purification.

Compound (602) is dissolved in ethyl acetate, treated with a mixture of sodium acetate and acetic acid, and heated to 45° C. for 4 hours. The reaction mixture is then washed with sodium bicarbonate solution, dried, filtered, evaporated, and purified by chromatography to afford the desired product (603).

Piperazine (5.0 mmol) is dissolved in 10 mL anhydrous tetrahydrofuran and stirred under nitrogen in a dry ice/acetone bath. A solution of 1.0 M butyl lithium (11 mmol) is added via syringe, and the mixture is stirred for 15 minutes. At this point a solution of ethylene sulfide (11 mmol) in 1 mL anhydrous tetrahydrofuran is added dropwise via syringe over 5 minutes. The reaction mixture is then removed from the cooling bath and allowed to slowly rise to room temperature, where it is stirred for 2 hours. The reaction mixture is then quenched with ammonium chloride. Volatiles are then removed under reduced pressure and the crude product is fractionated by silica gel chromatography to afford piperazine thiol (604). A solution of 10 mmols of (603) in acetone with 5 mmols of (604) in acetone is cooled to −20° C. and the reaction followed by TLC. When judged complete, volatiles are removed under vacuum and the crude is fractionated by reverse-phase HPLC to afford the title product after lyopholization of the appropriate fractions.

The chemistry is detailed below in the following reaction scheme:

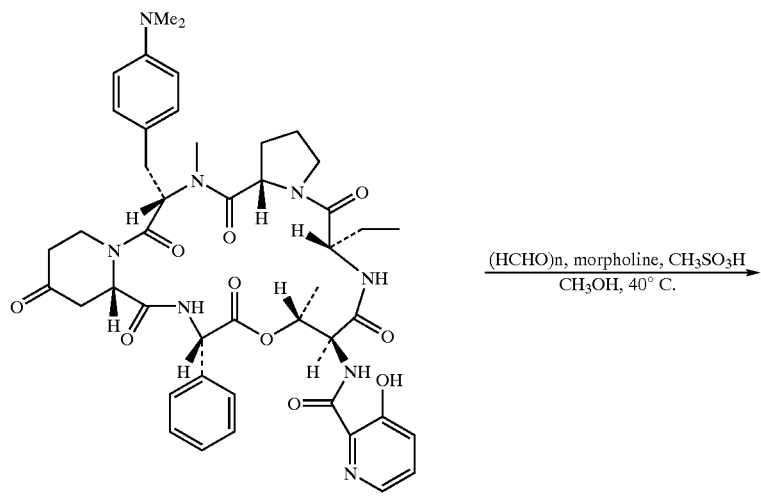
(601)
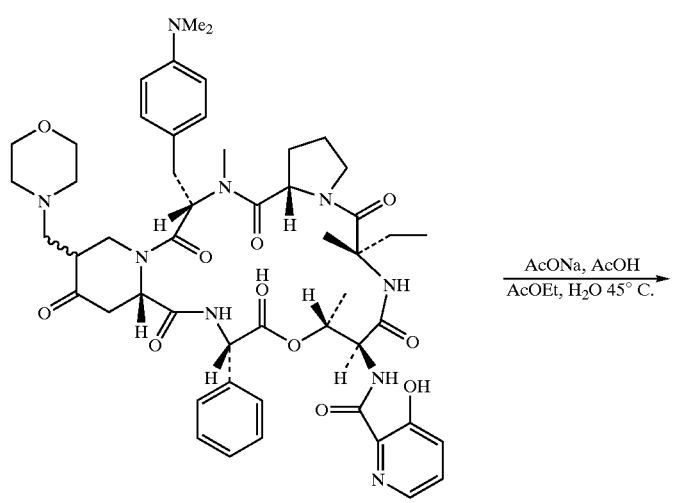
(602)
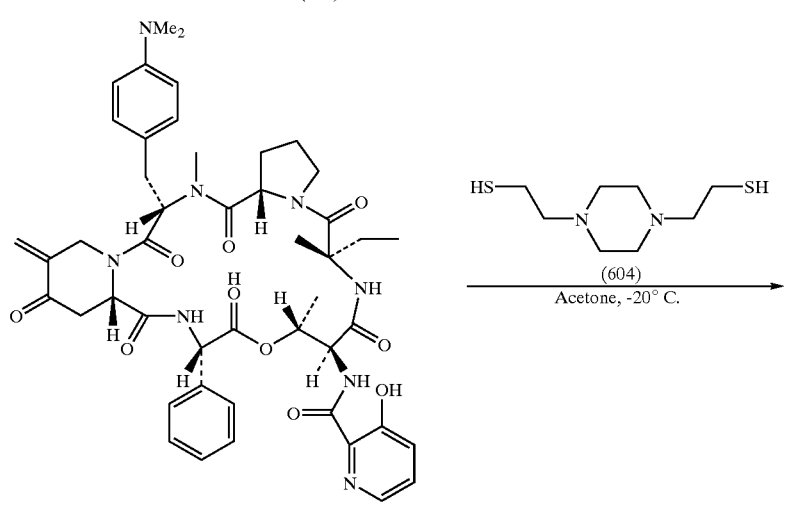
(603)

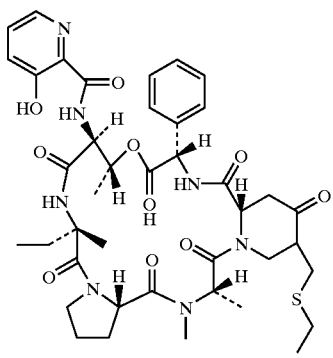

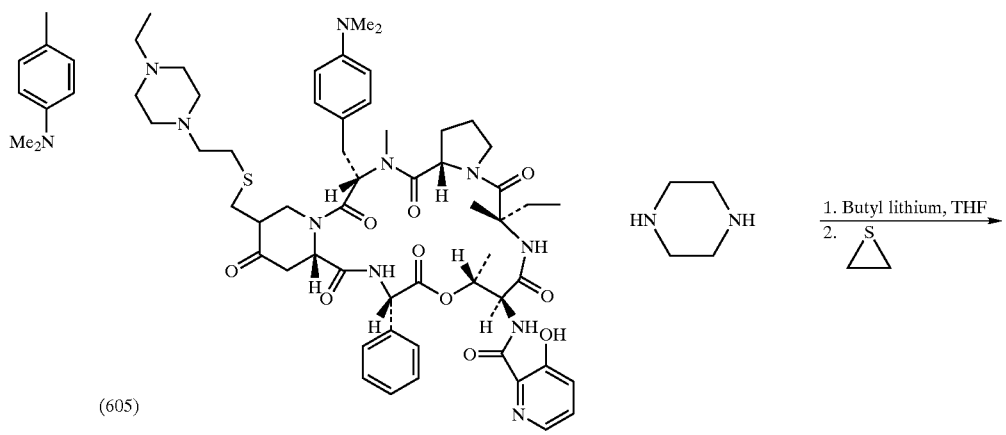

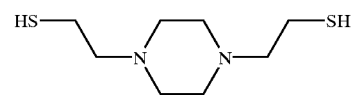

Example 16

Preparation of (608), a Compound of Formula XV via Scheme O

To a solution of Quinupristin (606) (5 mmol) in water acidified to pH 2 with HCl is added zinc (40 mmol). The reaction mixture is filtered and the filtrate is diluted with $Na_2CO_3$, extracted with $CH_2Cl_2$, dried over $MgSO_4$ and concentrated. The crude product is purified by chromatography over silica gel to afford compound (601).

Adipic acid (205) (2.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated diacid is treated with compound (607) (4.0 mmol) and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

147 148
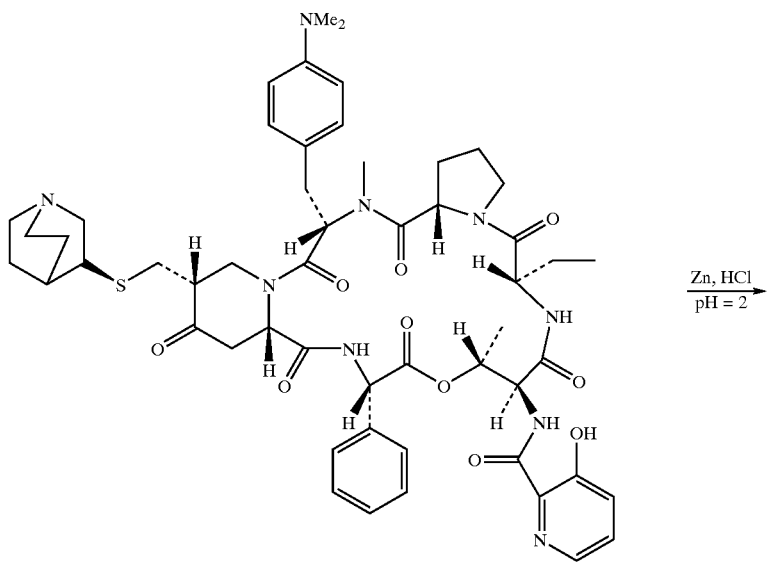
(606)
Zn, HCl
―――――→
pH = 2
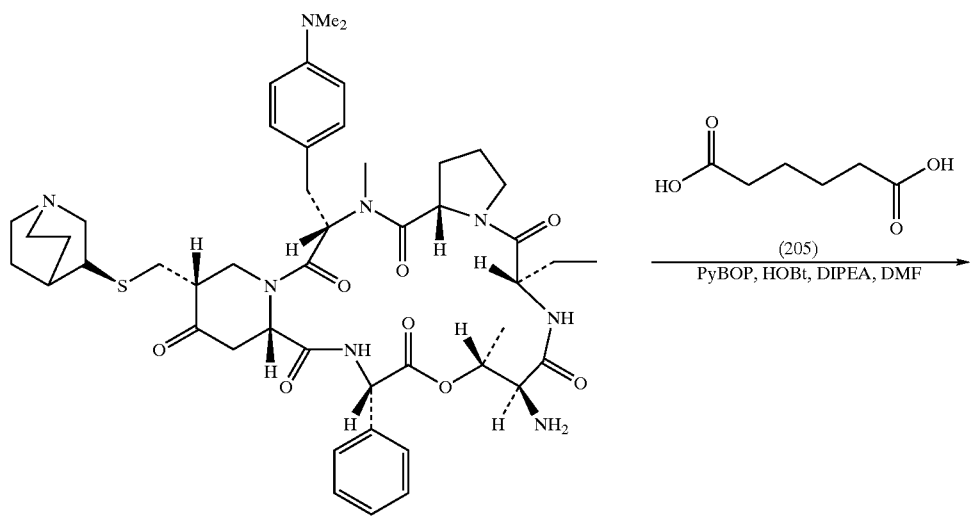
(607)
(205)
―――――――――――→
PyBOP, HOBt, DIPEA, DMF -continued

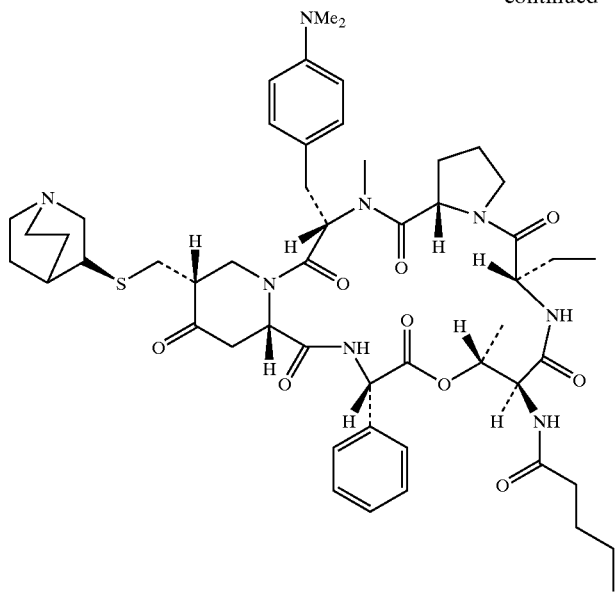

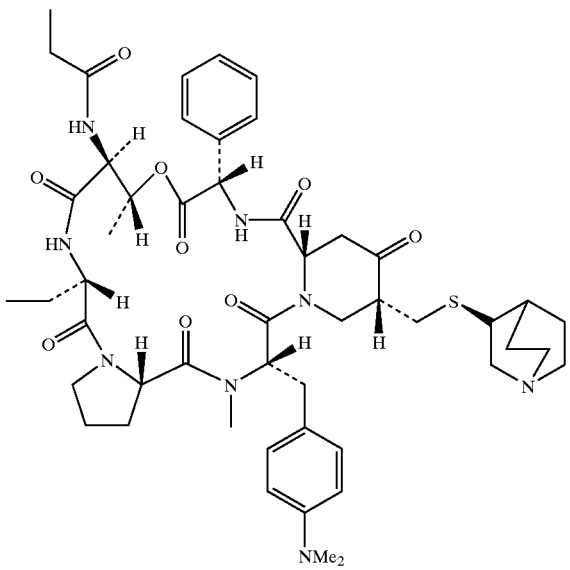

(608)

Example 17

Preparation of (611), a Compound of Formula XVI via Scheme P

A solution of 20 mmols of (603), prepared as described in Example 15, in acetone with 20 mmols of 3-mercaptopropionic acid (609) is cooled to –20° C. and the reaction followed by TLC. When judged complete, volatiles are removed under vacuum and the crude product is purified by chromatography to afford the desired product (610).

Compound (610) (4.0 mmol) is dissolved in 10 mL anhydrous dimethylformamide and treated sequentially with compound (607) (4.0 mmol), prepared as described in Example 16, hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:
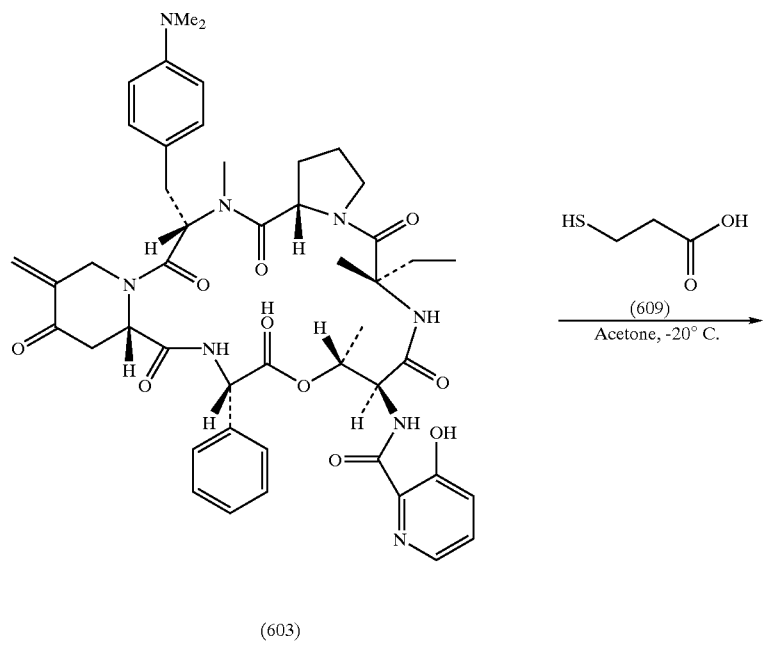
(603)
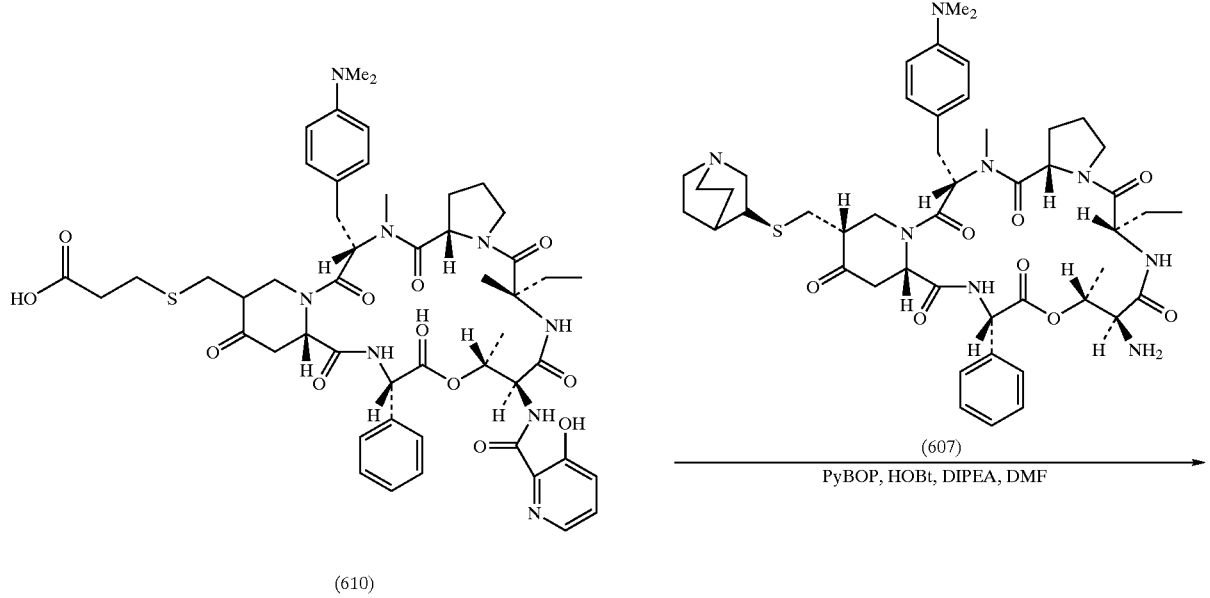
(610)

-continued

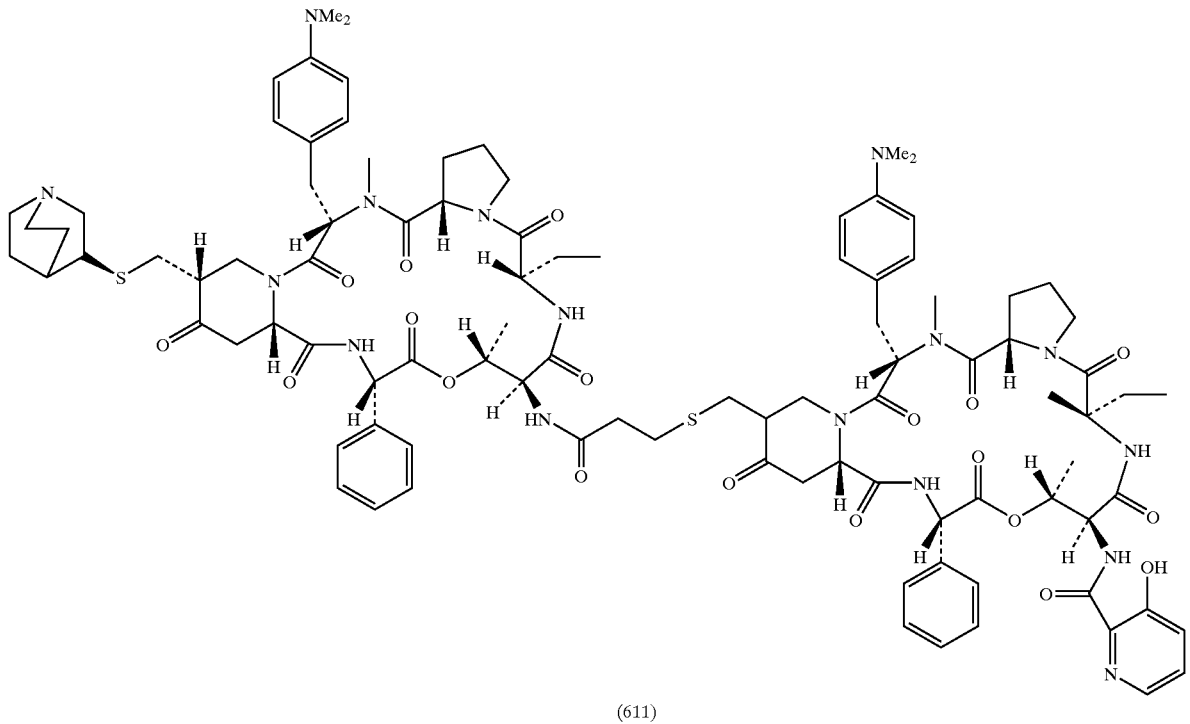

(611)

Example 18

Preparation of (613), a Compound of Formula XVII via Scheme Q

A solution of 20 mmols of Pristinamycin II (612) in acetone with 10 mmols of (604), prepared as described in Example 15, is cooled to -20° C. and the reaction followed by TLC. When judged complete, the mixture is partitioned between ethyl acetate and water and the organic phase washed with water, dried over sodium sulfate and the solvent removed in vacuo. The residue is purified by chromatography to afford the title structure.

The chemistry is detailed below in the following reaction scheme:

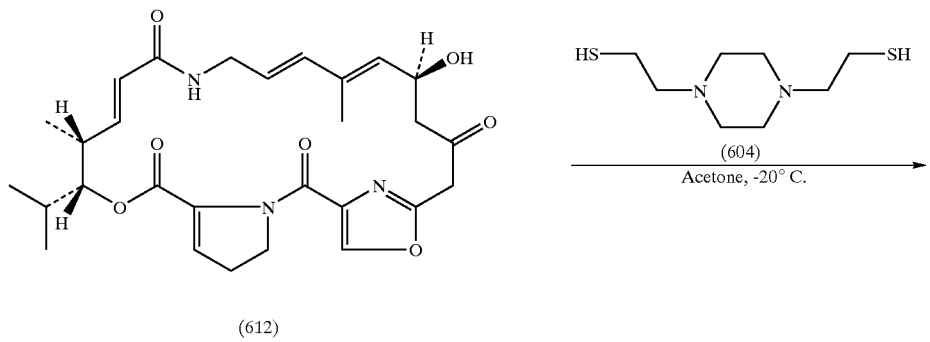

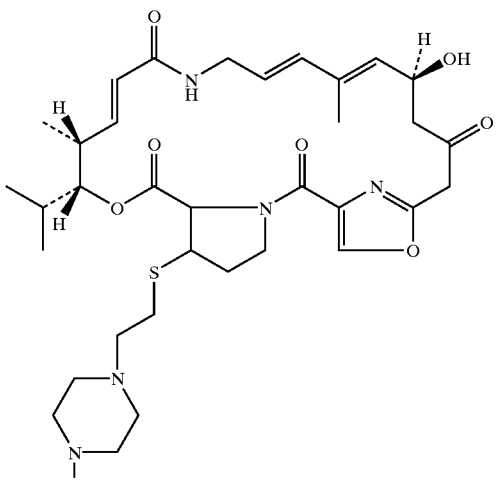

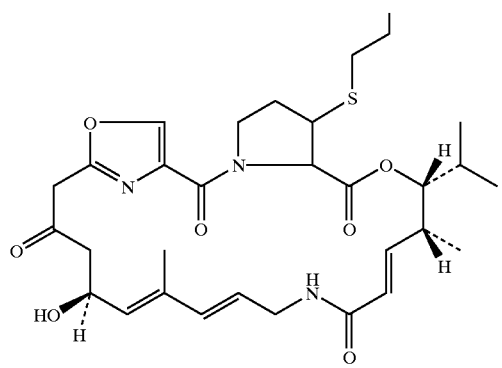

(613)

Example 19

Preparation of (616), a Compound of Formula XVIII via Scheme R

A solution of 20 mmols of (603) in acetone with 20 mmols of 1,6-hexanedithiol (614) is cooled to −20° C. and the reaction followed by TLC. When judged complete, volatiles are removed under vacuum and the crude is fractionated by reverse-phase HPLC to afford the desired product (615) after lyopholization of the appropriate fractions.

A solution of 20 mmols of (615) in acetone with 20 mmols of Pristinamycin II (612) is cooled to −20° C. and the reaction followed by TLC. When judged complete, volatiles are removed under vacuum and the crude is fractionated by reverse-phase HPLC to afford the title product after lyopholization of the appropriate fractions.

The chemistry is detailed below in the following reaction scheme:

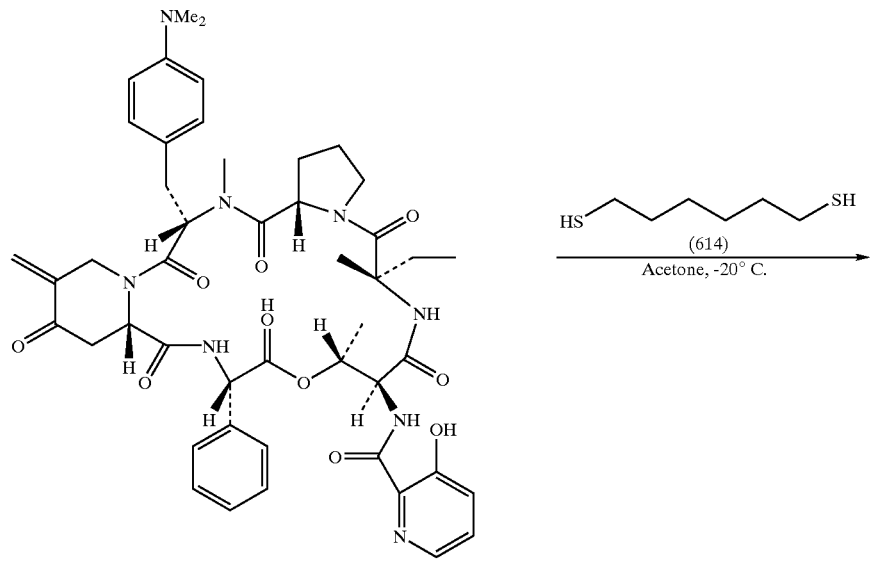
(603)
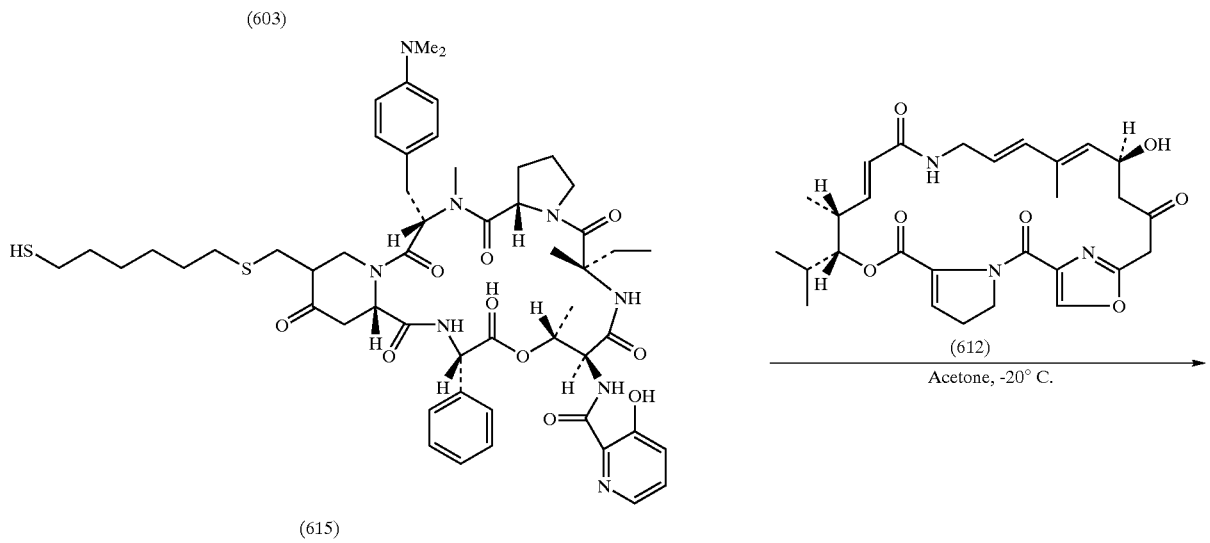
(615)
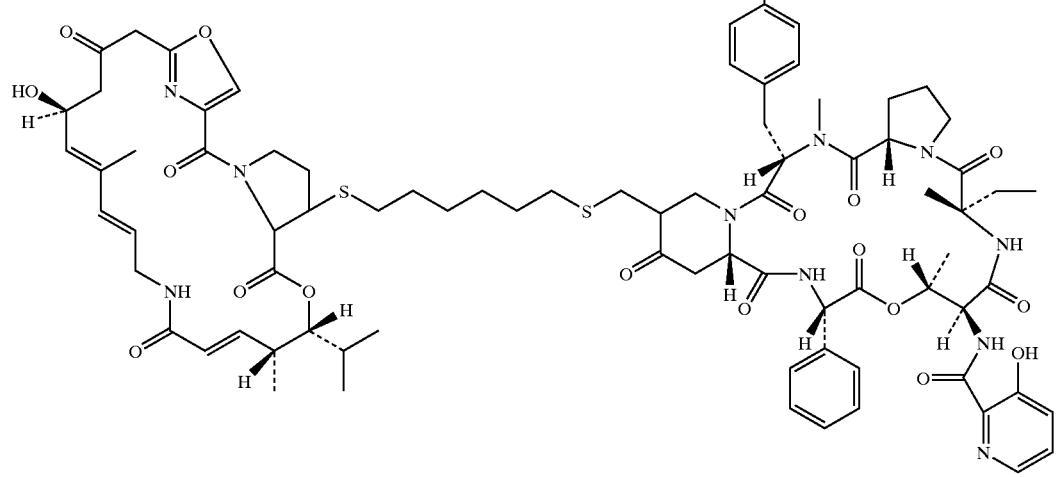
(616)

Example 20

Preparation of (618), a Compound of Formula XIX via Scheme S

A solution of 20 mmols of Pristinamycin II (612) in acetone with 20 mmols of 3-mercaptopropionic acid (609) is cooled to −20° C. and the reaction followed by TLC. When judged complete, volatiles are removed under vacuum and the crude is fractionated by reverse-phase HPLC to afford the desired product (617) after lyopholization of the appropriate fractions.

Compound (617) (4.0 mmol) is dissolved in 10 mL anhydrous dimethylformamide and treated with compound (607) (4.0 mmol), prepared as described in Example 16, hydroxybenzotriazole (5.0 mmol), diisopropylphenyl amine (4.0 mmol) and PyBOP (4.0 mmol) and the coupling reaction mixture is stirred overnight at room temperature. Volatiles are removed under vacuum and the crude is fractionated by reverse-phase. HPLC to afford the title product after lyopholization of the appropriate fractions.

The chemistry is detailed below in the following reaction scheme:

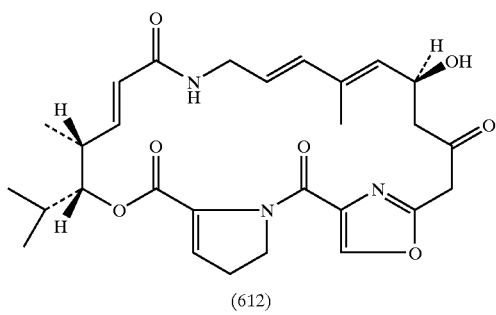
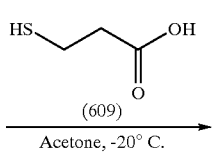
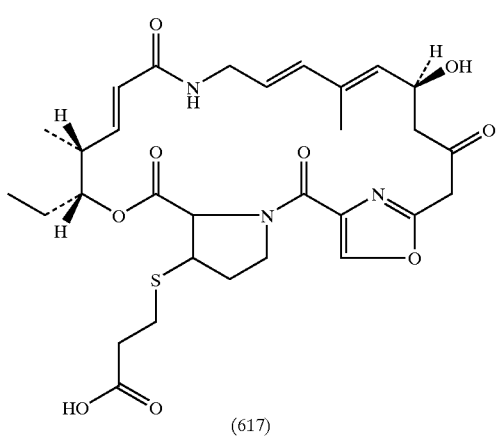
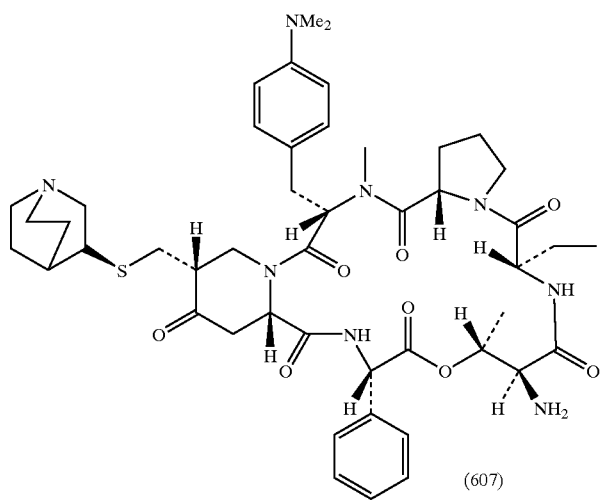

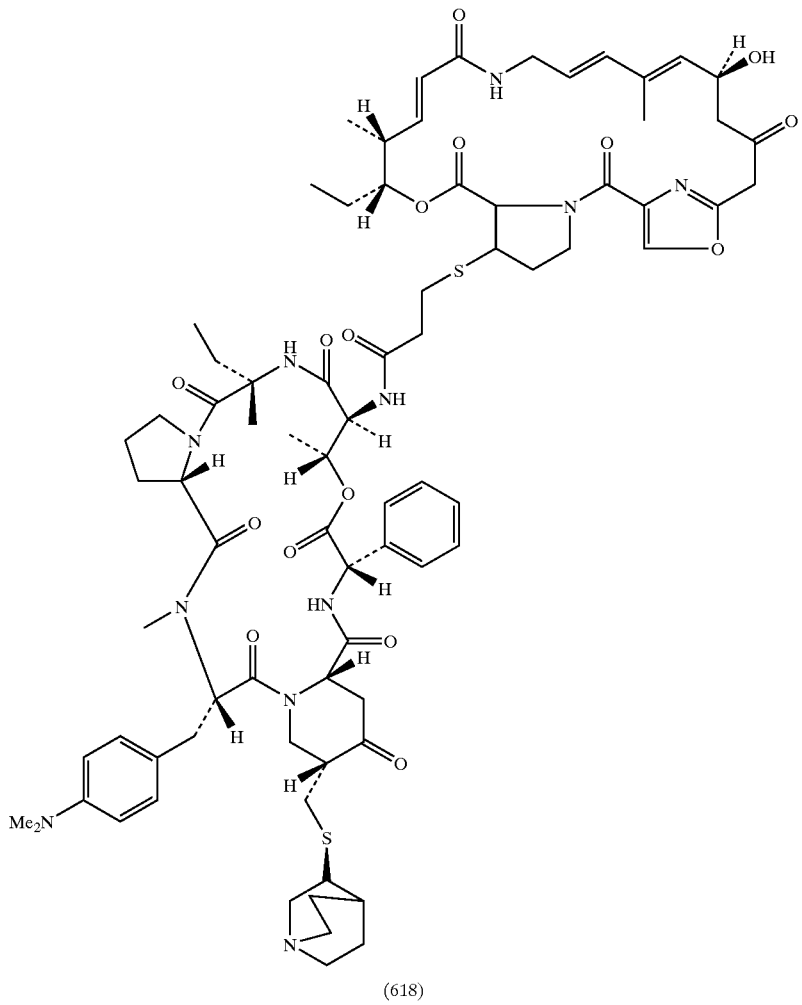

(618)

Example 21

Preparation of (702), (703), and (704), Compounds of Formula XX via Scheme T A solution of 20 mmols of Spectinomycin (701) in DMF with 10 mmols of α,α'-dibromo-p-xylene and 40 mmols of potassium carbonate is heated as necessary and the reaction followed by TLC. When judged complete, volatiles are removed under vacuum and the crude is fractionated by reverse-phase HPLC to afford the title products after lyopholization of the appropriate fractions.

The chemistry is detailed belong in the following reaction scheme:

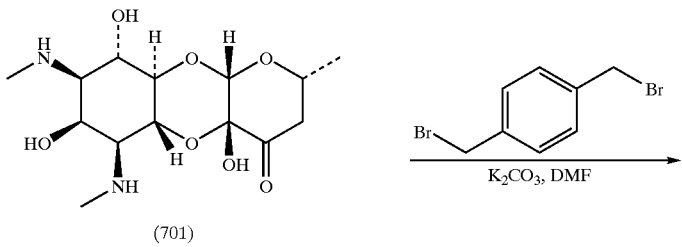

(701)

-continued

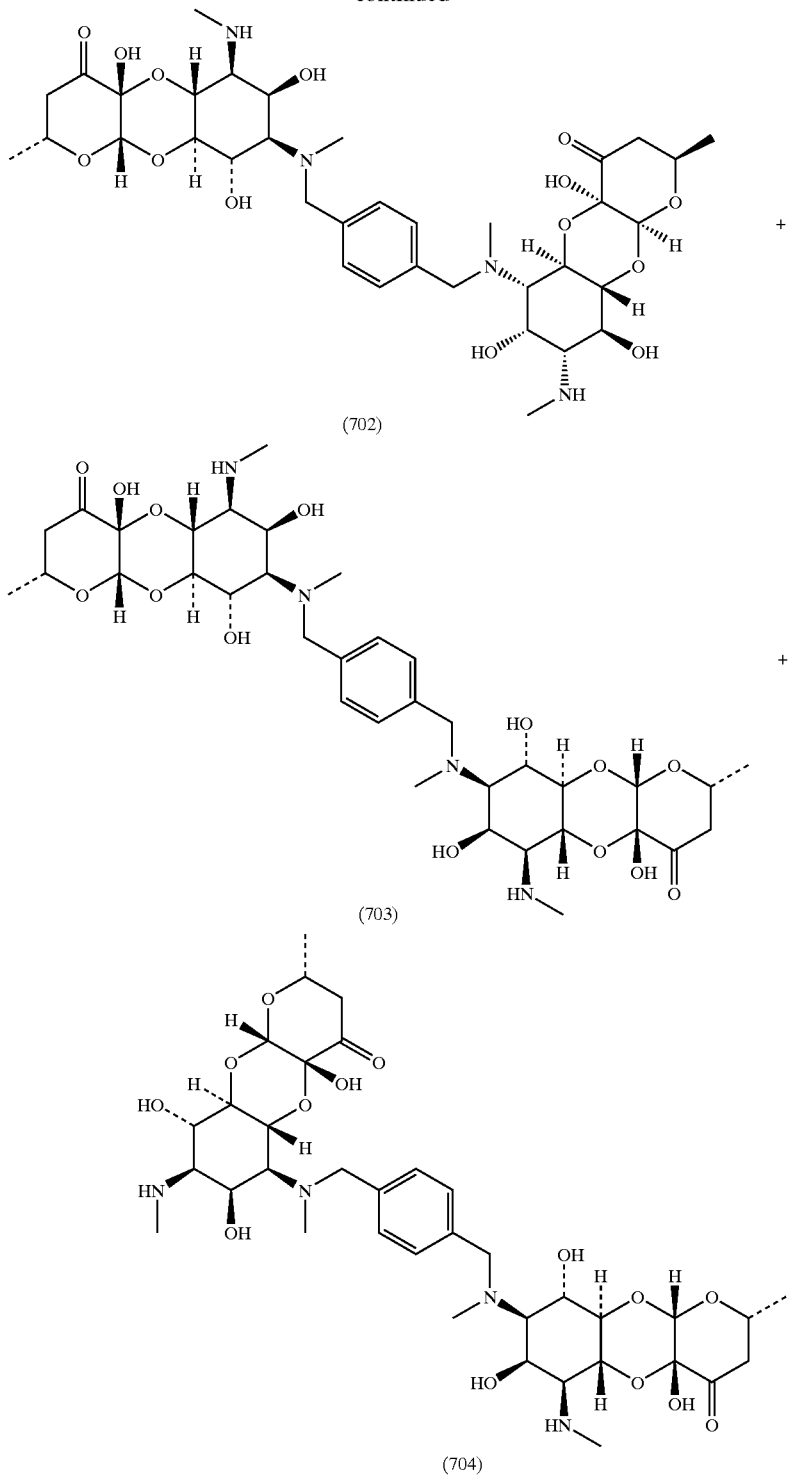

(702)

+

(703)

+

(704)

Example 22

Preparation of (806), (807), and (808)

Gentamicin $C_1$ (801) (10 mol) is slurried in methanol:anhydrous dimethylformamide, stirred at room temperature, and treated sequentially with diisopropylethyl amine (60 mmol) and benzaldehyde (50 mmol). After 2 hours the reaction mixture is cooled in an ice water bath and treated further with sodium cyanoborohydride (20 mmol) and trifluoroacetic acid (70 mmol). After 2 additional hours the crude product is precipitated by dropwise addition to a ten-fold volume of acetonitrile, and then fractionated by reverse-phase HPLC to afford the desired product (802).

Compound (802) (10 mmol) is slurried in methanol:anhydrous dimethylformamide, stirred at room temperature, and treated sequentially with diisopropylethyl amine (20 mmol) and Fmoc glycinal (101) (10 mmol) (prepared as described by Salvi et al. *Tetrahedron Lett.* 1994, 35, 1181–1184). After 2 hours the reaction mixture is cooled in an ice water bath and treated further with sodium cyanoborohydride (4.0 mmol) and trifluoroacetic acid (30 mmol). After 2 additional hours the crude product is precipitated by dropwise addition to a ten-fold volume of acetonitrile, and then fractionated by reverse-phase HPLC to afford the desired products (803), (804), and (805).

The above separated products (803), (804), and (805) are then individually dissolved in anhydrous dimethylformamide (10 mL), stirred at room temperature and treated with excess piperidine (1.0 mL). After one hour, the crude products are concentrated under reduced pressure and then fractionated by reverse-phase HPLC to afford compounds (806), (807), and (808).

The chemistry is detailed below in the following reaction scheme:

Example 23

Preparation of (803), (804), (805), (813), (814), (815), (816), and (817)

Gentamicin $C_2$ (809) (10 mmol) is slurried in methanol:anhydrous dimethylformamide, stirred at room temperature, and treated sequentially with diisopropylethyl amine (60 mmol) and benzaldehyde (50 mmol). After 2 hours the reaction mixture is cooled in an ice water bath and treated further with sodium cyanoborohydride (20 mmol) and trifluoroacetic acid (70 mmol). After 2 additional hours the crude product is precipitated by dropwise addition to a ten-fold volume of acetonitrile, and then fractionated by reverse-phase HPLC to afford the desired product (811). Compound (812) is prepared in the same manner from Gentamicin $C_3$ (810).

Compound (811) (10 mmol) is slurried in methanol:anhydrous dimethylformamide, stirred at room temperature,

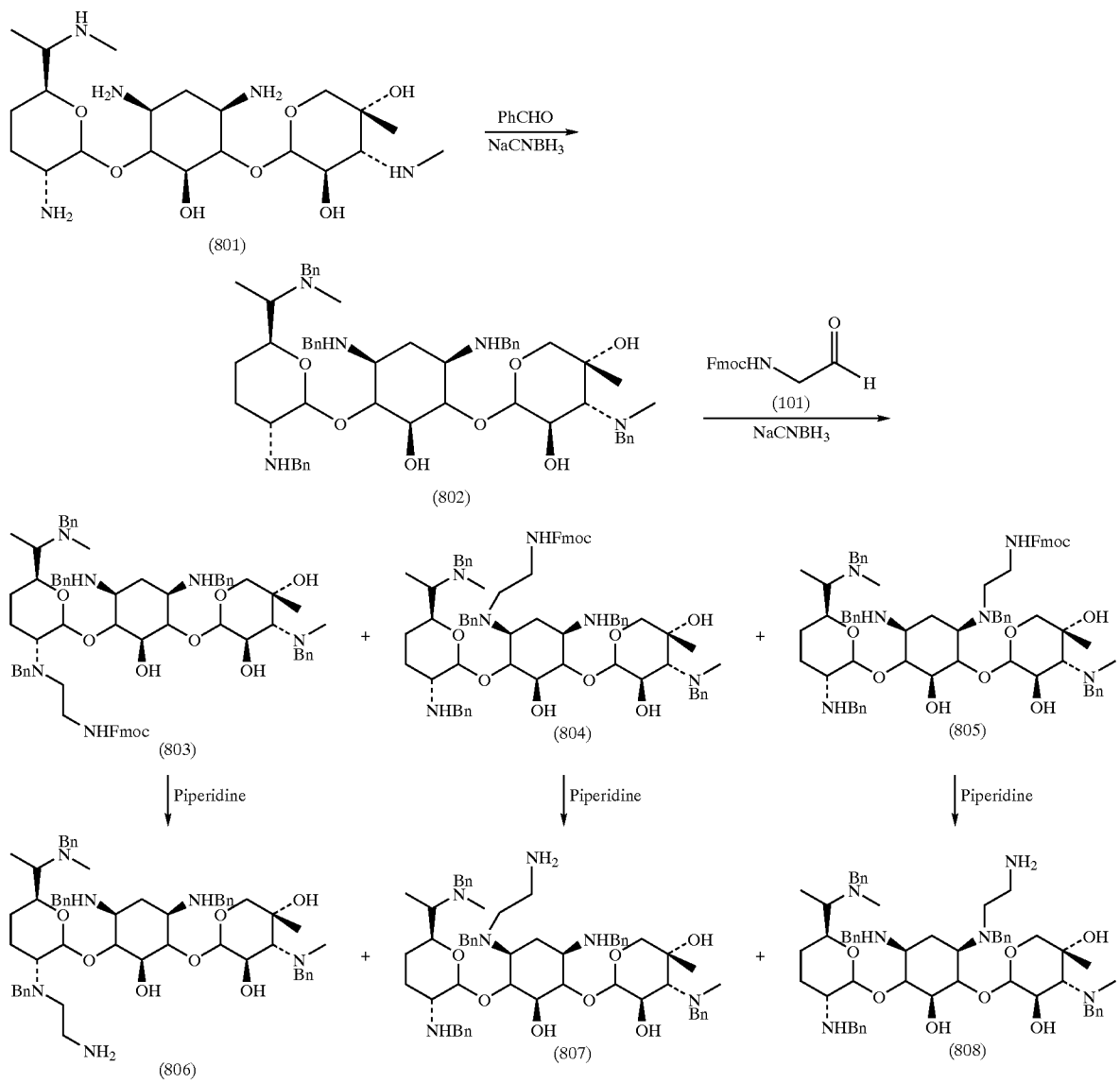

and treated sequentially with diisopropylethyl amine (20 mmol) and Fmoc glycinal (101) (10 mmol) (prepared as described by Salvi et al. *Tetrahedron Lett.* 1994, 35, 1181–1184). After 2 hours the reaction mixture is cooled in an ice water bath and treated further with sodium cyanoborohydride (4.0 mmol) and trifluoroacetic acid (30 mmol). After 2 additional hours the crude product is precipitated by dropwise addition to a ten-fold volume of acetonitrile, and then fractionated by reverse-phase HPLC to afford the desired products (803), (804), (805), and (813), which are then separated by reverse phase chromatography. Compounds (814), (815), (816), and (817) are prepared and separated in the same manner from (812).

The above separated products (803), (804), (805), and (813) are then individually dissolved in anhydrous dimethylformamide (10 mL), stirred at room temperature and treated with excess piperidine (1.0 mL). After one hour, the crude products are fractionated by reverse-phase HPLC to afford compounds (806), (807), (808), and (818). Compounds (820), (821), and (822) are prepared and separated in the same manner from (814), (815), (816), and (817), respectively.

The chemistry is detailed below in the following reaction scheme:

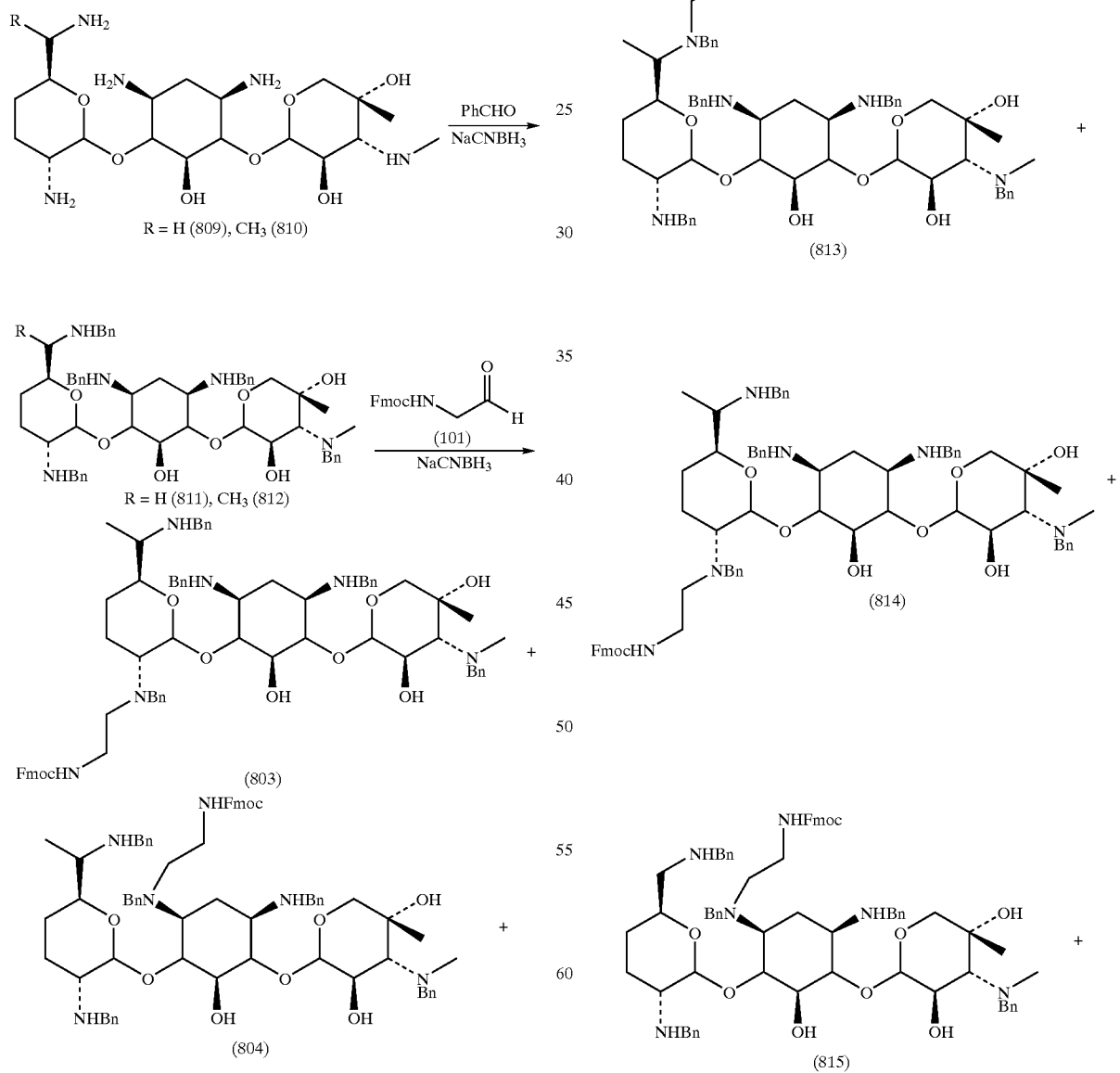

-continued
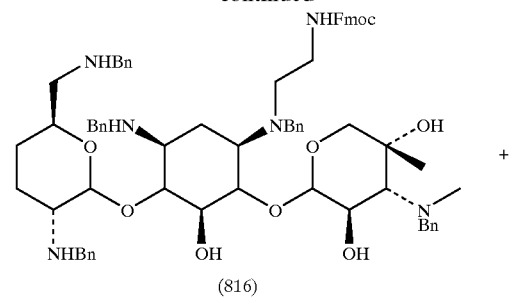
(816)
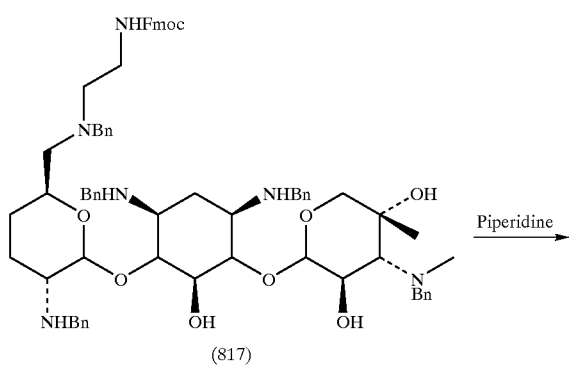
(817) →Piperidine
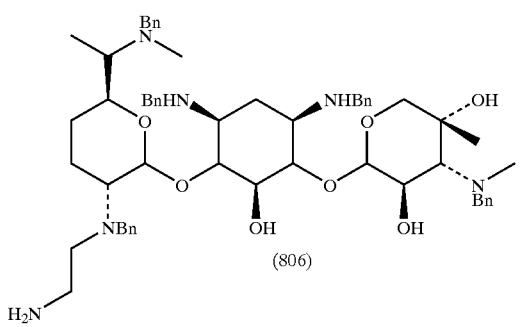
(806)
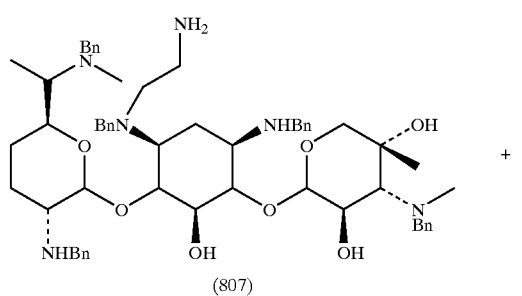
(807)
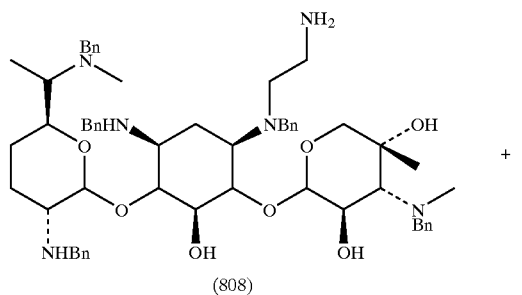
(808)
+
-continued
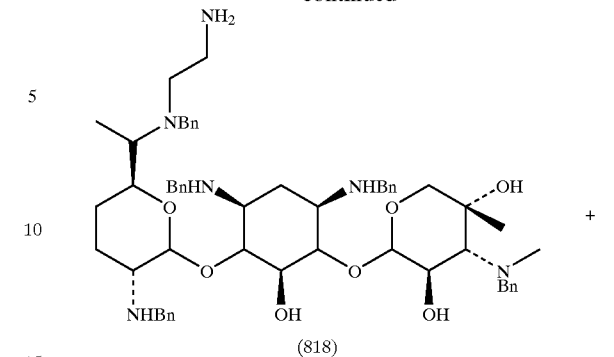
(818)
+
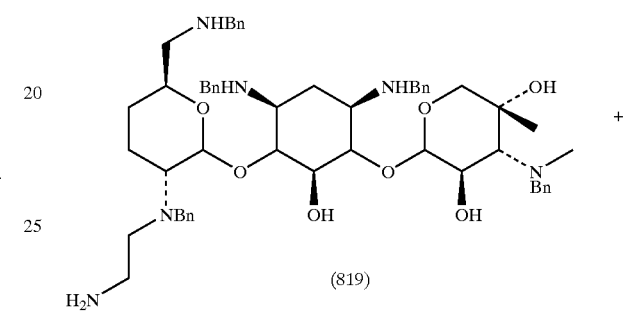
(819)
+
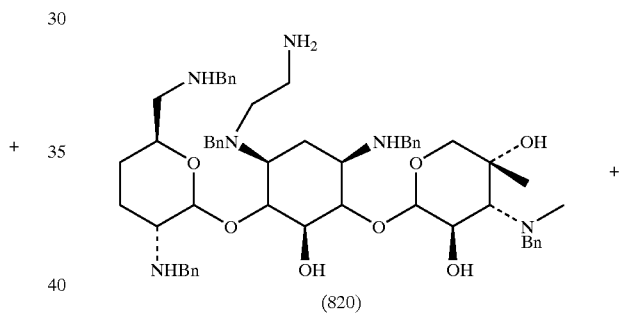
(820)
+
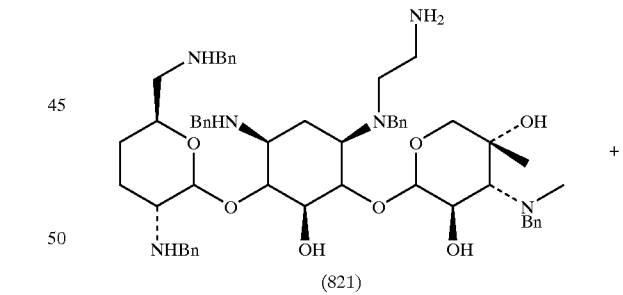
(821)
+
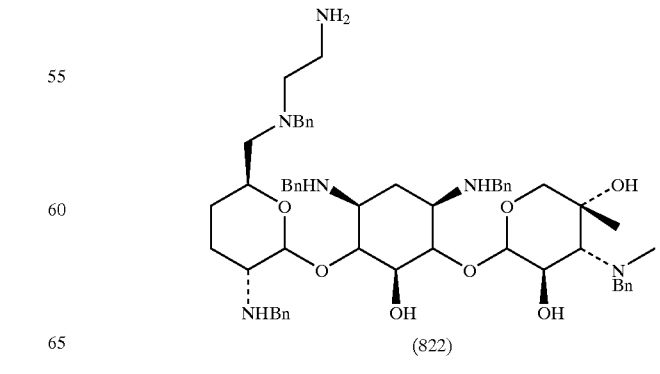
(822)

Example 24

Preparation of (824), a Compound of Formula XXI via Scheme U

Compound (806) (10 mmol), prepared as described in Example 22, is slurried in methanol:anhydrous dimethylformamide, stirred at room temperature, and treated sequentially with diisopropylethyl amine (20 mmol) and Streptomycin (401) (10 mmol). After 2 hours the reaction mixture is cooled in an ice water bath and treated further with sodium cyanoborohydride (4.0 mmol) and trifluoroacetic acid (30 mmol). After 2 additional hours the crude product is precipitated by dropwise addition to a ten-fold volume of acetonitrile, and then fractionated by reverse-phase HPLC to afford the desired product (823).

A solution of (823) (5 mmol) in methanol is hydrogenated overnight at 35 psi, in the presence of 10% Pd/C. When judged complete, volatiles are removed under vacuum and the crude is fractionated by reverse-phase HPLC to afford the title product after lyopholization of the appropriate fractions.

***NOTE: Compound (806) is shown in the example, but the same procedure can be carried out on compounds (807), (808), (818), (819), (820), (821), (822), and (829) to provide their respective dimers with streptomycin.

The chemistry is detailed below in the following reaction scheme:

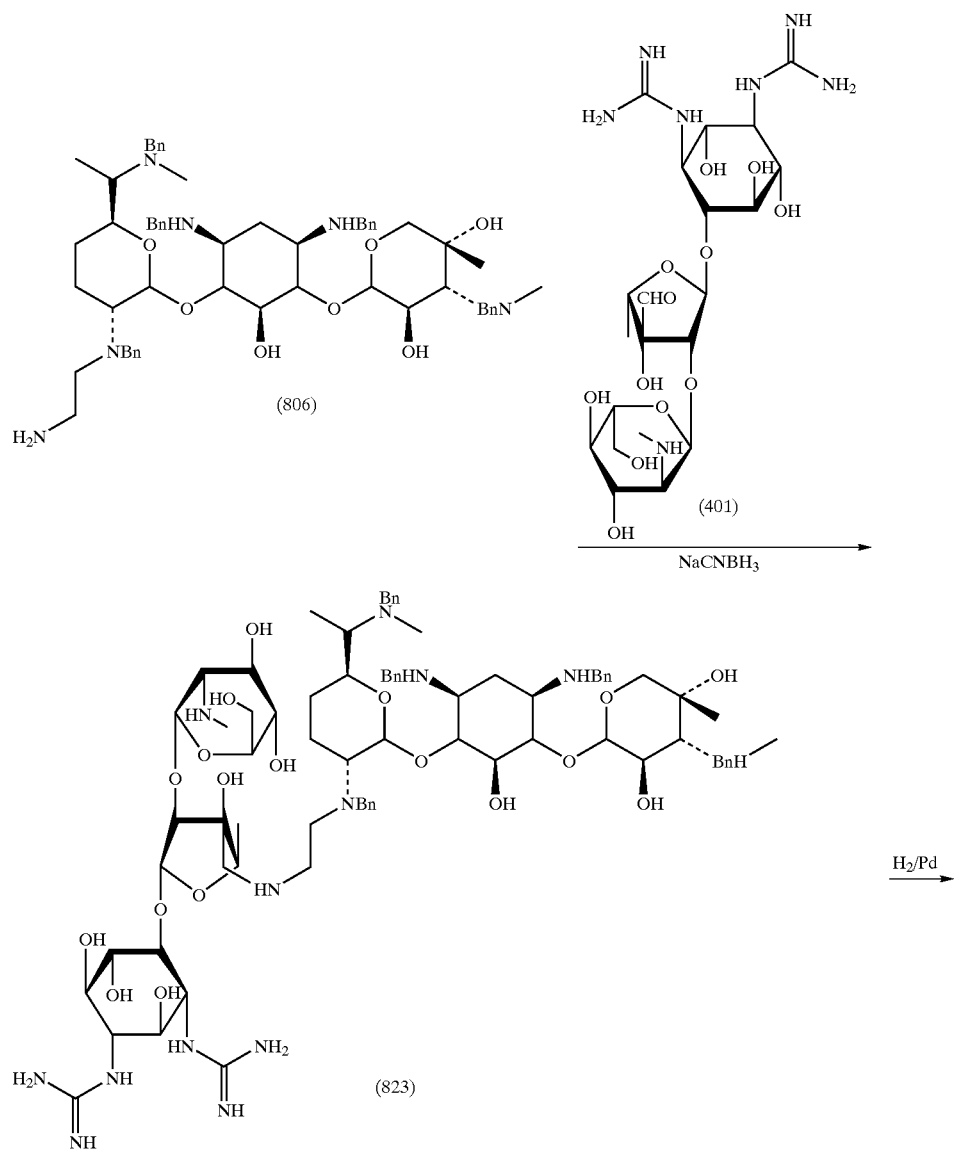

-continued

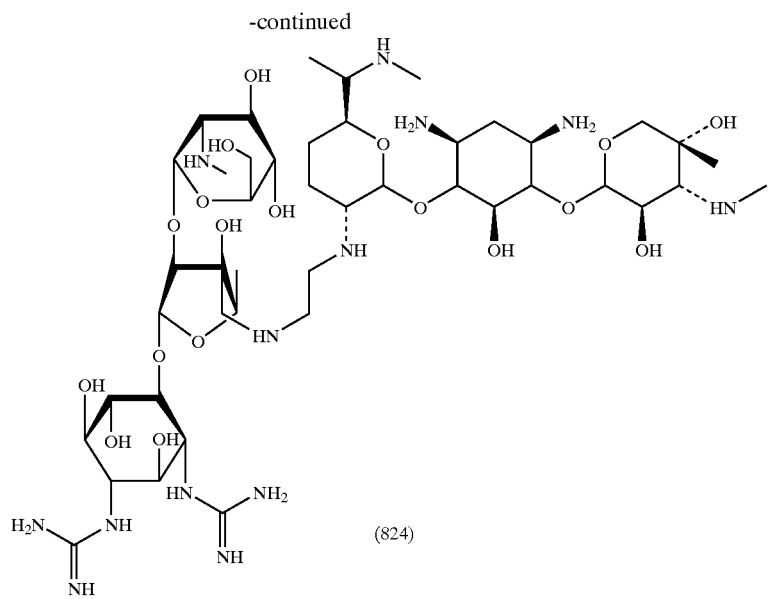

(824)

Example 25

Preparation of (828), a Compound of Formula XXII via Scheme V

Terephthalic acid (826) (2.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated diacid is treated with compound (806) (4.0 mmol), prepared as described in Example 22, and the coupling reaction mixture is stirred overweight at room temperature. Volatiles are removed under vacuum and the crude is fractionated by reverse-phase HPLC to afford the desired product (827) after lyopholization of the appropriate fractions.

A solution of (827) (5 mmol) in methanol is hydrogenated overnight at 35 psi, in the presence of 10% Pd/C. When judged complete, volatiles are removed under vacuum and the crude is fractionated by reverse-phase HPLC to afford the title product after lyopholization of the appropriate fractions.

***NOTE: Compound (806) is shown in the example, but the same procedure can be carried out on compounds (807), (808), (818), (819), (820), (821), and (822) to provide their respective dimers.

The chemistry is detailed belong in the following reaction scheme:

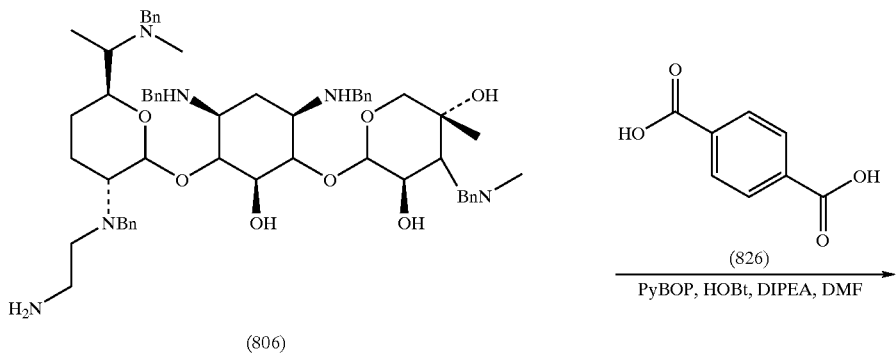

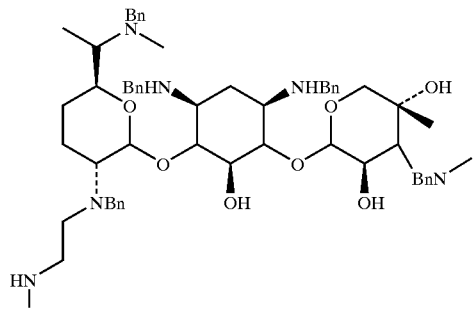

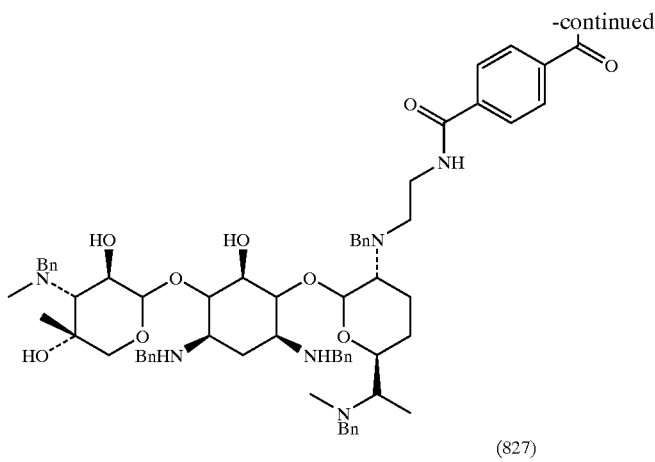

(827)

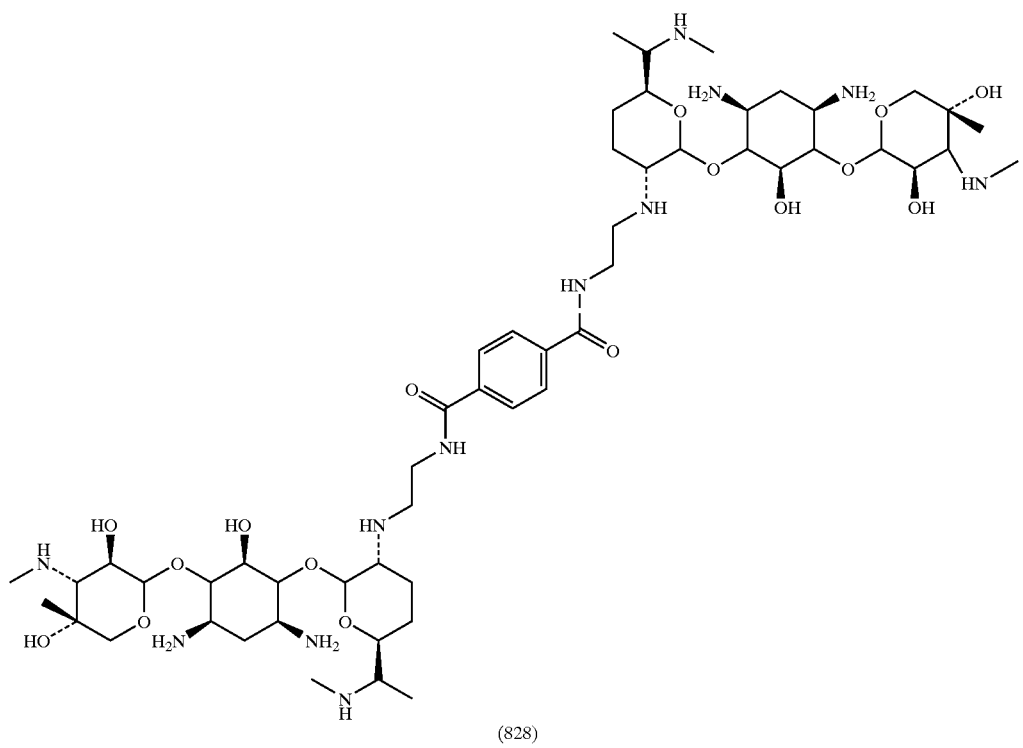

(828)

Example 26

Preparation of (830), a Compound of Formula XXIII via Scheme W

A solution of 20 mmols of (811), prepared as described in Example 23, in THF with 80 mmols of triethylamine is treated at room temperature with 40 mmols of trifluoroacetic anhydride for 1 hour. A solution of the resulting product (11.7 mmol) in methanol is hydrogenated overnight at 35 psi, in the presence of 10% Pd/C. The reaction mixture is filtered and the filtrate is concentrated to dryness. The crude product is purified by reverse-phase HPLC to afford the desired compound (829).

A solution of 20 mmols of compound (829) in DMF with 10 mmols of 1,6-dibromohexane (302) and 40 mmols of potassium carbonate is heated as necessary and the reaction followed by TLC. When judged complete, volatiles are removed under vacuum and the crude is fractionated by reverse-phase HPLC to afford the title product after lyopholization of the appropriate fractions.

***NOTE: Compound (811) is shown in the example, but the same procedure can be carried out on compounds (802) and (812) to provide the respective products.

The chemistry is detailed below in the following reaction scheme:

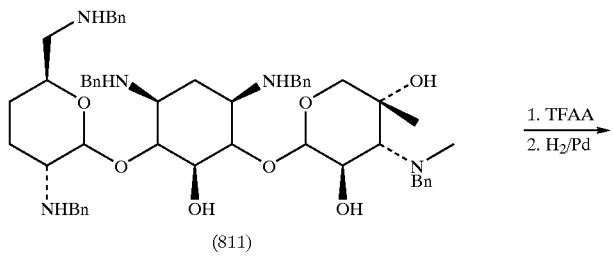

(811)

1. TFAA
2. H₂/Pd

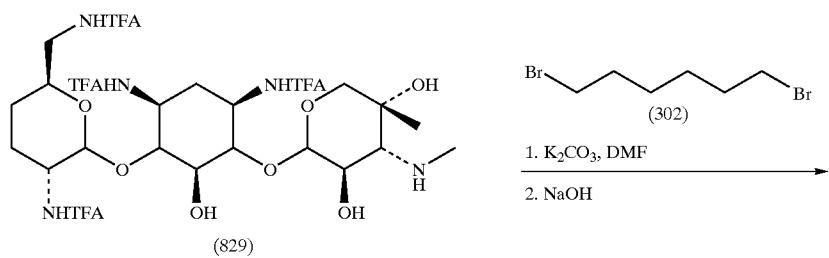

(829)

(302)

1. K₂CO₃, DMF
2. NaOH

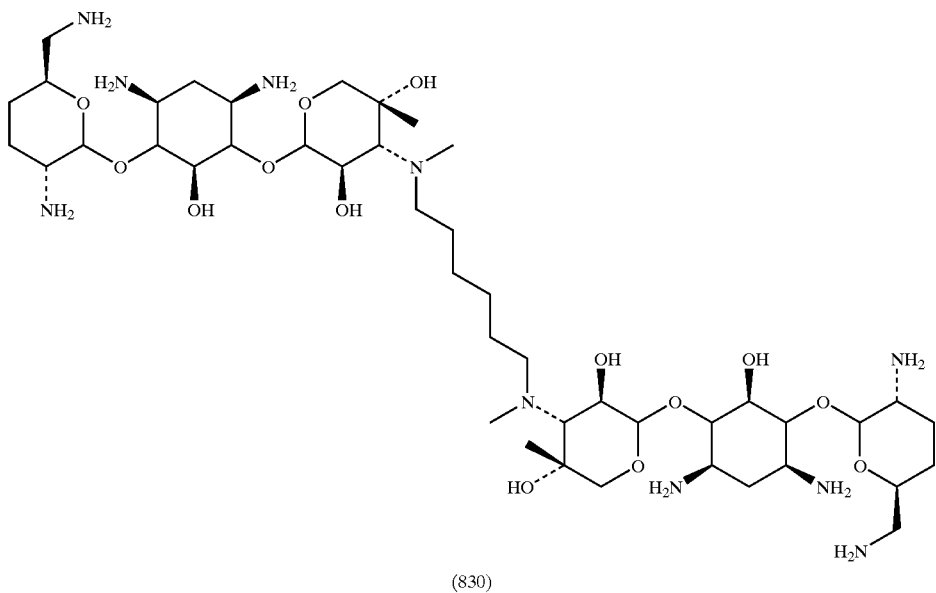

(830)

Example 27

Preparation of (831), a Compound of Formula XXIV via Scheme X

A solution of 20 mmols of compound (829), prepared as described in Example 26, in DMF with 20 mmols of 3-bromopropionic acid (833) and 200 mmols of potassium carbonate is heated as necessary and the reaction followed by TLC. When judged complete, volatiles are removed under vacuum and the crude is fractionated by reverse-phase HPLC to afford the desired product (834) after lyopholization of the appropriate fractions.

Compound (834) (4.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (806) (4.0 mmol) and the coupling reaction mixture is stirred overnight at room temperature. The mixture is diluted two-fold with an aqueous NaOH solution (25 mmol) and heated to 50° C. for 1 hour. Volatiles are removed under vacuum and the crude is fractionated by reverse-phase HPLC to afford the title product after lyopholization of the appropriate fractions.

\*\*\*NOTE: Compound (806) is shown in the example, but the same procedure can be carried out on compounds (807), (808), (818), (819), (820), (821), and (822) to provide their respective dimers with compound (829).

The chemistry is detailed below in the following reaction scheme:

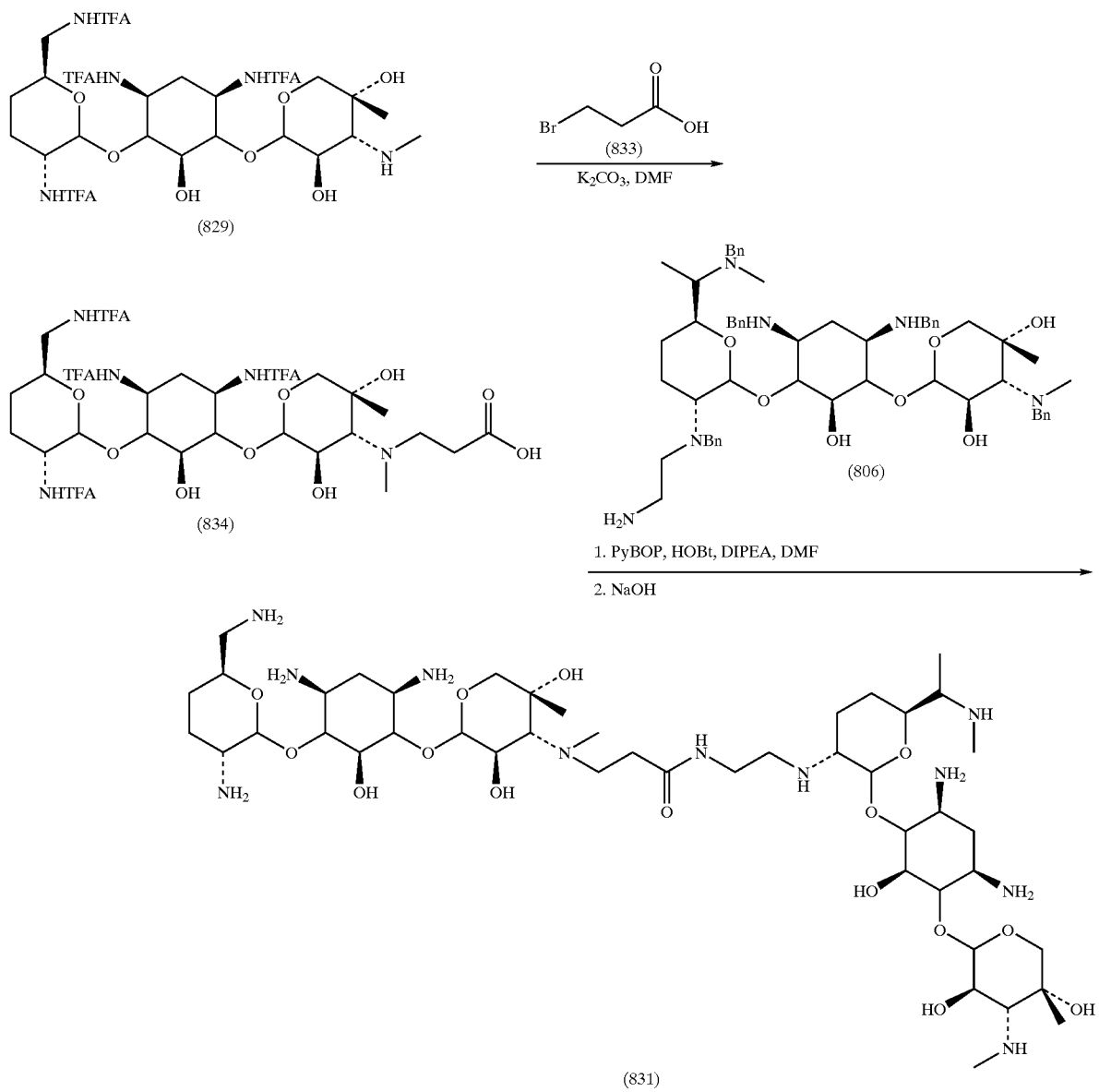

Example 28

Preparation of (832), a Compound of Formula XXV via Scheme Y

Succinic acid (104) (2.0 mmol) is dissolved in 10 mL anhydrous dimethylformamide and treated sequentially with hydroxybenzotriazole (2.0 mmol), diisopropylethyl amine (2.0 mmol) and PyBOP (2.0 mmol). After stirring for 15 minutes at room temperature, the activated diacid is treated with compound (408) (2.0 mmol), prepared as described in Example 11, and the coupling reaction mixture is stirred overnight at room temperature. Volatiles are removed under vacuum and the crude is fractionated by reverse-phase HPLC to afford the desired product (835) after lyopholization of the appropriate fractions.

Compound (835) (4.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated diacid is treated with compound (806) (4.0 mmol), prepared as described in Example 22, and the coupling reaction mixture is stirred overnight at room temperature. Volatiles are removed under vacuum and the crude is fractionated by reverse-phase HPLC to afford the title product after lyopholization of the appropriate fractions. A solution of the resulting product (11.7 mmol) in methanol is hydrogenated overnight at 35 psi, in the presence of 10% Pd/C. The reaction mixture is filtered and the filtrate is concentrated to dryness. The crude product is purified by reverse-phase HPLC to afford the title product.

\*\*\*NOTE: Compound (806) is shown in the example, but the same procedure can be carried out on compounds (807), (808), (818), (819), (820), (821), and (822) to provide their respective dimers with compound (408).

The chemistry is detailed below in the following reaction scheme:

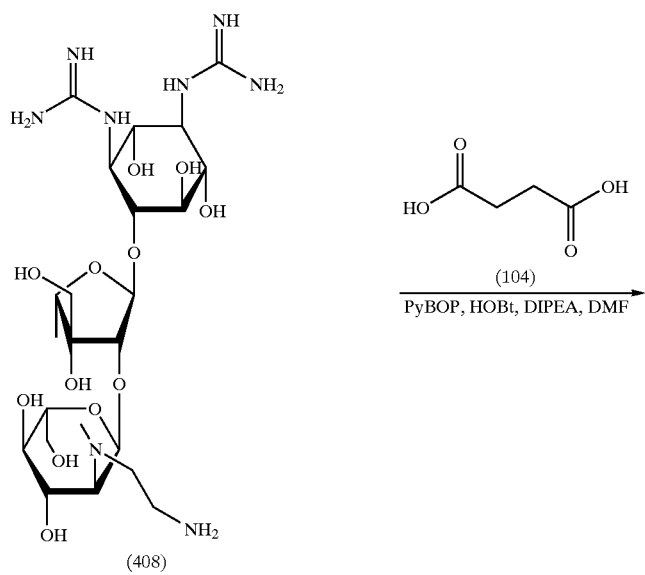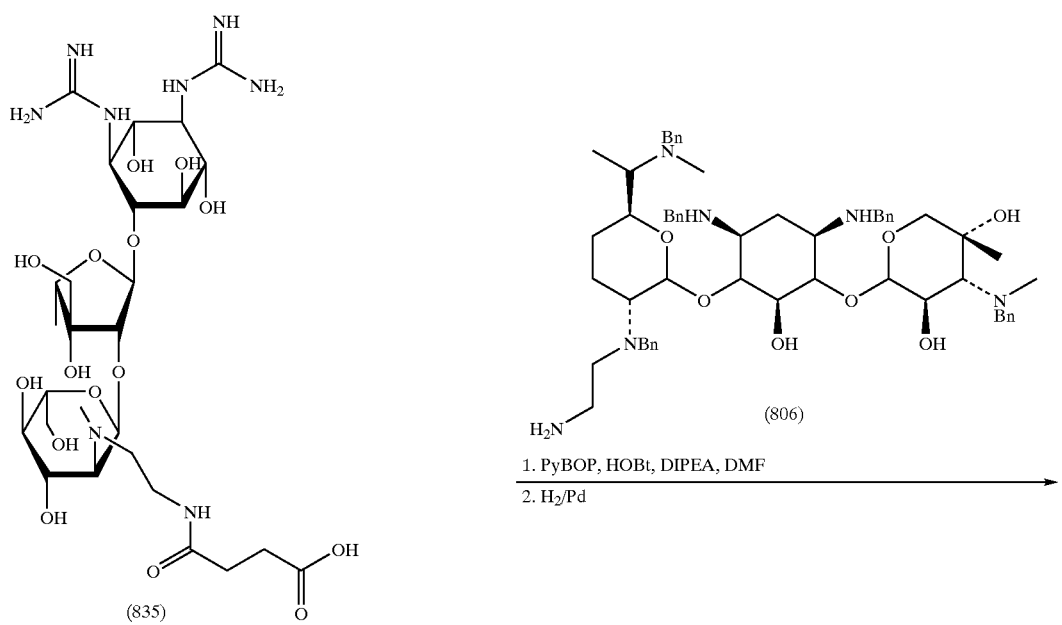

-continued

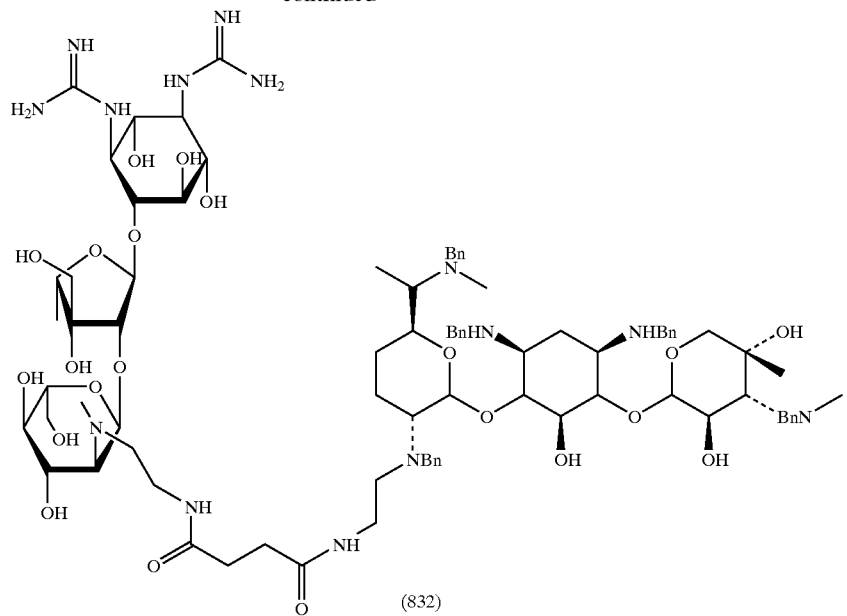

(832)

Example 29

Preparation of (902), a Compound of Formula XXVI via Scheme Z

A solution of 10 mmols of compound (301) in DMF with 10 mmols of 3-bromopropionic acid (833) and 20 mmols of potassium carbonate is heated as necessary and the reaction followed by TLC. When judged complete, volatiles are removed under vacuum and the crude is fractionated by reverse-phase HPLC to afford the desired product (901) after lyopholization of the appropriate fractions.

Compound (901) (4.0 mmol) is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (103) (4.0 mmol), prepared as described in Example 1, and the coupling reaction mixture is stirred overnight at room temperature. Volatiles are removed under vacuum and the crude is fractionated by reverse-phase HPLC to afford the title product after lyopholization of the appropriate fractions.

Compound (301) is U-57930E and is reported in *Antimicrobial Agents Chemother,* 21:902–905 (19892).

The chemistry is detailed below in the following reaction scheme:

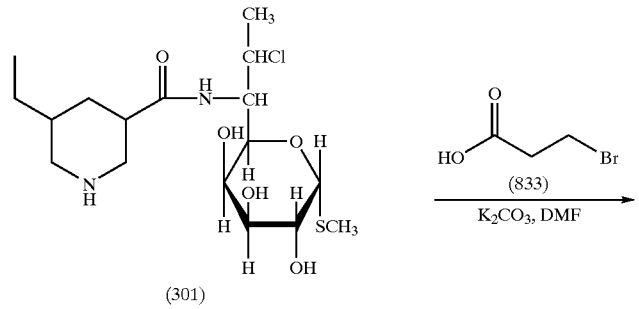

-continued

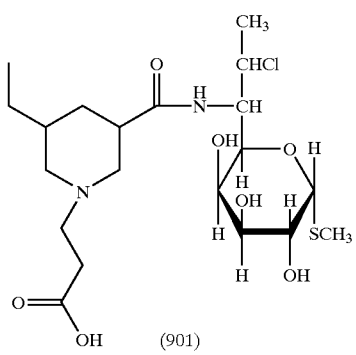
(901)

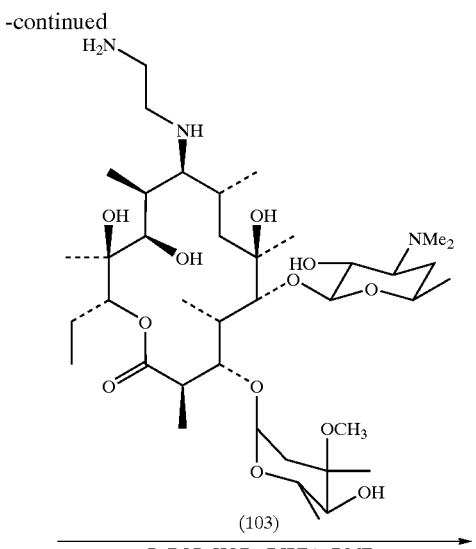
(103)

PyBOP, HOBt, DIPEA, DMF

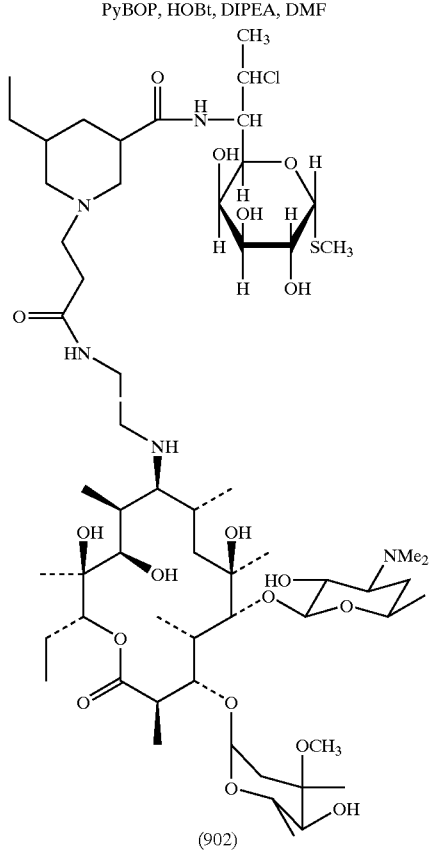
(902)

Example 30

Preparation of (905), a Compound of Formula XXVII via Scheme AA 1,4-Diaminobutane (106) (4.0 mmol) is dissolved in DMF, stirred at room temperature, and treated sequentially with diisopropylethyl amine (4.0 mmol) and imidazolide (105) (4.0 mmol), prepared as described in Example 2. After 2 hours, volatiles are removed under vacuum and the crude product is purified by reverse-phase HPLC to afford the desired product (903).

Compound (903) (2.0 mmol) is dissolved in DMF, stirred at room temperature, and treated sequentially with diisopropylethyl amine (4.0 mmol) and imidazolide (202) (2.0 mmol), prepared as described in Example 4. After 2 hours, volatiles are removed under vacuum and the crude product is purified by reverse-phase HPLC to afford the desired product (904).

Compound (904) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at refux for 1 hour. Volatiles are removed under vacuum and the crude is fractionated by reverse-phase HPLC to afford the title product after lyopholization of the appropriate fractions.
The chemistry is detailed below in the following reaction scheme:
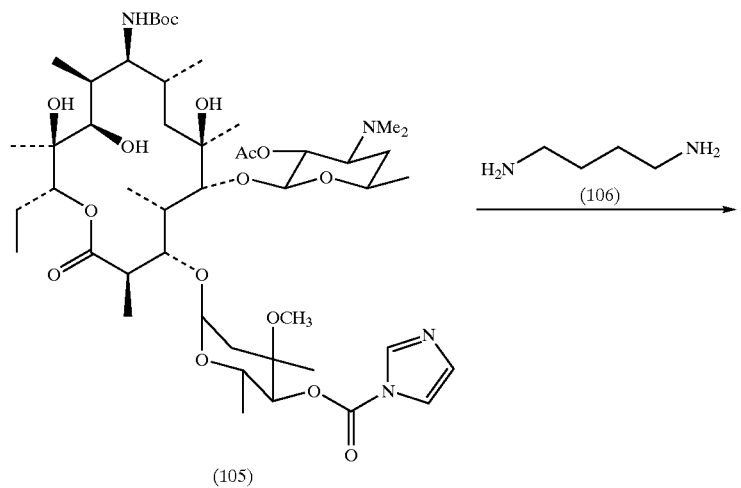
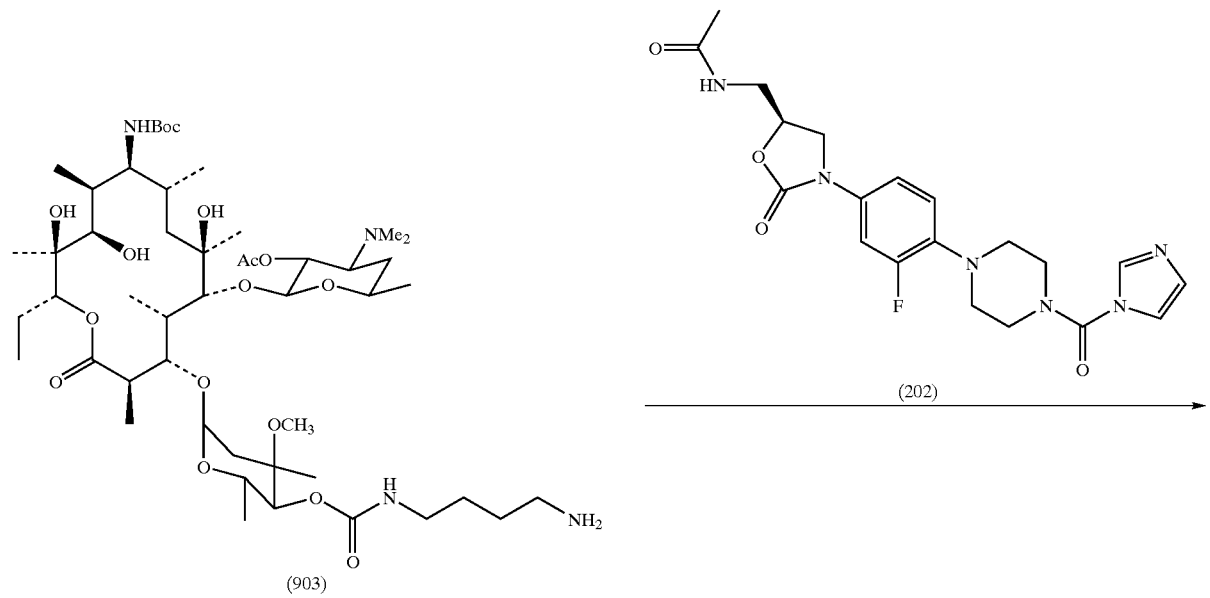

-continued

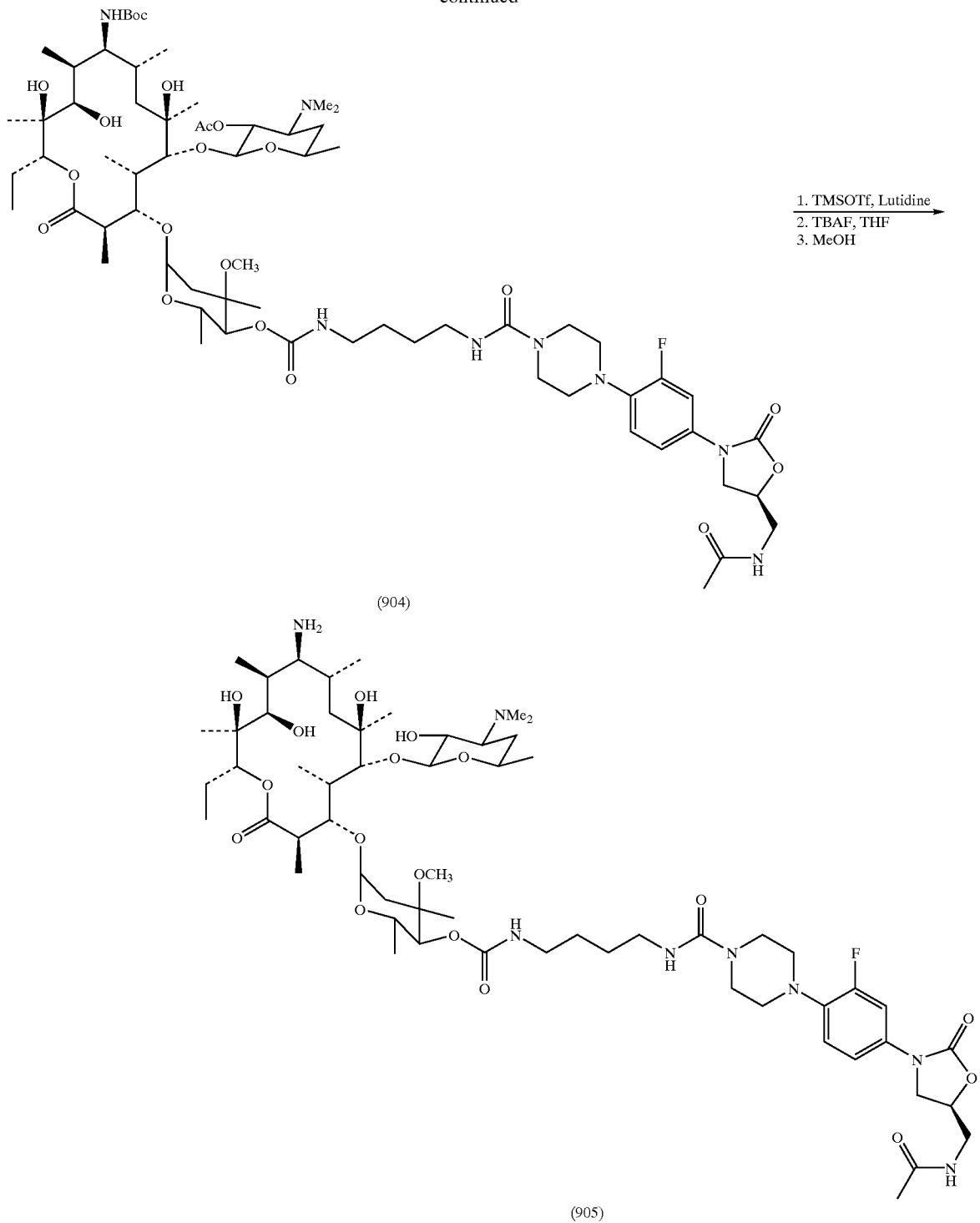

Example 31

Preparation of (905), a Compound of Formula XXIII via Scheme BB

Succinic acid (104) (8.0 mmol) is dissolved in 10 mL anhydrous dimethylformamide and treated sequentially with hydroxybenzotriazole (10 mmol), diisopropylethyl amine (8.0 mmol) and PyBOP (8.0 mmol). After stirring for 15 minutes at room temperature, the diacid is treated with compound (103) (8.0 mmol), prepared as described in Example 1, and the coupling reaction mixture is stirred overnight at room temperature. Volatiles are removed under vacuum and the crude is fractionated by reverse-phase HPLC to afford the desired product (906) after lyopholization of the appropriate fractions.

Compound (906) (2.0 mmol) is dissolved in 10 mL anhydrous dimethylformamide and treated sequentially with hydroxybenzotriazole (2.5 mmol), diisopropylethyl amine (2.0 mmol) and PyBOP (2.0 mmol). After stirring for 15 minutes at room temperature, the activated acid is treated with compound (204) (2.0 mmol) and the coupling reaction mixture is stirred overnight at room temperature. Volatiles are removed under vacuum and the crude is fractionated by reverse-phase HPLC to afford the title product after lyopholization of the appropriate fractions.

Compound (204) is reported in J. Med. Chem. 1996, 49, 673–679.

The chemistry is detailed below in the following reaction scheme:

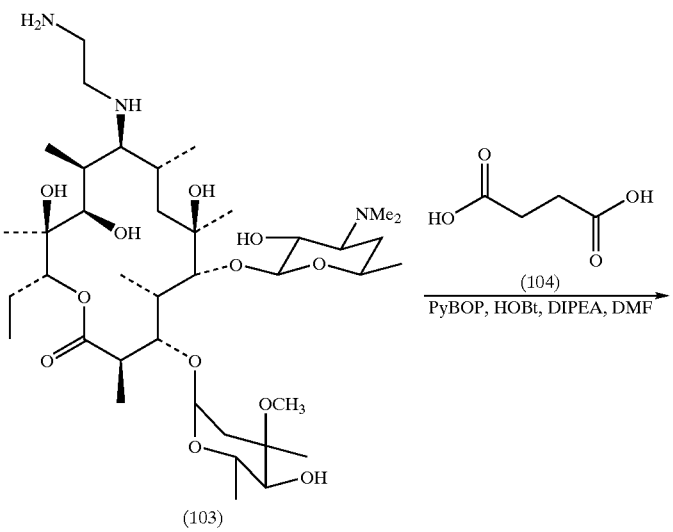

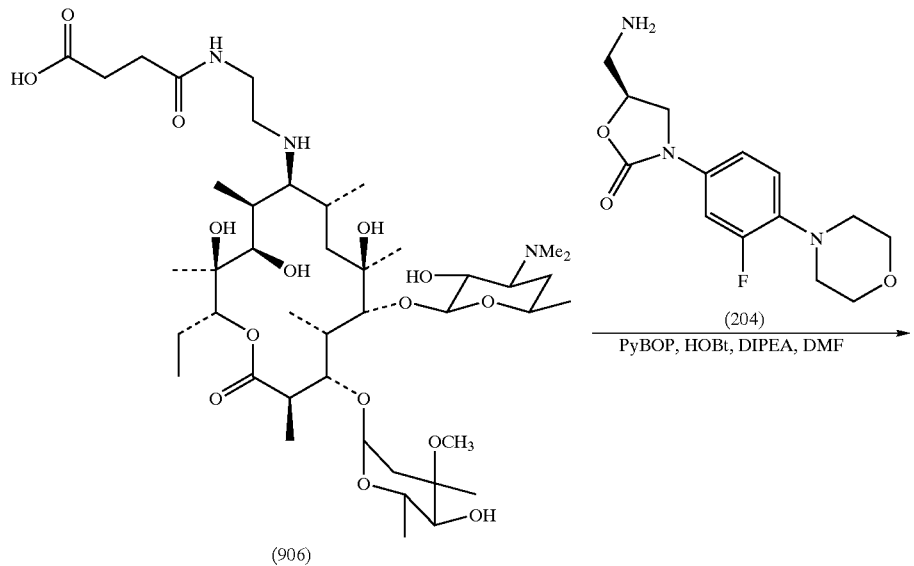

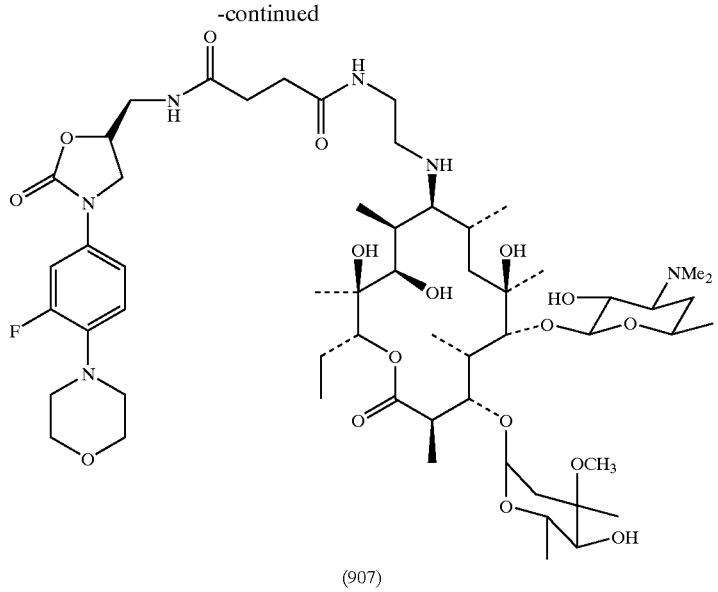

(907)

Example 32

Preparation of (909), a compound of Formula XXIX via Scheme CC

Compound (110) (4.0 mmol), prepared as described in Example 3, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (204) (4.0 mmol) and the coupling reaction mixture is stirred overnight at room temperature. Volatiles are removed under vacuum and the crude is fractionated by reverse-phase HPLC to afford the desired product (908) after lyopholization of the appropriate fractions.

Compound (908) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at reflux for 1 hour. Volatiles are removed under vacuum and the crude is fractionated by reverse-phase HPLC to afford the title product after lyopholization of the appropriate fractions.

Compound (204) is reported in J. Med. Chem. 1996, 49, 673–679.

The chemistry is detailed below in the following reaction scheme:

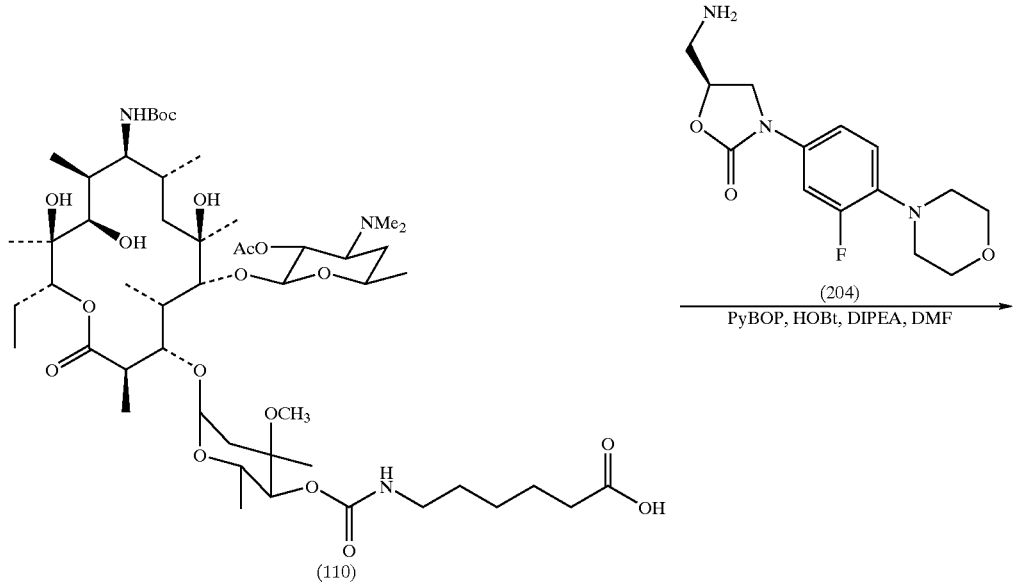

-continued

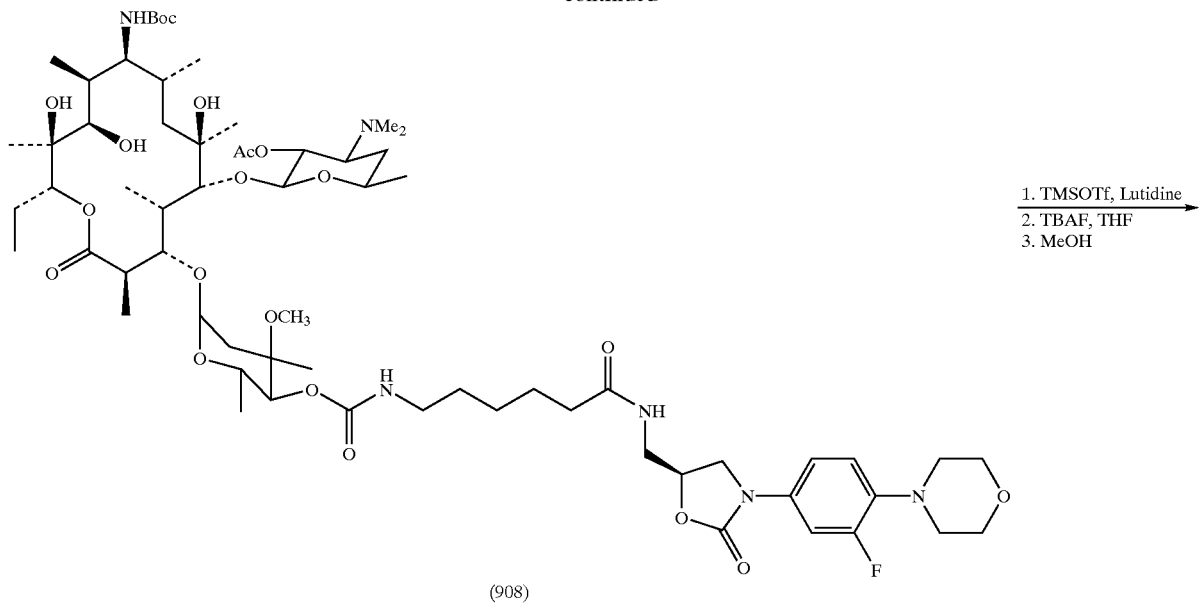

(908)

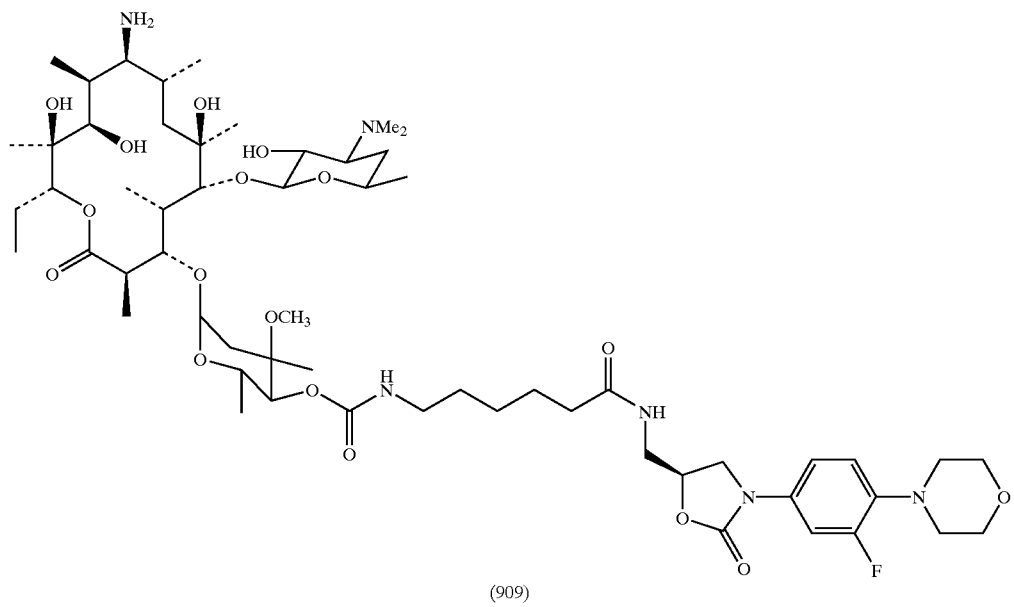

(909)

Example 33

Preparation of (911), a Compound of Formula XXX via Scheme DD

A solution of (105) (2.0 mmol), prepared as described in Example 2, in toluene/DMF with 1,4-diaminobutane (106) (2.0 mmol) is heated as necessary in a sealed vessel and the reaction followed by TLC. When judged complete, volatiles are removed under vacuum and the crude is fractionated by reverse-phase HPLC to afford the desired product (922) after lyopholization of the appropriate fractions.

A solution of the above product (922) (1.0 mmol) in DMF with compound (202) (1.0 mmol), prepared as described in Example 4, is heated as necessary in a sealed vessel and the reaction followed by TLC. When judged complete, volatiles are removed under vacuum and the crude is fractionated by reverse-phase HPLC to afford the desired product (910) after lyopholization of the appropriate fractions.

Compound (910) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at reflux for 1 hour. Volatiles are removed under vacuum and the crude is fractionated by reverse-phase HPLC to afford the title product after lyopholization of the appropriate fractions.

The chemistry is detailed below in the following reaction scheme:

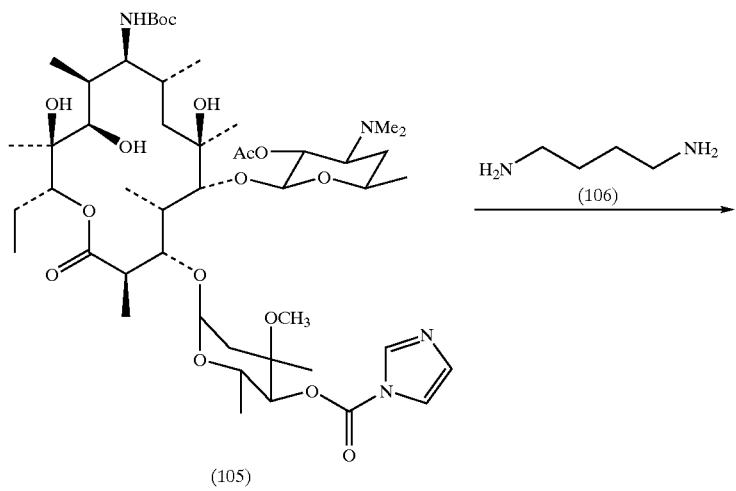
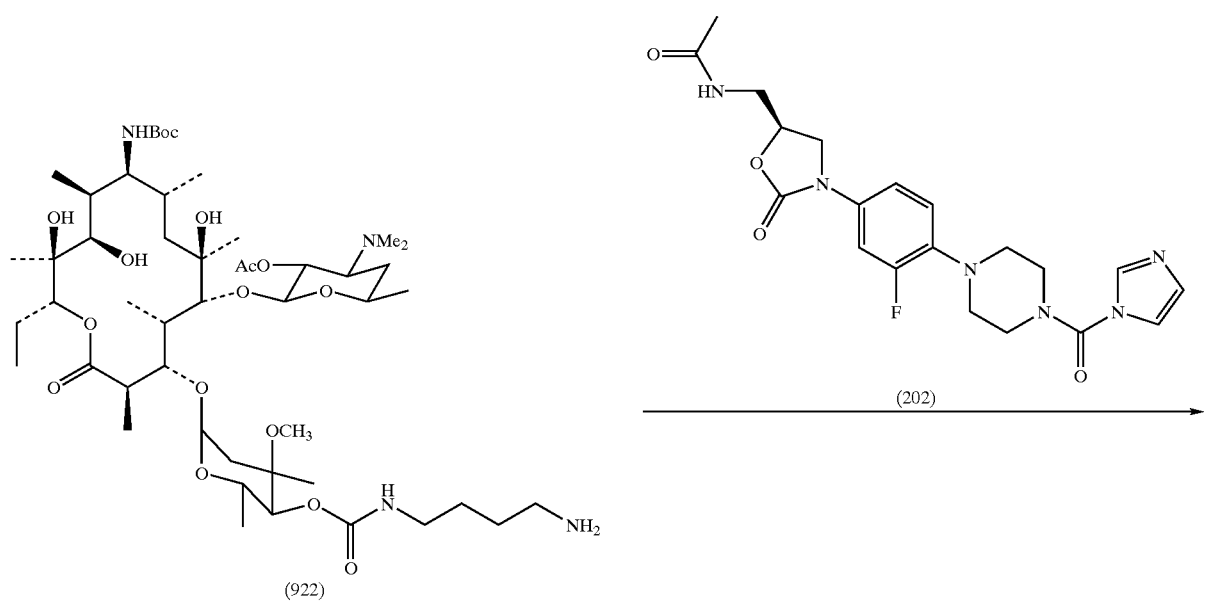

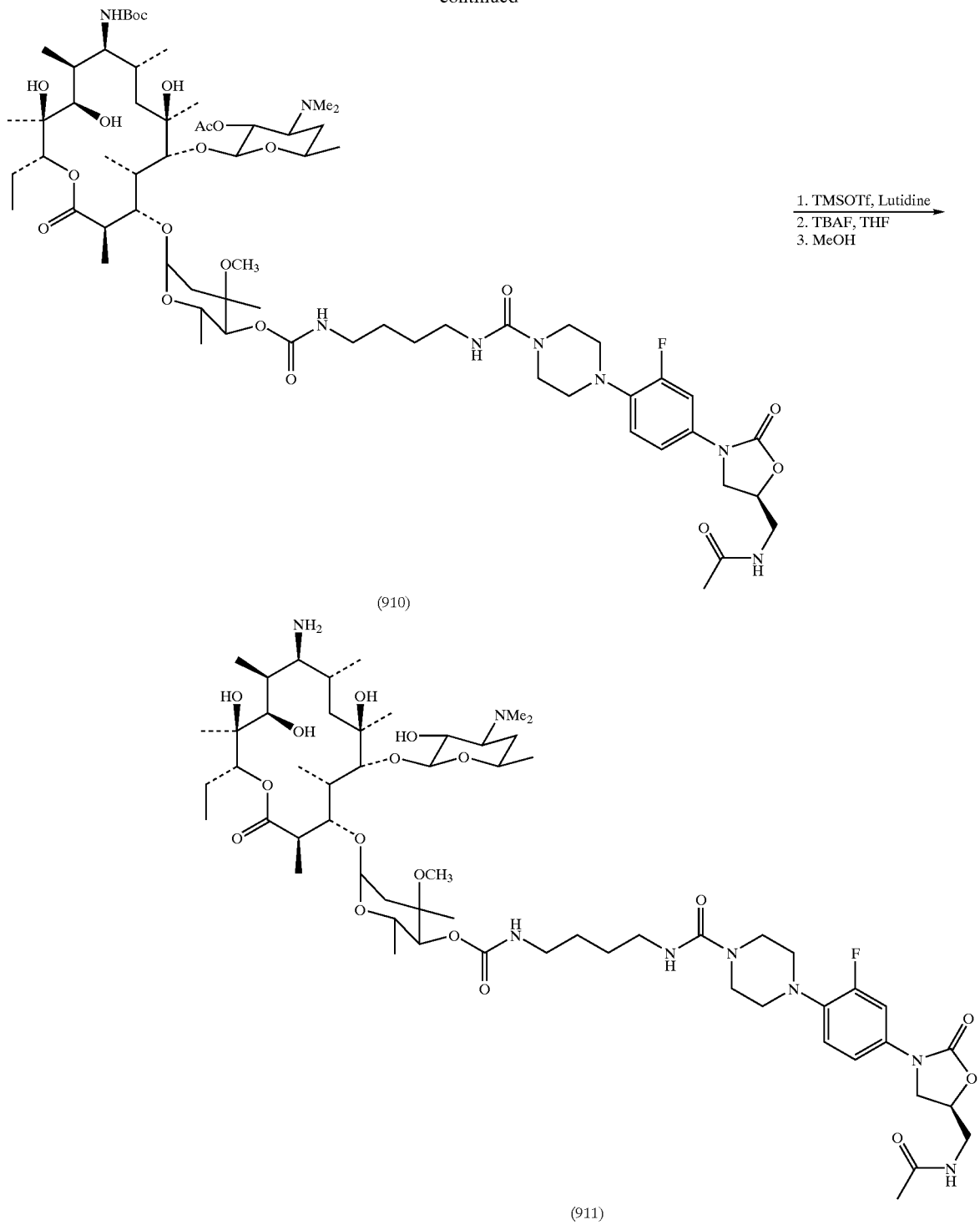

Example 34

Preparation of (923) and (924), Compounds of Formula XXXI via Scheme EE

A solution of 10 mmols of Spectinomycin (701) in DMF with 10 mmols of 3-bromopropionic acid (833) and 20 mmols of potassium carbonate is heated as necessary and the reaction followed by TLC. When judged complete, volatiles are removed under vacuum and the crude is fractionated by reverse-phase HPLC to afford the desired products (912) and (913) after lyopholization of the appropriate fractions.

Compounds (912) (4.0 mmol) and (913) (4.0 mmol) are individually dissolved in anhydrous dimethylformamide and treated sequentially with compound (103) (4.0 mmol), prepared as, described in Example 1, hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the crude is fractionated by reverse-phase HPLC to afford the title products after lyopholization of the appropriate fractions.
The chemistry is detailed below in the following reaction scheme:
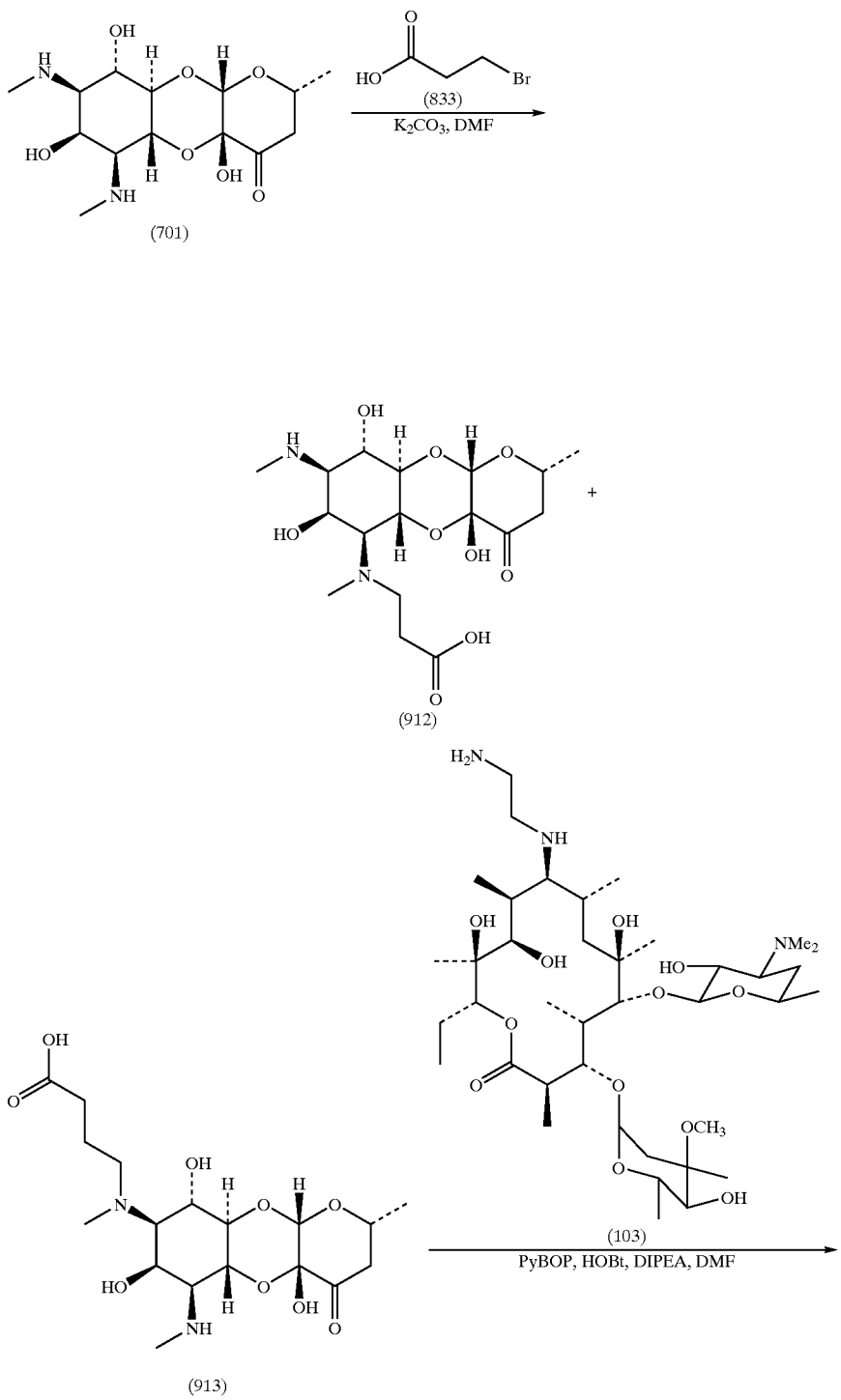

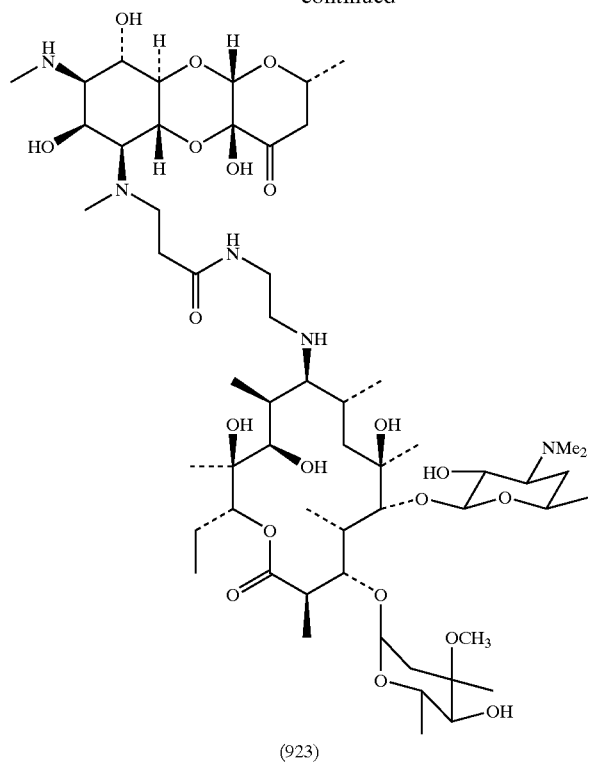
(923)
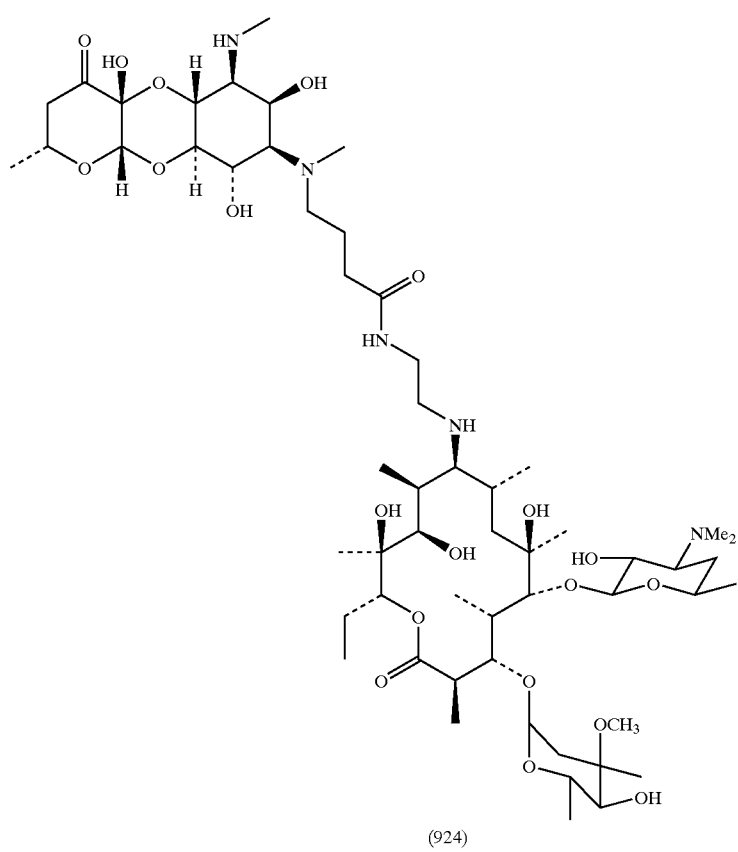
(924)

Example 35

Preparation of (915), a Compound of Formula XXXII via Scheme FF 1,4-Diaminobutane (106) (4.0 mmol) is dissolved in toluene/DMF, stirred at room temperature, and treated sequentially with diisopropylethyl amine (4.0 mmol) and imidazolide (105) (4.0 mmol), prepared as described in Example 2. After 2 hours, volatiles are removed under vacuum and the crude is fractionated by reverse-phase HPLC to afford the desired product (903) after lyopholization of the appropriate fractions.

Compound (903) (2.0 mmol) is dissolved in toluene, stirred at room temperature, and treated sequentially with diisopropylethyl amine (4.0 mmol) and imidazolide (506) (2.0 mmol), prepared as described in Example 13. After 2 hours, volatiles are removed under vacuum and the crude is fractionated by reverse-phase HPLC to afford the desired product (914) after lyopholization of the appropriate fractions.

Compound (914) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at reflux for 1 hour. Volatiles are removed under vacuum and the crude is fractionated by reverse-phase HPLC to afford the title product after lyopholization of the appropriate fractions.

The chemistry is detailed below in the following reaction scheme:

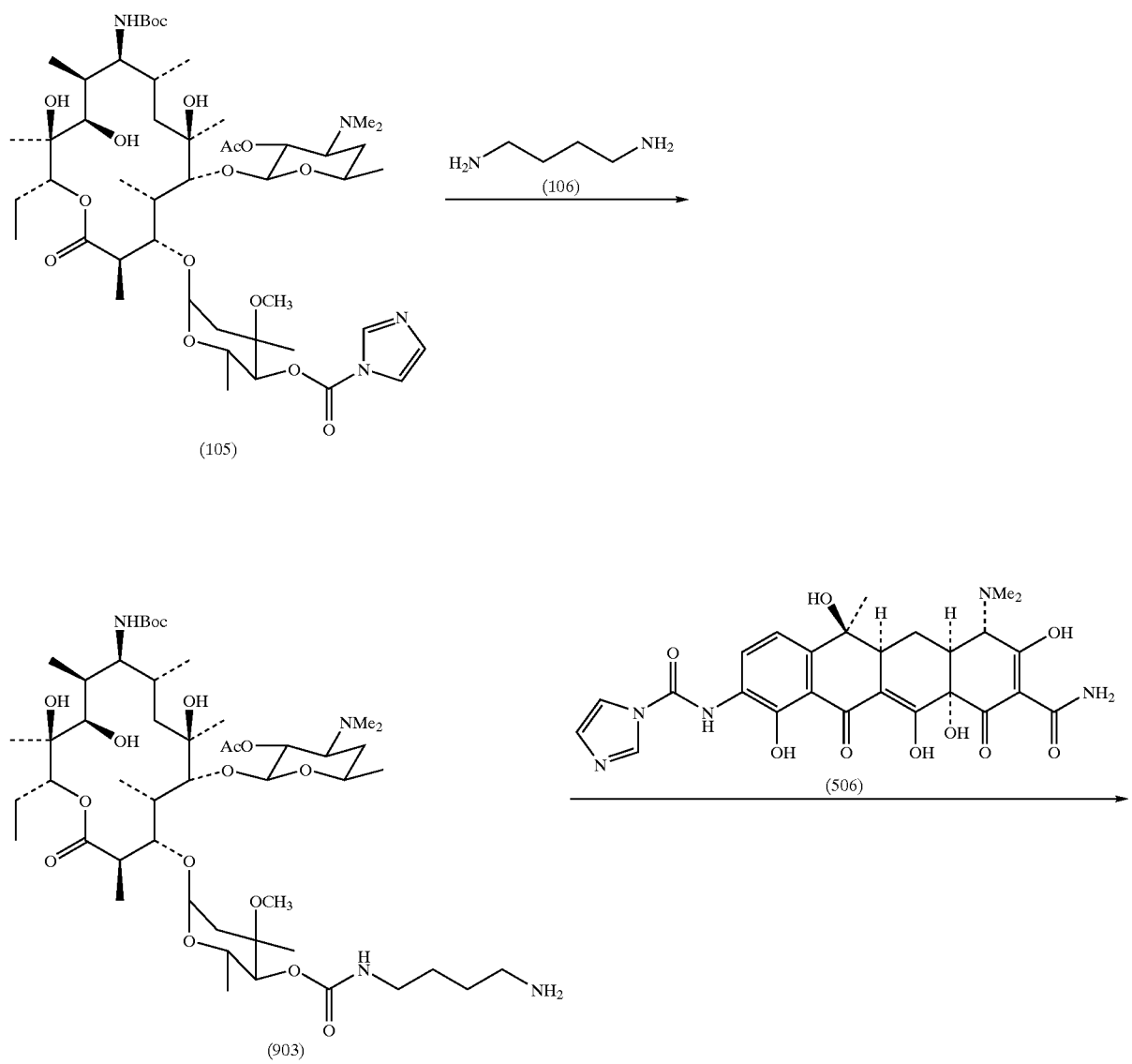

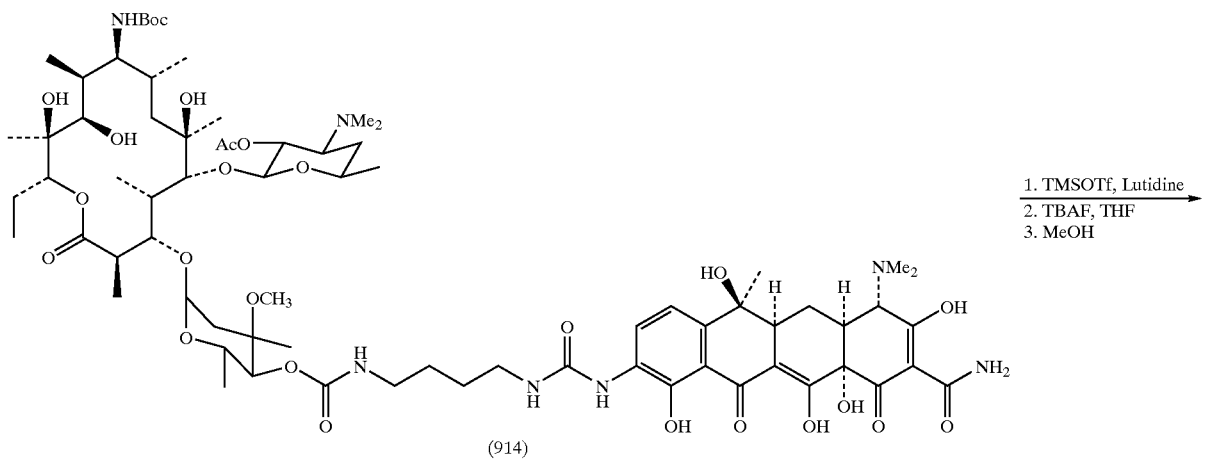

(914)

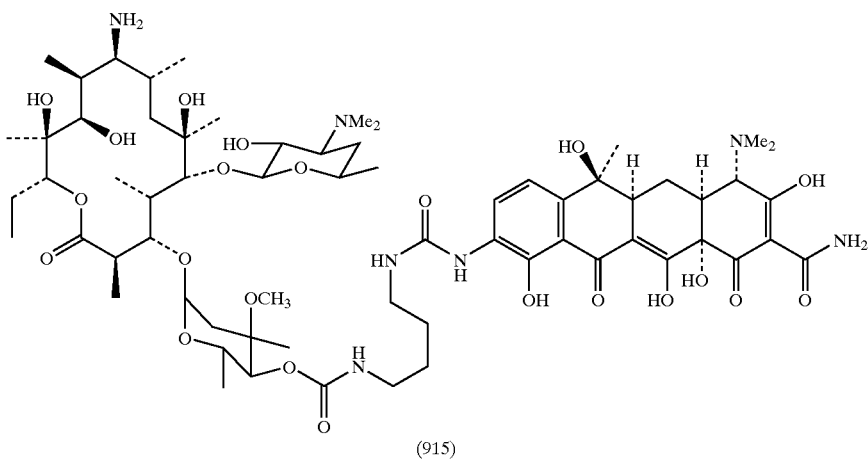

(915)

Example 36

Preparation of (916), a Compound of Formula XXXII via Scheme GG

Compound (906) (2.0 mmol), prepared as described in Example 31, is dissolved in 10 mL anhydrous dimethylformamide and treated sequentially with hydroxybenzotriazole (2.5 mmol), diisopropylethyl amine (2.0 mmol) and PyBOP (2.0 mmol). After stirring for 15 minutes at room temperature, the activated acid is treated with compound (503) (2.0 mmol), prepared as described in Example 12, and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

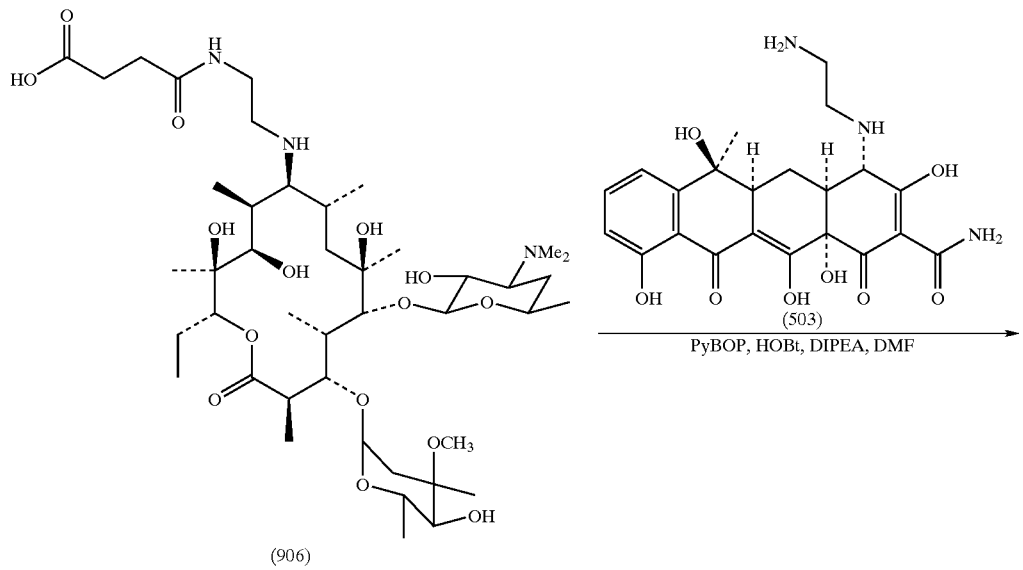

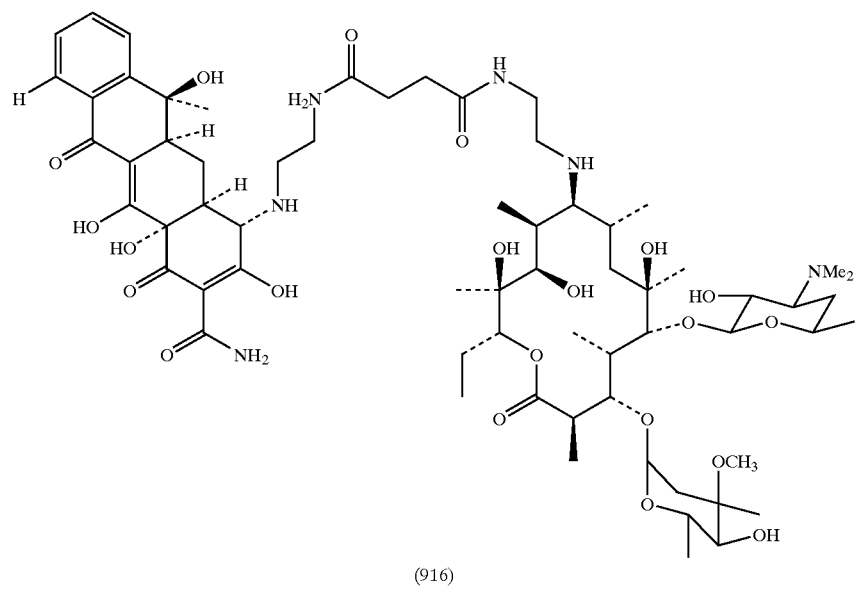

Example 37

Preparation of (918), a Compound of Formula XXXIV via Scheme HH

Compound (110) (4.0 mmol), prepared as described in Example 3, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (503) (4.0 mmol), prepared as described in Example 12, and the coupling reaction mixture is stirred overnight at room temperature. Volatiles are removed under vacuum and the crude is fractionated by reverse-phase HPLC to afford the desired product (908) after lyopholization of the appropriate fractions.

Compound (908) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at reflux for 1 hour. Volatiles are removed under vacuum and the crude is fractionated by reverse-phase HPLC to afford the title product after lyopholization of the appropriate fractions.

The chemistry is detailed below in the following reaction scheme:

211
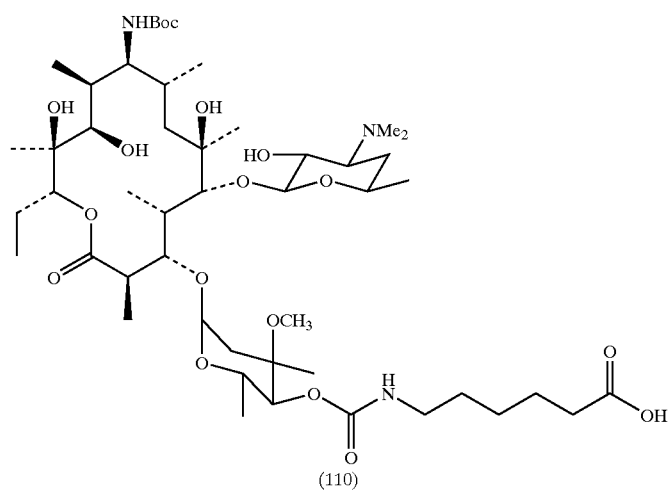
(110)
212
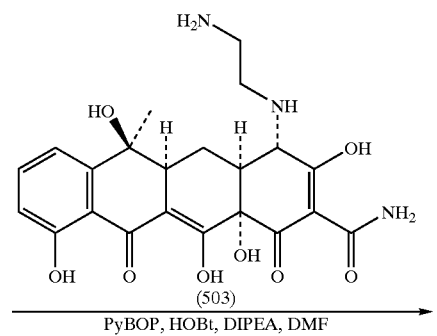
(503)
PyBOP, HOBt, DIPEA, DMF
1. TMSOTf, Lutidine
2. TBAF, THF
3. MeOH
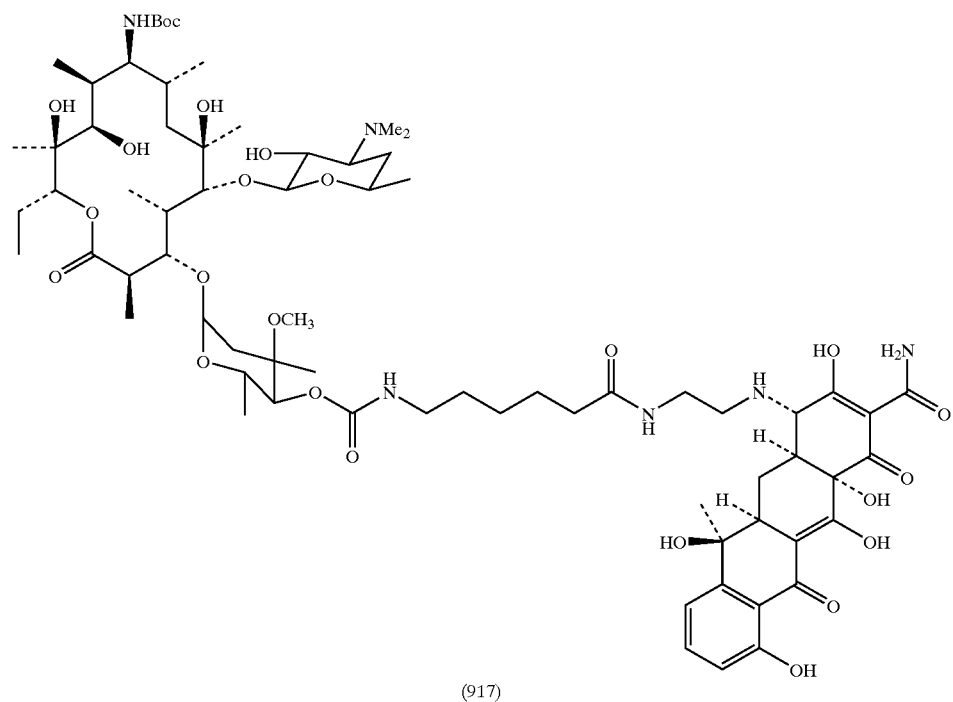
(917)

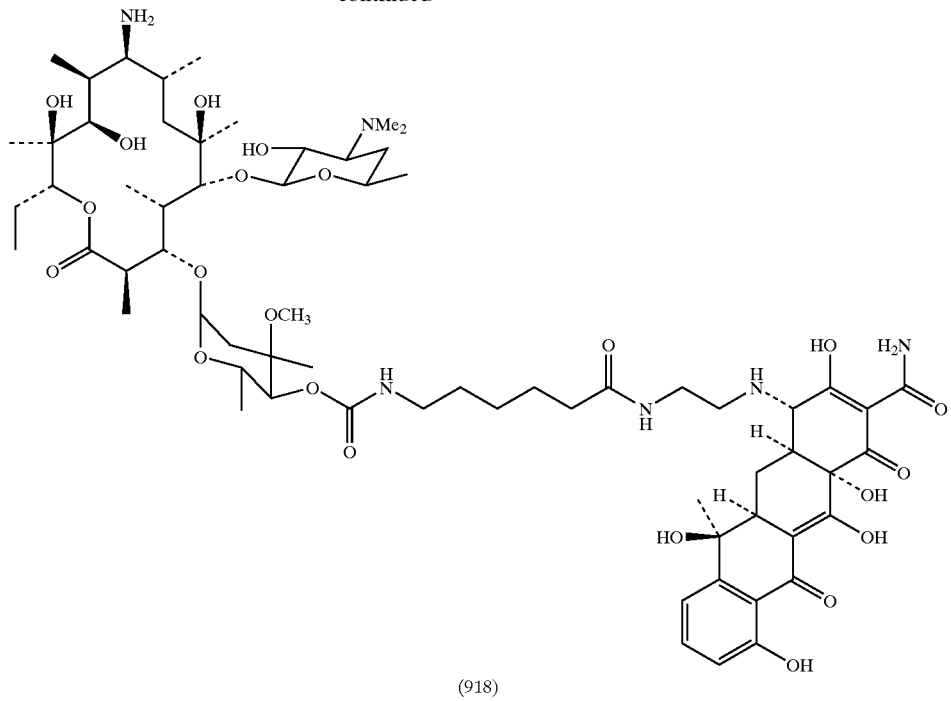

(918)

Example 38

Preparation of (921), a Compound of Formula XXXV via Scheme II

A solution of compound (922) (1.0 mmol), prepared as described in Example 33, in DMF with compound (506) (1.0 mmol), prepared as described in Example 13, is heated as necessary in a sealed vessel and the reaction followed by TLC. When judged complete, volatiles are removed under vacuum and the crude is fractionated by reverse-phase HPLC to afford the desired product (920) after lyopholization of the appropriate fractions.

Compound (920) (2.0 mmol) is dissolved in THF. Trimethylsilyl triflate (20 mmol) and lutidine (30 mmol) are added and the reaction is followed by TLC. When judged complete, the mixture is treated with tetrabutylammonium fluoride (30 mmol) and the reaction is followed by TLC. When judged complete, the mixture is diluted two-fold with methanol and heated at reflux for 1 hour. Volatiles are removed under vacuum and the crude is fractionated by reverse-phase HPLC to afford the title product after lyopholization of the appropriate fractions.

The chemistry is detailed below in the following reaction scheme:

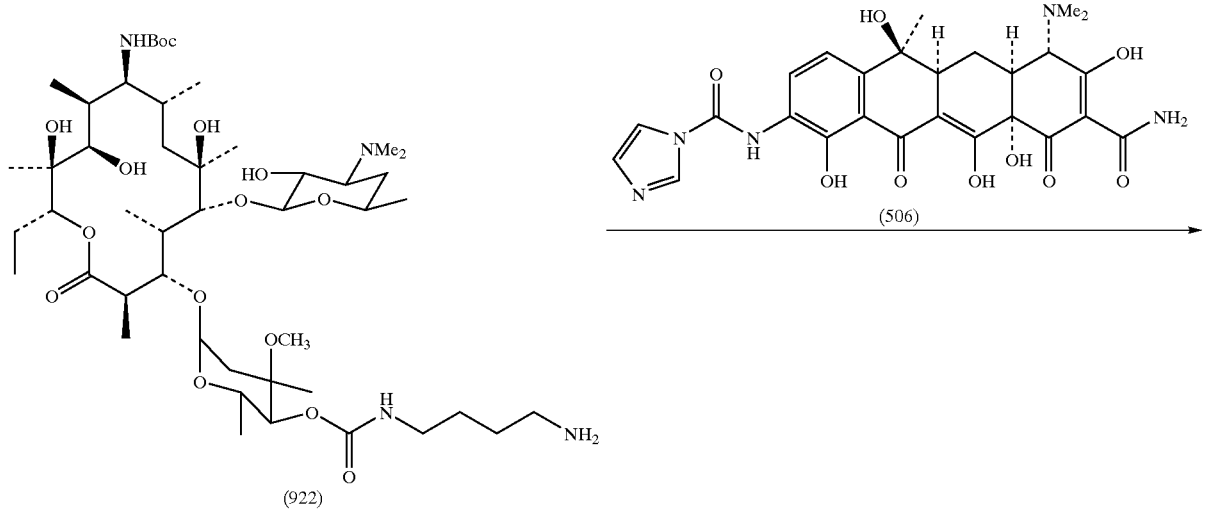

-continued

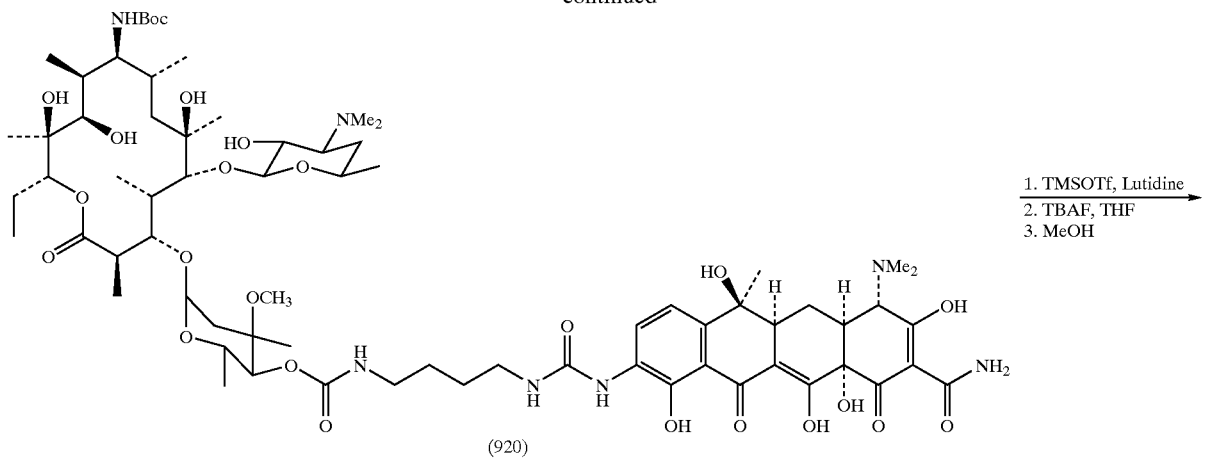

(920)

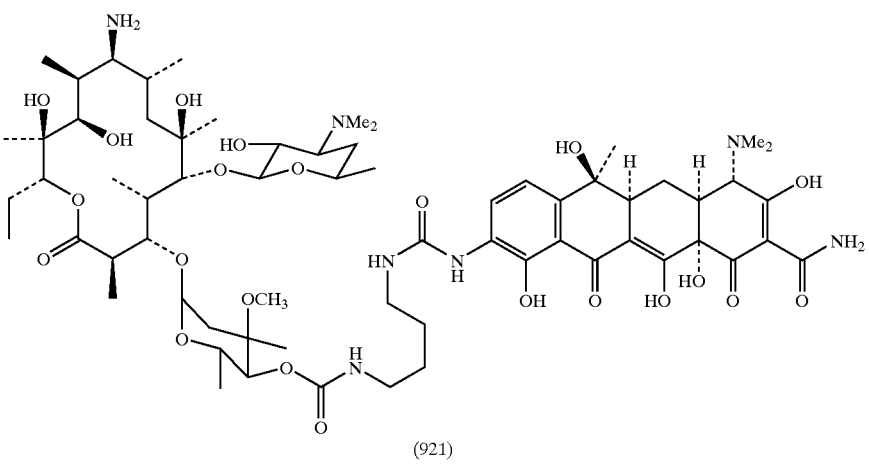

(921)

Example 39

Preparation of (1001), a Compound of Formula XXXVI via Scheme JJ

3-Bromopropionic acid (833) (4.0 mmol) is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (204) (4.0 mmol) and the coupling reaction mixture is stirred overnight at room temperature. Volatiles are removed under vacuum and the crude product is purified by silica gel chromatography to afford the desired product (1000).

A solution of 2 mmols of the above compound (1000) in DMF with 2 mmols compound (301) and 20 mmols of potassium carbonate is heated as necessary and the reaction followed by TLC. When judged complete, volatiles are removed under vacuum and the crude is fractionated by reverse-phase HPLC to afford the title product after lyopholization of the appropriate fractions.

Compound (204) is reported in *J. Med. Chem,* 49:673–679 (1996).

Compound (301) is U-57930E and is reported in *Antimicrobial Agents Chemother.,* 21:902–905 (1982).

The chemistry is detailed below in the following reaction scheme:

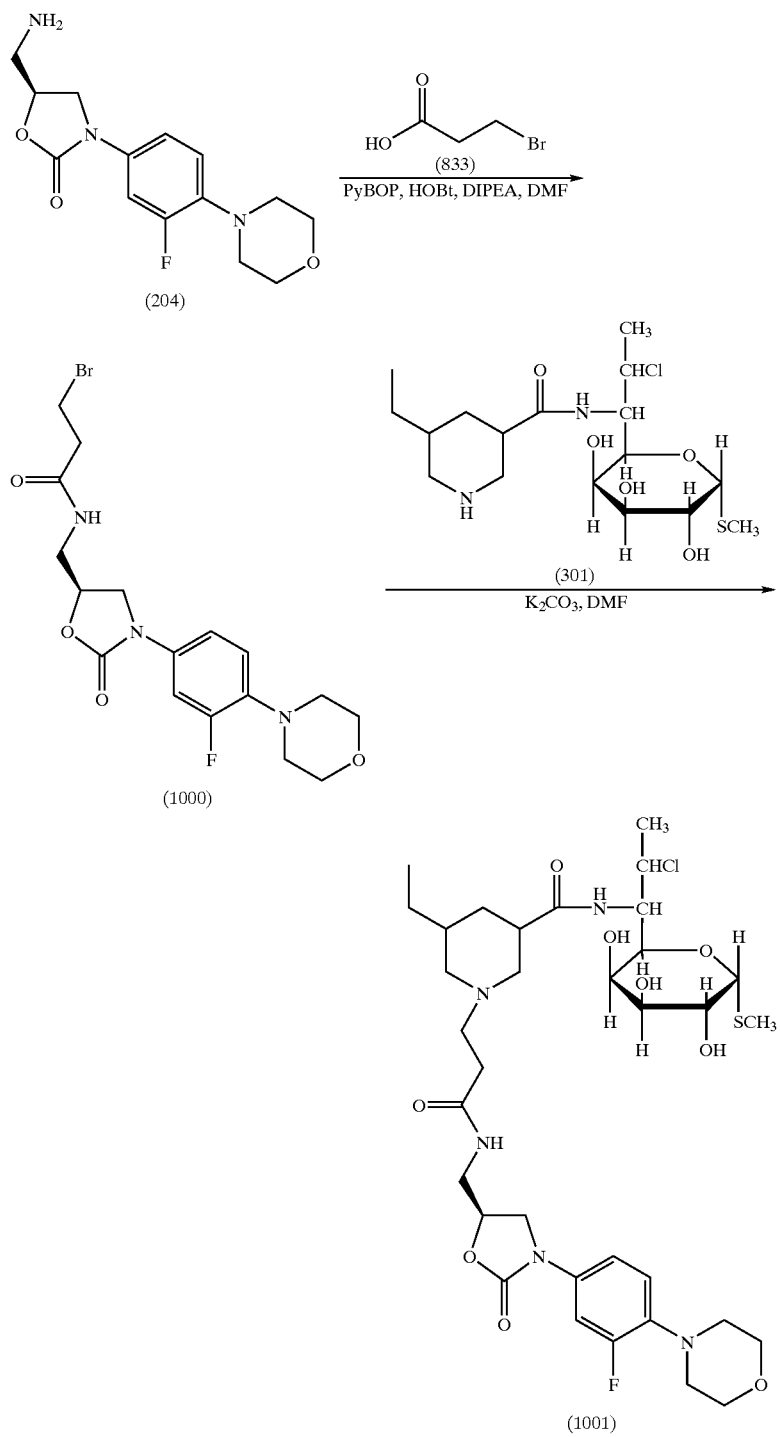

Example 39A

Preparation of (1012), a Compound of Formula XXXVII via Scheme KK

A solution of (202) (20 mmol), prepared as described in Example 4, in DMF with 3-bromopropylamine hydrobromide (1011) (20 mmol) is heated as necessary in a sealed vessel and the reaction followed by TLC. When judged complete, the mixture is partitioned between ethyl acetate and water and the organic phase washed with water, dried over sodium sulfate and the solvent removed in vacuo. The residue is purified by chromatography to afford the desired product (1002).

A solution of 10 mmols of the above compound (1002) in DMF with 10 mmols of compound (301) and 20 mmols of potassium carbonate is heated as necessary and the reaction followed by TLC. When judged complete, volatiles are removed under vacuum and the crude is fractionated by reverse-phase HPLC to afford the title product after lyopholization of the appropriate fractions.

Compound (301) is U-57930E and is reported in Antimicrobial Agents Chemother. 1982, 21, 902–905.

The chemistry is detailed below in the following reaction scheme:

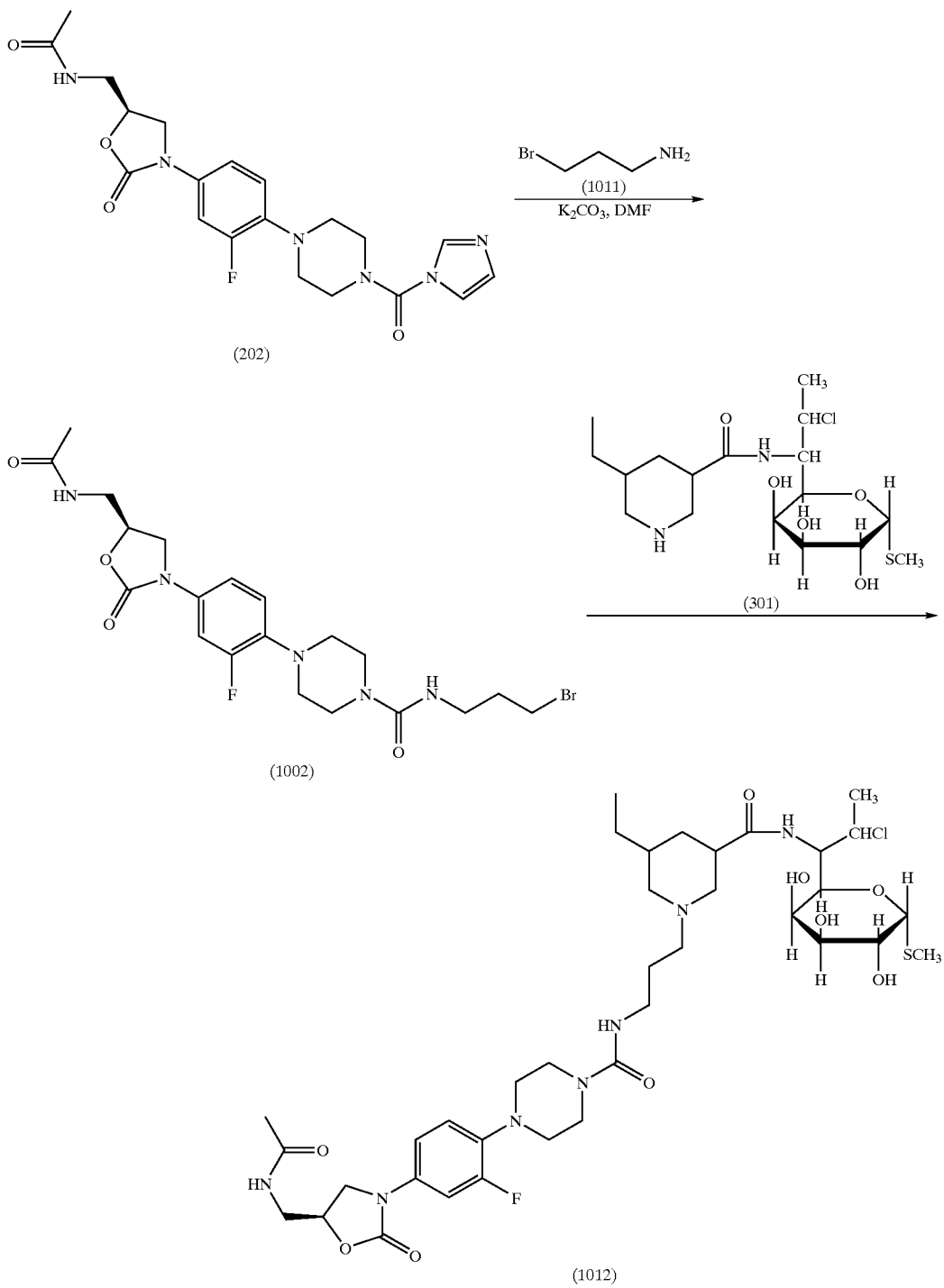

Example 40

Preparation of (1004), a Compound of Formula XXXVIII via Scheme LL

A solution of 20 mmols of the compound (301) in DMF with 20 mmols 3-bromoropionic acid (833) and 40 mmols of potassium carbonate is heated as necessary and the reaction followed by TLC. When judged complete, the mixture is partitioned between ethyl acetate and water and the organic phase washed with water, dried over sodium sulfate and the solvent removed in vacuo. The residue is purified by chromatography to afford the desired product (1003).

The above product (1003) (4.0 mmol) is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (503) (4.0 mmol), prepared as described in Example 12, and the coupling reaction mixture is stirred overnight at room temperature. Volatiles are removed under vacuum and the crude is fractionated by reverse-phase HPLC to afford the title product after lyopholization of the appropriate fractions.

Compound (301) is U-57930E and is reported in Antimicrobial Agents Chemother. 1982, 21, 902–905.

The chemistry is detailed below in the following reaction scheme:

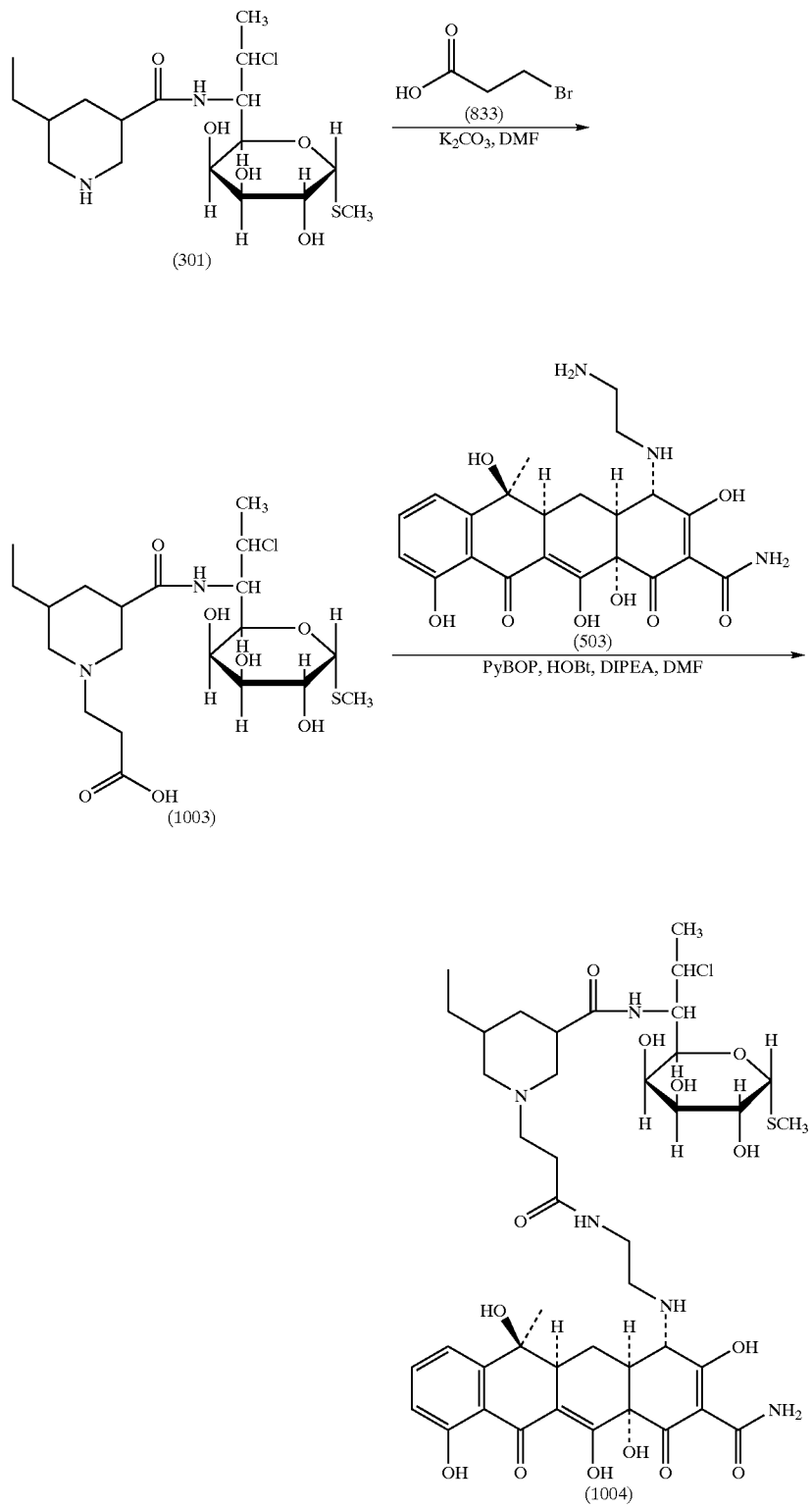

Example 41

Preparation of (1006) and (1007), Compounds of Formula XXXIX via Scheme MM

A solution of 20 mmols of compound (301) in DMF with 20 mmols of 1,6-diaminohexane (302) and 40 mmols of potassium carbonate is heated as necessary and the reaction followed by TLC. When judged complete, volatiles are removed under vacuum and the crude is fractionated by reverse-phase HPLC to afford the desired product (1005) after lyopholization of the appropriate fractions.

A solution of 10 mmols of the above compound (1005) in DMF with 10 mmols of Spectinomycin (701) and 20 mmols of potassium carbonate is heated as necessary and the reaction followed by TLC. When judged complete, volatiles are removed under vacuum and the crude is fractionated by reverse-phase HPLC to afford the title product after lyopholization of the appropriate fractions.

Compound (301) is U-57930E and is reported in Antimicrobial Agents Chemother. 1982, 21, 902–905.

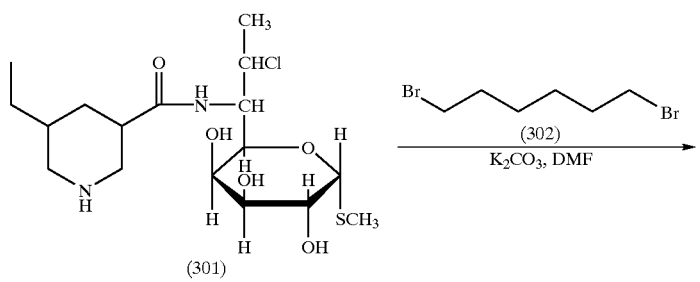

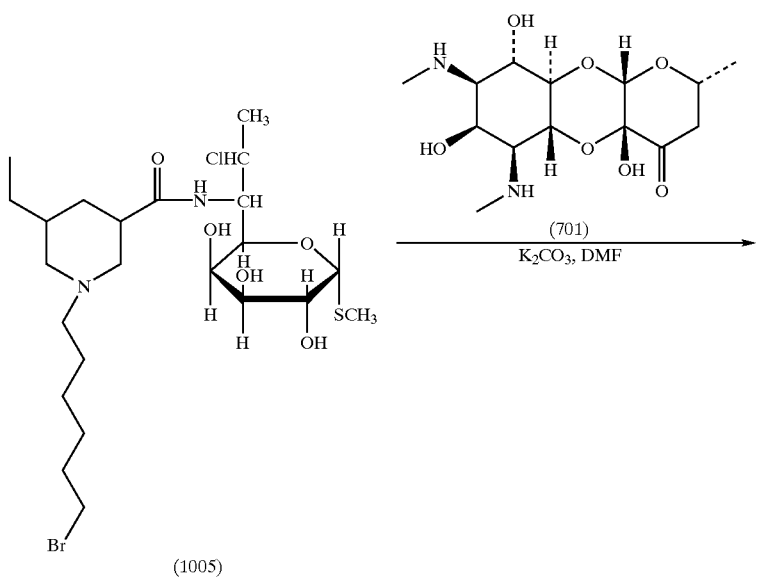

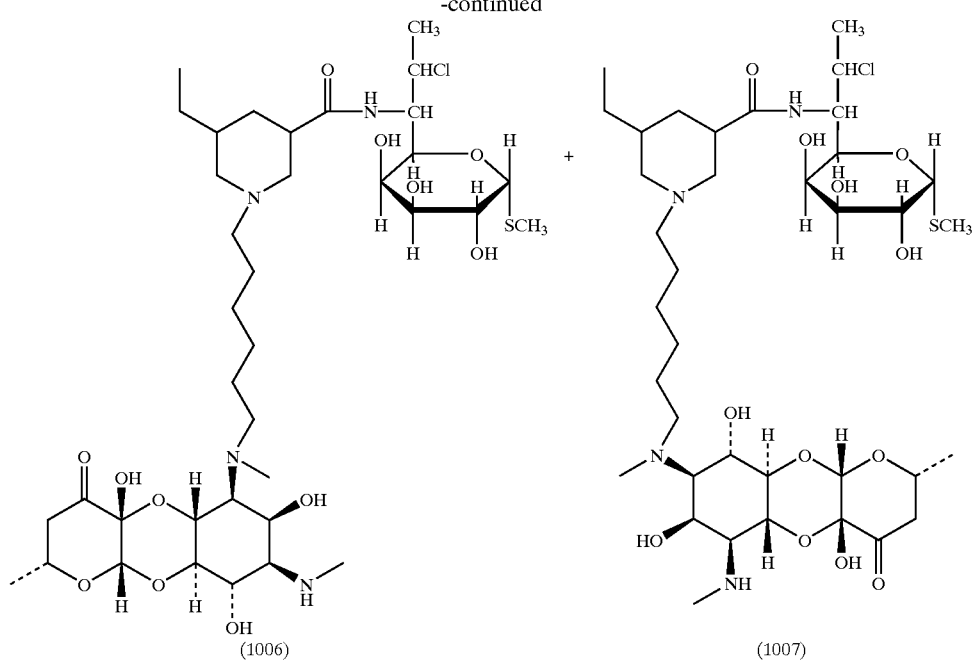

(1006) + (1007)

Example 42

Preparation of (1010), a Compound of Formula XL via Scheme NN

A solution of 20 mmols of 6-bromohexanoic acid (1008) in DMF with 20 mmols of compound (301) and 40 mmols of potassium carbonate is heated as necessary and the reaction followed by TLC. When judged complete, the reaction mixture is concentrated under reduced pressure and the residue purified by chromatography to afford the desired product (1009).

The above compound (1009) (4.0 mmol) is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (503) (4.0 mmol), prepared as described in Example 12, and the coupling reaction mixture is stirred overnight at room temperature. Volatiles are removed under vacuum and the crude is fractionated by reverse-phase HPLC to afford the title product after lyopholization of the appropriate fractions.

Compound (301) is U-57930E and is reported in Antimicrobial Agents Chemother. 1982, 21, 902–905.

The chemistry is detailed below in the following reaction scheme:

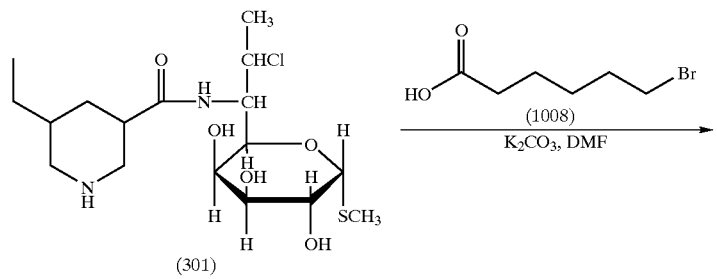

-continued

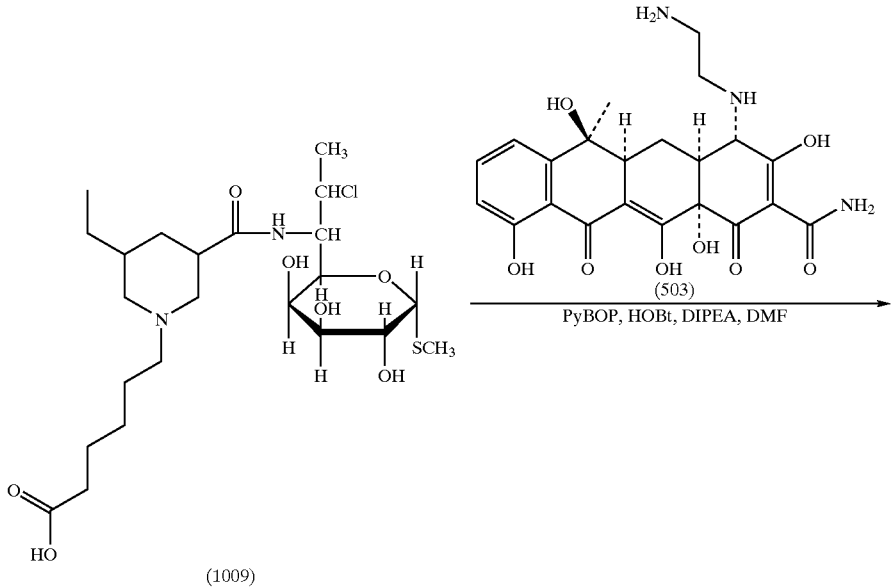

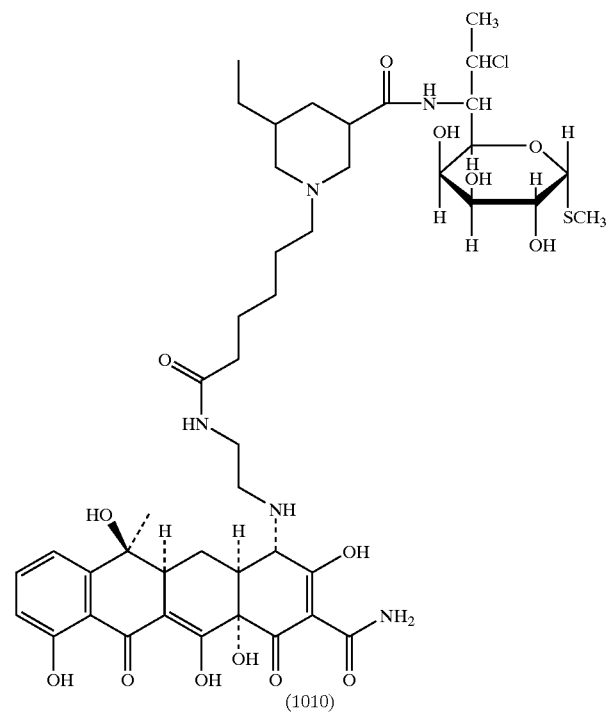

Example 43

Preparation of (1101), a Compound of Formula XLI via Scheme OO

Compound (906) (4.0 mmol), prepared as described in Example 31, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (607) (4.0 mmol), prepared as described in Example 16, and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme.

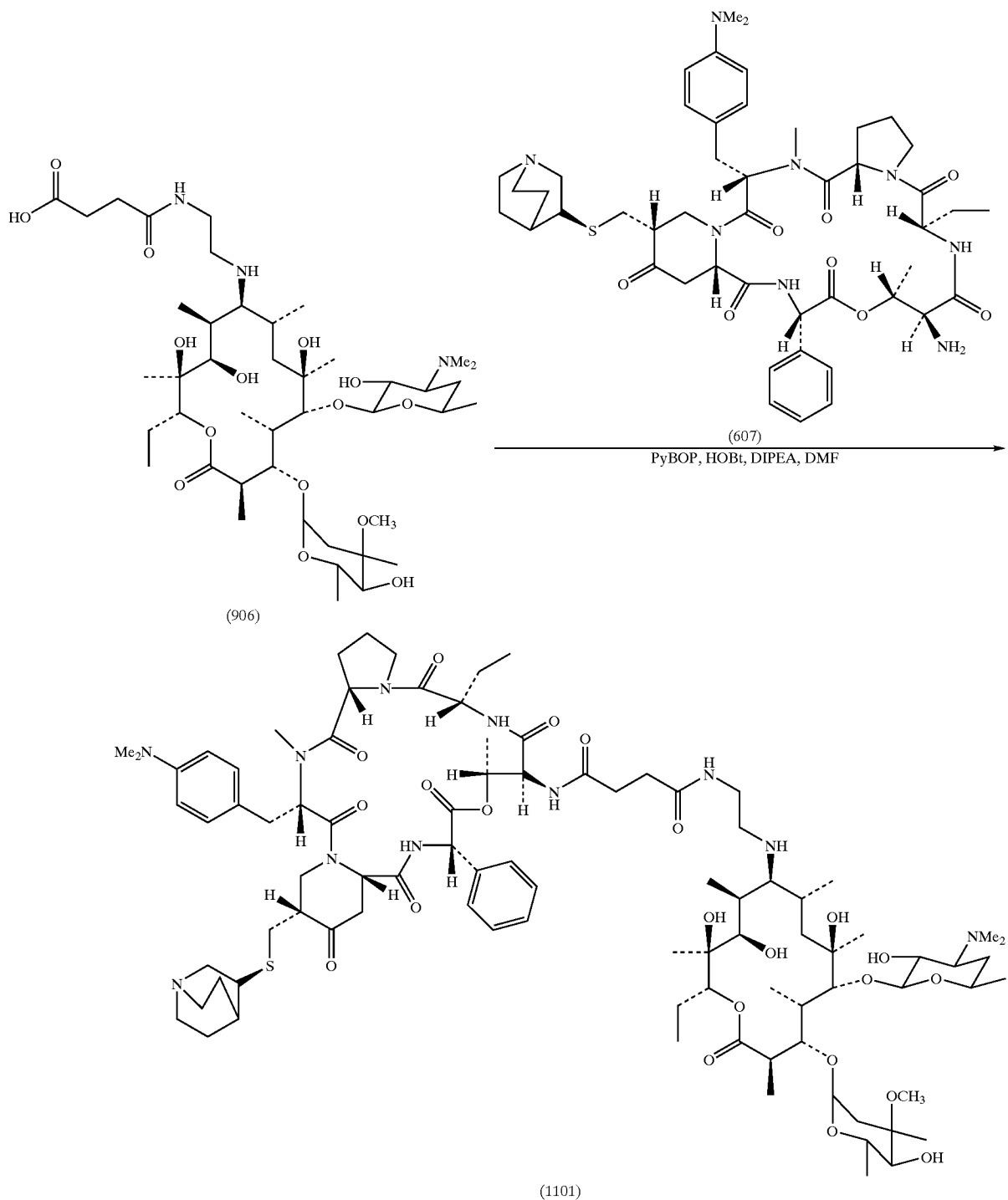

Example 44

Preparation of (1102), a Compound of Formula XLII via Scheme PP

Compound (610) (4.0 mmol), prepared as described in Example 17, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (103) (4.0 mmol), prepared as described in Example 1, and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

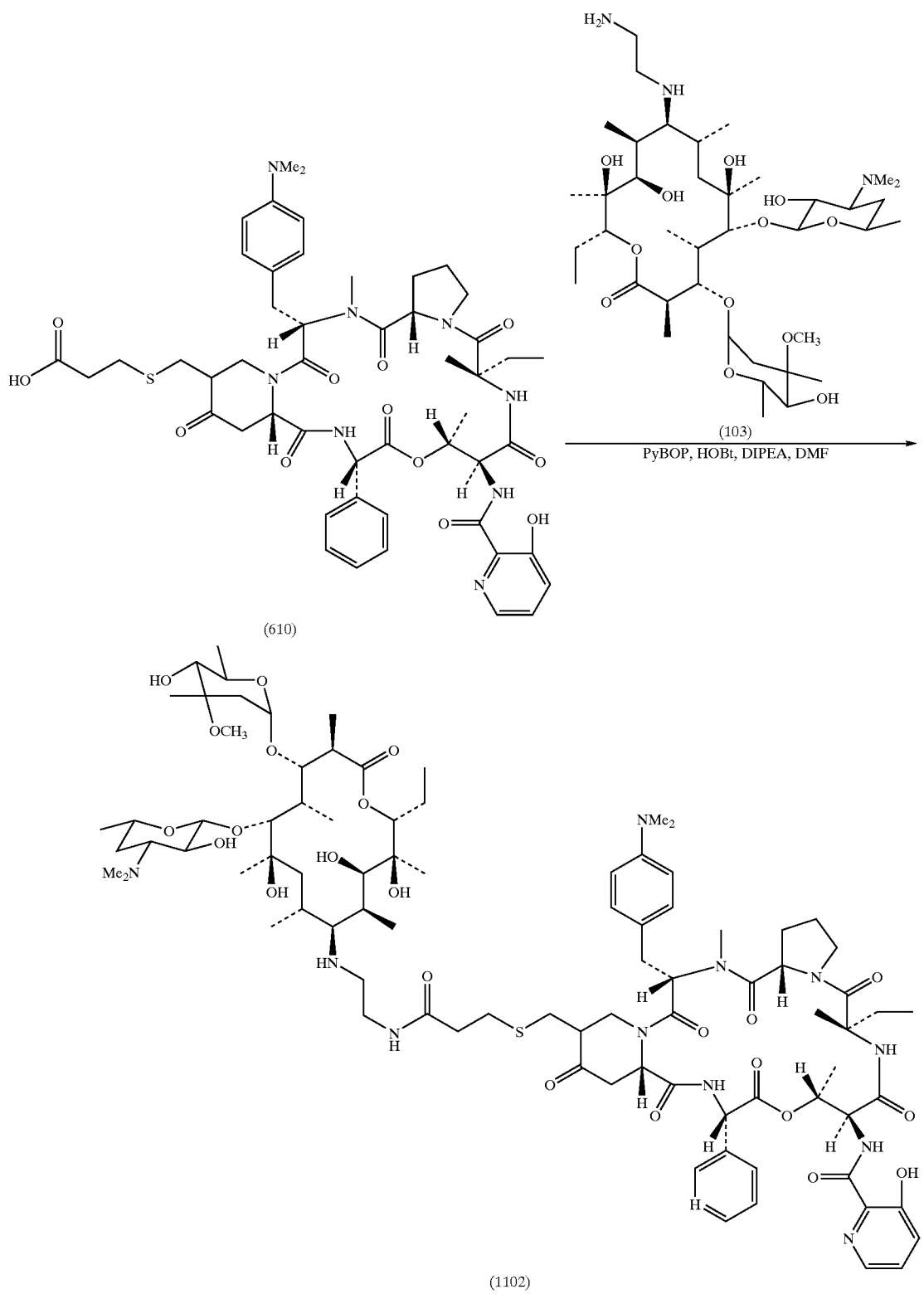

Example 45

Preparation of (1103), a Compound of Formula XLIII via Scheme QQ

Compound (617) (4.0 mmol), prepared as described in Example 16, is dissolved in anhydrous dimethylformamide and treated sequentially with hydroxybenzotriazole (5.0 mmol), diisopropylethyl amine (14.0 mmol) and PyBOP (4.0 mmol), After stirring for 15 minutes at room temperature, the activated acid is treated with compound (103) (4.0 mmol), prepared as described in Example 1, and the coupling reaction mixture is stirred overnight at room temperature. Volatiles are removed under vacuum and the crude is fractionated by reverse-phase HPLC to afford the title product after lyopholization of the appropriate fractions.
The chemistry is detailed below in the following reaction scheme:
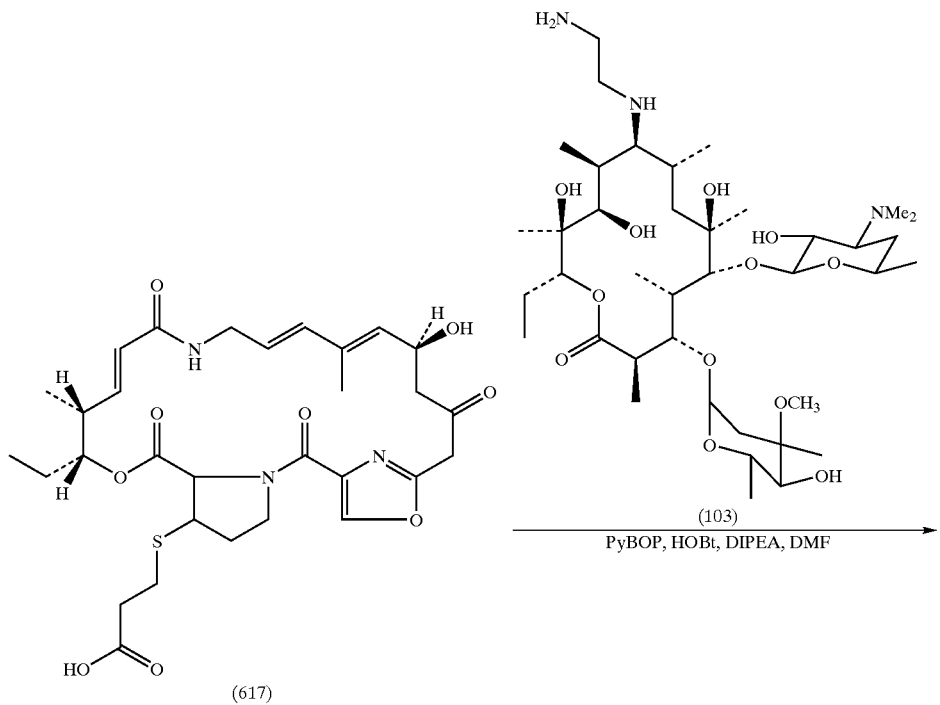
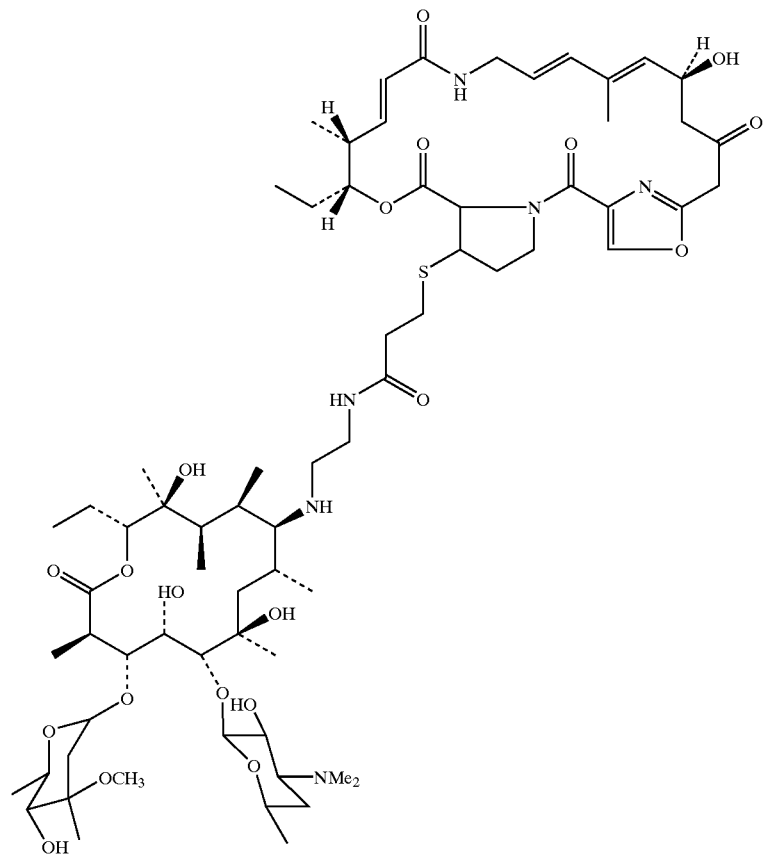

Example 46

Preparation of (1105), a Compound of Formula XLIV via Scheme RR

Compound (901) (4.0 mmol), prepared as described in Example 29, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (607) (4.0 mmol), prepared as described in Example 16, and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

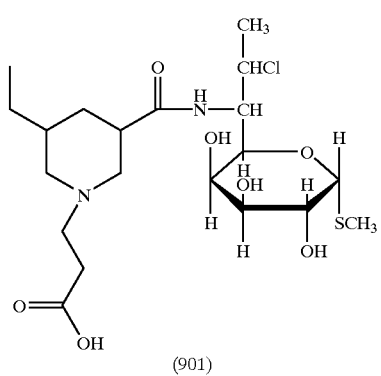
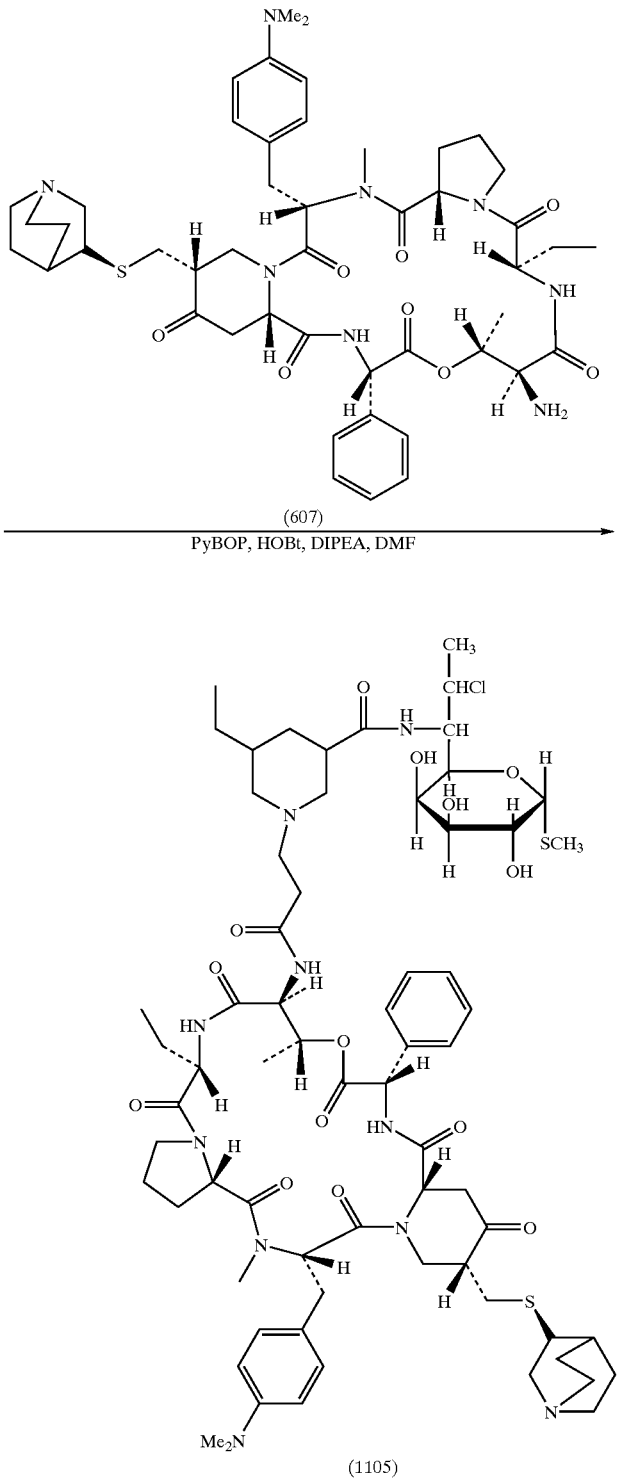

Example 47

Preparation of (1113), a Compound of Formula XLV via Scheme SS

Compound (301) (10 mmol) is slurried in methanol:anhydrous dimethylformamide, stirred at room temperature, and treated sequentially with diisopropylethyl amine (20 mmol) and Fmoc glycinal (101) (10 mmol) (prepared as described by Salvi et al. Tetrahedron Lett. 1994, 35, 1181–1184). After 2 hours the reaction mixture is cooled in an ice water bath and treated further with sodium cyanoborohydride (4.0 mmol) and trifluoroacetic acid (30 mmol). After 2 additional hours, volatiles are removed under vacuum and the crude is fractionated by reverse-phase HPLC to afford the desired product (1106) after lyopholization of the appropriate fractions.

The above product (1106) is then dissolved in anhydrous dimethylformamide (10 mL), stirred at room temperature and treated with excess piperidine (1.0 mL). After one hour the crude products are fractionated by reverse-phase HPLC to afford the desired product (1112).

Compound (617) (4.0 mmol), prepared as described in Example 20, is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (1112) (4.0 mmol) and the coupling reaction mixture is stirred overnight at room temperature. Volatiles are removed under vacuum and the crude is fractionated by reverse-phase HPLC to afford the title product after lyopholization of the appropriate fractions.

Compound (301) is U-57930E and is reported in Antimicrobial Agents Chemother. 1982, 21, 902–905.

The chemistry is detailed below in the following reaction scheme:

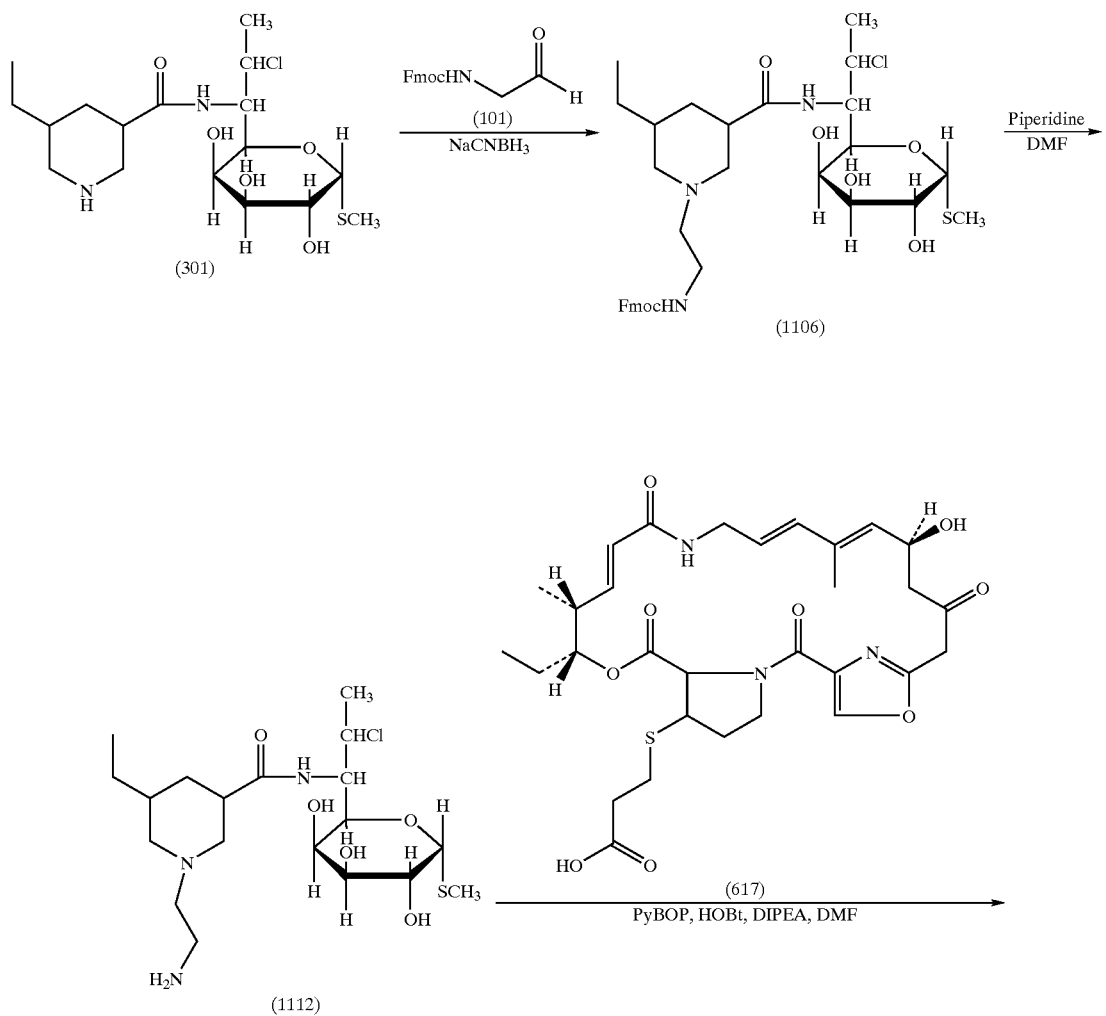

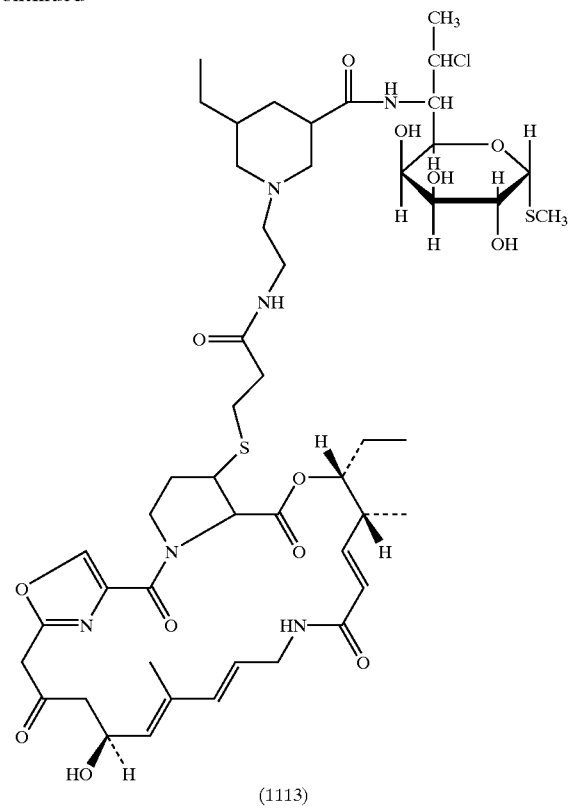

(1113)

Example 48

Preparation of (1108), a Compound of Formula XLVI via Scheme TT

Compound (204) (10 mmol) is dissolved in anhydrous dimethylformamide and treated with adipic acid (205) (10 mmol), hydroxybenzotriazole (10 mmol), diisopropylethyl amine (20 mmol) and PyBOP (10 mmol) and the coupling reaction mixture is stirred overnight at room temperature. After deprotection with NaOH, volatiles are removed under vacuum and the crude is fractionated by reverse-phase HPLC to afford the desired product (1107) after lyopholization of the appropriate fractions.

The above compound (1107) (4.0 mmol) is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (607) (4.0 mmol), prepared as described in Example 16, and the coupling reaction mixture is stirred overnight at room temperature. Volatiles are removed under vacuum and the crude is fractionated by reverse-phase HPLC to afford the title product after lyopholization of the appropriate fractions.

Compound (204) is reported in J. Med. Chem. 1996, 49, 673–679.

The chemistry is detailed below in the following reaction scheme:

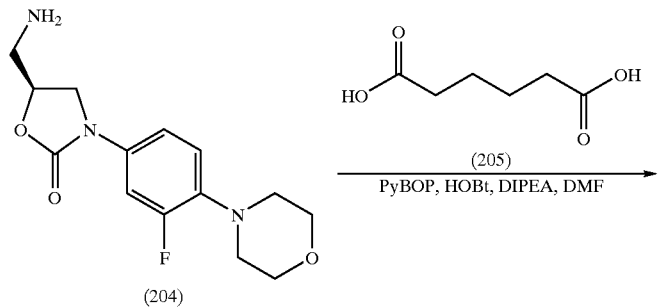

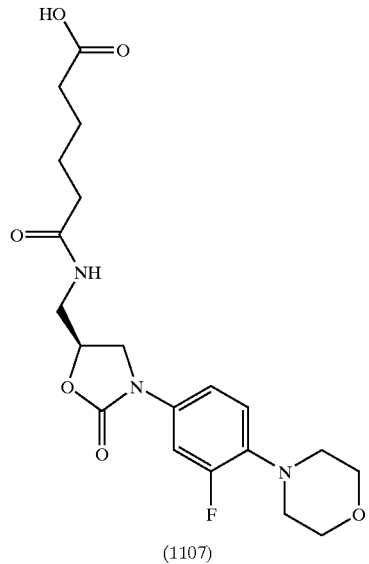
(1107)
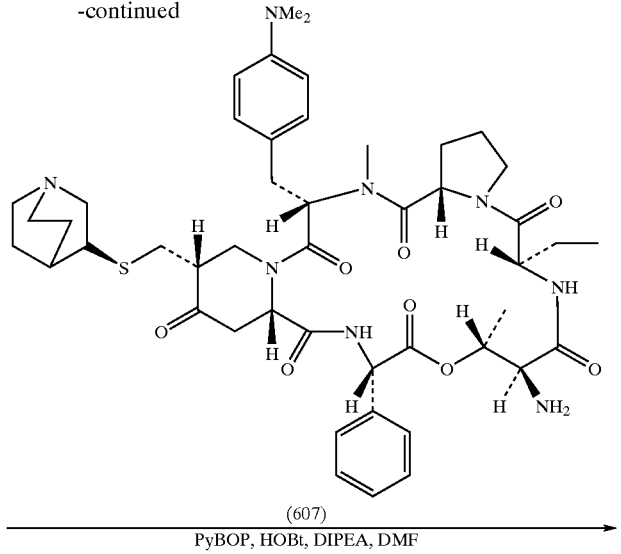
(607)
PyBOP, HOBt, DIPEA, DMF
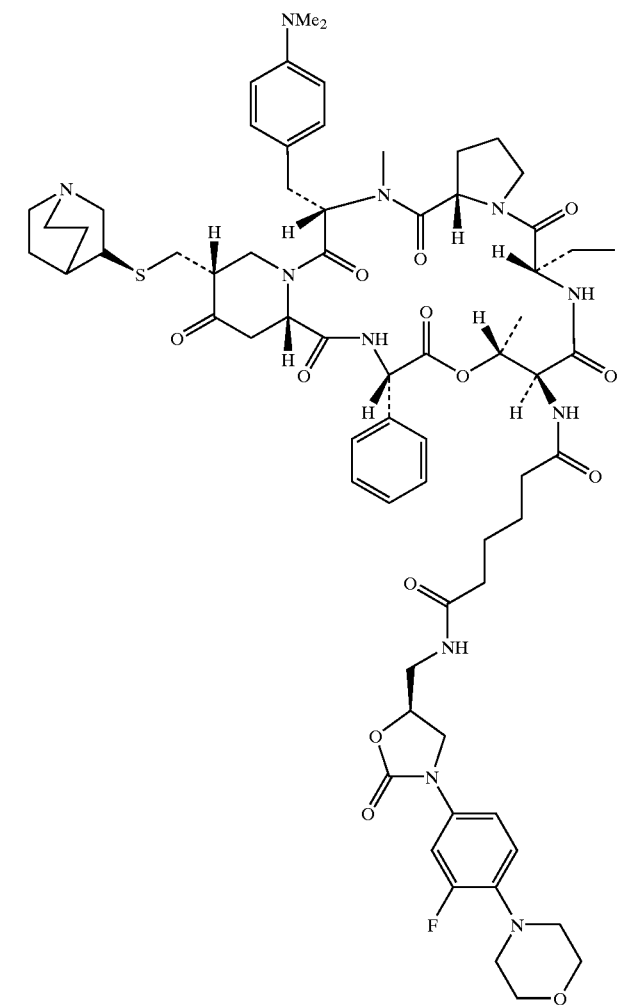
(1108)

Example 49

Preparation of (1109), a Compound of Formula XLVII via Scheme UU

Compound (207) (4.0 mmol), prepared as described in Example 6, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (607) (4.0 mmol), prepared as described in Example 16, and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:

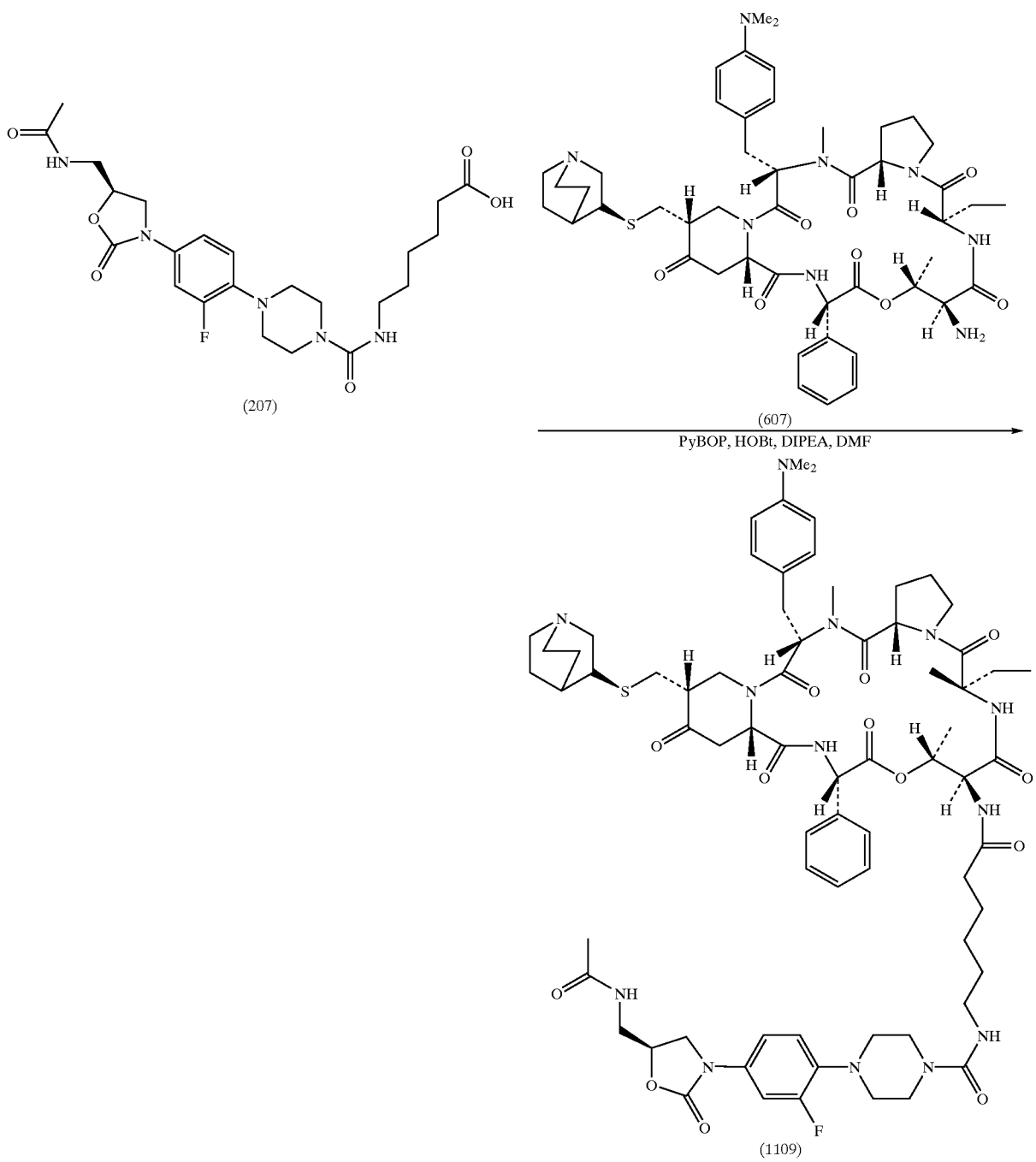

Example 50

Preparation of (1110), a Compound of Formula XLVIII via Scheme VV

Compound (610) (4.0 mmol), prepared as described in Example 17, is dissolved in anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (204) (4.0 mmol), prepared as described in Example 16, and the coupling reaction mixture is stirred overnight at room temperature. Volatiles are removed under vacuum and the crude is fractionated by reverse-phase HPLC to afford the title product after lyopholization of the appropriate fractions.

Compound (204) is reported in J. Med. Chem. 1996, 49, 673–679.

The chemistry is detailed below in the following reaction scheme:

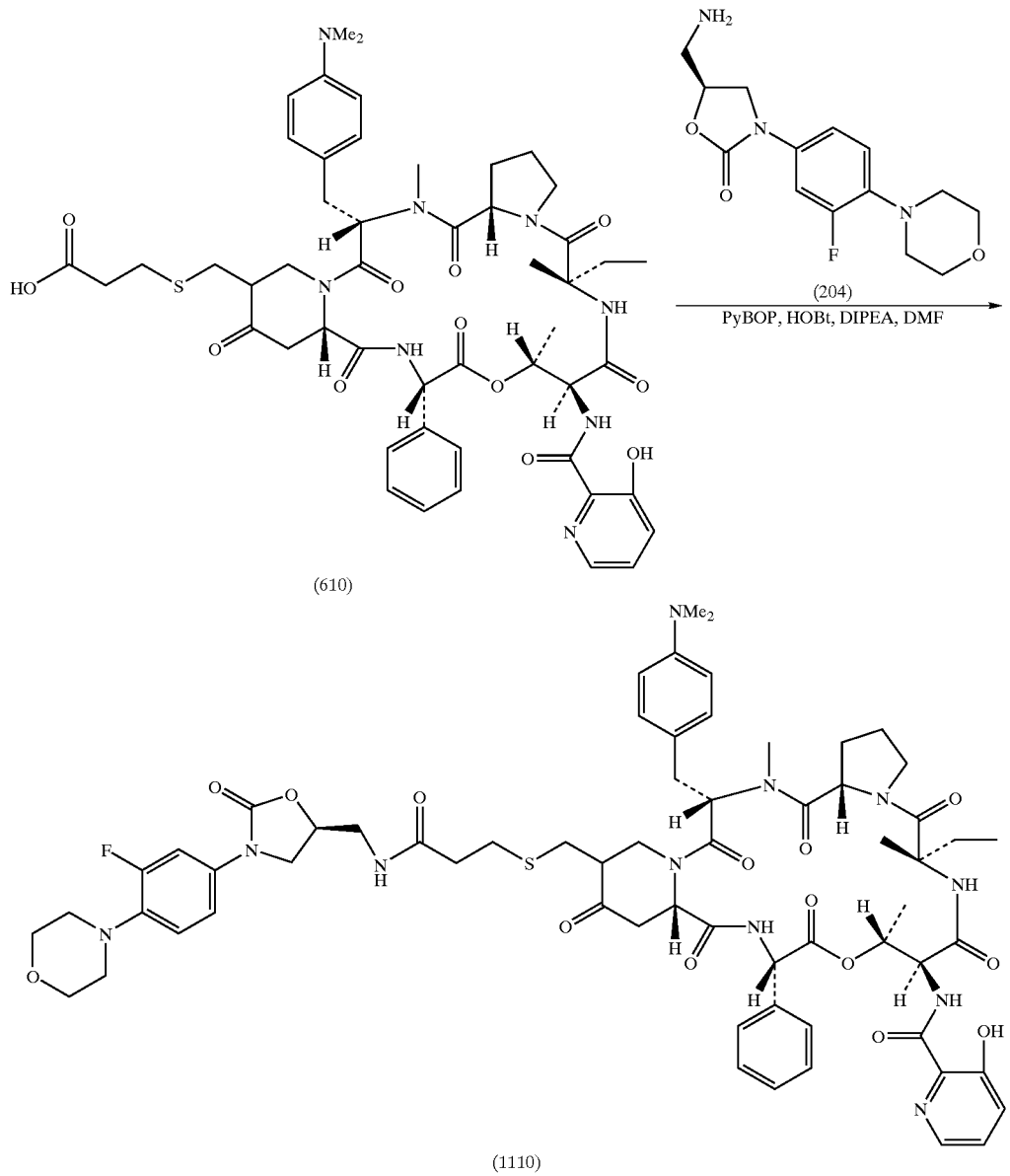

(610)

(1110)

Example 51

Preparation of (1111), a Compound of Formula XLIX via Scheme WW

Compound (617) (4.0 mmol), prepared as described in Example 20, is dissolved in anhydrous dimethylformamide

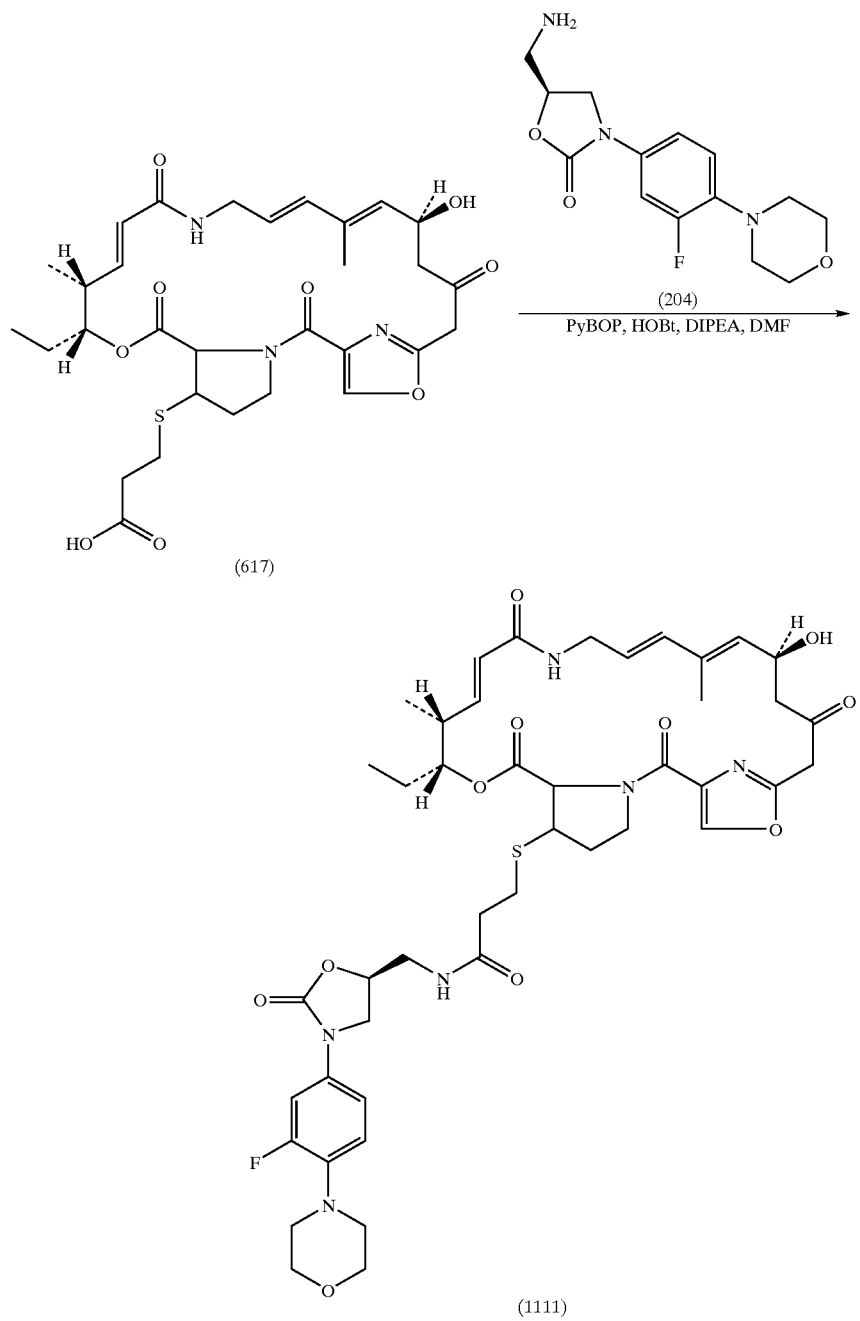

Example 52

Preparation of (1201), a Compound of Formula L via Scheme XX

A solution of 20 mmols of compound (829), prepared as described in Example 26, in DMF with 20 mmols of 1,6-dibromohexane (302) and 40 mmols of potassium carbonate is heated as necessary and the reaction followed by TLC. When judged complete, the crude product is purified by chromatography to afford the desired product (1200).

A solution of 10 mmols of the above compound (1200) in DMF with 10 mmols of compound (301) and 20 mmols of potassium carbonate is heated as necessary and the reaction followed by TLC. When judged complete, the reaction mixture is diluted two-fold with water, treated with NaOH (50 mmol), and heated as necessary to effect deprotection. The crude product is fractionated by reverse-phase HPLC to afford the title product after lyopholization of the appropriate fractions.

Compound (301) is U-57930E and is reported in Antimicrobial Agents Chemother. 1982, 21, 902–905.

The chemistry is detailed below in the following reaction scheme:

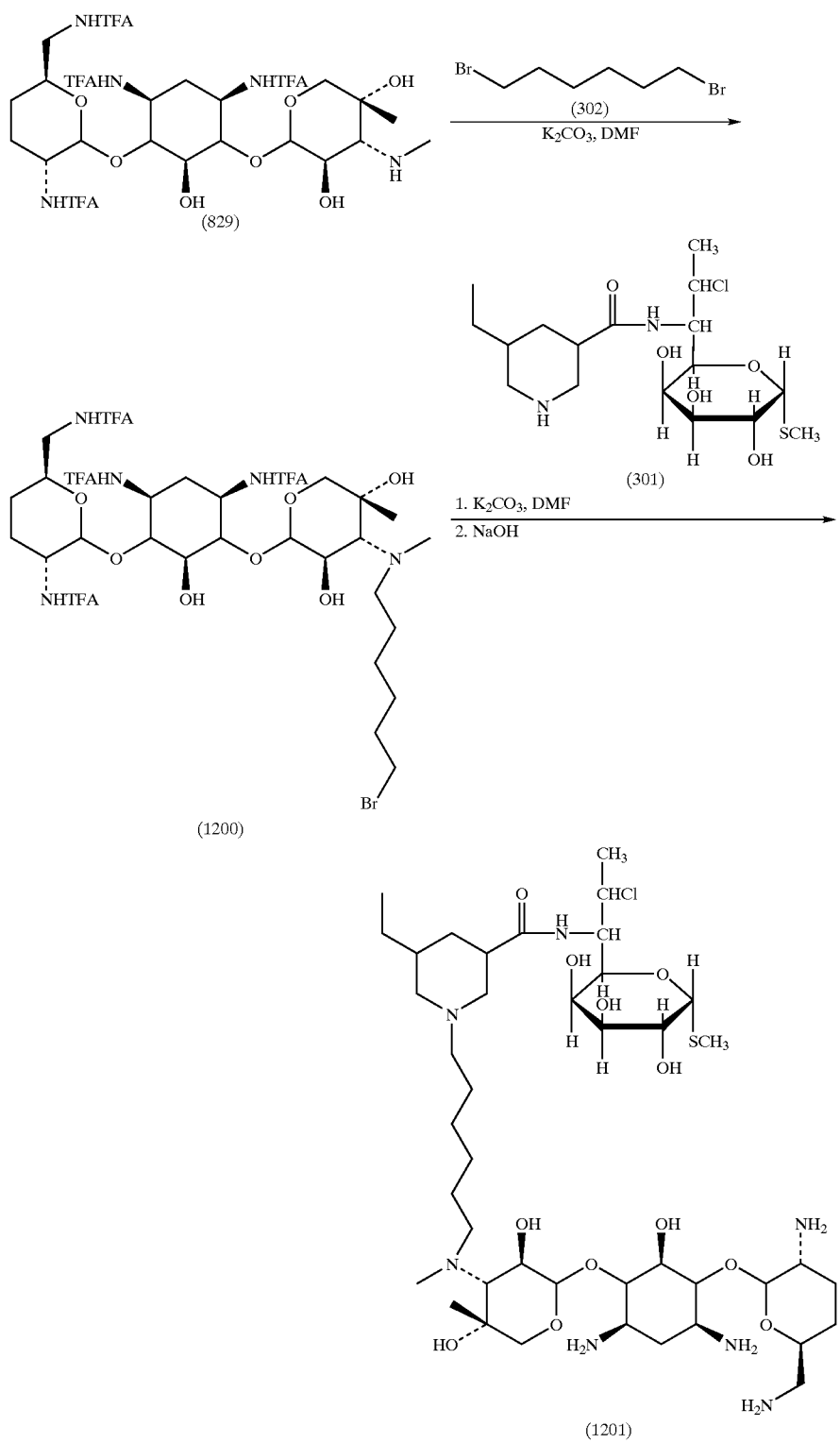

Example 53

Preparation of (1202) and (1203), Compounds of Formula LI via Scheme YY

A solution of 20 mmols of the compound (1200), prepared as described in Example 52, in DMF with 20 mmols of Spectinomycin (701) and 20 mmols of potassium carbonate is heated as necessary and the reaction followed by TLC. When judged complete, the reaction mixture is diluted two-fold with water, treated with NaOH (50 mmol), and heated as necessary to effect deprotection. The crude product is fractionated by reverse-phase HPLC to afford the title product after lyopholization of the appropriate fractions.

The chemistry is detailed below in the following reaction scheme:

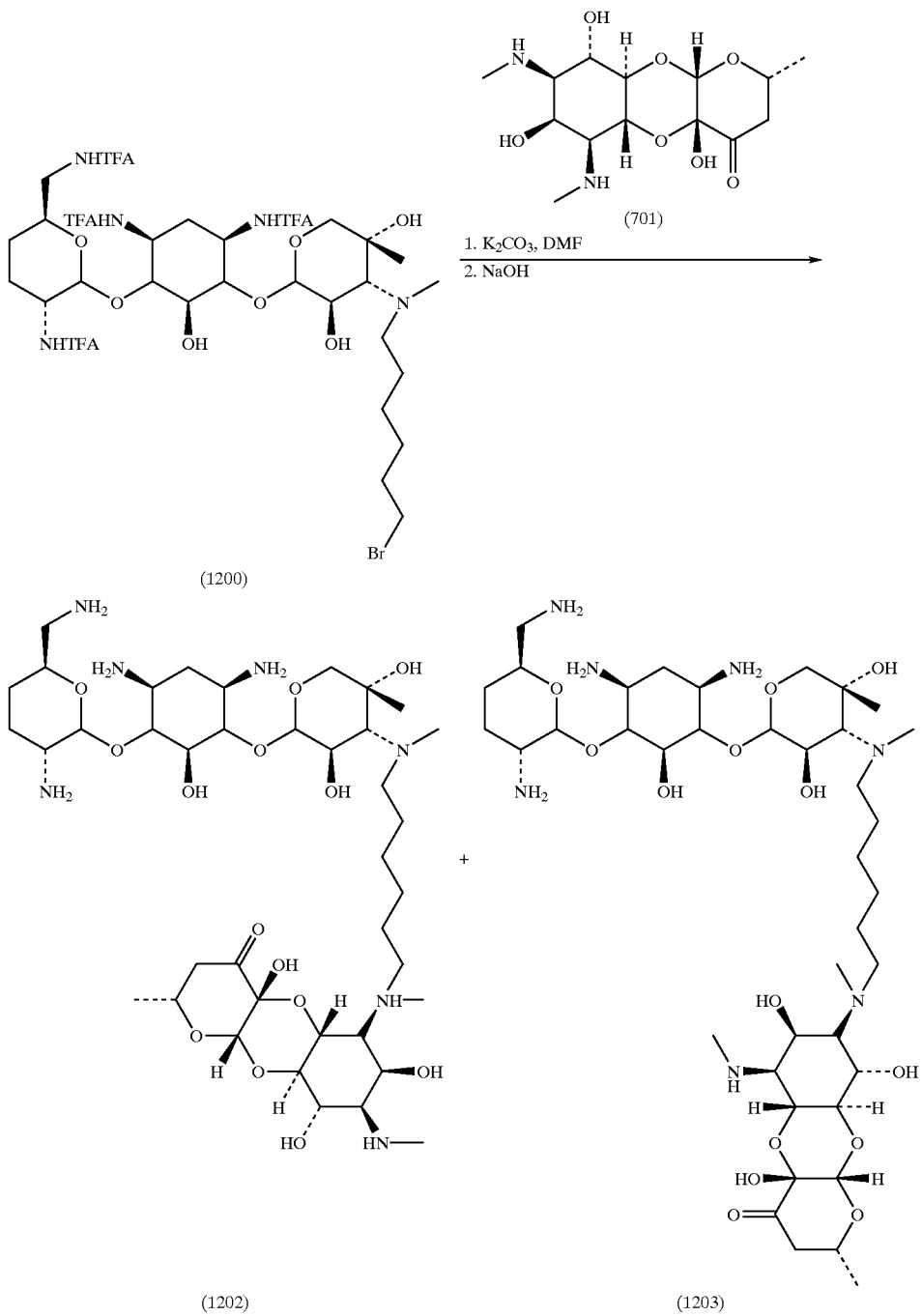

Example 54

Preparation of (1205) and (1206), Compounds of Formula LII via Scheme ZZ

A solution of 20 mmols of compound (301) in DMF with 20 mmols of 1,6-dibromohexane (302) and 40 mmols of potassium carbonate is heated as necessary and the reaction followed by TLC. When judged complete, volatiles are removed under reduced pressure to afford the desired product (1204), which is used in the next step without any further purification.

A solution of 10 mmols of the above compound (1204) in DMF with 10 mmols of Spectinomycin (701) and 20 mmols of potassium carbonate is heated as necessary and the reaction followed by TLC. When judged complete, volatiles are removed under vacuum and the crude is fractionated by reverse-phase HPLC to afford the title product after lyopholization of the appropriate fractions.

Compound (301) is U-57930E and is reported in Antimicrobial Agents Chemother. 1982, 21, 902–905.

The chemistry is detailed below in the following reaction scheme:

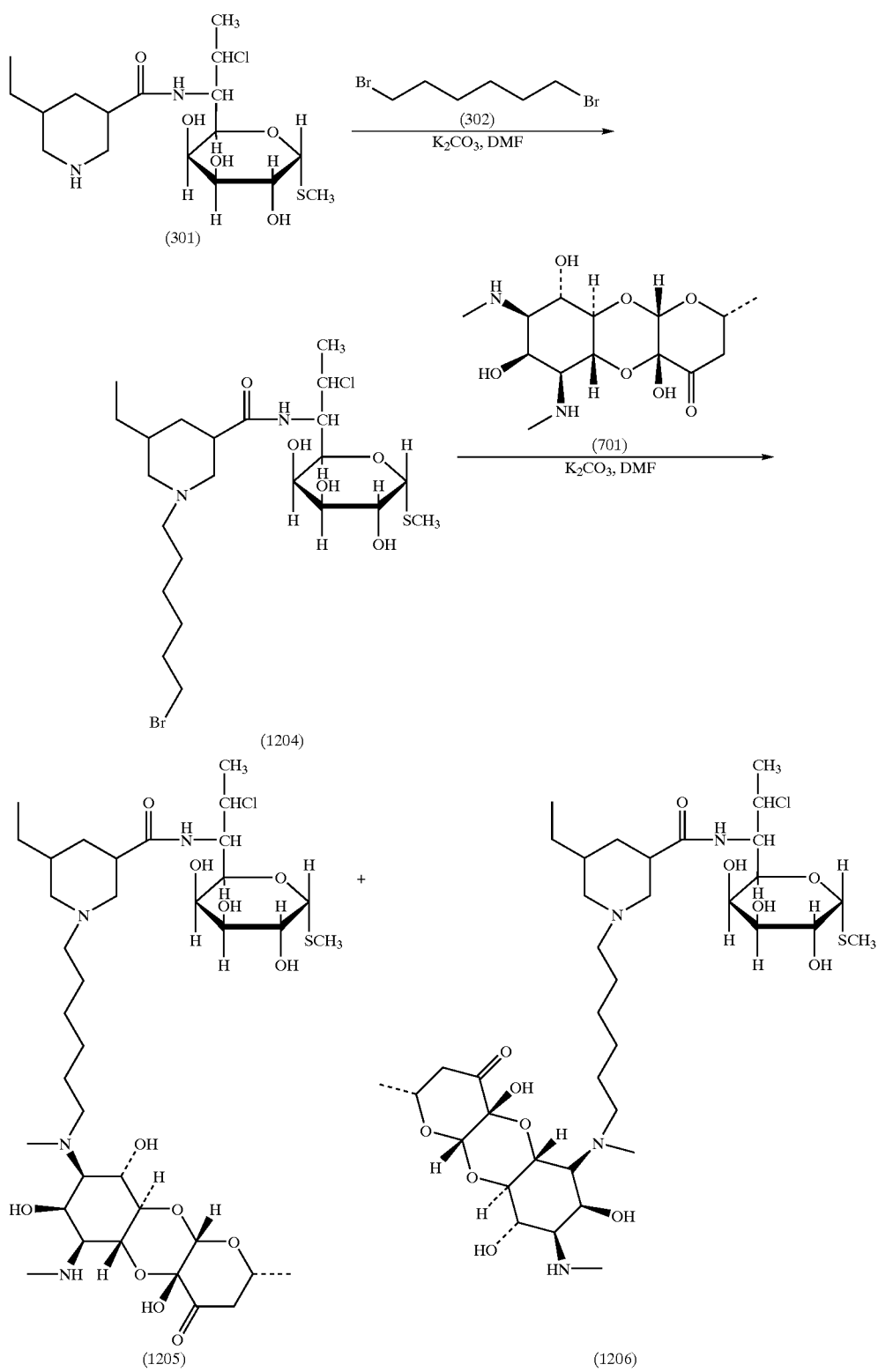

Example 55

Preparation of (1207) and (1208), Compounds of Formula LIII via Scheme AAA

Compounds (912) (4.0 mmol) and (913) (4.0 mmol), prepared as described in Example 34, are individually dissolved in anhydrous dimethylformamide and treated with compound (408) (4.0 mmol), prepared as described in Example 11, hydroxybenzotriazole (5.0 mmol), diisopropylethyl amine (4.0 mmol) and PyBOP (4.0 mmol) and the coupling reaction mixture is stirred overnight at room temperature. Volatiles are removed under vacuum and the crude is fractionated by reverse-phase HPLC to afford the title products after lyopholization of the appropriate fractions.
The chemistry is detailed below in the following reaction scheme:
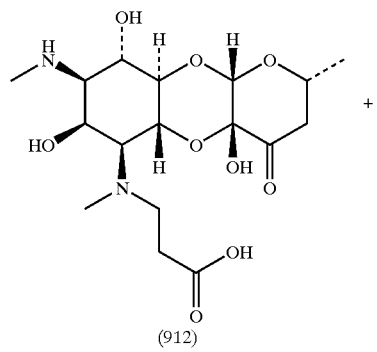
(912)
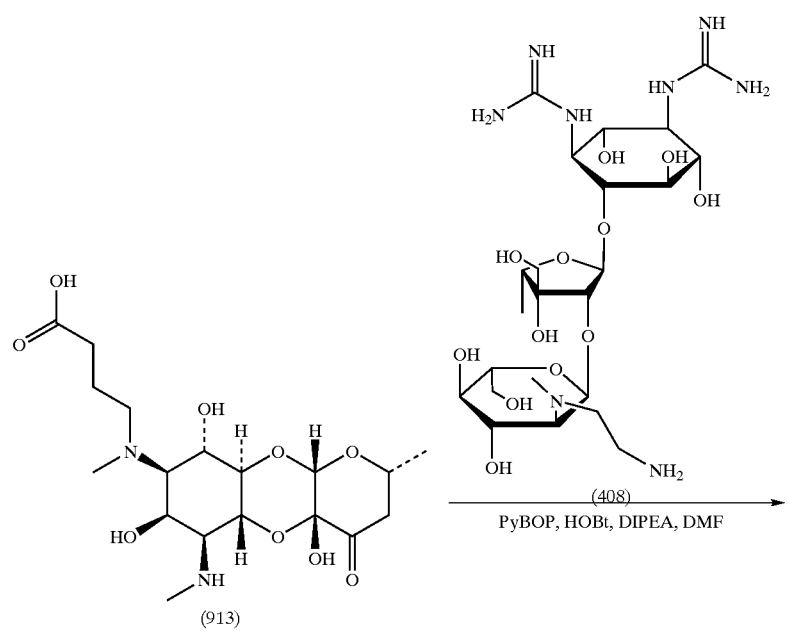
(913)

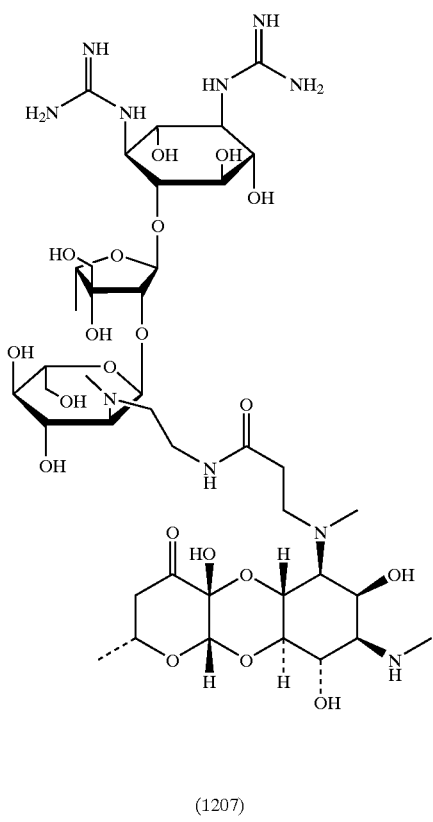

(1207)

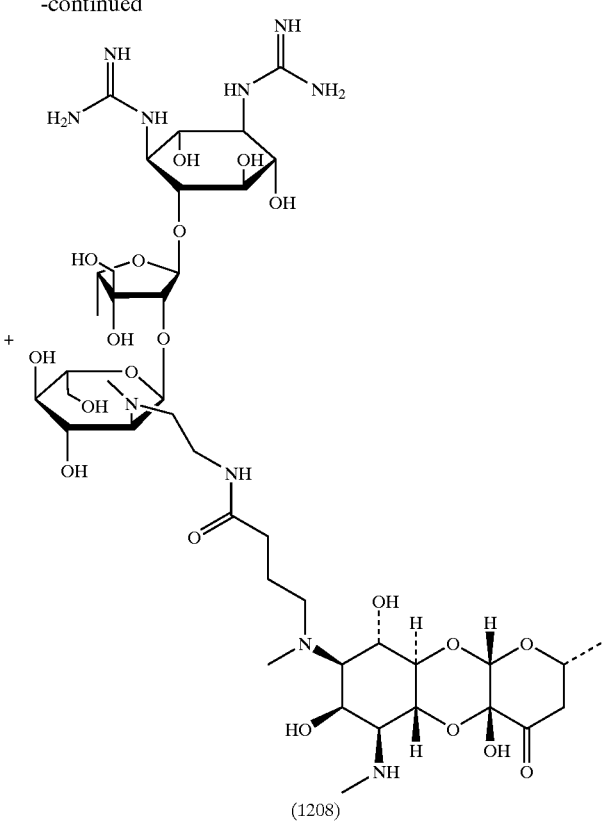

(1208)

Example 56

Preparation of (1211), a Compound of Formula LIV via Scheme BBB

In a sealed tube, 1,3-phenylenediisocyanate (1209) (41.0 mmol) is dissolved in anhydrous acetonitrile. To this solution is added compound (408) (41.0 mmol), prepared as described in Example 11, and the tube is partially immersed in a silicon oil bath and heated to 65° C. and allowed to stir for 16 h. The reaction mixture is cooled and then evaporated to afford the crude product (1210), which is used in the next step without any further purification.

In a sealed tube, compound (1210) (30.0 mmol) is dissolved in anhydrous acetonitrile. To this solution is added compound (503) (30.0 mmol), prepared as described in Example 12, and the tube is partially immersed in a silicon oil bath and heated to 85° C. and allowed to stir for 16 h. The reaction mixture is cooled and then evaporated to afford the crude product, which is purified by reverse-phase HPLC to afford the title product.

The chemistry is detailed below in the following reaction scheme:

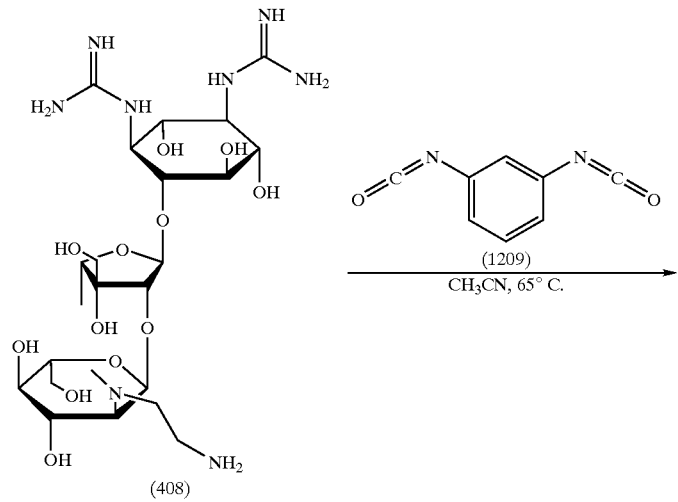

-continued

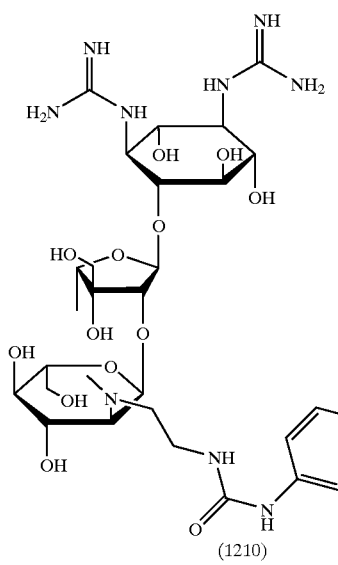
(1210)

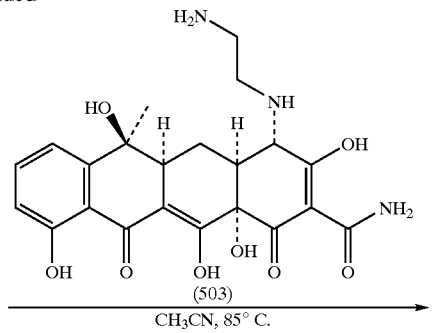
(503)
$\xrightarrow{CH_3CN, 85°\ C.}$

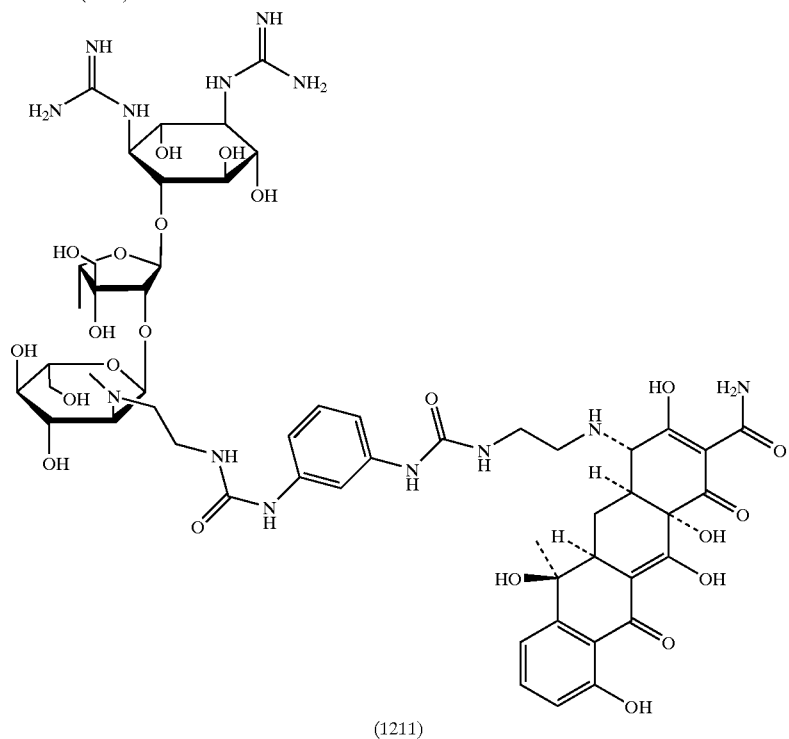
(1211)

Example 56A

Preparation of (1213), a Compound of Formula LV via Scheme CCC

Succinic acid (104) (8.0 mmol) is dissolved in 10 mL anhydrous dimethylformamide and treated sequentially with hydroxybenzotriazole (10.0 mmol), diisopropylethyl amine (8.0 mmol) and PyBOP (8.0 mmol). After stirring for 15 minutes at room temperature, the activated acid is treated with compound (835) (8.0 mmol), prepared as described in Example 28, and the coupling reaction mixture is stirred overnight at room temperature. Volatiles are removed under vacuum and the crude is fractionated by reverse-phase HPLC to afford the desired product (1212) after lyopholization of the appropriate fractions.

The above compound (1212) (4.0 mmol) is dissolved in 10 mL anhydrous dimethylformamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (503) (4.0 mmol), prepared as described in Example 12, and the coupling reaction mixture is stirred overnight at room temperature. Volatiles are removed under vacuum and the crude is fractionated by reverse-phase HPLC to afford the title product after lyopholization of the appropriate fractions.

The chemistry is detailed below in the following reaction scheme:
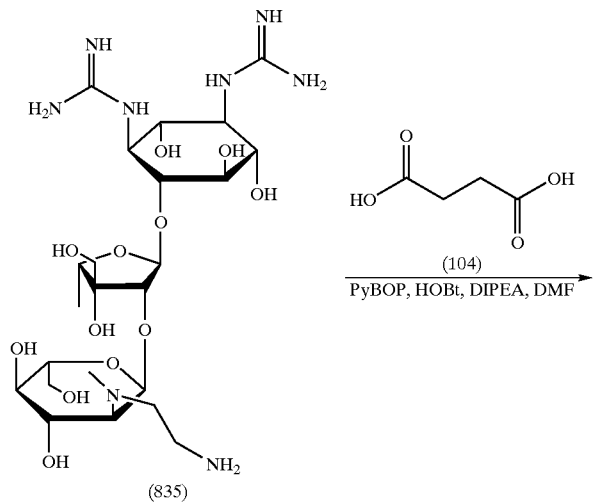
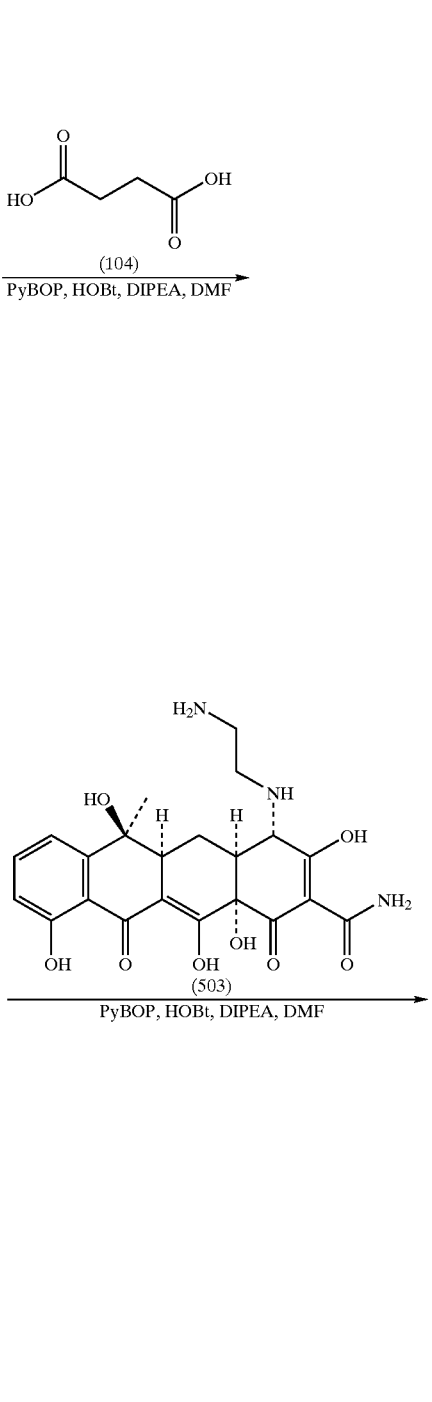

-continued

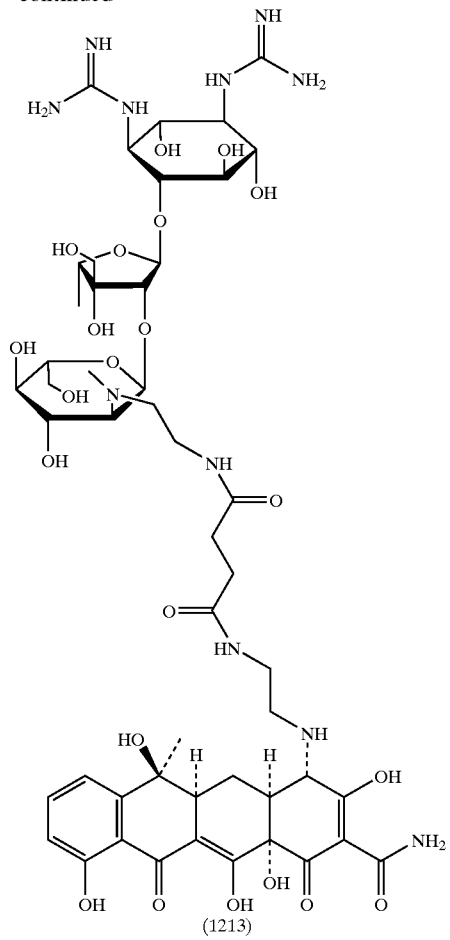

(1213)

Example 57

Preparation of (1215), a Compound of Formula LVI via Scheme DDD

A solution of 10 mmols of compound (829), prepared as described in Example 26, in DMF with 10 mmols of 6-bromohexanoic acid (1008) and 20 mmols of potassium carbonate is heated as necessary and the reaction followed by TLC. When judged complete, the reaction mixture is concentrated under reduced pressure and the residue purified by chromatography to afford the desired product (1214).

The above compound (1214) (4.0 mmol) is dissolved in anhydrous dimethylfornamide and treated sequentially with hydroxybenzotriazole (5.0 mmol), diisopropylethyl amine (4.0 mmol) and PyBOP (4.0 mmol). After stirring for 15 minutes at room temperature, the activated acid is treated with compound (503) (4.0 mmol), prepared as described in Example 12, and the coupling reaction mixture is stirred overnight at room temperature. The reaction mixture is diluted two-fold with water, treated with NaOH (50 mmol), and heated as necessary to effect deprotection. The crude product is fractionated by reverse-phase HPLC to afford the title product after lyopholization of the appropriate fractions.

The chemistry is detailed below in the following reaction scheme:

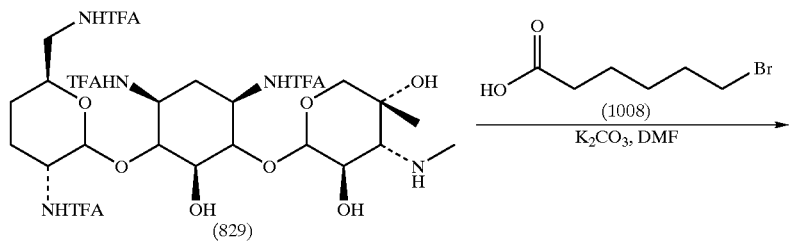

-continued
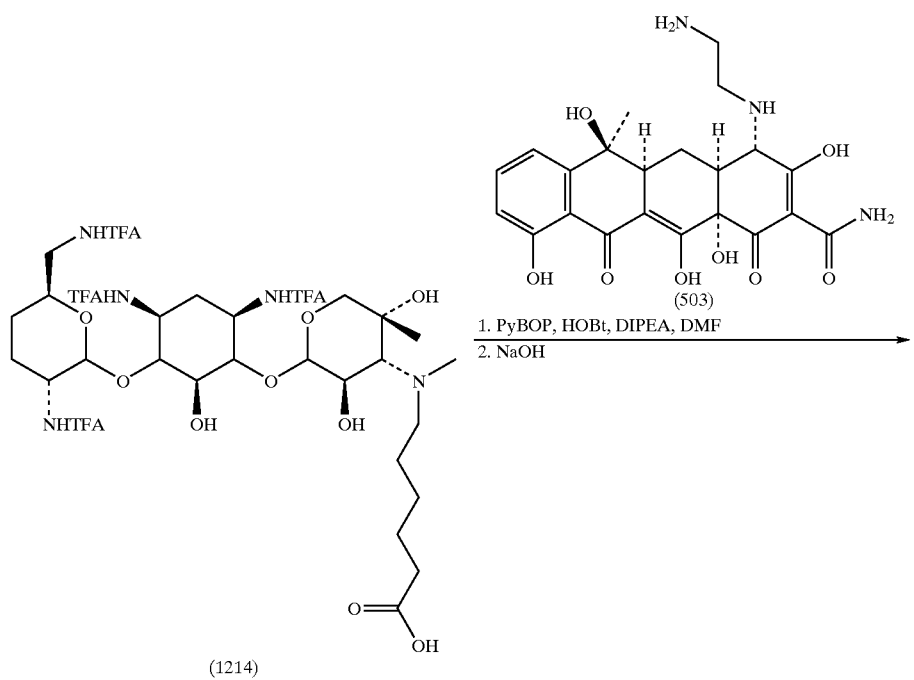
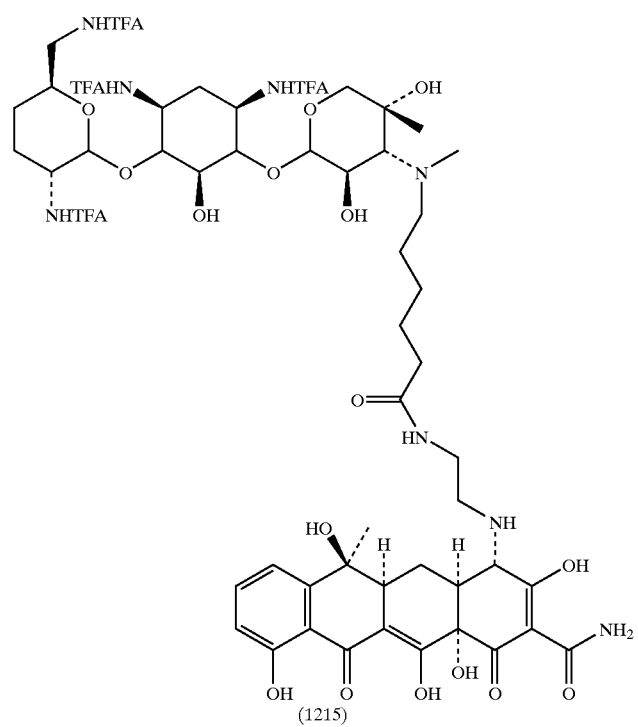

What is claimed is:
1. A compound of the formula:
L'—X'—L"
or a pharmaceutically-acceptable salt thereof; wherein L' is selected from the group consisting of:
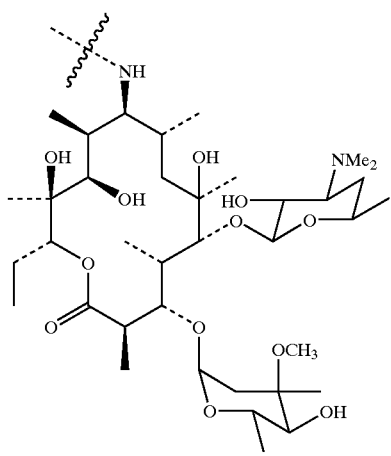
(i)
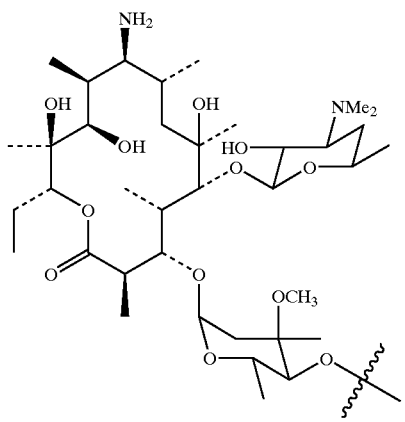
(ii)
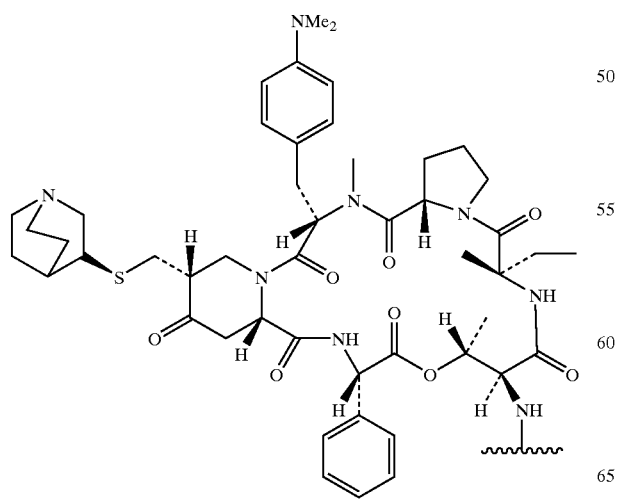
(iii)
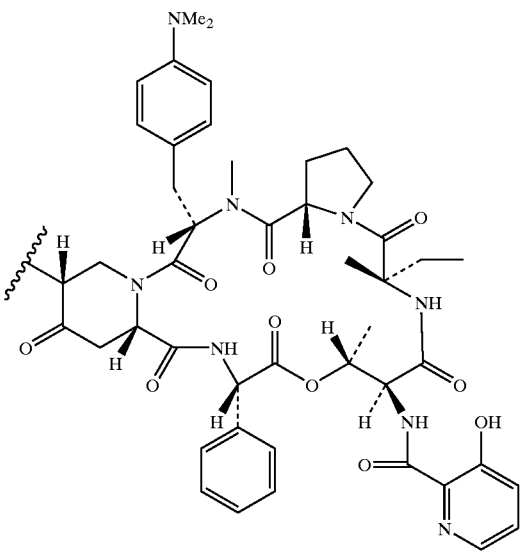
(iv)
and
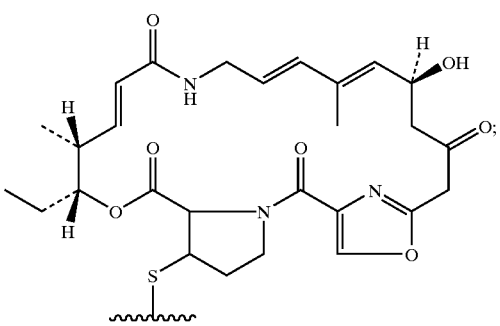
(v)
L" is a moiety of formula:
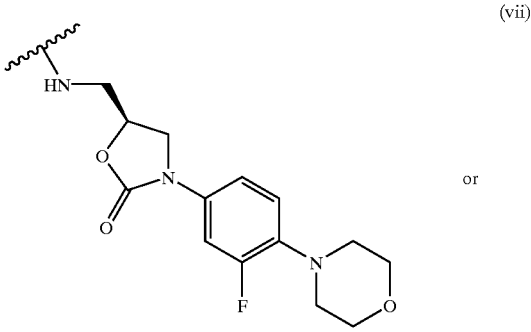
(vii)
or

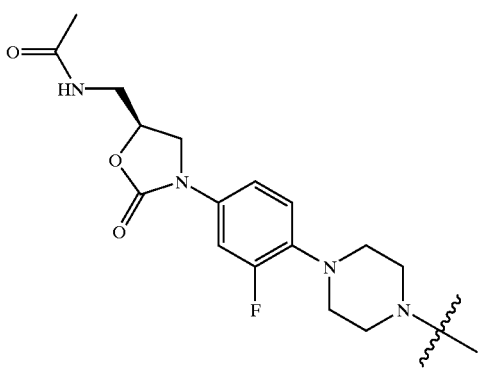

; and

X' has the formula:

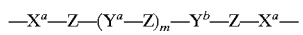

wherein m is an integer of from 0 to 20;

$X^a$ at each separate occurrence is selected from the group consisting of —O—, —S—, —NR—, —C(O)—, —C(O)O—, —C(O)NR—, —C(S), —C(S)O—, —C(S)NR— and a covalent bond where R is as defined below;

Z is at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, and a covalent bond;, $Y^a$ and $Y^b$ at each separate occurrence are selected from the group consisting of —C(O)NR'—, —NR'C(O)—, —NR'C(O)NR'—, —C(=NR')—NR'—, —NR'C(=NR')—, —NR'C(O)—O—, —P(O)(OR')—O—, —S(O)$_n$CR'R"—, —S(O)$_n$—NR'—, —S—S— and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

2. The compound of claim 1, wherein L' is formula (i).
3. The compound of claim 1, wherein L' is formula (ii).
4. The compound of claim 1, wherein L' is formula (iii).
5. The compound of claim 1, wherein L' is formula (iv).
6. The compound of claim 1, wherein L' is formula (v).
7. A pharmaceutical composition comprising a pharmaceutically acceptable carrier and an effective amount of a compound of any of claims 1 and 2–6.

* * * * *